(12) United States Patent
Mun et al.

(10) Patent No.: US 10,468,606 B2
(45) Date of Patent: Nov. 5, 2019

(54) COMPOUND FOR ORGANIC ELECTRIC ELEMENT, ORGANIC ELECTRIC ELEMENT COMPRISING THE SAME, AND ELECTRONIC DEVICE THEREOF

(71) Applicant: DUK SAN NEOLUX CO., LTD., Cheonan-si, Chungcheongnam-do (KR)

(72) Inventors: Soung Yun Mun, Cheonan-si (KR); Yeon Hee Choi, Cheonan-si (KR); Sun-Hee Lee, Hwaseong-si (KR); Seul-gi Kim, Daejeon (KR); Sunpil Hwang, Ansan-si (KR)

(73) Assignee: Duk San Neolux Co., Ltd., Cheonan-si, Chungcheon (KR)

( * ) Notice: Subject to any disclaimer, the term of this patent is extended or adjusted under 35 U.S.C. 154(b) by 0 days.

(21) Appl. No.: 16/068,378

(22) PCT Filed: Dec. 27, 2016

(86) PCT No.: PCT/KR2016/015324
§ 371 (c)(1),
(2) Date: Jul. 6, 2018

(87) PCT Pub. No.: WO2017/119654
PCT Pub. Date: Jul. 13, 2017

(65) Prior Publication Data
US 2019/0019962 A1    Jan. 17, 2019

(30) Foreign Application Priority Data

Jan. 6, 2016  (KR) .................. 10-2016-0001687

(51) Int. Cl.
*H01L 51/00*    (2006.01)
*C07D 495/04*   (2006.01)
(Continued)

(52) U.S. Cl.
CPC ........ *H01L 51/0071* (2013.01); *C07D 495/04* (2013.01); *C07D 519/00* (2013.01);
(Continued)

(58) Field of Classification Search
CPC ............. H01L 51/0071; H01L 51/0074; H01L 51/0073; H01L 51/0052; C07D 519/00
See application file for complete search history.

(56) References Cited

U.S. PATENT DOCUMENTS

2009/0128012 A1* 5/2009 Song .................. H01L 51/0092
                                                    313/504
2016/0365517 A1* 12/2016 Mun ..................... C07D 209/86
(Continued)

FOREIGN PATENT DOCUMENTS

KR    10-2011-0066766 A    6/2011
KR    10-2015-0003566 A    1/2015
(Continued)

*Primary Examiner* — John P. Dulka
(74) *Attorney, Agent, or Firm* — Vorys, Sater, Seymour & Pease LLP; Mih Suhn Koh

(57) ABSTRACT

The present invention provides the compound represented by Formula 1, an organic electric element comprising a first electrode, a second electrode, and an organic material layer formed between the first electrode and the second electrode, and electronic device thereof, and by comprising the compound represented by Formula 1 in the organic material layer, the driving voltage of the organic electronic device can be lowered, and the luminous efficiency and life time of the organic electronic device can be improved.

12 Claims, 1 Drawing Sheet

(51) Int. Cl.
*C09K 11/06* (2006.01)
*C07D 519/00* (2006.01)
*H01L 51/50* (2006.01)

(52) U.S. Cl.
CPC .......... *C09K 11/06* (2013.01); *H01L 51/0052* (2013.01); *H01L 51/0072* (2013.01); *H01L 51/0073* (2013.01); *H01L 51/0074* (2013.01); *C09K 2211/1007* (2013.01); *C09K 2211/1011* (2013.01); *C09K 2211/1018* (2013.01); *C09K 2211/1029* (2013.01); *C09K 2211/1037* (2013.01); *C09K 2211/1048* (2013.01); *C09K 2211/1051* (2013.01); *C09K 2211/1092* (2013.01); *H01L 51/5016* (2013.01); *H01L 51/5056* (2013.01); *H01L 51/5088* (2013.01)

(56) References Cited

U.S. PATENT DOCUMENTS

2017/0062728 A1* 3/2017 Mun .................... H01L 51/0061
2018/0123048 A1* 5/2018 So ........................ C07D 307/93

FOREIGN PATENT DOCUMENTS

| KR | 10-1561566 B1 | 10/2015 |
| KR | 10-2015-0133998 A | 12/2015 |
| KR | 10-2015-0136942 A | 12/2015 |

* cited by examiner

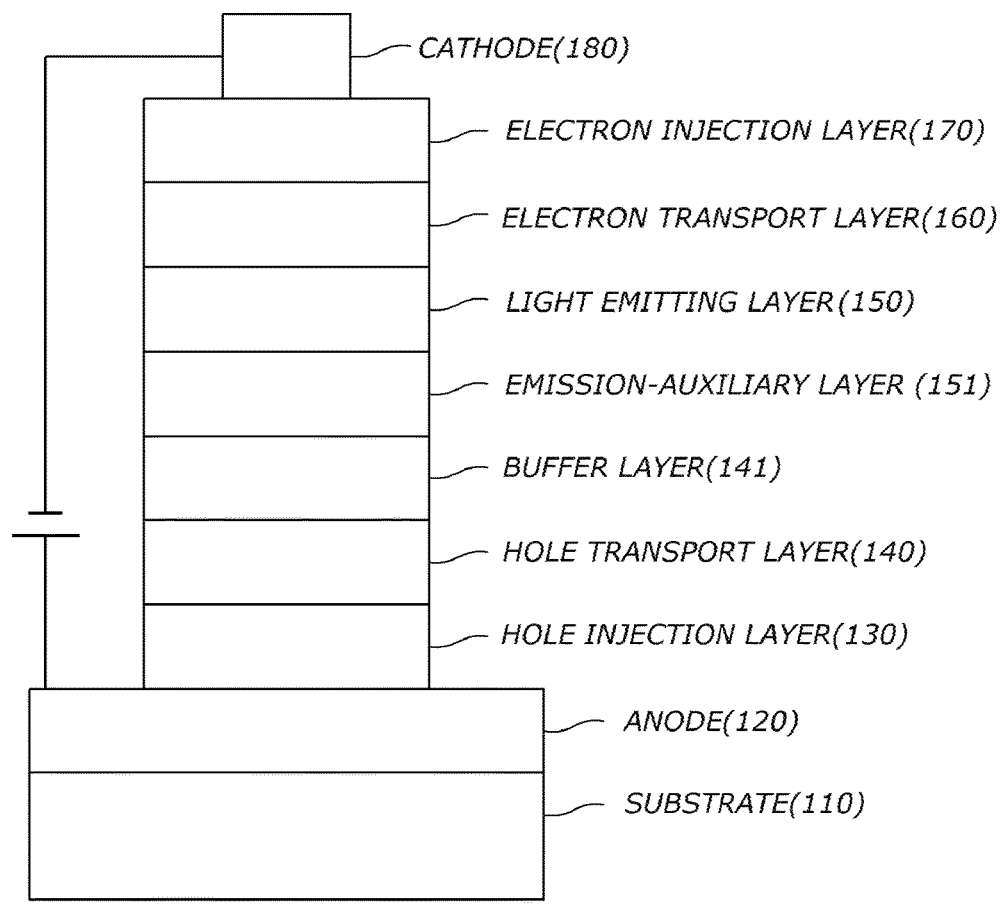

COMPOUND FOR ORGANIC ELECTRIC ELEMENT, ORGANIC ELECTRIC ELEMENT COMPRISING THE SAME, AND ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2016-0001687, filed on Jan. 6, 2016, which is hereby incorporated by reference for all purposes as if fully set forth herein. Further, this application claims the benefit of priority in countries other than U.S.A, which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given. In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. Therefore, there is a continuous need to develop new material, in particular, there are strong needs to develop host material for a light emitting layer.

OBJECT, TECHNICAL SOLUTION AND EFFECTS OF THE INVENTION

The present invention is to provide a compound improving luminous efficiency and lifetime of the element, an organic electric element comprising the same, and an electronic device thereof.

In an aspect of the present invention, the present invention provides the compound represented by the following formula.

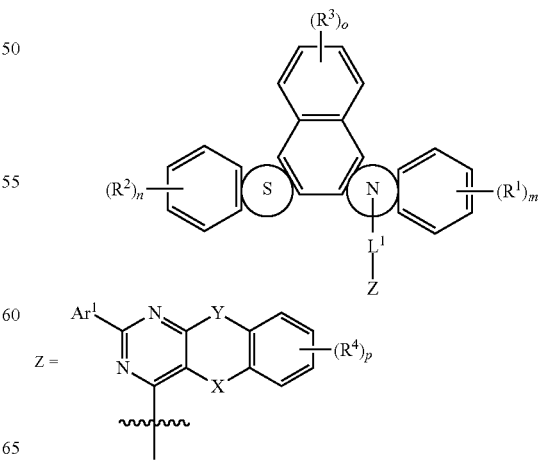

In another aspect of the present invention, the present invention provides an organic electric element using the compound represented by formula above and an electric device thereof.

By using the compound according to embodiments of the present invention, the luminous efficiency and lifetime of the element can be improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means the saturated aliphatic functional radicals including a linear alkyl group, a branched chain alkyl group, a cycloalkyl group (alicyclic), or an alkyl group substituted with a cycloalkyl or with a cycloalkyl substituted with an alkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means an oxygen radical attached to an alkyl group, but not limited to, and has 1 to 60 carbon atoms.

Unless otherwise stated, the term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises spiro compound formed by linking R and R' together with the carbon bonded to them.

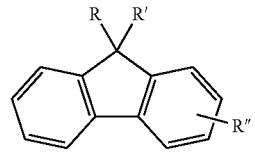

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the following compound.

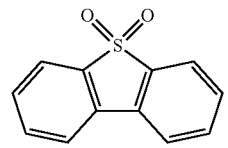 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic ring" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted with deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula:

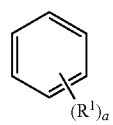

Wherein, when a is an integer of zero, the substituent $R^1$ is absent, that is, hydrogen atoms are bonded to all the carbon constituting the benzene ring, and chemical formulas or compounds may be written without explicitly describing the hydrogen. In addition, one substituent $R^1$ is bonded to any carbon of the carbons forming the benzene ring when "a" is an integer of 1. When "a" is an integer of 2 or 3, for example, substituents $R^1$s are bonded to the carbon of the benzene ring as followings. Also, substituents $R^1$s are bonded to the carbon of the benzene ring when "a" is an integer of 4 to 6 in a similar manner. Further, when "a" is an integer of 2 or more, $R^1$s may be the same or different from each other.

(a = 2)

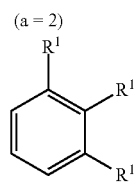

(a = 3)

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

Although not shown, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170 and the like, as a host or a dopant material of a light emitting layer 150, or as a material of a layer for improving luminous efficiency. For example, the inventive compound may be used as material of the light emitting layer 150, preferably, as phosphorescent host material of the light emitting layer 150.

On the other hand, even if the core is the same core, the band gap, the electrical characteristics, the interface characteristics, and the like may be different depending on which substituent is bonded at which position. Therefore, it is necessary to study the selection of the core and the combination of the core and the sub-substituent bonded to the core. Specially, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, according to the present invention, energy level and $T_1$ value between the respective layers of the organic material layer, inherent material properties (mobility, interfacial properties, etc.) and the like can be optimized by forming a light emitting layer 150 which comprises the compound represented by the Formula 1, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by the following formula 1.

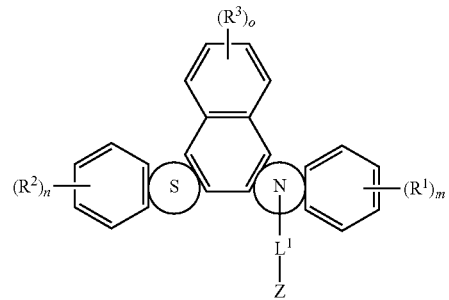

In the formula 1, each of symbols may be defined as follows.

Z may be represented by the following formula.

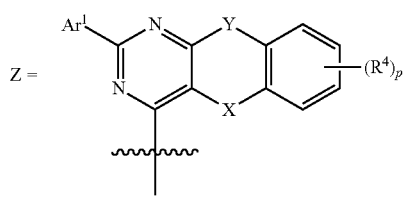

In the Formula 1, S ring is a $C_4$ heterocyclic group comprising S (Sulfur), and N ring is a $C_4$ heterocyclic group comprising N (Nitrogen). For example, S ring may be a thiophene and N ring may be a pyrrole.

$R^1$ to $R^4$ may be each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-$N(R^a)(R^b)$, a $C_1$-$C_{30}$ alkoxyl group and a $C_6$-$C_{30}$ aryloxy group.

When $R^1$ to $R^4$ are an aryl group, $R^1$ to $R^4$ may be preferably a $C_6$-$C_{30}$ aryl group, more preferably a $C_6$-$C_{14}$ aryl group, for example, phenyl, biphenyl, naphthyl, phenanthrene or the like; when $R^1$ to $R^4$ are a heterocyclic group, $R^1$ to $R^4$ may be preferably a $C_2$-$C_{30}$ heterocyclic group, more preferably a $C_2$-$C_{16}$ heterocyclic group, for example, pyridine, carbazole, benzocarbazole, pyridoindole, dibenzothiophene, dibenzofuran, benzonaphthofuran or the like; when $R^1$ to $R^4$ are a fluorenyl group, $R^1$ to $R^4$ may be 9,9-dimethyl-9H-fluorene, 9,9'-spirofluorene or the like; when $R^1$ to $R^4$ are an alkyl group, $R^1$ to $R^4$ may be preferably a $C_1$-$C_{10}$ alkyl group, more preferably a $C_1$-$C_4$ alkyl group, for example, t-butyl; when $R^1$ to $R^4$ are an alkenyl group, $R^1$ to $R^4$ may be preferably a $C_2$-$C_{10}$ alkenyl group, more preferably a $C_2$-$C_3$ alkenyl group, for example, ethene, propenyl or the like; and when $R^1$ to $R^4$ are an aryloxy group, $R^1$ to $R^4$ may be preferably a $C_6$-$C_{12}$ aryloxy group, for example, a phenoxy group.

Further, neighboring $R^1$s to $R^4$s may be optionally linked to each other to form at least one ring, and $R^1$ to $R^4$ not forming a ring may be the same as defined above. Here, the ring formed by bonding between the neighboring groups may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring, for example, the formed ring may be benzene ring or naphthalene or the like.

m, n, o and p are each an integer of 0 to 4, and when each of them is an integer of 2 or more, each of the plurality of $R^1$s to $R^4$s may be the same or different from each other, $Ar^1$ may be selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

Preferably, $Ar^1$ may be selected from the group consisting of a $C_6$-$C_{30}$ aryl group, a fluorenyl group, a fused ring group of a $C_3$-$C_{30}$ aliphatic ring and a $C_6$-$C_{30}$ aromatic ring, and a $C_2$-$C_{30}$ heterocyclic group containing at least one heteroatom selected from the group consisting of O, N, S, Si, and P.

When $Ar^1$ is an aryl group, $Ar^1$ may be preferably a $C_6$-$C_{30}$ aryl group, more preferably a $C_6$-$C_{18}$ aryl group, for example, phenyl, biphenyl, terphenyl, naphthyl, phenanthrene, triphenylene, benzo[d]anthracene, pyrene or the like; when $Ar^1$ is a heterocyclic group, $Ar^1$ may be preferably a $C_2$-$C_{30}$ heterocyclic group, more preferably a $C_2$-$C_{22}$ heterocyclic group, for example, furan, thiophene, pyridine, indole, benzimidazole, isoquinoline, carbazole, indolocarbazole, benzocarbazole, dibenzothiophene, benzonaphthothiophene, dibenzofuran, thianthrene, phenoxazine, dihydroacridine, benzothienopyridine, phenoxathine, phenothiazine, benzothienobenzocarbazole derivatives or the like; and when $Ar^1$ is a fluorenyl group, $Ar^1$ may be 9,9-dimethyl-9H-fluorene or the like.

$L^1$ and $L^a$ may be are each independently selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring.

When $L^1$ and $L^a$ are an arylene group, they may be preferably a $C_6$-$C_{30}$ arylene group, more preferably a $C_6$-$C_{12}$ arylene group, for example, phenyl, biphenyl, naphthalene or the like; when $L^1$ and $L^a$ are a heterocyclic group, $L^1$ and $L^a$ may be preferably a $C_2$-$C_{30}$ heterocyclic group, more preferably a $C_2$-$C_{12}$ heterocyclic group, for example, carbazole, dibenzofuran, dibenzothiophene or the like, and when $L^1$ and $L^a$ are a fluorenyl group, $L^1$ and $L^a$ may be 9,9-dimethyl-9H-fluorene or the like.

$R^a$ and $R^b$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, and a $C_2$-$C_{20}$ alkenyl group, X and Y may be each independently a single bond, O or S, with the proviso that one of X and Y is a a single bond and the other is O or S, The above aryl group, arylene group, fluorenyl group, fluorenylene group, heterocyclic group, fused ring group, alkyl group, alkenyl group, alkynyl group, alkoxyl group and aryloxyl group may be each further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

Specifically, the above Formula 1 may be represented by one of the following Formulas 2 to 5.

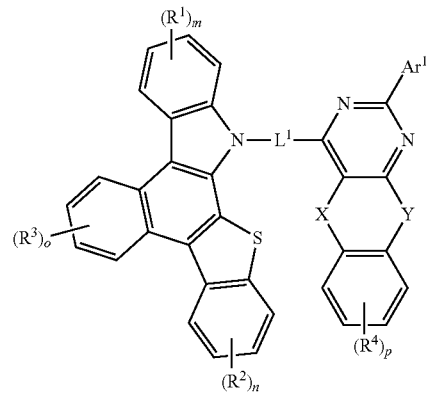

<Formula 2>

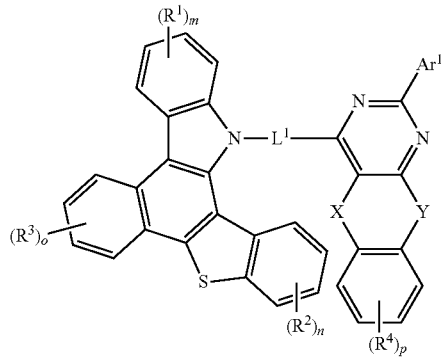

<Formula 3>

<Formula 4>

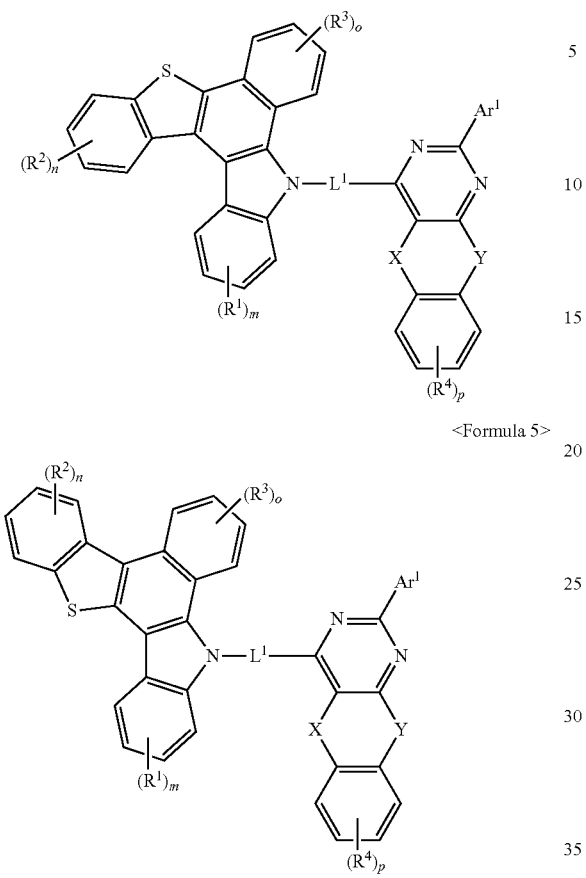

<Formula 5>

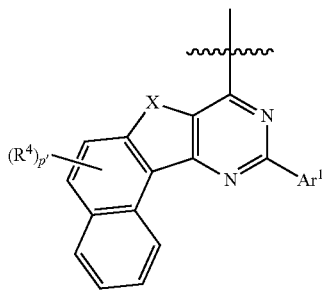


In Formulas 2 to 5, X, Y, $R^1$ to $R^4$, $L^1$, $Ar^1$, m, n, o and p may be the same as defined in Formula 1 above.

Further, Z of the formula 1 may be represented by one of the following formulas Z-1 to Z-8.

Z-1

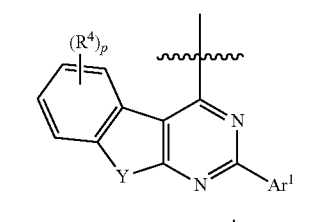

Z-2

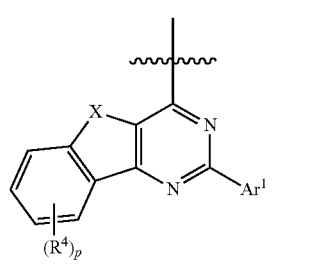

Z-3

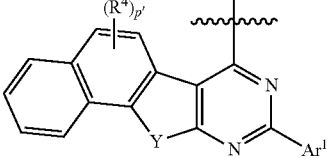

Z-4

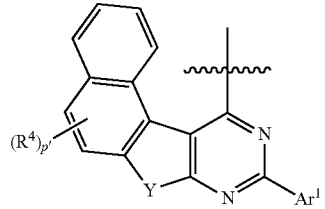

Z-5

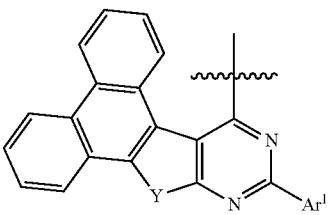

Z-6

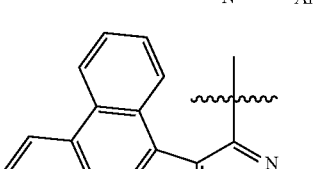

Z-7

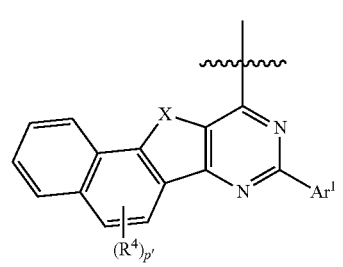

Z-8

In the formulas Z-1 to Z-8, $R^4$ and $Ar^1$ may be the same as defined for Formula 1.

X and Y may be each independently S(Sulfur) or O(Oxygen).

Further, p may be each independently an integer of 0 to 4, and p' may be each independently an integer of 0 to 2. Here, when p and p' are an integer of 2 or more, the plurality of $R^4$ may be the same or different from each other.

More specifically, the above Formula 1 may be represented by one of the following Formulas 2-1 to 5-4.
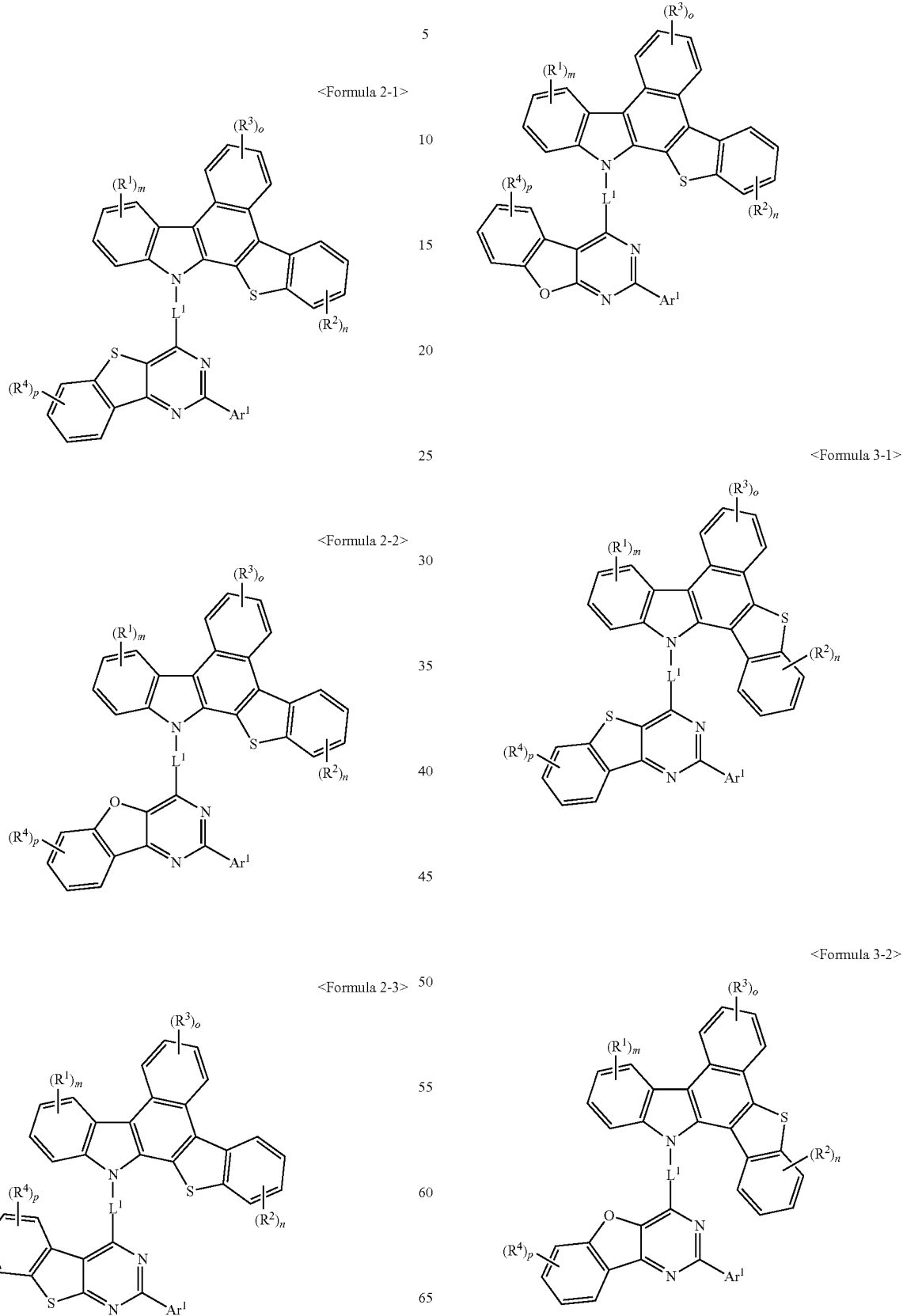

<Formula 3-3>
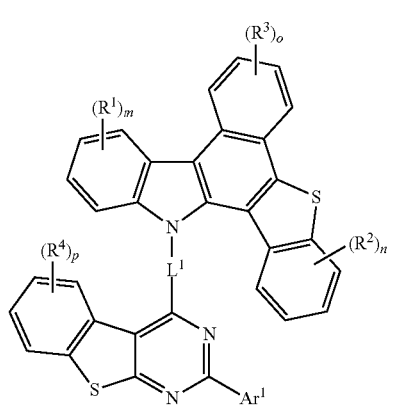
<Formula 3-4>
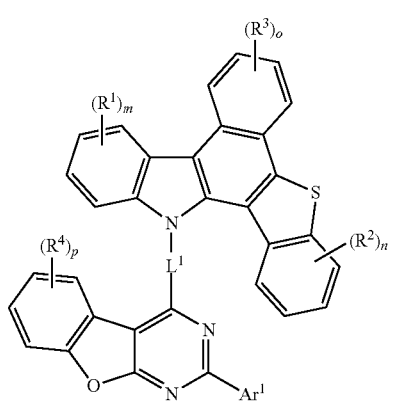
<Formula 4-1>
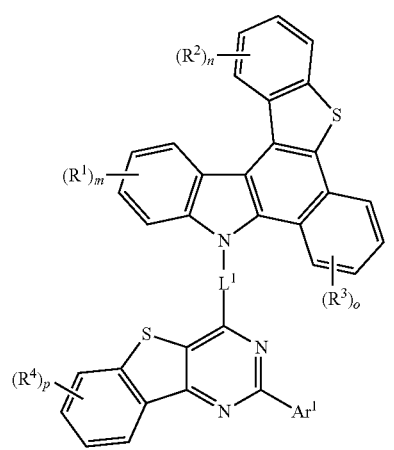
<Formula 4-2>
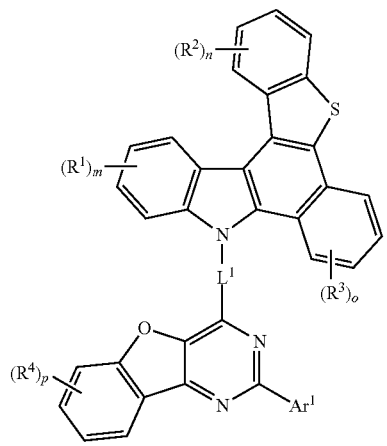
<Formula 4-3>
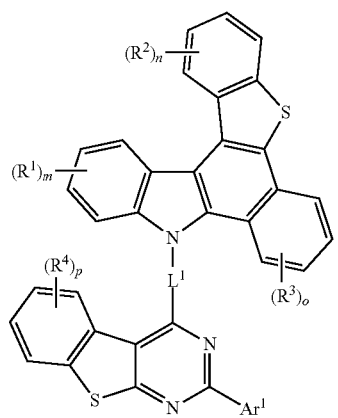
<Formula 4-4>
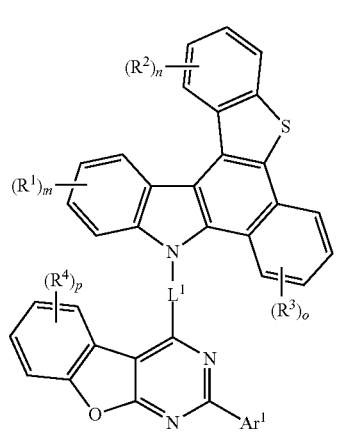

<Formula 5-1>
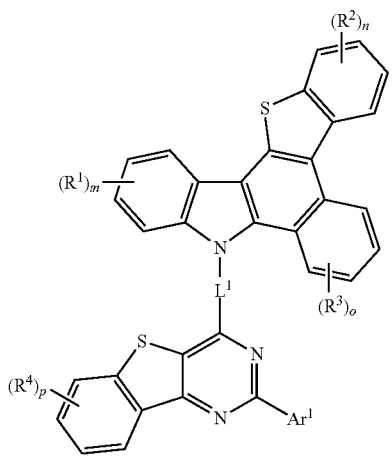
<Formula 5-2>
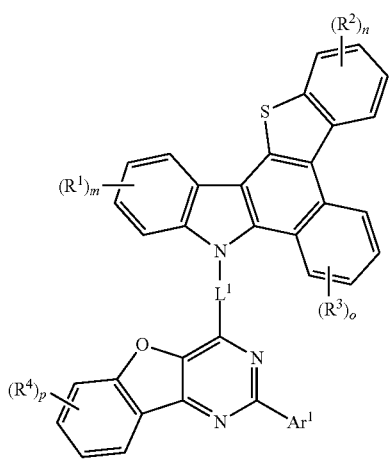
<Formula 5-3>
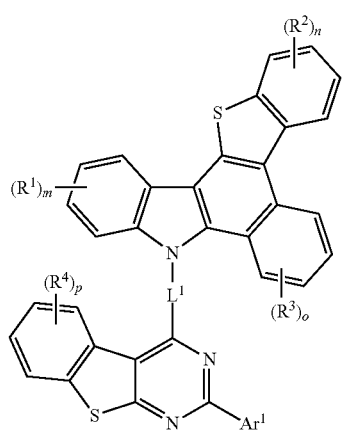
<Formula 5-4>
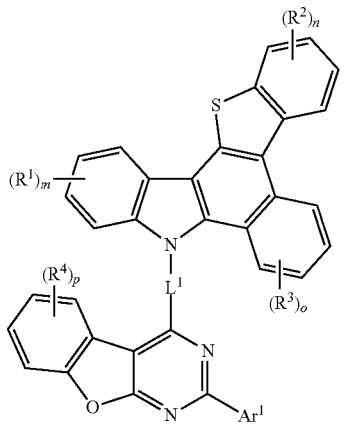
In the formulas 2-1 to 2-4, 3-1 to 3-4, 4-1 to 4-4, and 5-1 to 5-4, $R^1$ to $R^4$, $L^1$, Ar, m, n, o and p may be the same as defined for the formula 1.
Meanwhile, $Ar^1$ in the formula 1 may be represented by one of the following formulas Ar-1 to Ar-10.
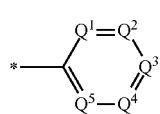
Ar-1
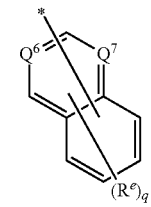
Ar-2
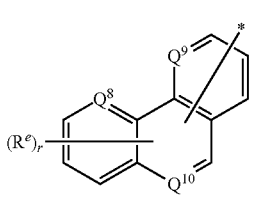
Ar-3
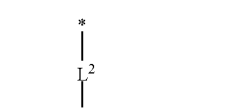
Ar-4
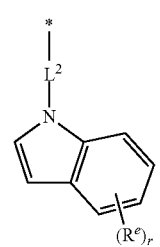
Ar-5

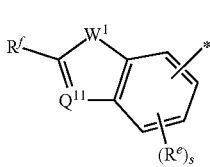
Ar-6

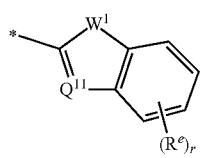
Ar-7

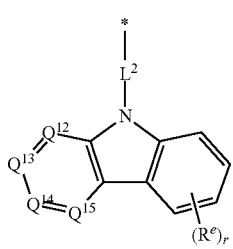
Ar-8

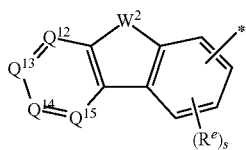
Ar-9

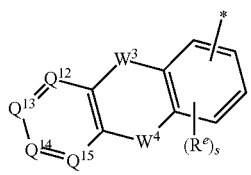
Ar-10

In the Formulas Ar-1 to Ar-10, $L^2$ may be the same as $L^1$ defined for the formula 1.

$Q^1$ to $Q^{15}$ may be each independently $C(R^g)$ or N. Here, $R^g$ may be selected from the group consisting of hydrogen, deuterium, a $C_6$-$C_{20}$ aryl group, a fluorenyl group, a fused ring group of a $C_3$-$C_{20}$ aliphatic ring and a $C_6$-$C_{20}$ aromatic ring, a $C_2$-$C_{20}$ heterocyclic group containing at least one heteroatom selected from the group consisting of O, N, S, Si, and P, a $C_1$-$C_{20}$ alkyl group, a $C_2$-$C_{20}$ alkenyl group, a $C_2$-$C_{20}$ alkynyl group, and a $C_1$-$C_{30}$ alkoxyl group.

$W^1$ is S, O or $N(R^h)$, and $W^2$ to $W^4$ are S, O, $N(R^h)$ or $C(R^i)(R^j)$. Here, $R^h$ to $R^j$ may be each independently selected from the group consisting of a $C_6$-$C_{20}$ aryl group, a $C_2$-$C_{20}$ heterocyclic group containing at least one heteroatom selected from the group consisting of O, N, S, Si, and P, a $C_1$-$C_{20}$ alkyl group, a $C_2$-$C_{20}$ alkenyl group, a $C_1$-$C_{30}$ alkoxyl group, and a fluorenyl group.

$R^e$ may be selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group. Further, neighboring $R^e$ groups are optionally linked to each other to form a ring, wherein the ring formed by bonding between the neighboring groups may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring, for example, the formed ring may be benzene ring or naphthalene and the like.

$R^f$ may be selected from the group consisting of hydrogen, deuterium, a $C_6$-$C_{20}$ aryl group, a fluorenyl group, a fused ring group of a $C_3$-$C_{20}$ aliphatic ring and a $C_6$-$C_{20}$ aromatic ring, a $C_2$-$C_{20}$ heterocyclic group containing at least one heteroatom selected from the group consisting of O, N, S, Si, and P, a $C_1$-$C_{20}$ alkyl group, a $C_2$-$C_{20}$ alkenyl group, a $C_2$-$C_{20}$ alkynyl group, and a $C_1$-$C_{30}$ alkoxyl group.

q may be each independently an integer of 0 to 5, r may be each independently an integer of 0 to 4, s may be each independently an integer of 0 to 3, and when each of q, r and s is an integer of 2 or more, each of the plurality of $R^e$s may be the same or different from each other, and "*" indicates the bonding position.

Further, more specifically, the compound represented by the Formula 1 may be one of the following compounds P 1-1 to P 4-50.

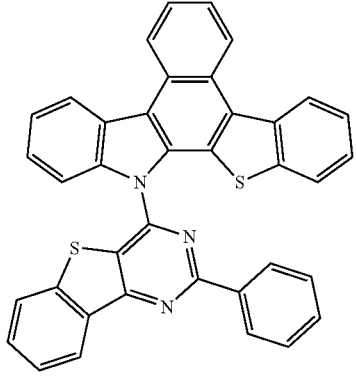
P 1-1

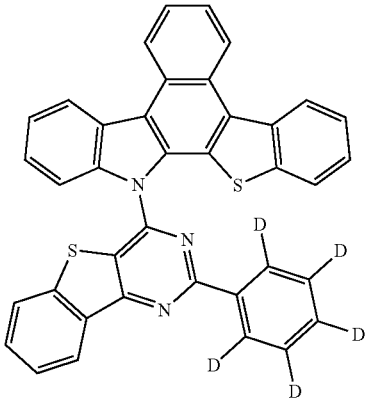
P 1-2

-continued
P 1-3
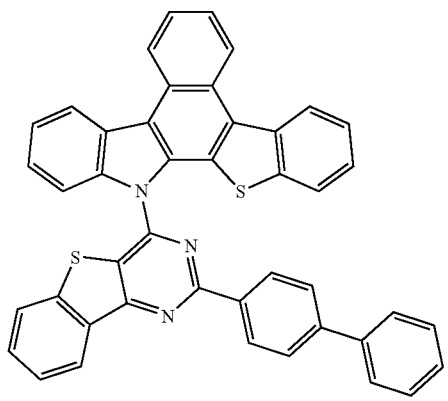
P 1-4
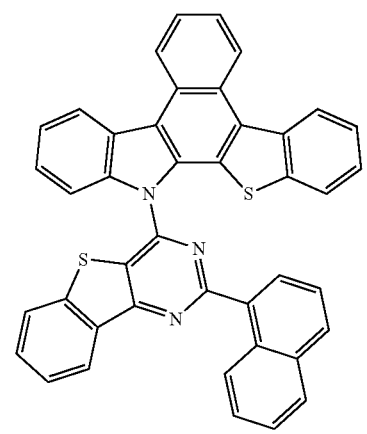
P 1-5
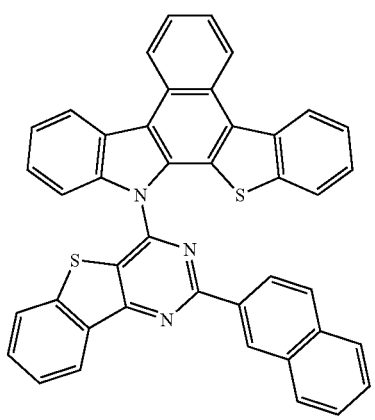
P 1-6
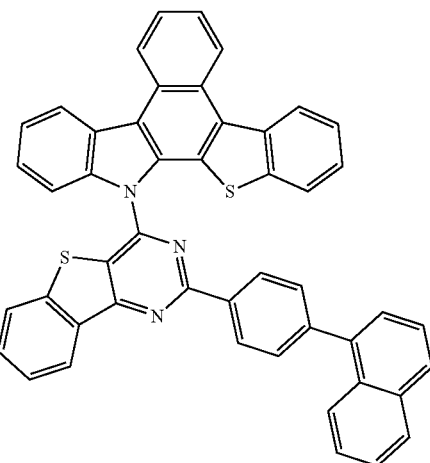
P 1-7
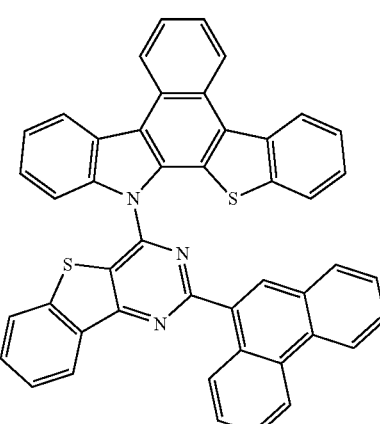
P 1-8
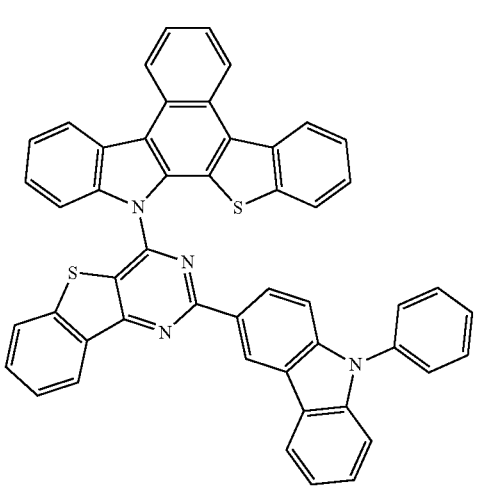

P 1-9
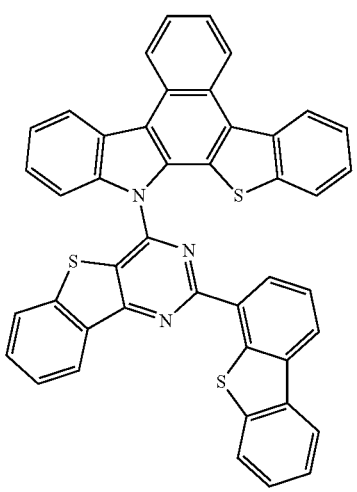
P 1-10
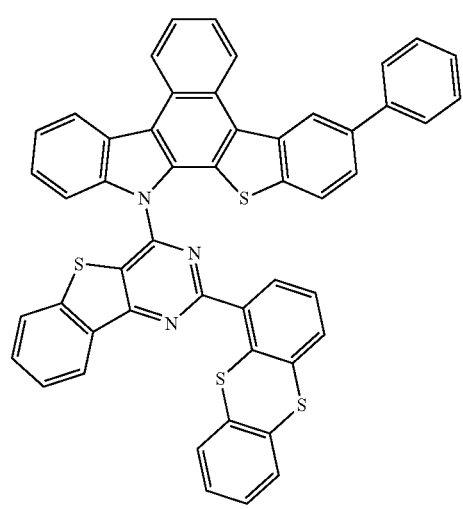
P 1-11
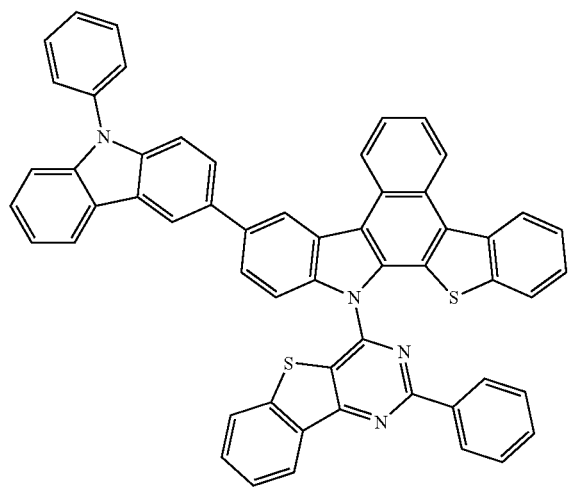
P 1-12
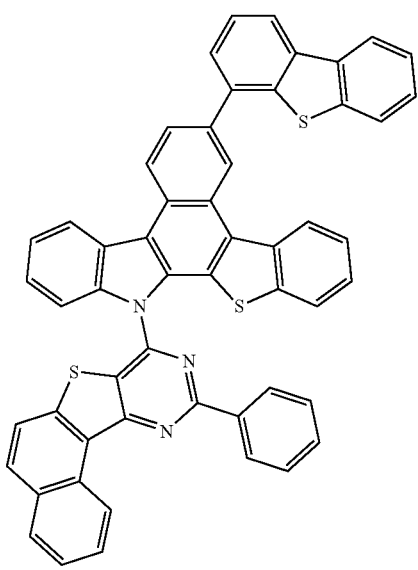
P 1-13
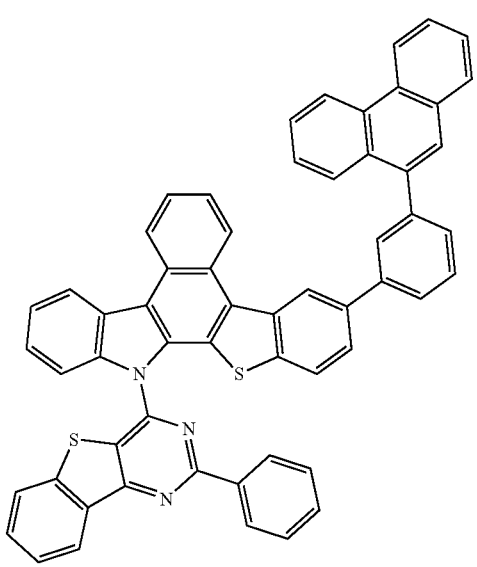
P 1-14
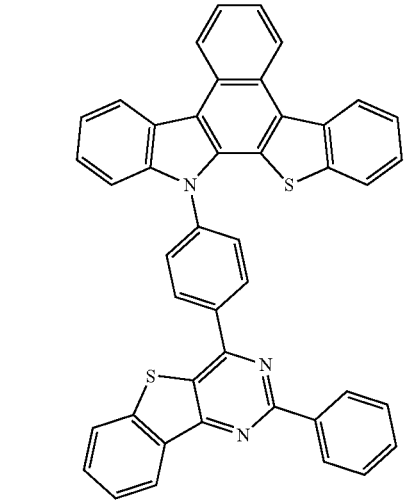

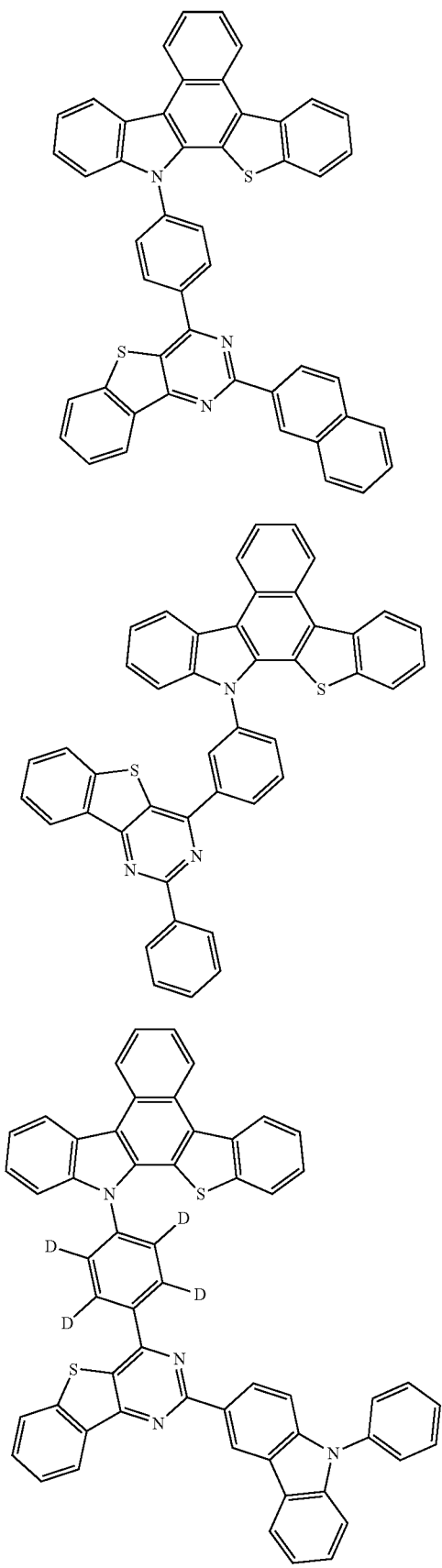

-continued
P 1-20
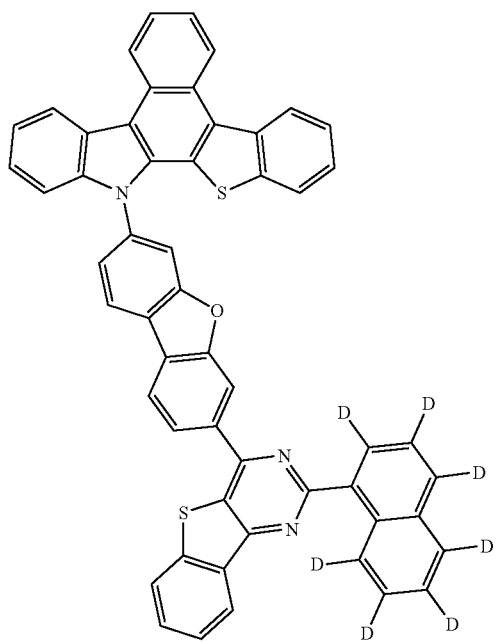
P 1-21
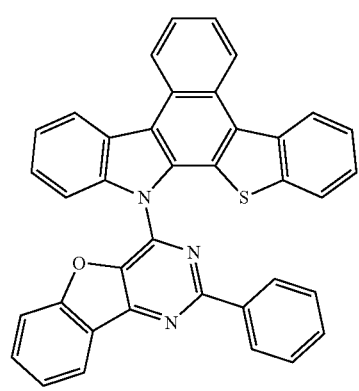
P 1-22
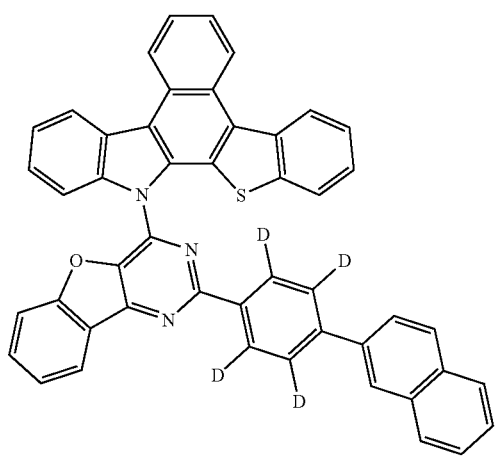
-continued
P 1-23
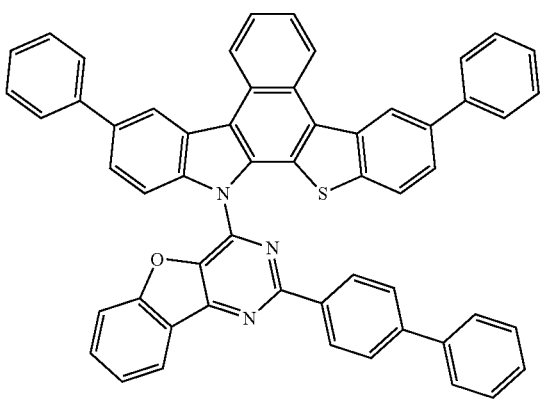
P 1-24
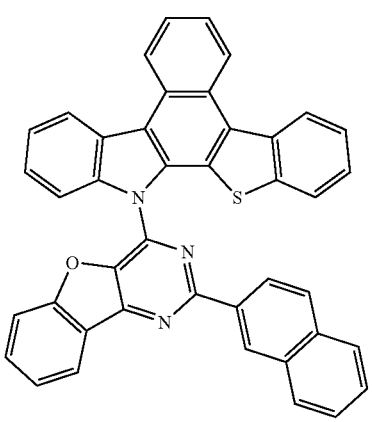
P 1-25
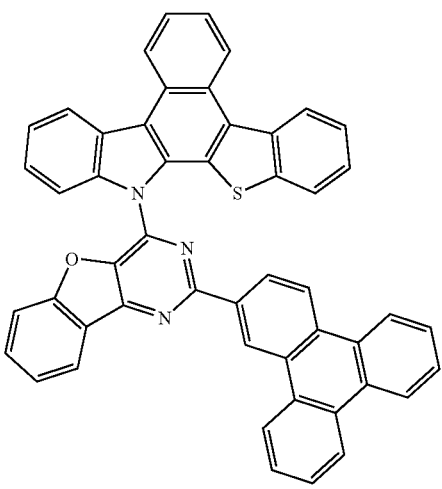

P 1-26
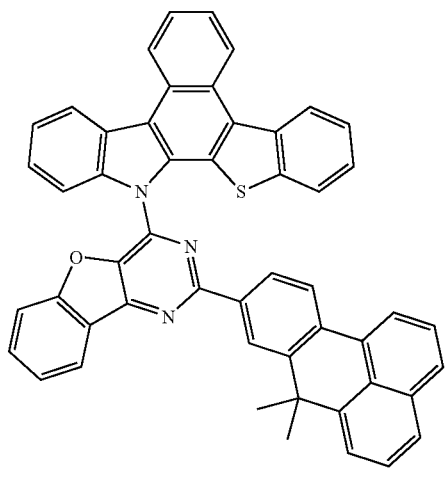
P 1-27
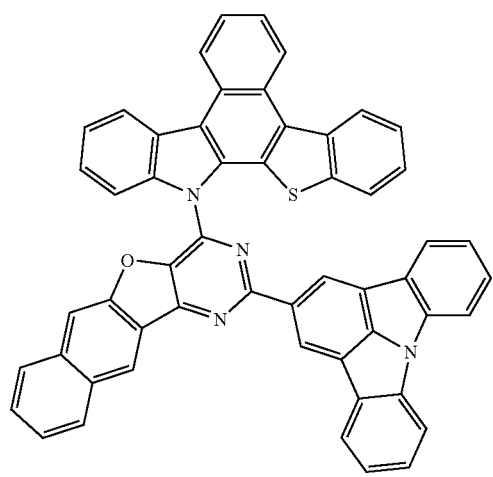
P 1-28
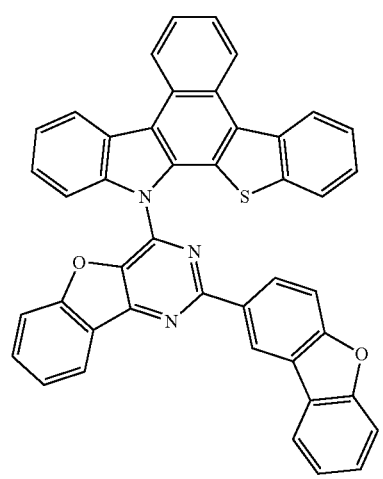
P 1-29
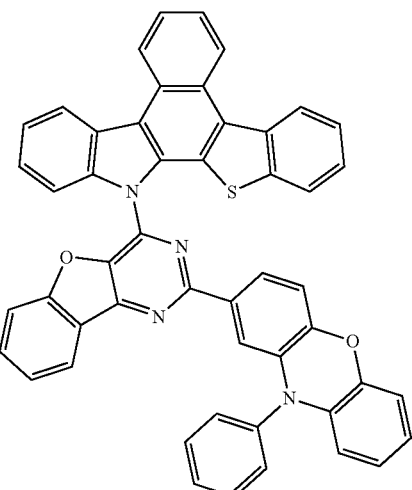
P 1-30
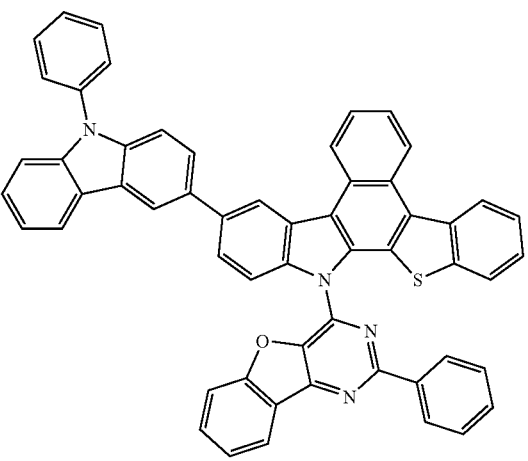
P 1-31
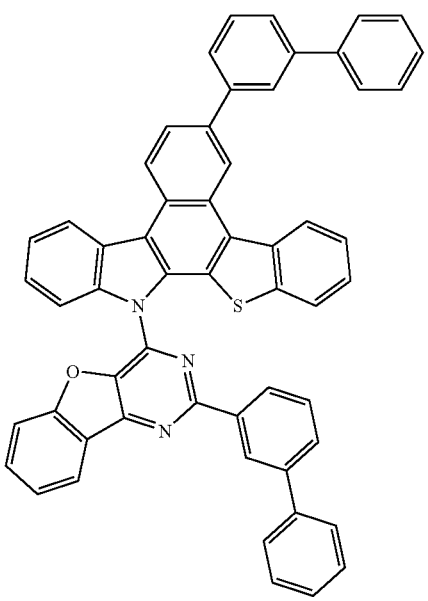

P 1-32
P 1-33
P 1-34
P 1-35
P 1-36
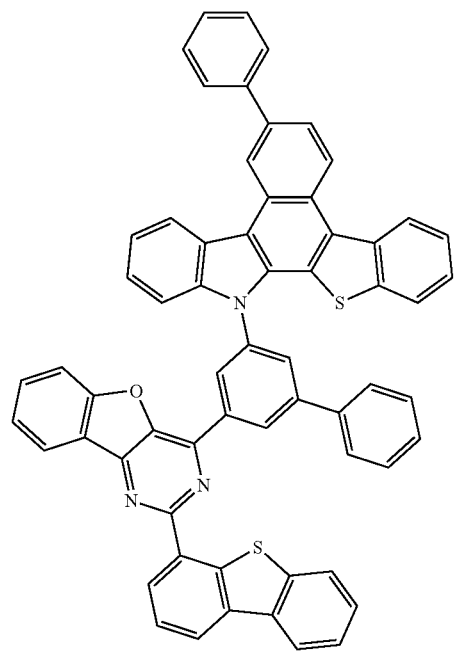
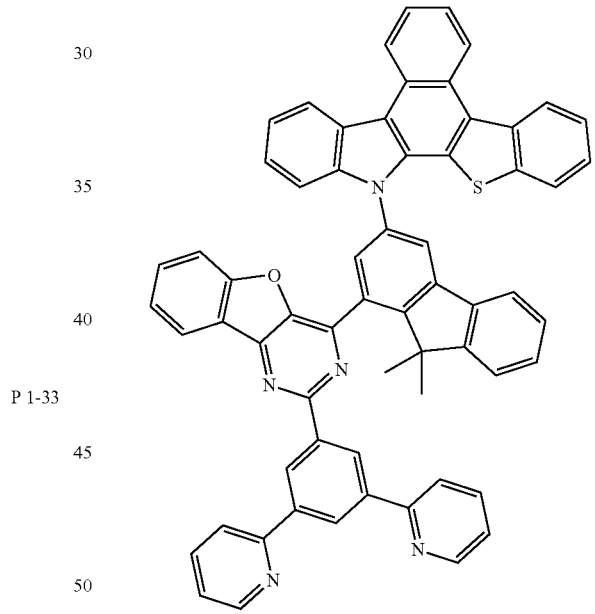
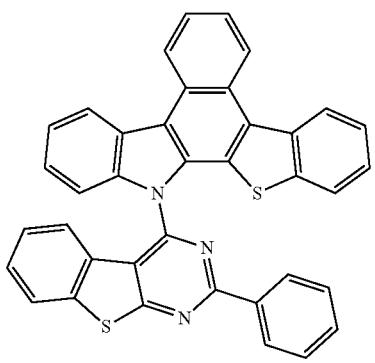

-continued
P 1-37
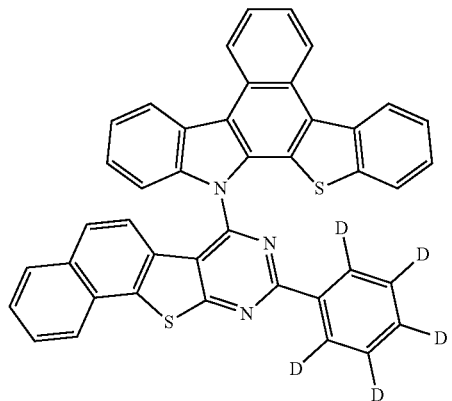
P 1-38
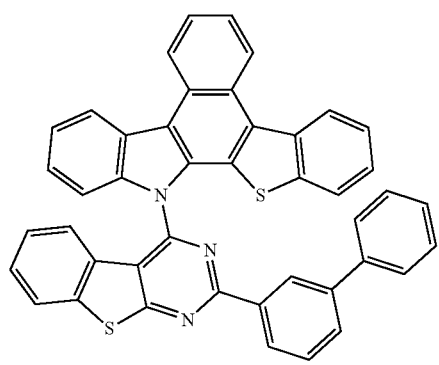
P 1-39
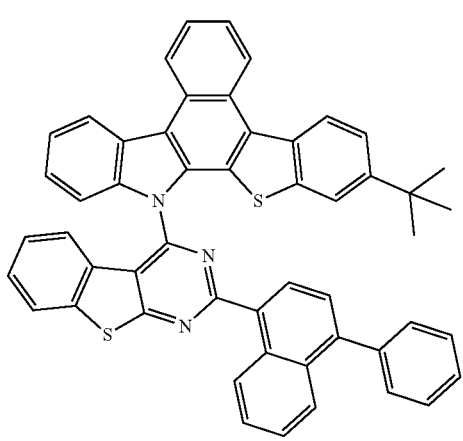
P 1-40
-continued
P 1-41
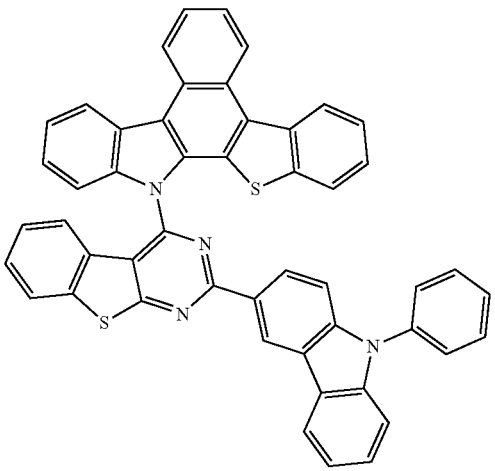
P 1-42
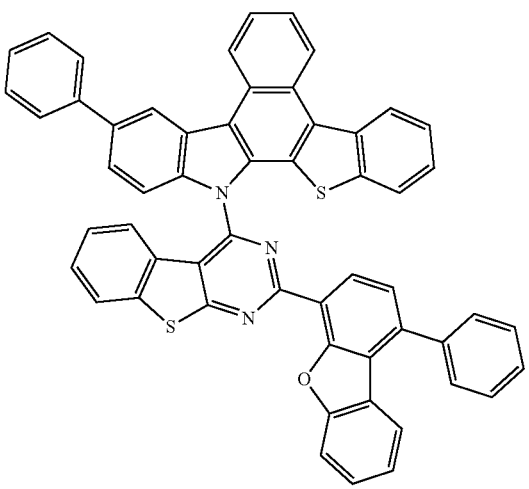
P 1-43
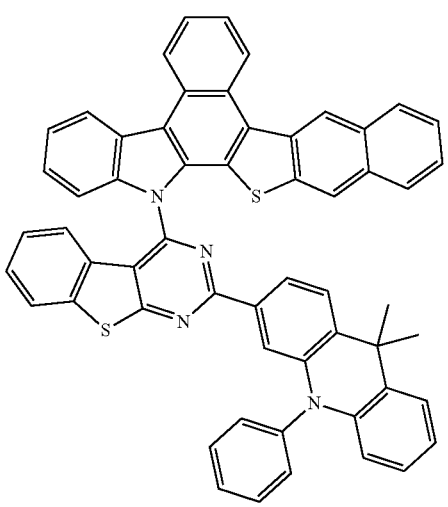

P 1-44
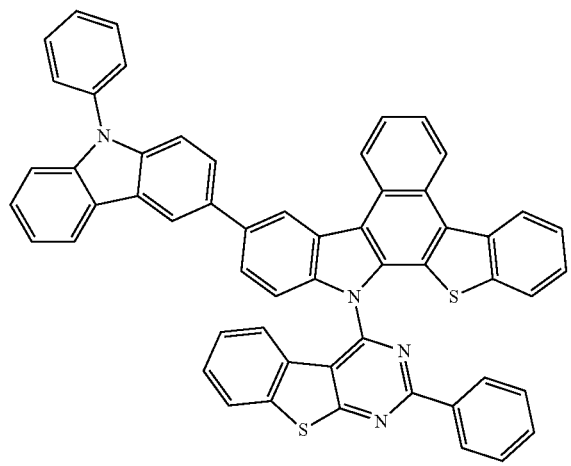
P 1-45
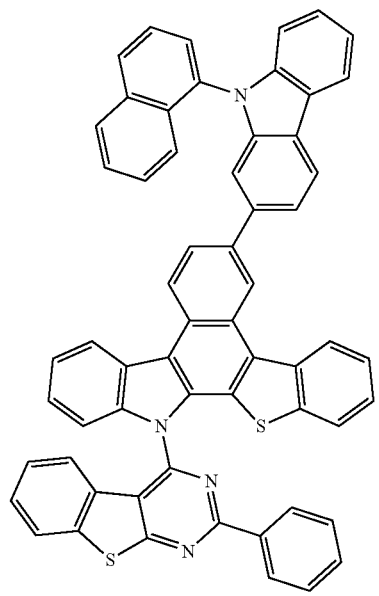
P 1-46
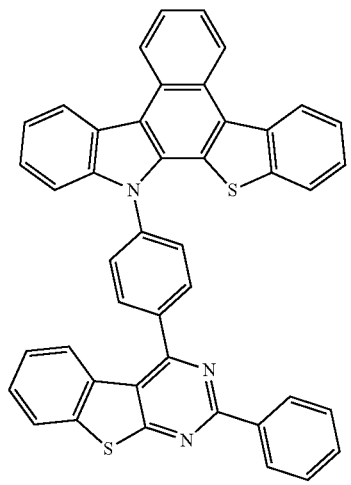
P 1-47
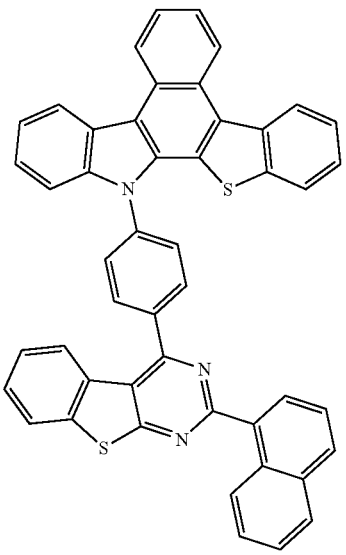
P 1-48
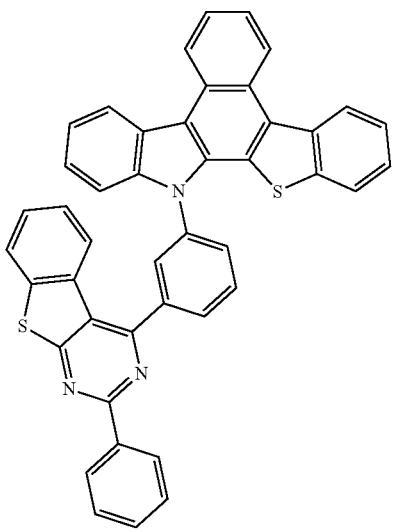
P 1-49
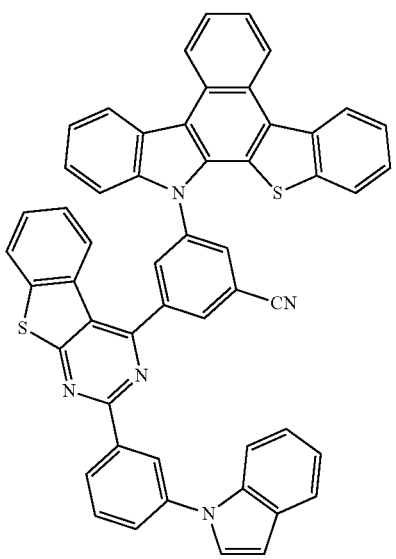

P 1-50
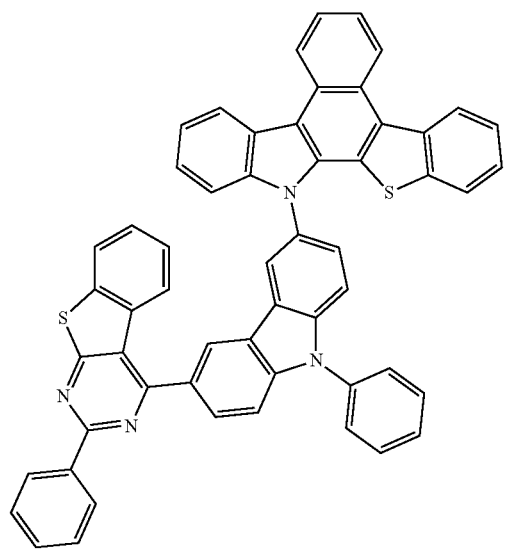
P 1-51
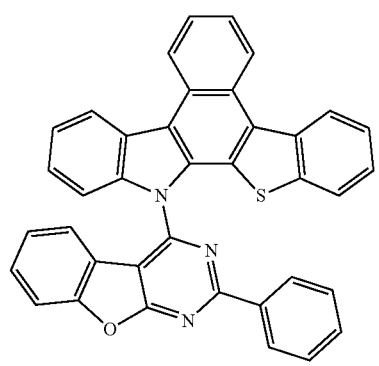
P 1-52
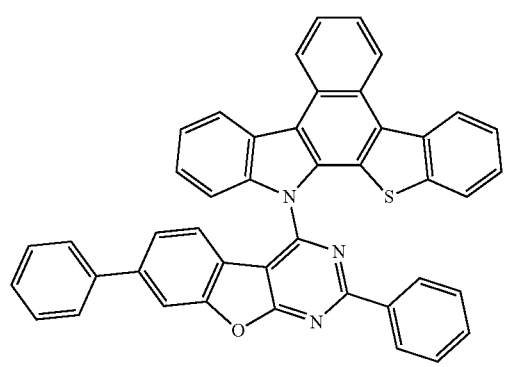
P 1-53
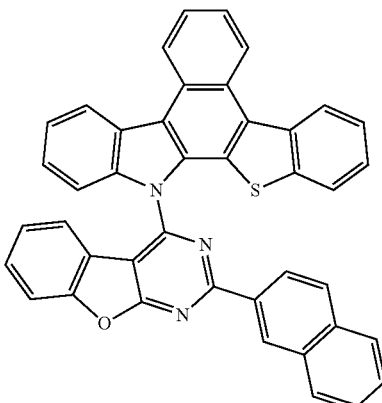
P 1-54
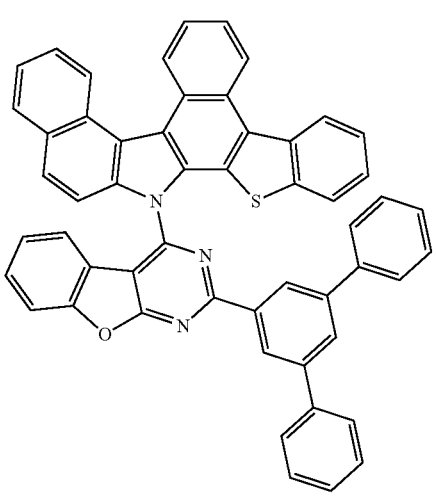
P 1-55
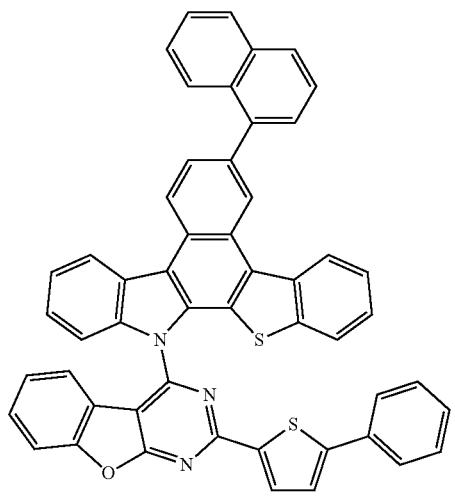

-continued
P 1-56
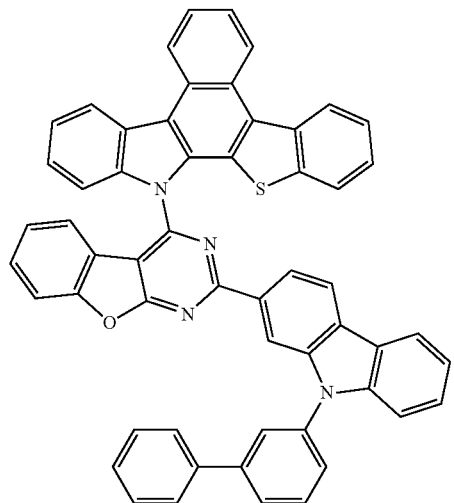
P 1-57
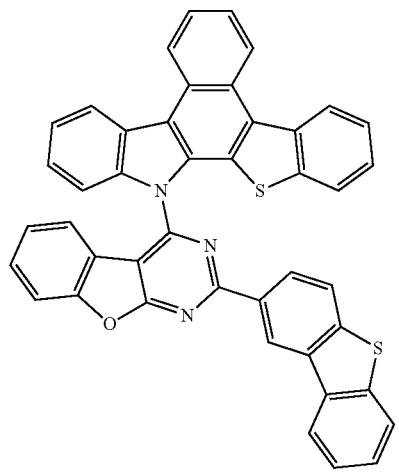
P 1-58
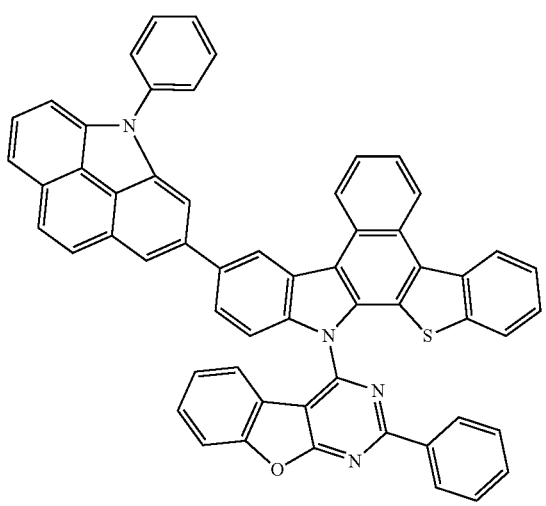
-continued
P 1-59
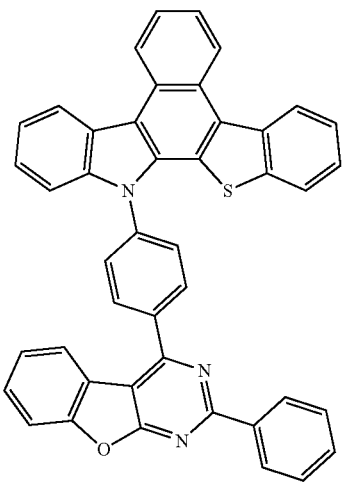
P 1-60
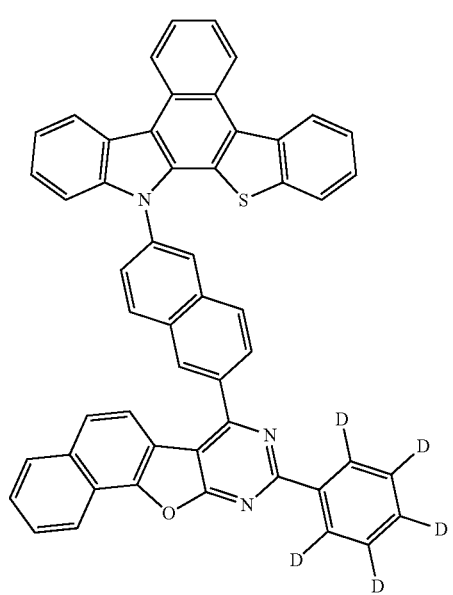
P 2-1
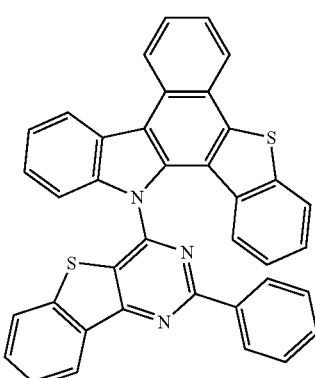

P 2-2
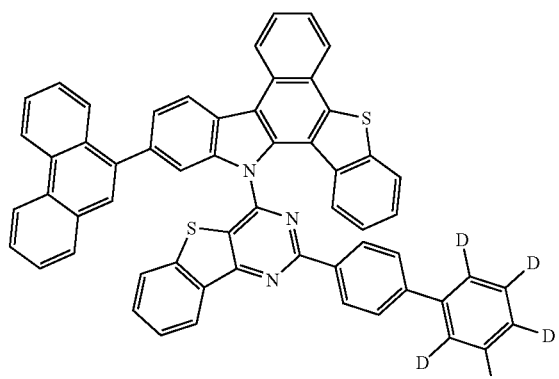
P 2-3
P 2-4
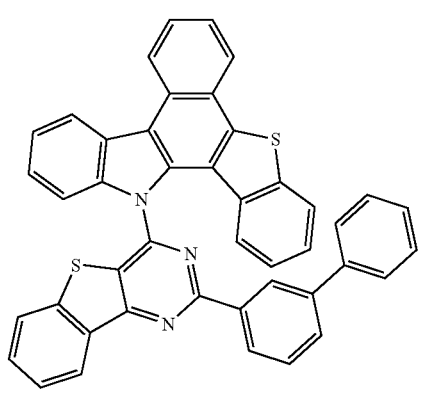
P 2-5
P 2-6
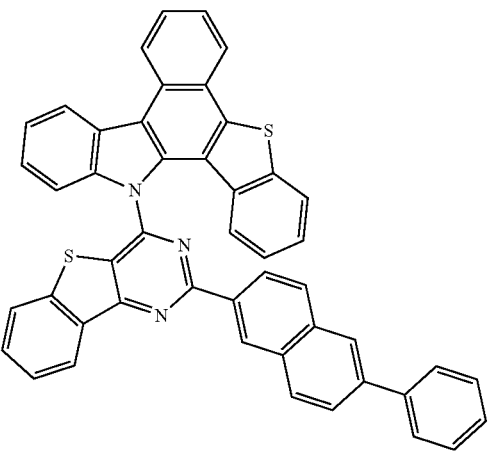
P 2-7
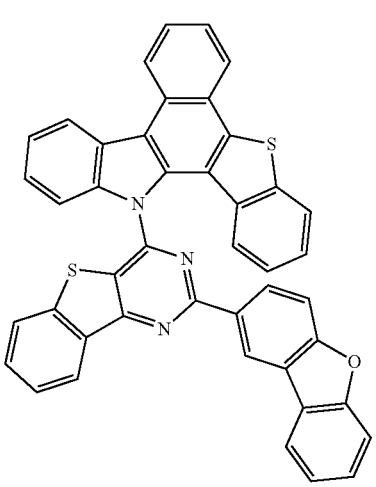
P 2-8
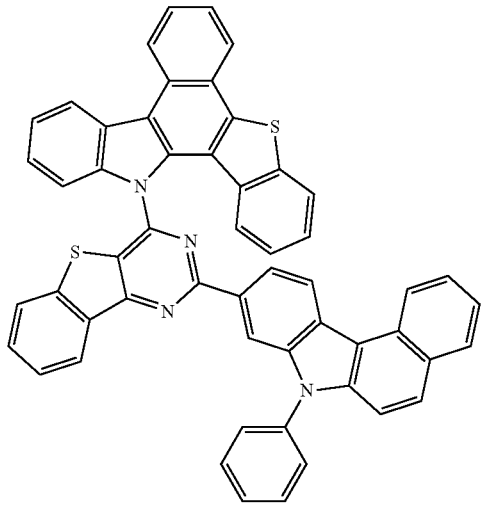

P 2-9
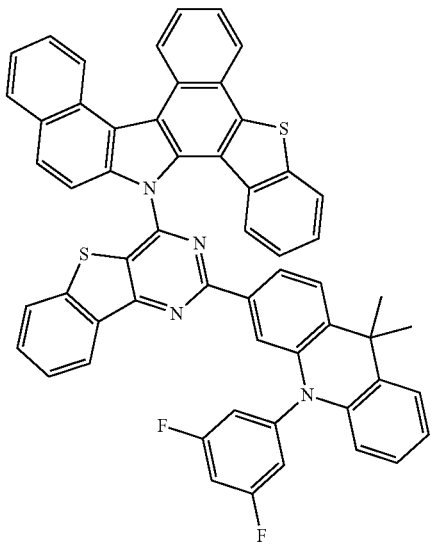
P 2-10
P 2-11
P 2-12
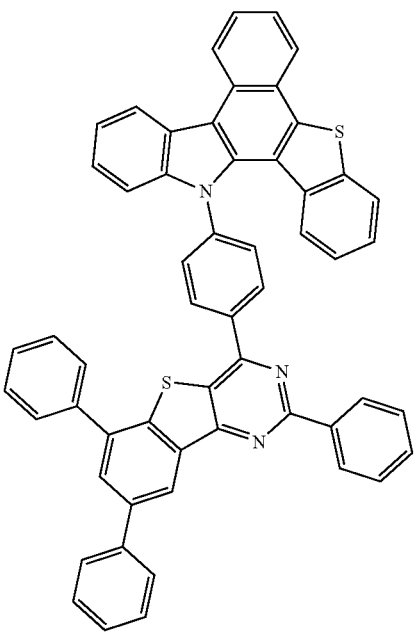
P 2-13
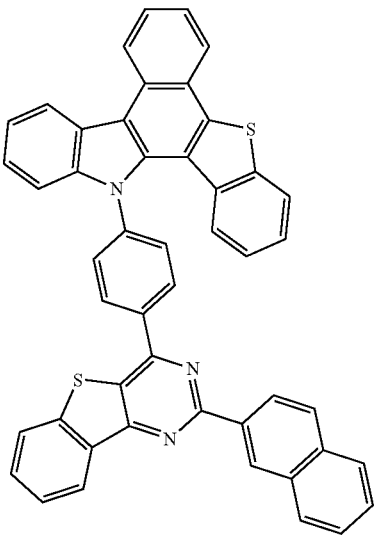

P 2-14
P 2-15
P 2-16
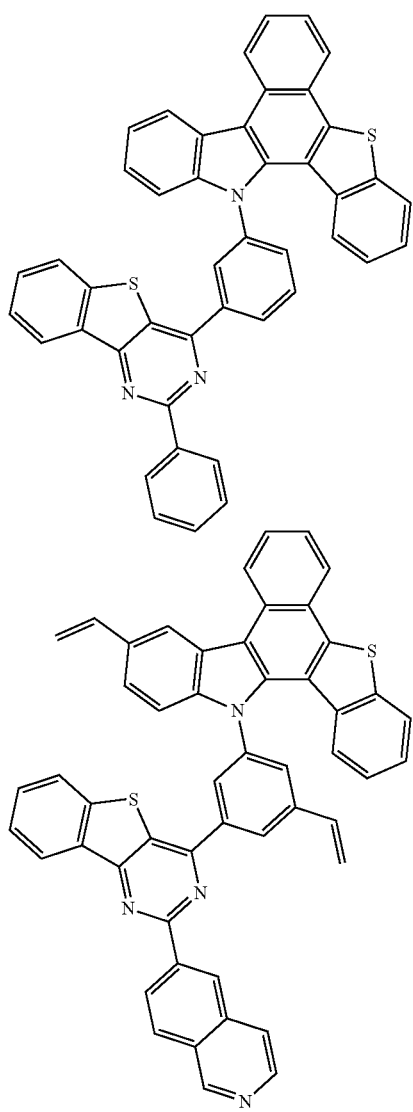
P 2-17
P 2-18
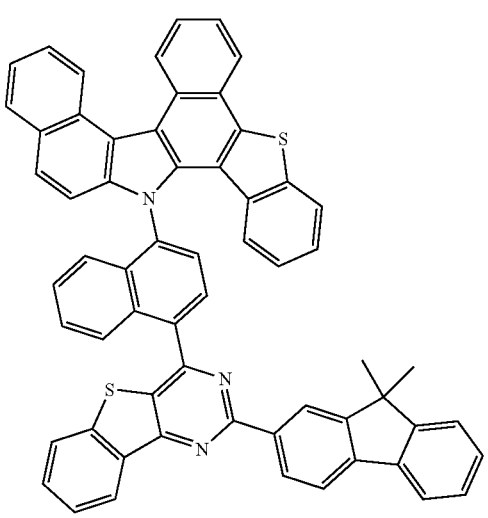

P 2-19
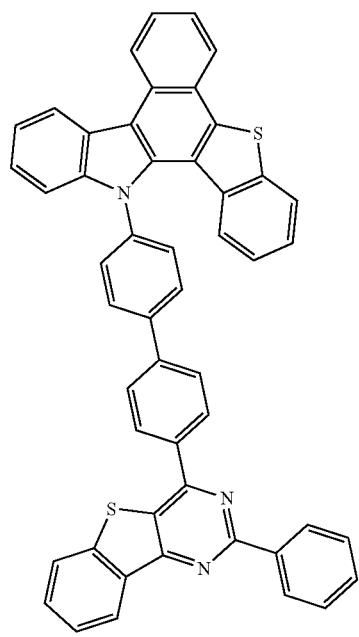
P 2-22
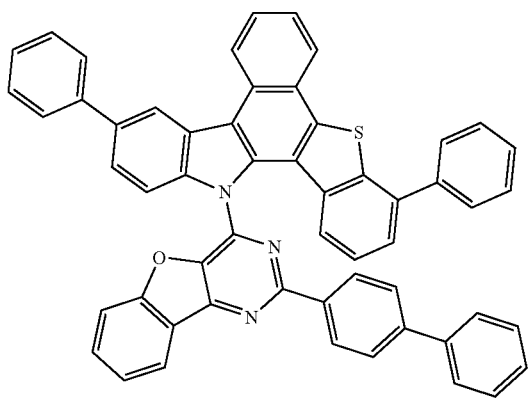
P 2-20
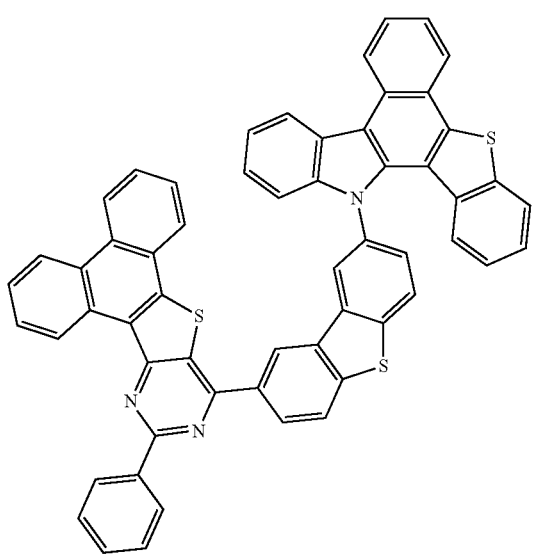
P 2-23
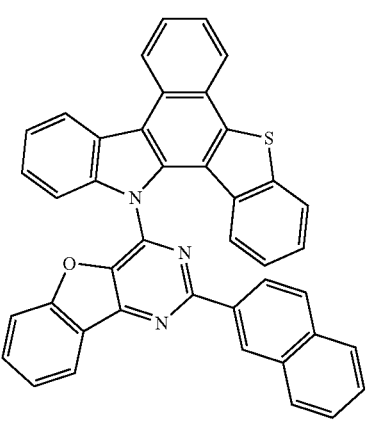
P 2-21
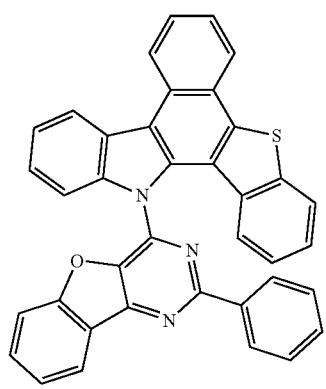
P 2-24
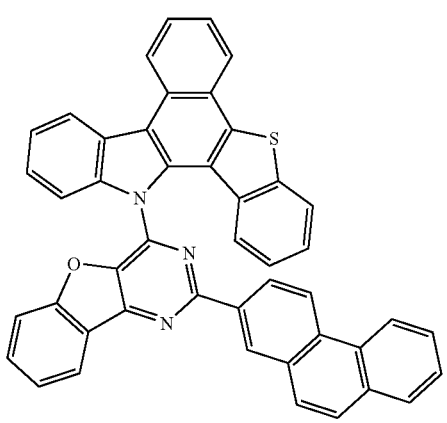

P 2-25
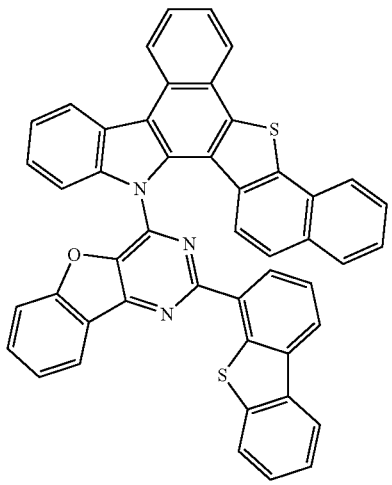
P 2-26
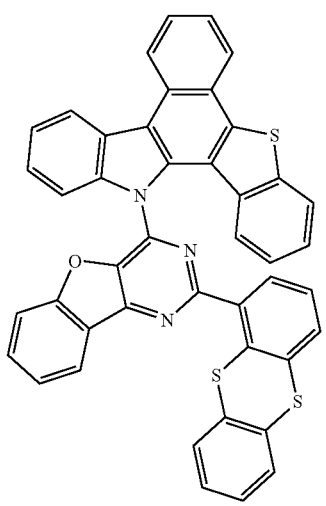
P 2-27
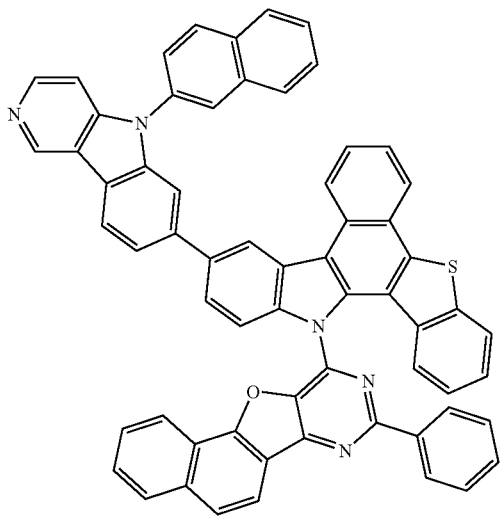
P 2-28
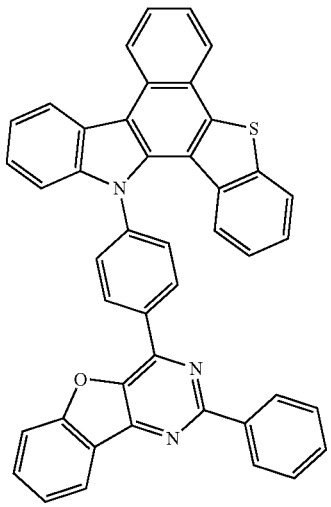
P 2-29
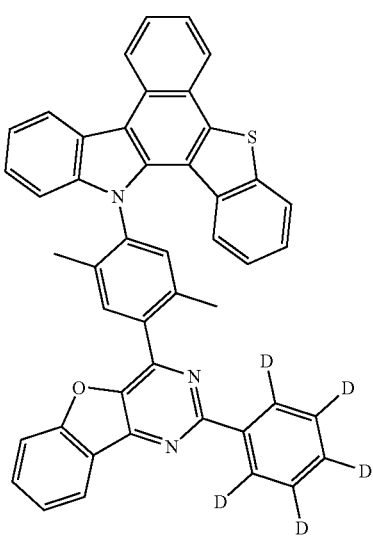
P 2-30
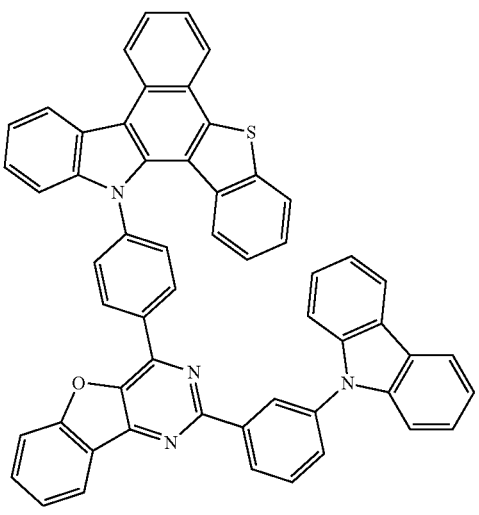

P 2-31
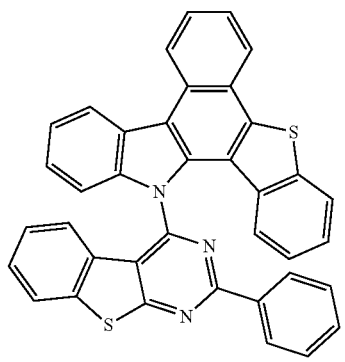
P 2-32
P 2-33
P 2-34
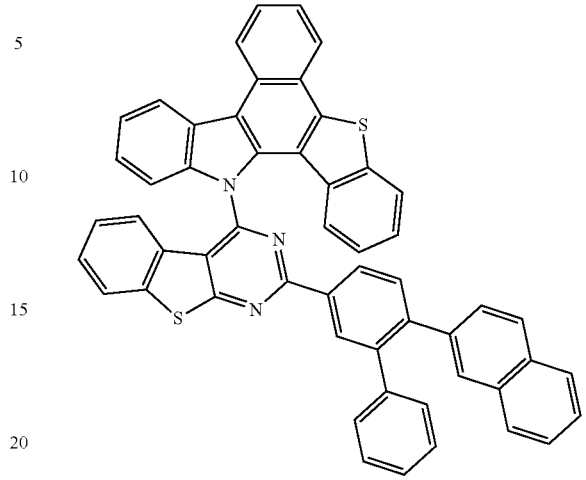
P 2-35
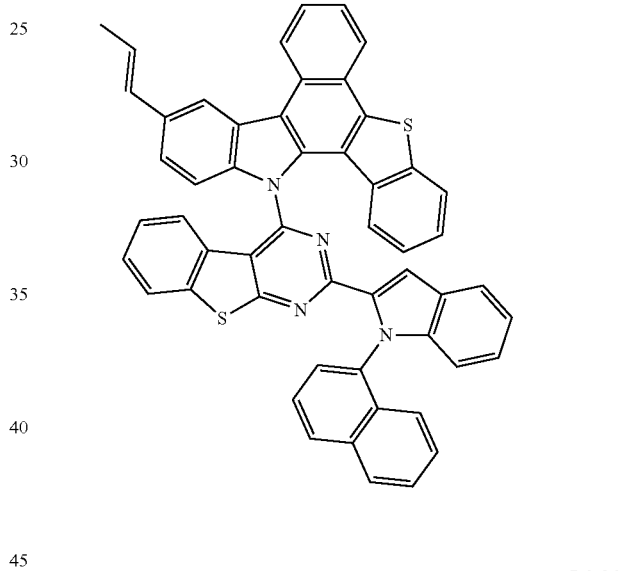
P 2-36
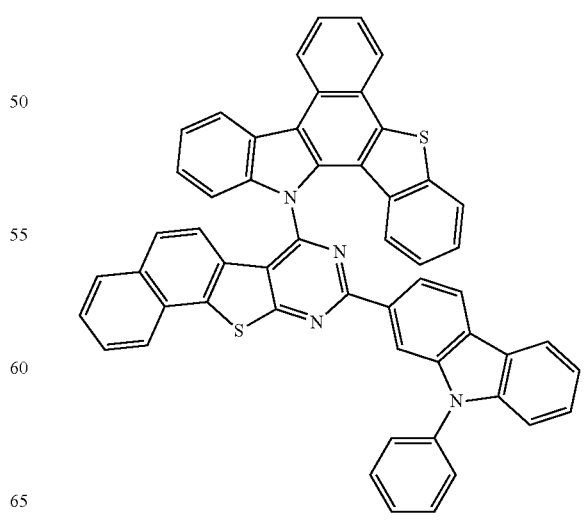

P 2-37
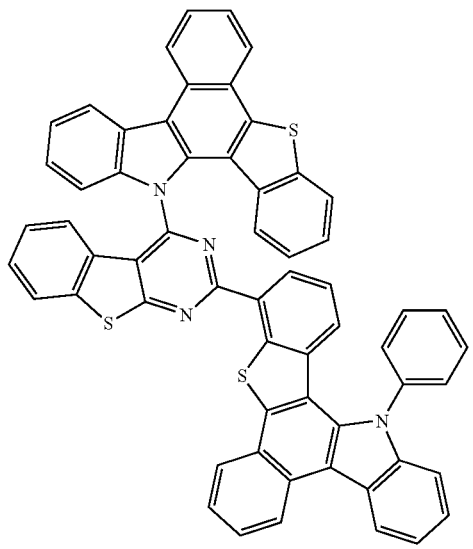
P 2-38
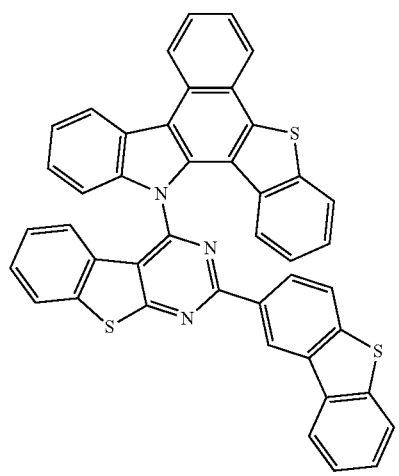
P 2-39
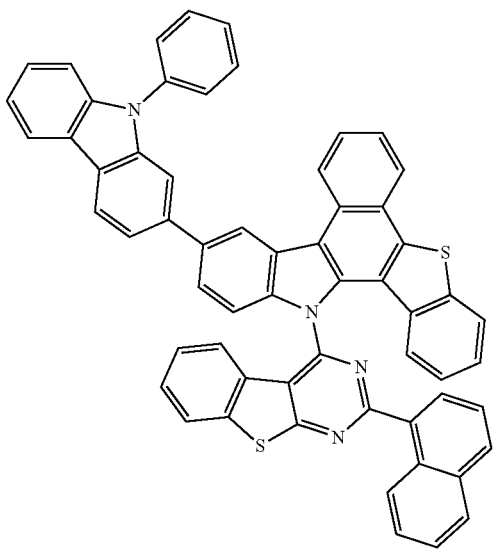
P 2-40
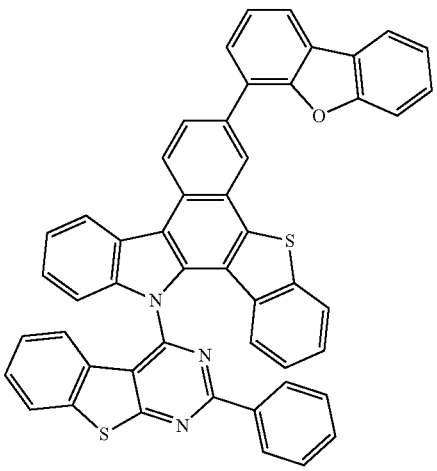
P 2-41
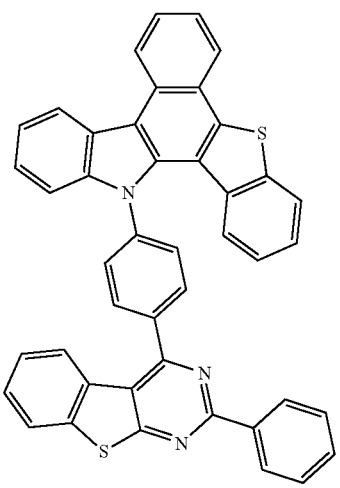
P 2-42
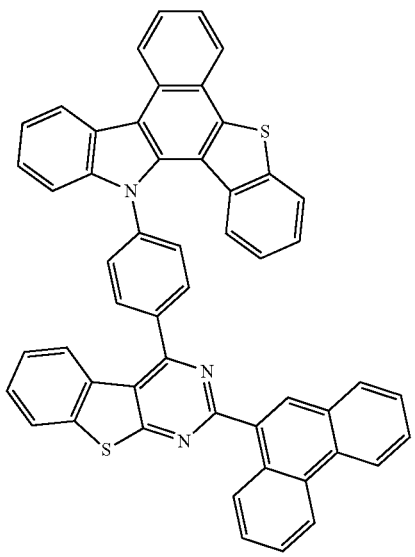

-continued
P 2-43
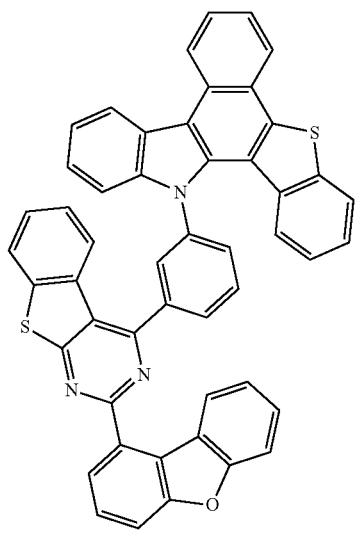
P 2-44
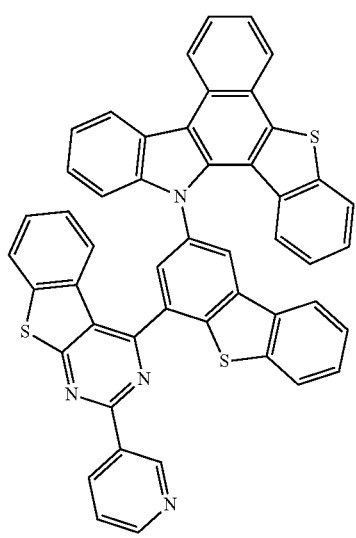
P 2-45
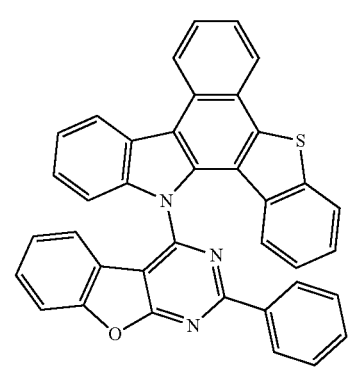
-continued
P 2-46
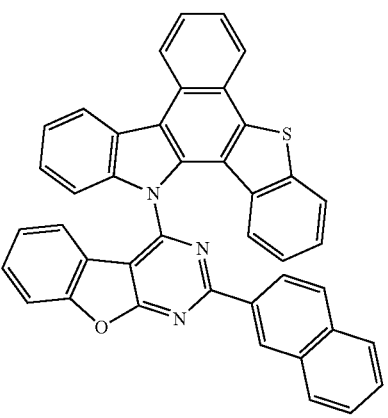
P 2-47
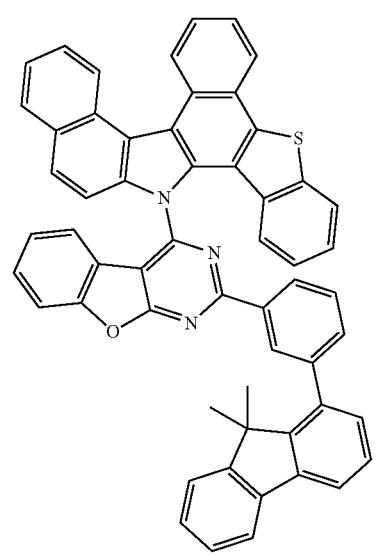
P 2-48
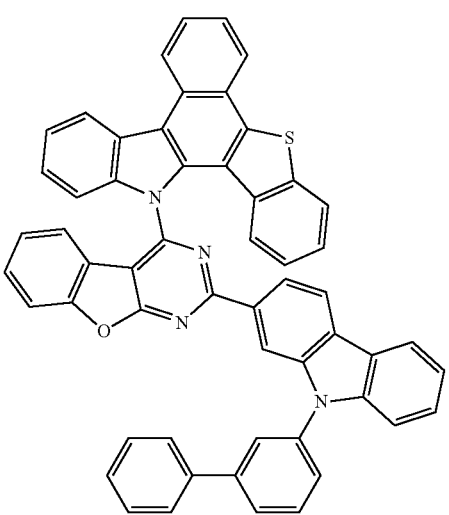

P 2-49
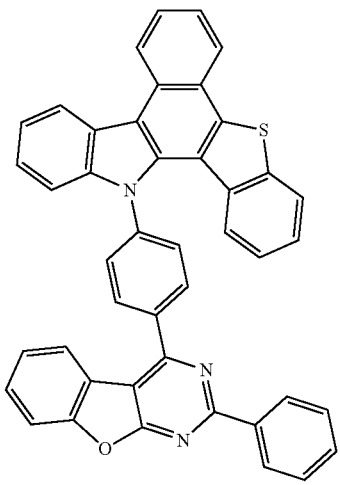
P 2-50
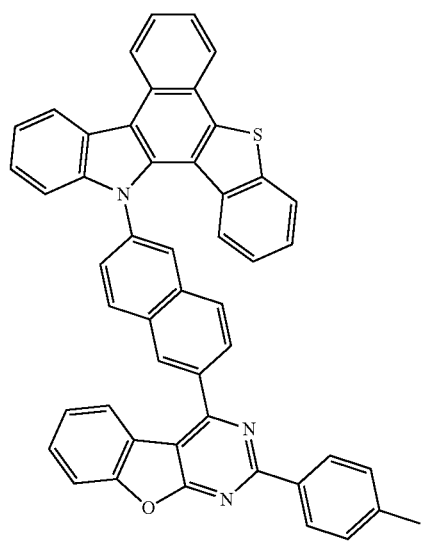
P 3-1
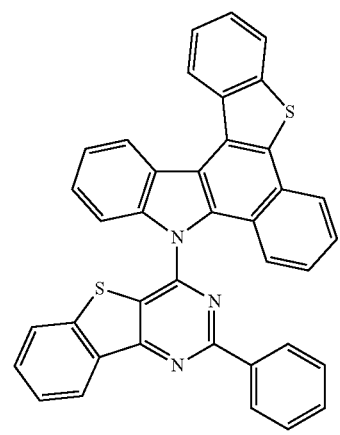
P 3-2
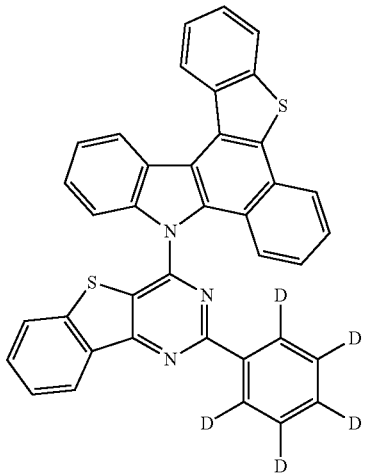
P 3-3
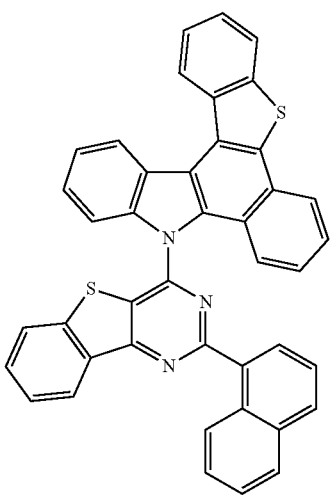
P 3-4
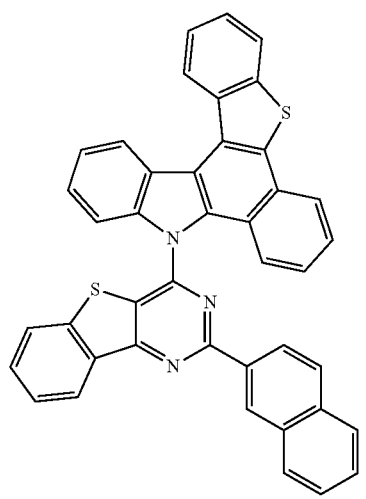

P 3-5
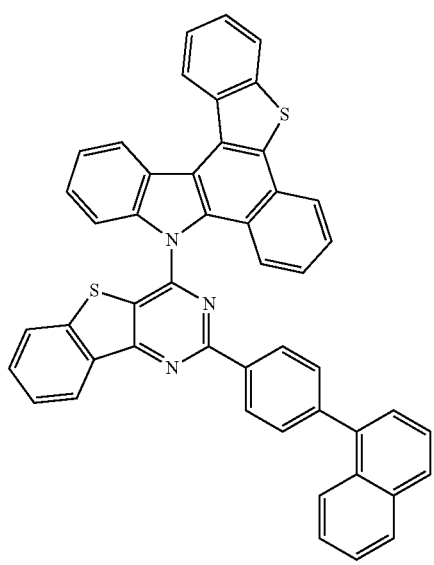
P 3-6
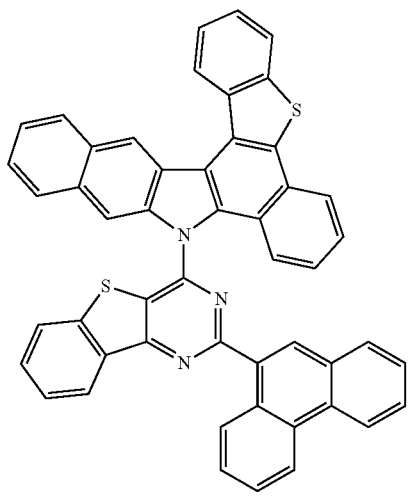
P 3-7
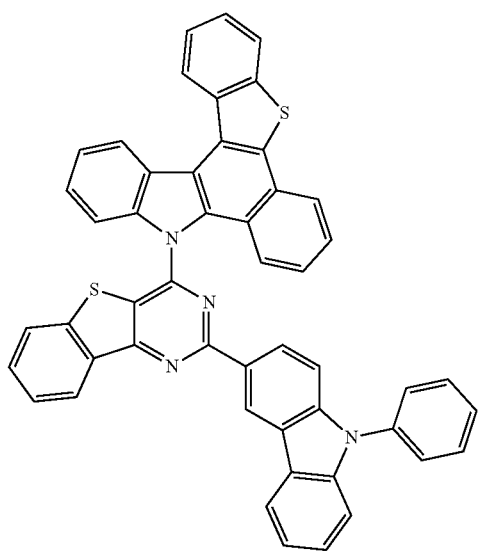
P 3-8
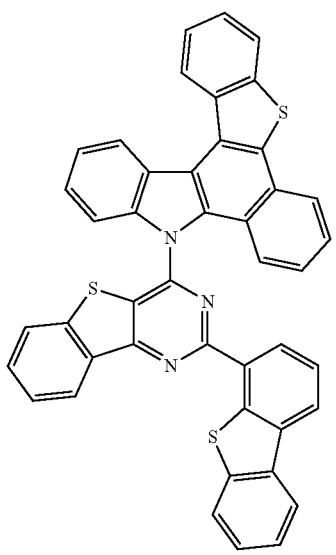
P 3-9
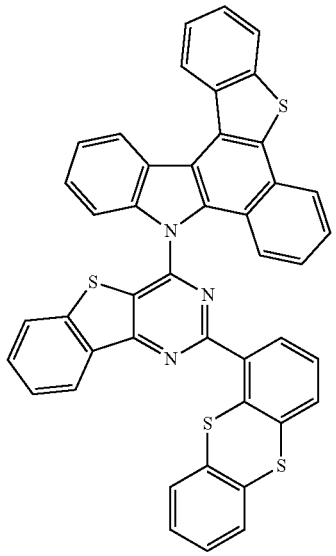
P 3-10
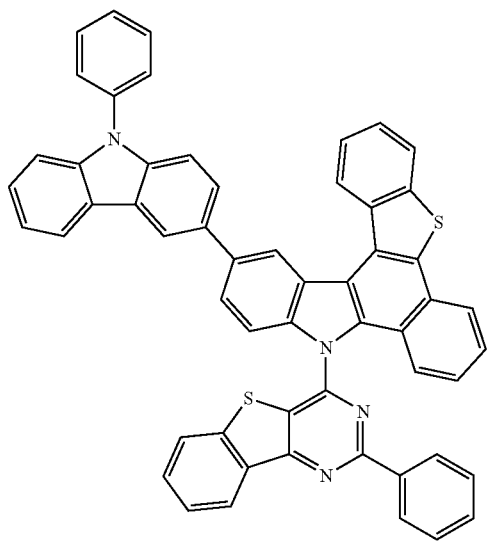

-continued
P 3-11
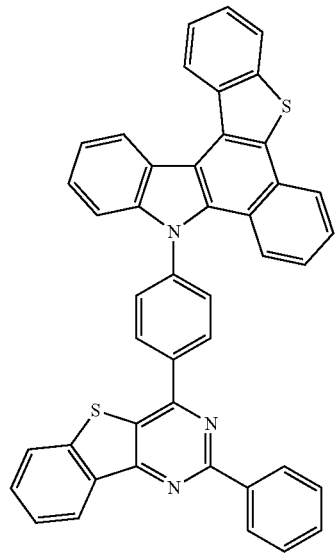
P 3-13
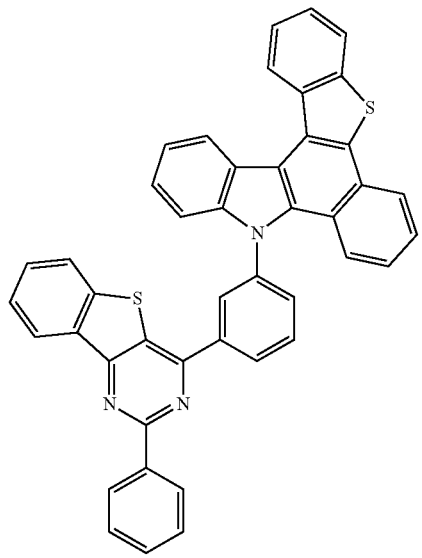
P 3-12
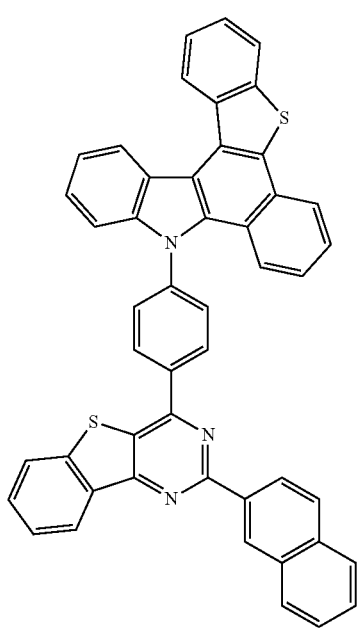
P 3-14
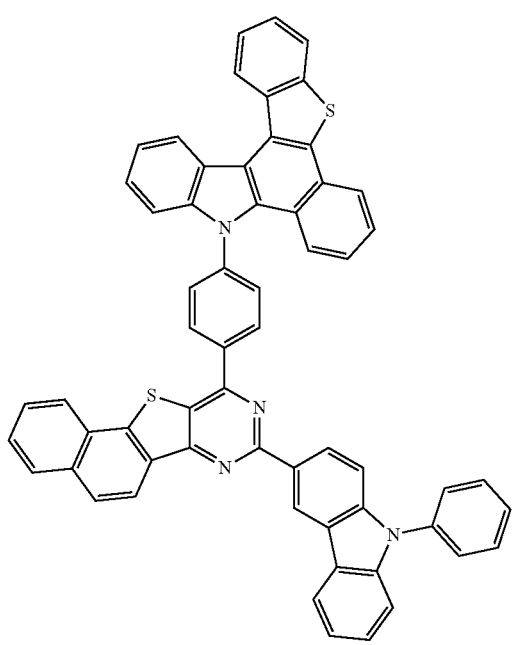

-continued
P 3-15
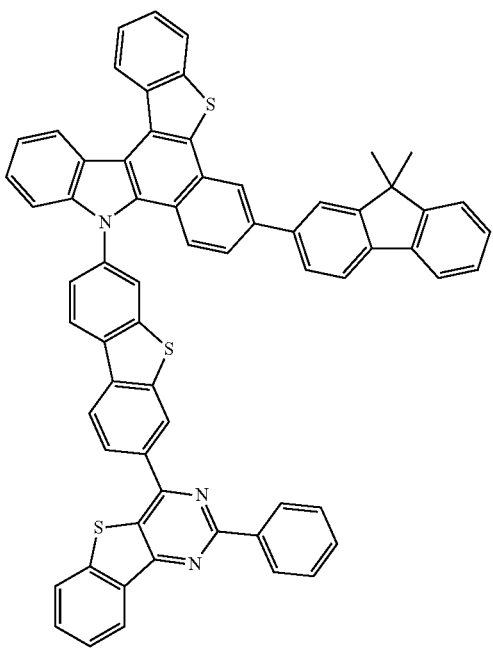
P 3-16
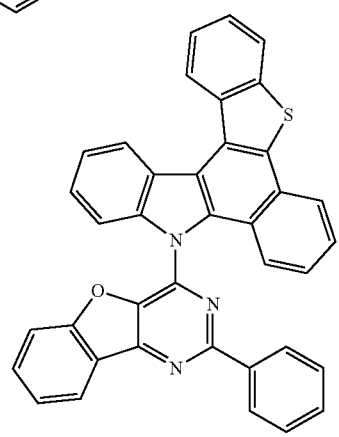
P 3-17
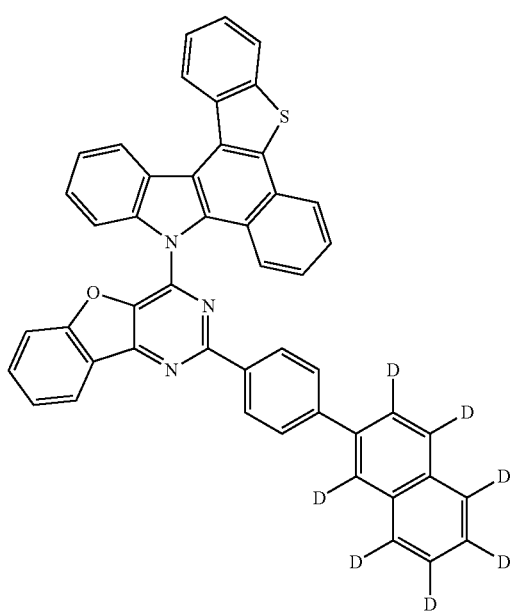
-continued
P 3-18
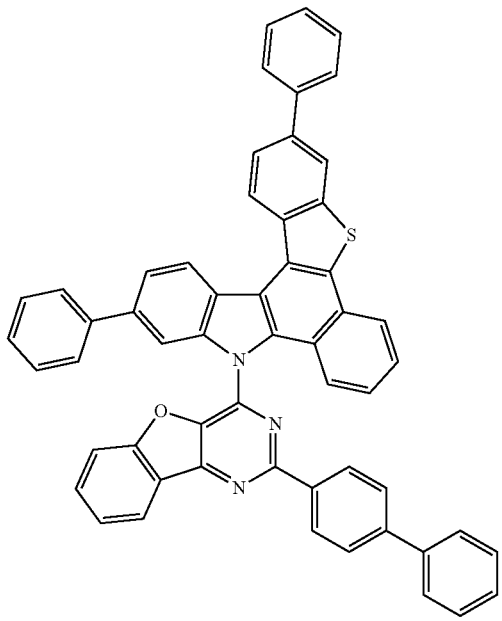
P 3-19
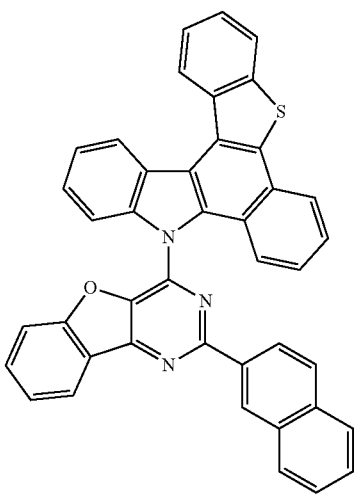
P 3-20
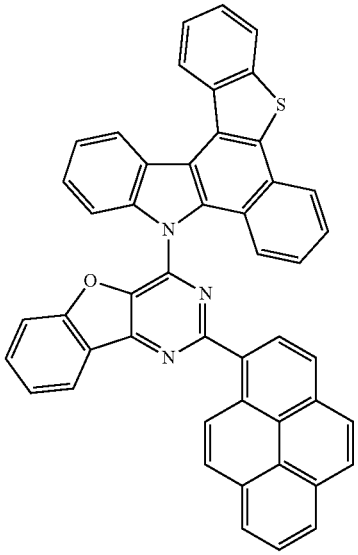

-continued
P 3-21
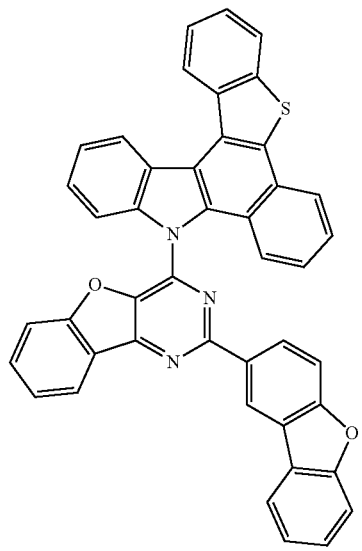
P 3-22
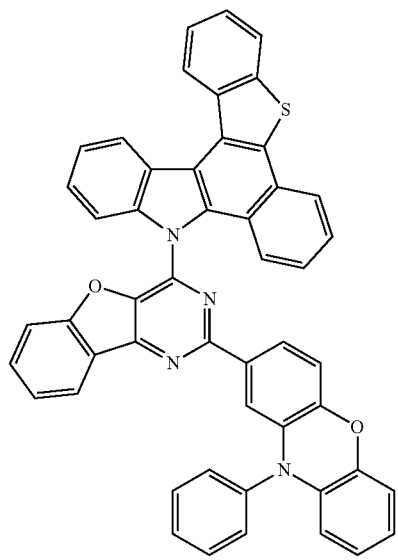
P 3-23
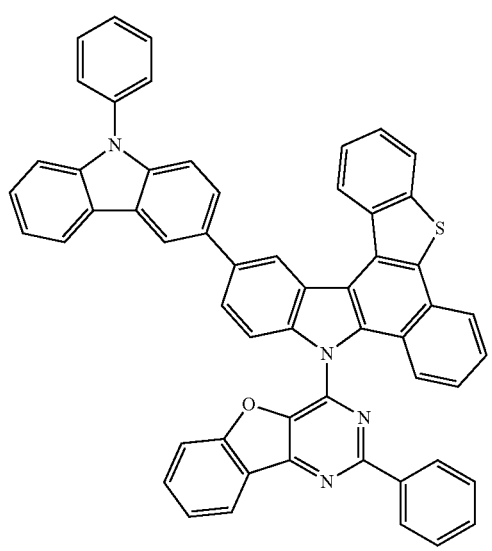
P 3-24
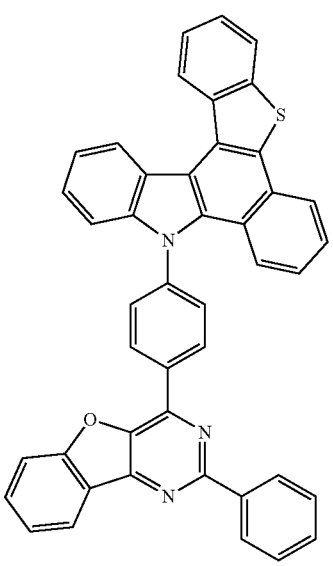
P 3-25
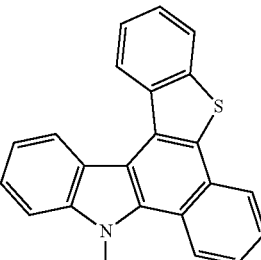
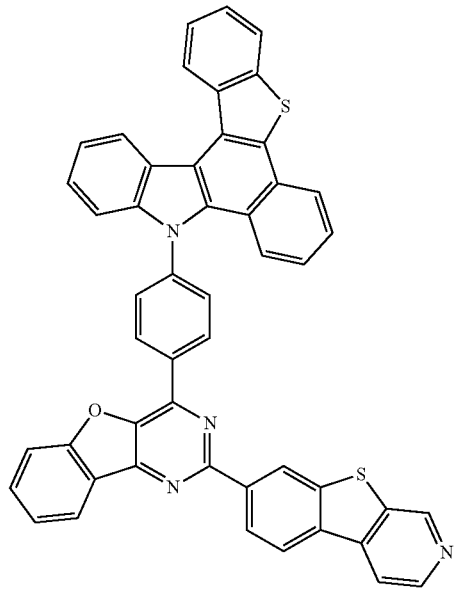
P 3-26
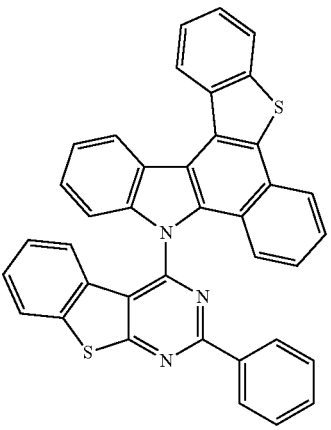

P 3-27
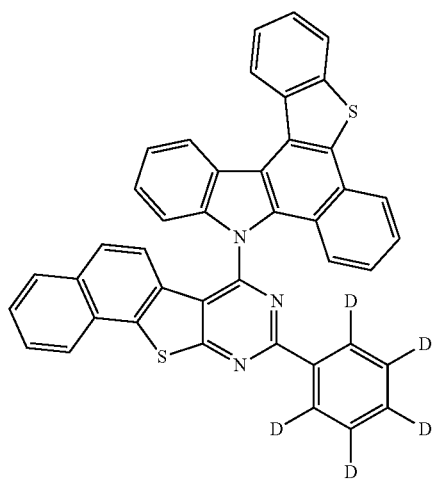
P 3-28
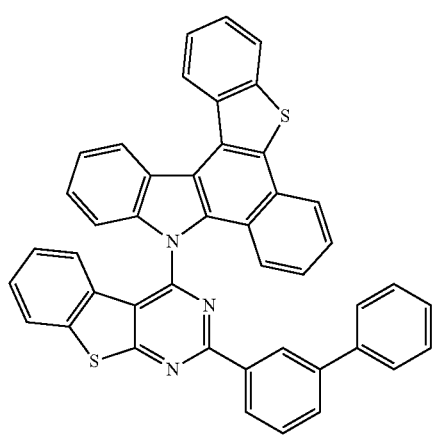
P 3-29
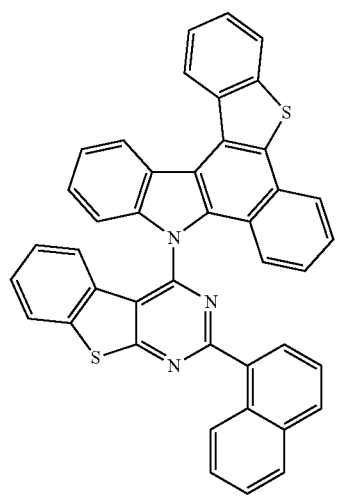
P 3-30
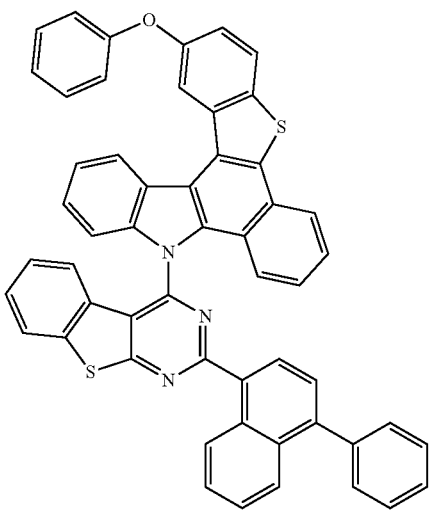
P 3-31
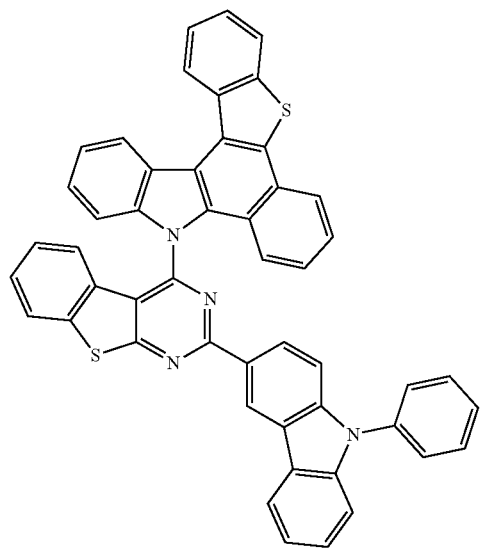
P 3-32
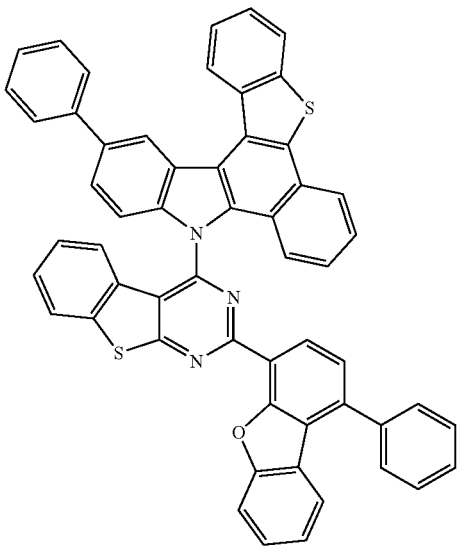

-continued
P 3-33
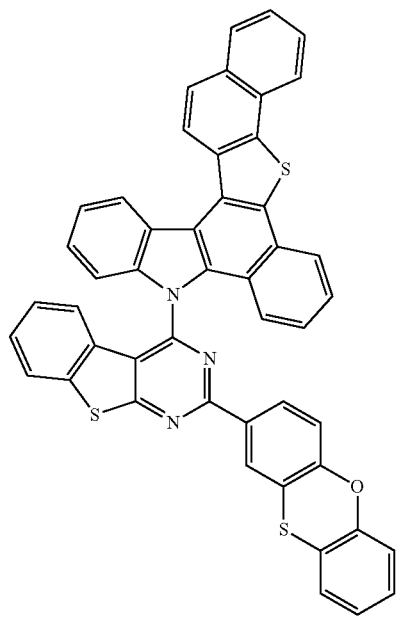
P 3-34
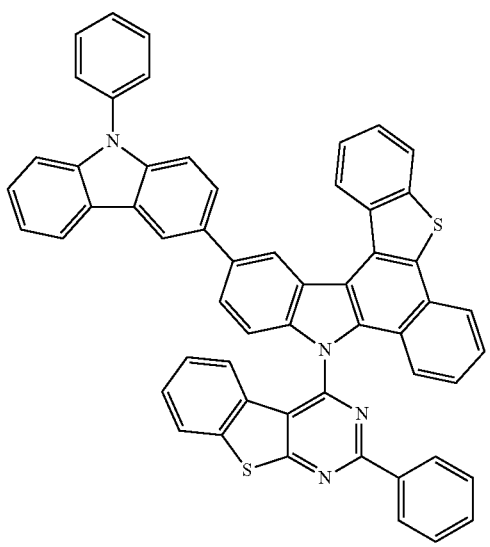
P 3-35
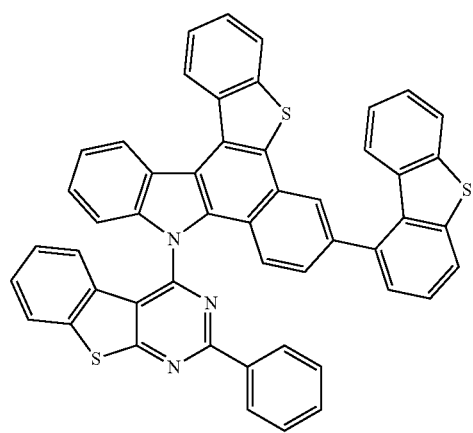
-continued
P 3-36
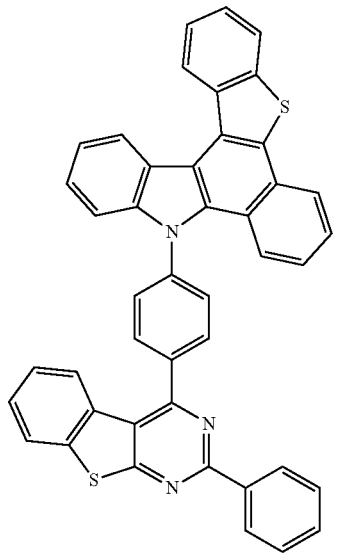
P 3-37
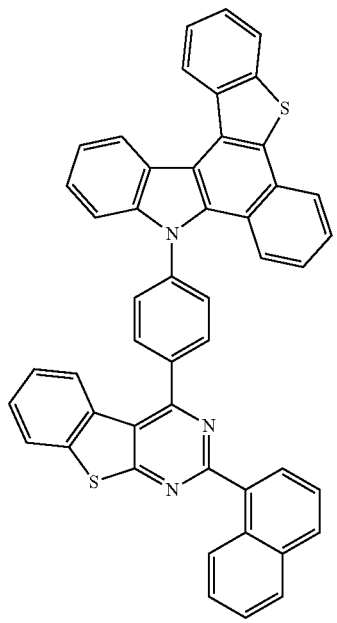

-continued
P 3-38
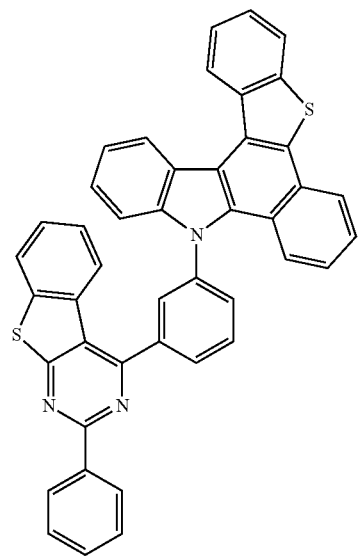
P 3-39
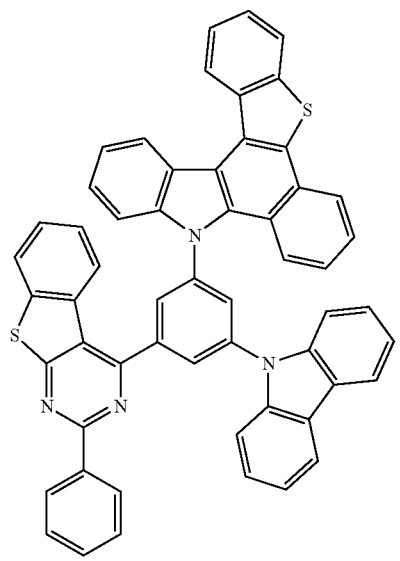
P 3-40
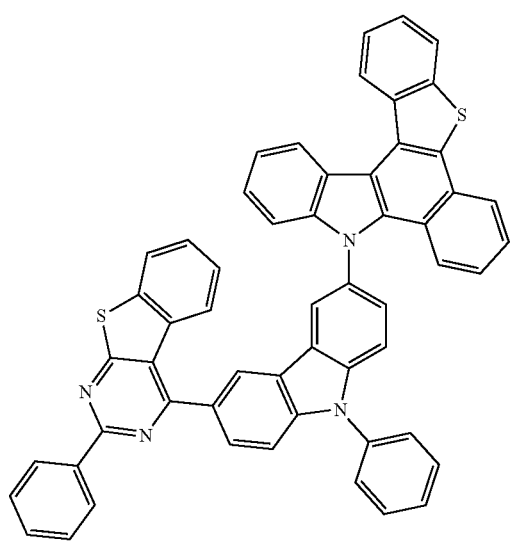
-continued
P 3-41
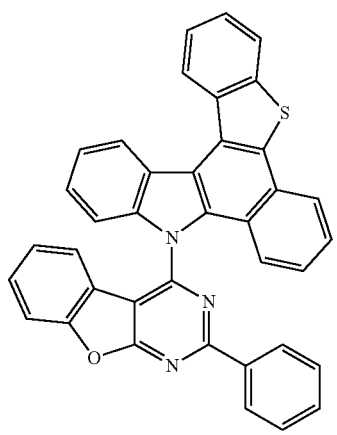
P 3-42
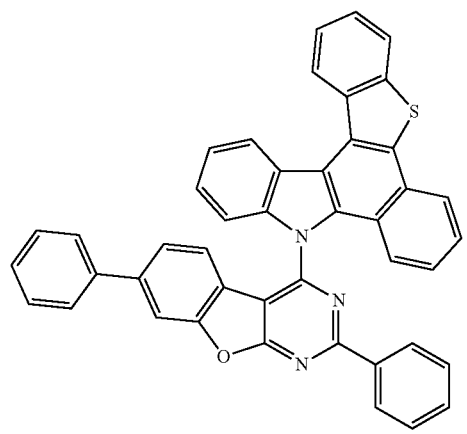
P 3-43
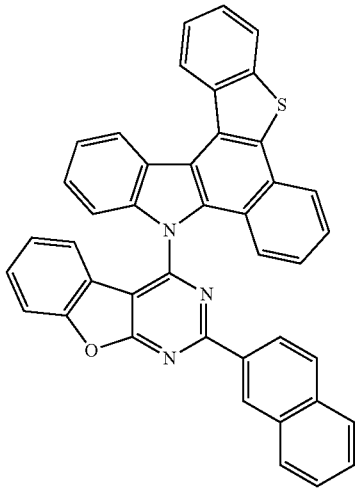

P 3-44
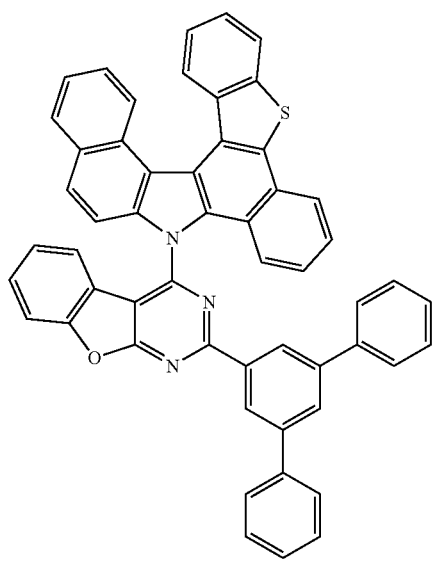
P 3-45
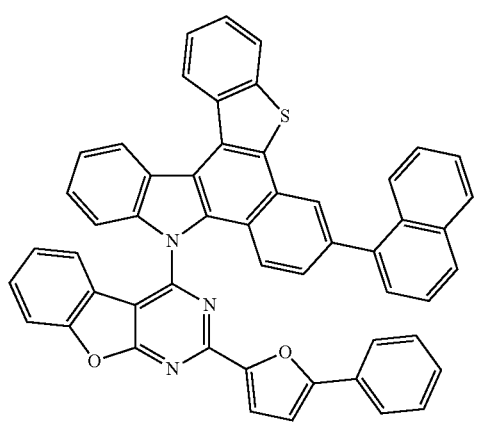
P 3-46
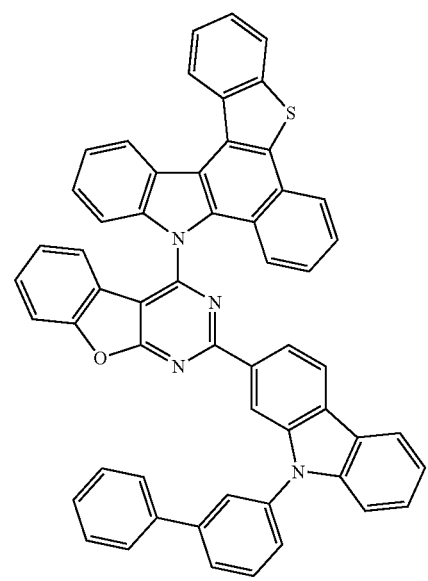
P 3-47
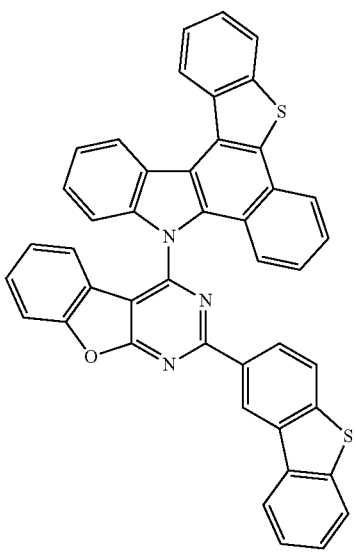
P 3-48
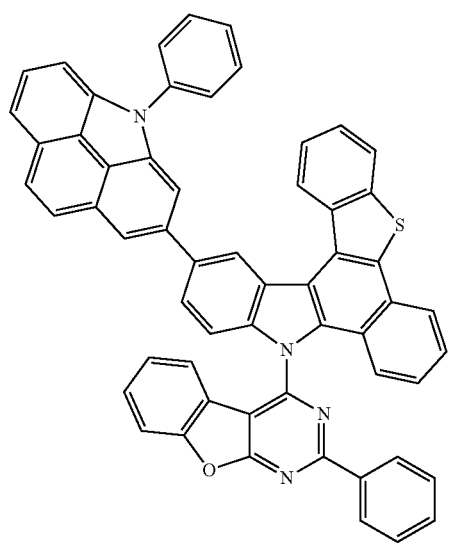
P 3-49
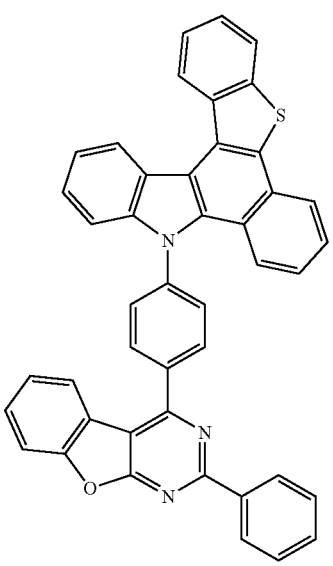

P 3-50
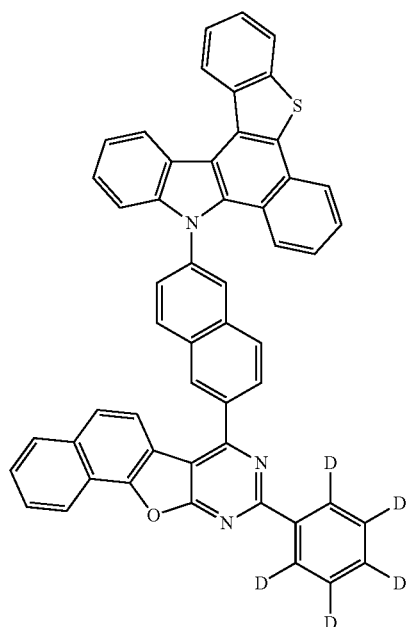
P 4-1
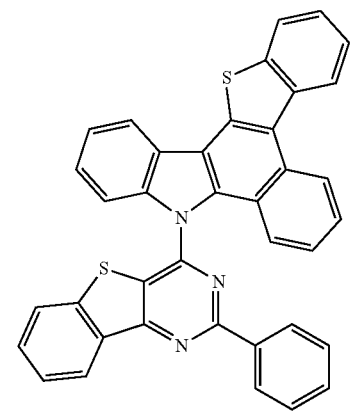
P 4-2
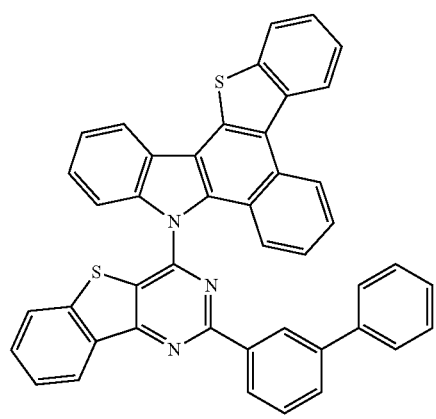
P 4-3
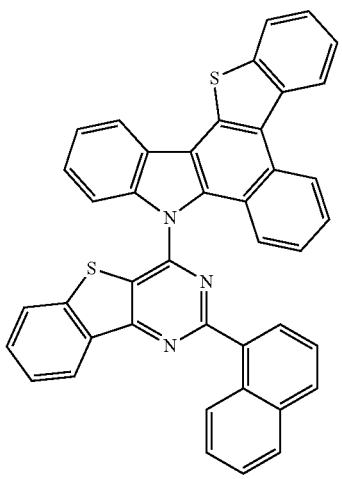
P 4-4
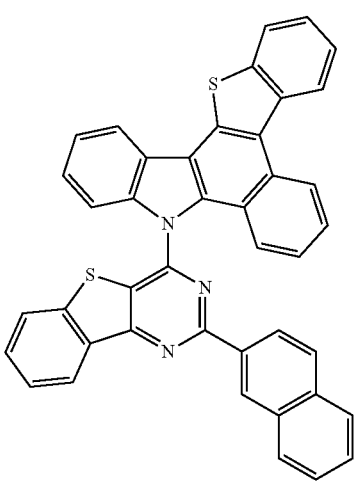
P 4-5
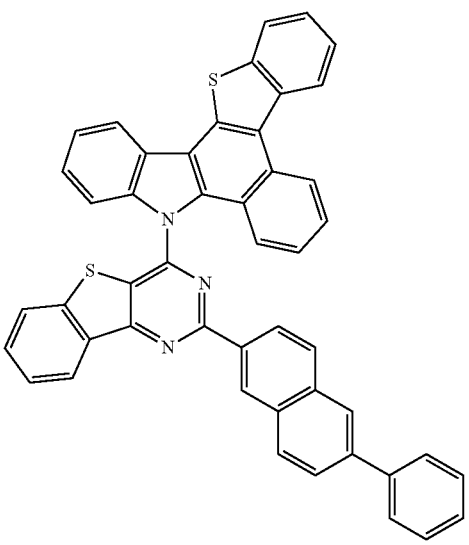

-continued
P 4-6
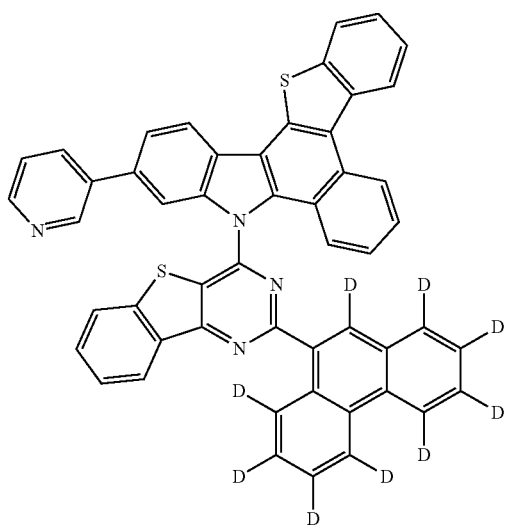
P 4-7
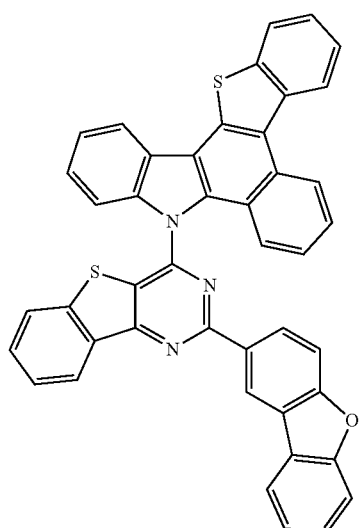
P 4-8
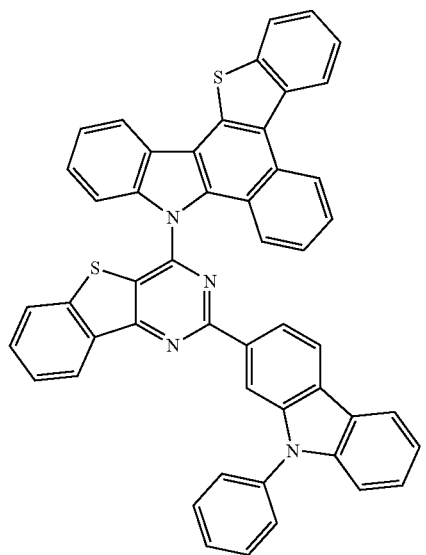
-continued
P 4-9
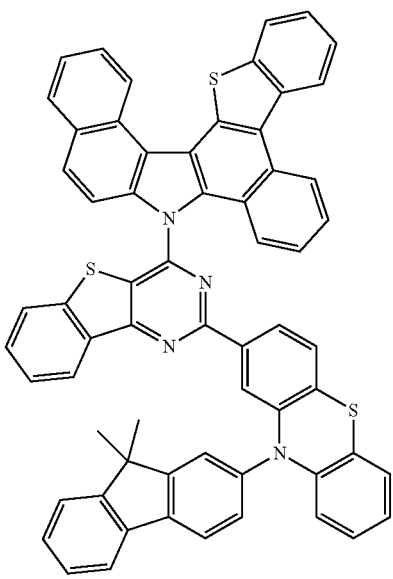
P 4-10
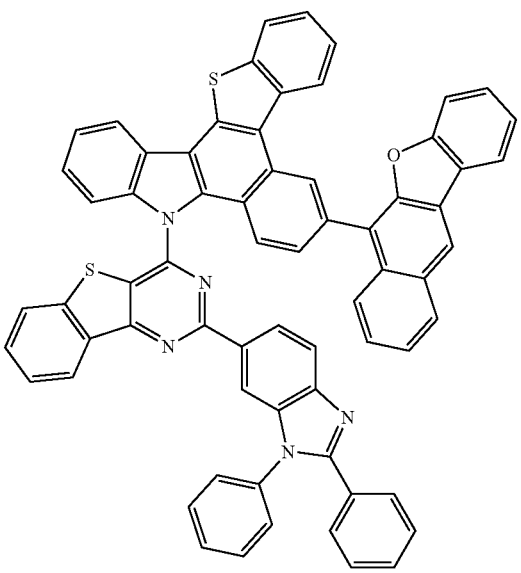
P 4-11
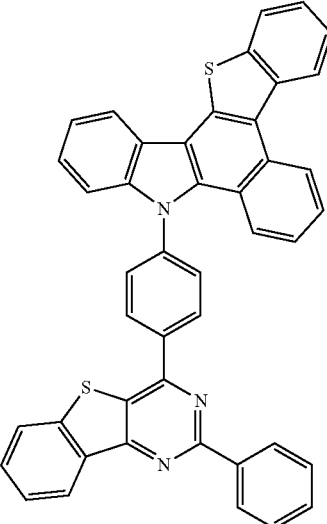

-continued
P 4-12
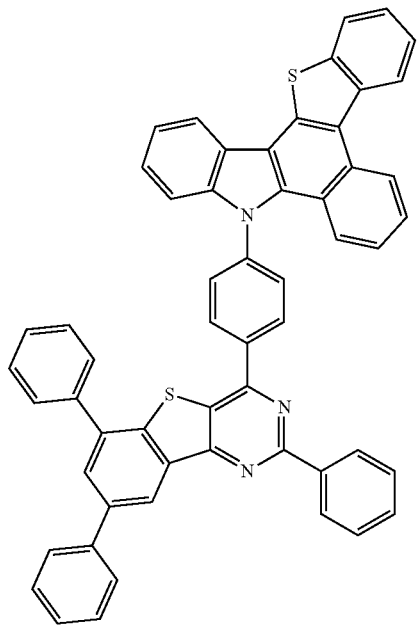
P 4-13
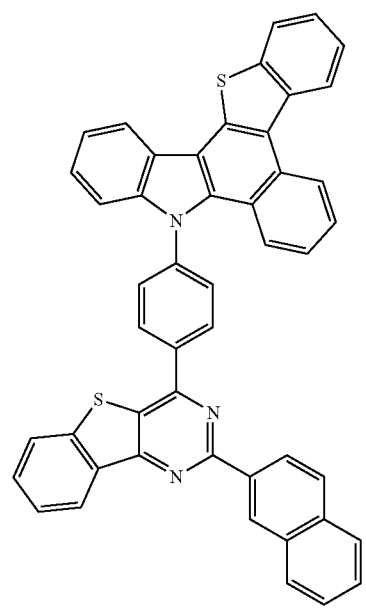
P 4-14
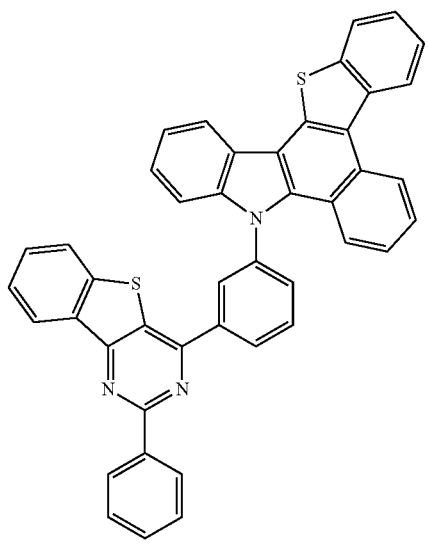
P 4-15
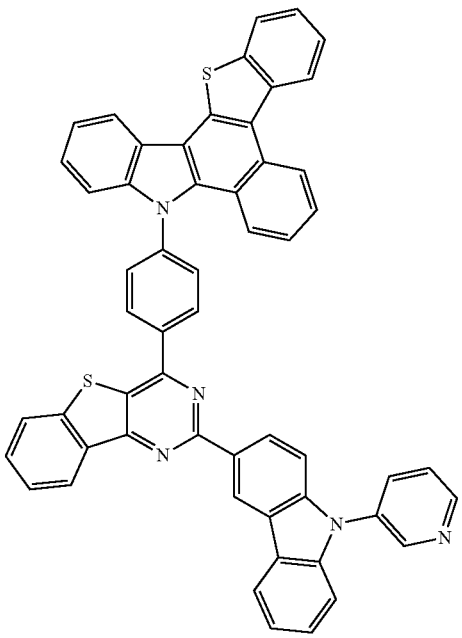
P 4-16

P 4-17
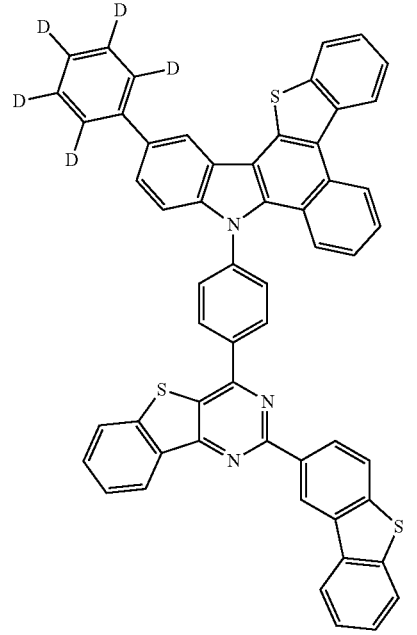
P 4-18
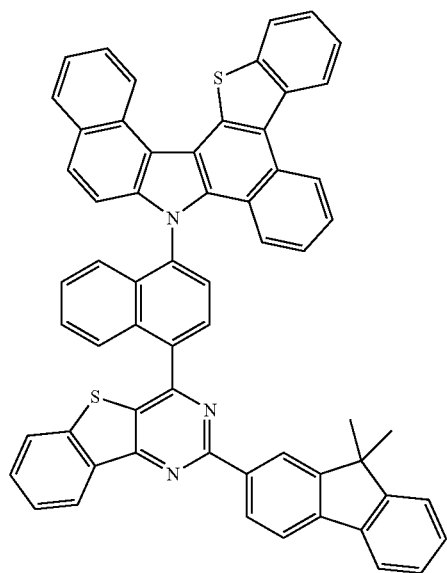
P 4-19
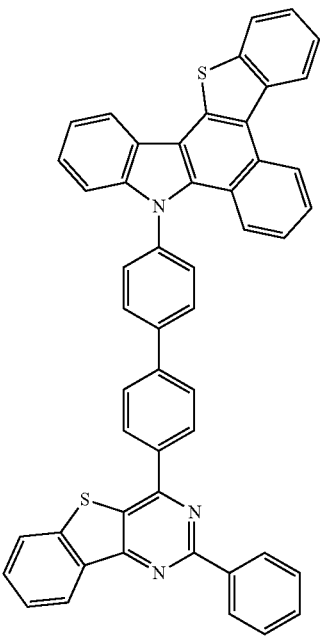
P 4-20
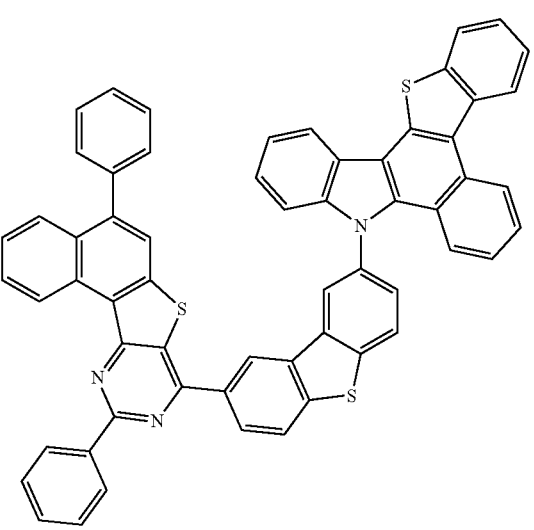
P 4-21
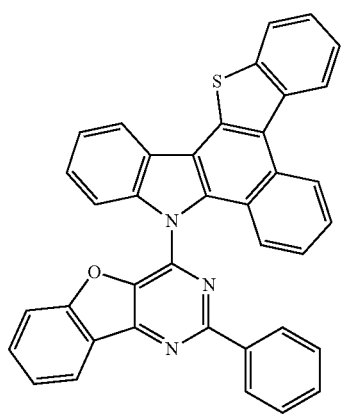

P 4-22
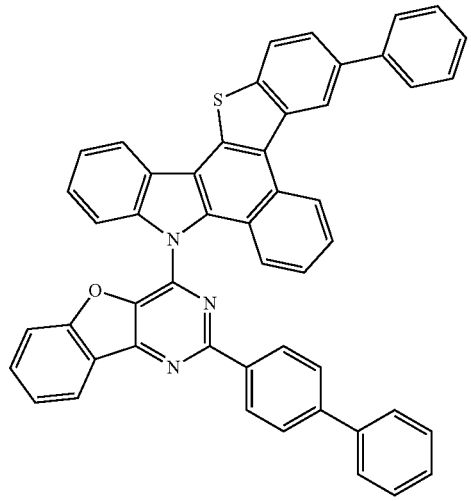
P 4-23
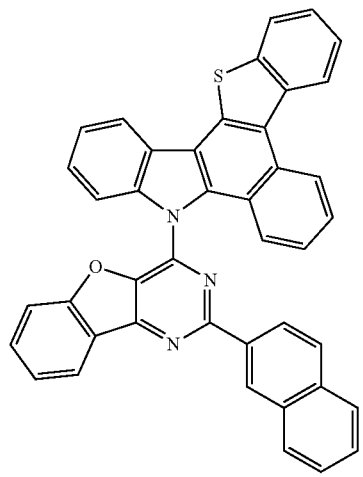
P 4-24
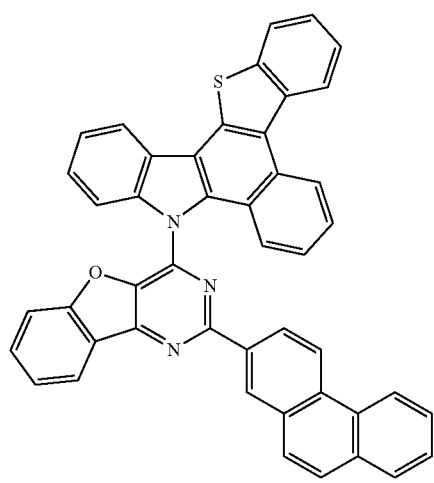
P 4-25
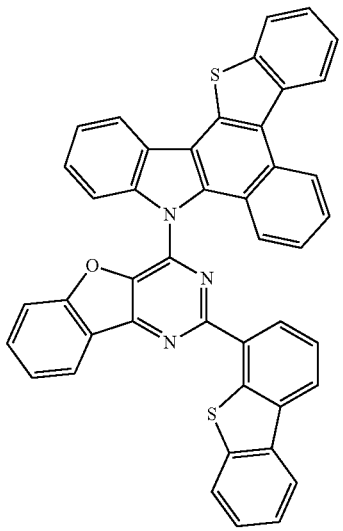
P 4-26
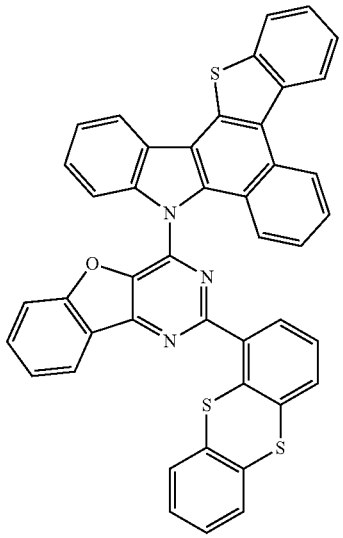
P 4-27
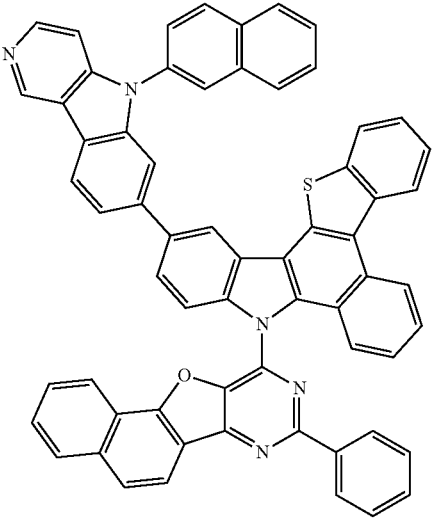

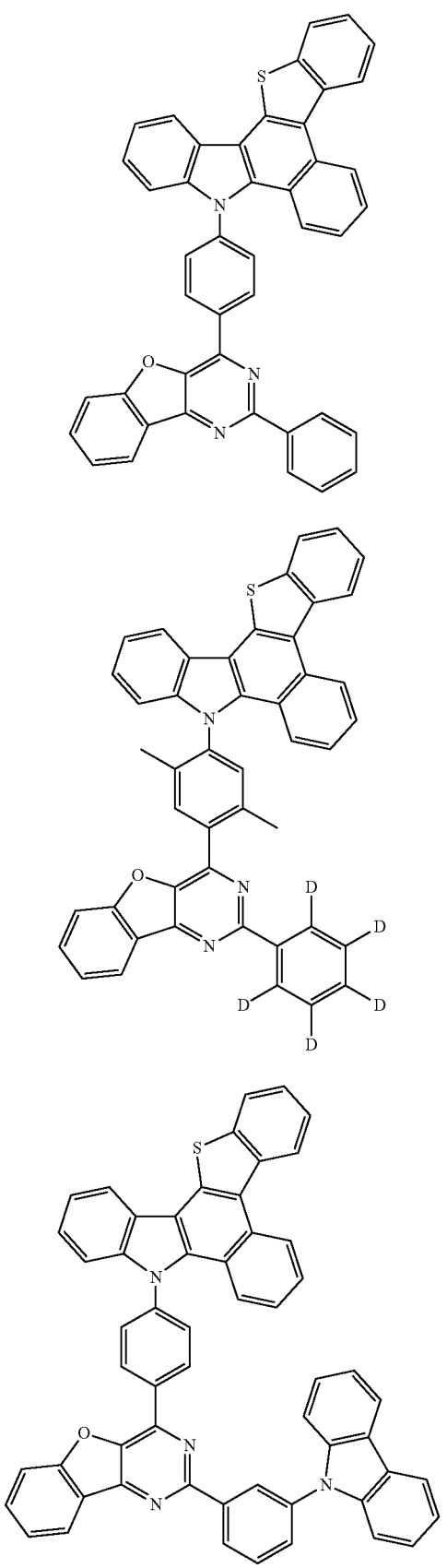
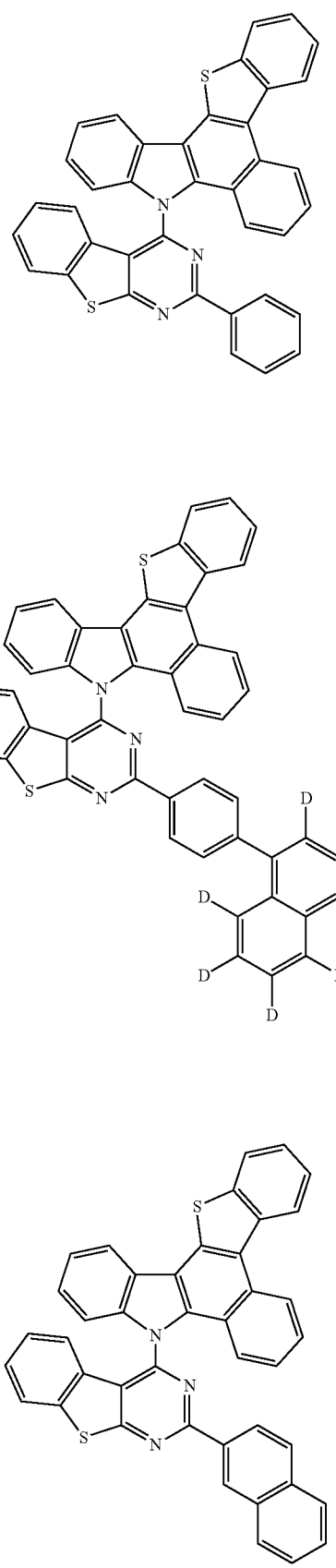

-continued
P 4-34
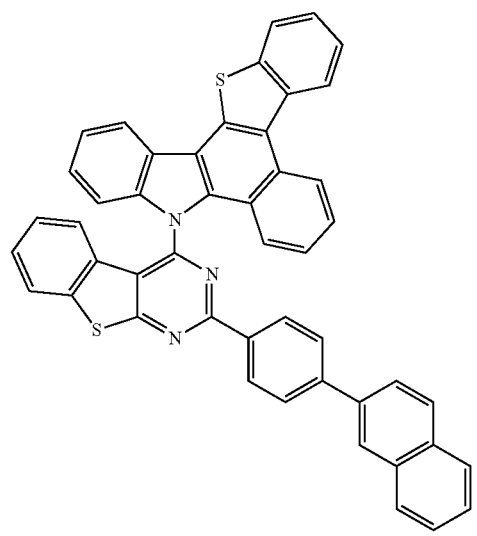
P 4-35
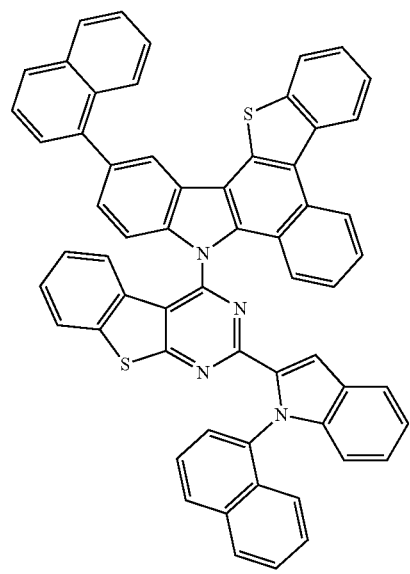
P 4-36
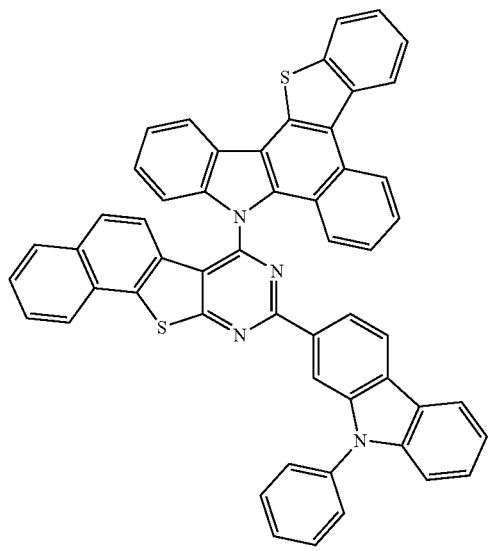
-continued
P 4-37
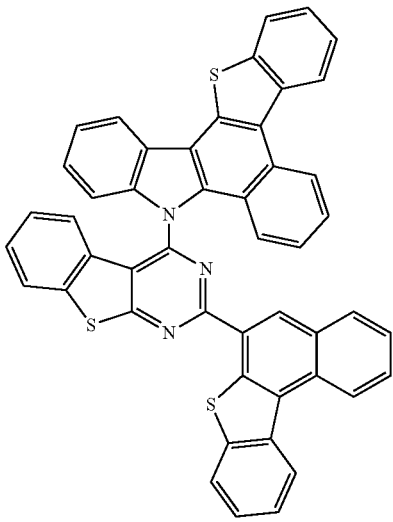
P 4-38
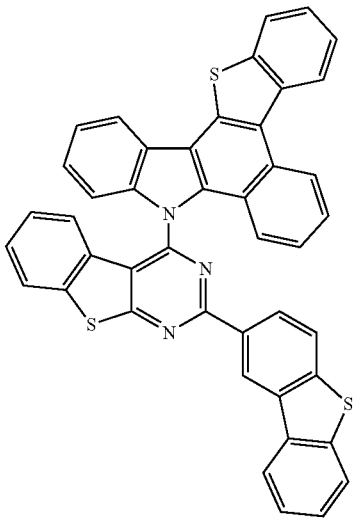
P 4-39
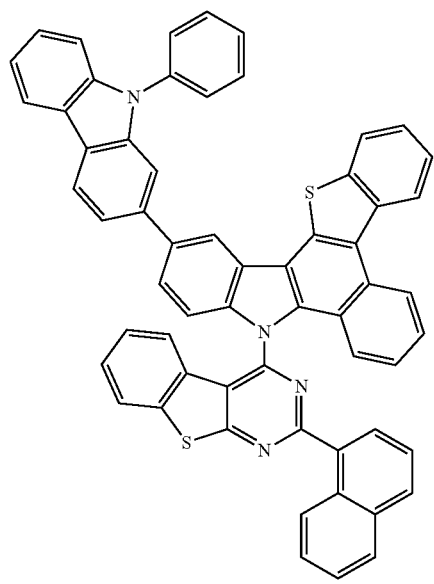

-continued
P 4-40
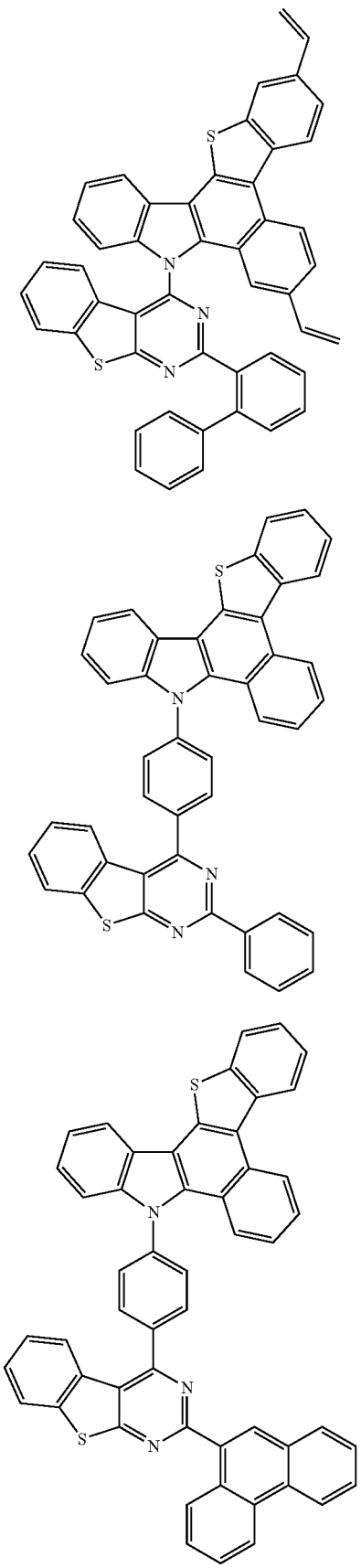
P 4-41
P 4-42
-continued
P 4-43
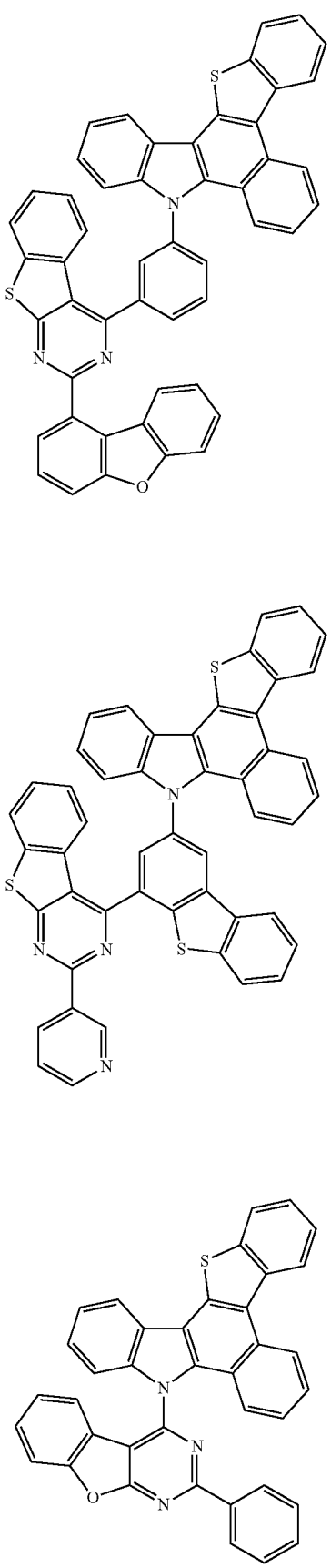
P 4-44
P 4-45

-continued

P 4-46
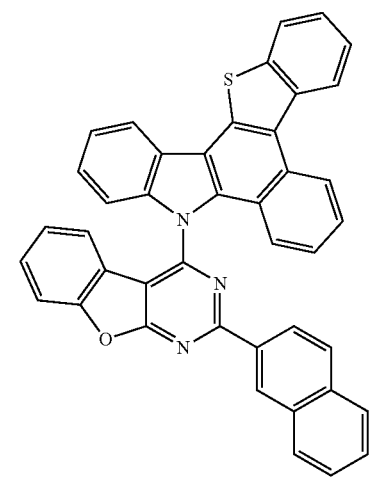

P 4-47
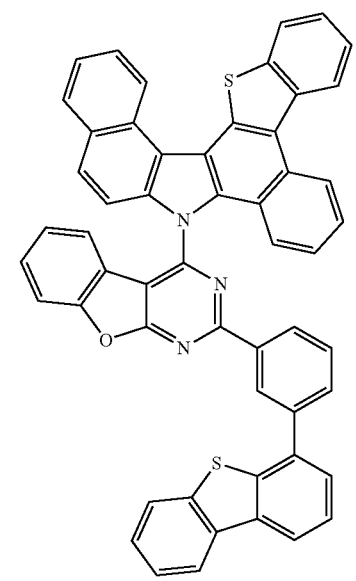

P 4-48
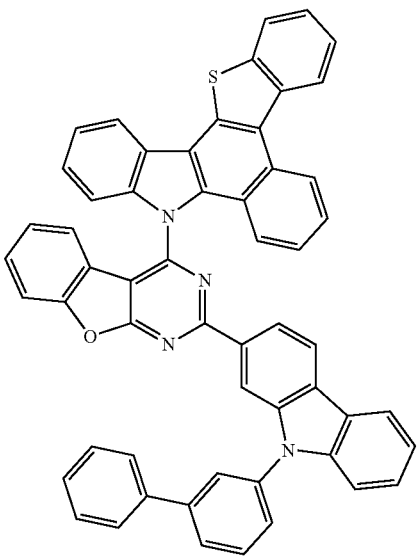

-continued

P 4-49
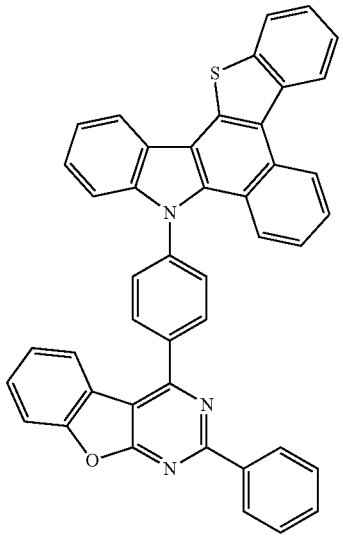

P 4-50
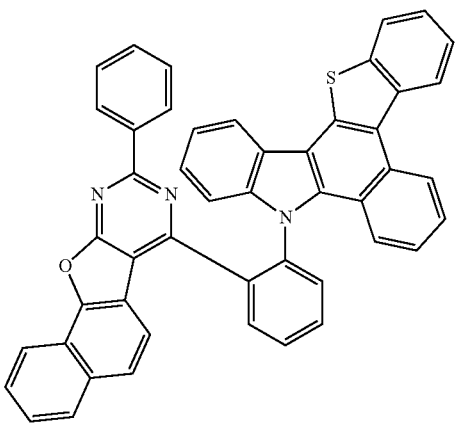

In another aspect of the present invention, the present invention provides compound for an organic electric element.

In another aspect of the present invention, the present invention provides an organic electric element comprising the compound represented by the formula 1. Here, the organic electric element may comprise a first electrode, a second electrode, and an organic material layer formed between the first electrode and the second electrode, wherein the organic material layer may comprise the compound represented by the formula 1, the compound may be comprised in at least one layer of a hole injection layer, a hole transport layer, an emission-auxiliary layer and a light emitting layer, and the compound may be comprised as a single compound or the component of the mixture of two or more kinds. That is, the compound represented by the formula 1 may be used as material of a hole injection layer, a hole transport layer, an emission-auxiliary layer or a light emitting layer. Preferably, the compound represented by the formula 1 may be used as phosphorescent host material of the light emitting layer.

In another aspect of the present invention, the present invention provides an organic electric element further comprising a layer for improving luminous efficiency formed on one side of the first electrode and/or one side of the second electrode, the side not facing the organic material layer.

Hereinafter, Synthesis method of the compound represented by Formula 1 and preparation method of an organic electric element according to one embodiment of the present invention will be described in detail by way of examples. However, the present invention is not limited to the following examples.

SYNTHESIS EXAMPLE

For example, as shown in Reaction Scheme 1 below, the compound (final products) represented by formula 1 according to the present invention is synthesized by reacting Sub 1 with Sub 2, but there is no limitation thereto.

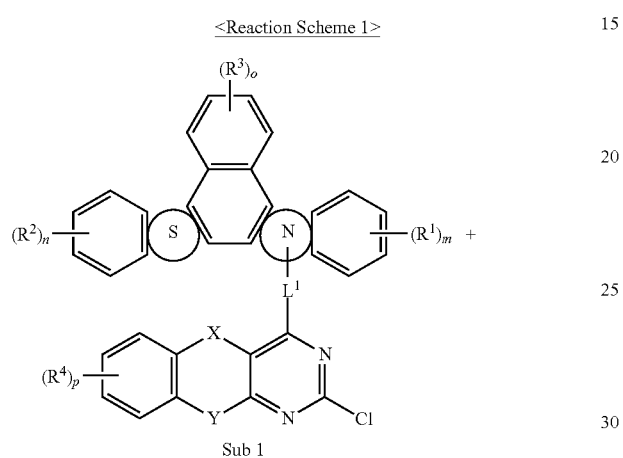

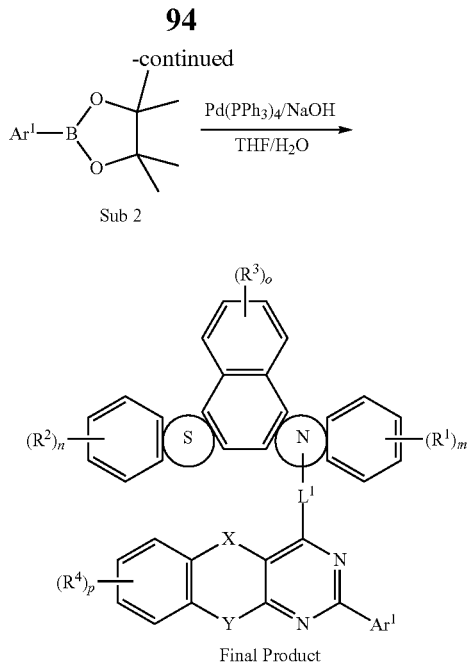

I. Synthesis of Sub 1

Sub 1 of the Reaction Scheme 1 can be synthesized according to, but not limited to, the reaction route of the following Reaction Schemes 2 and 3.

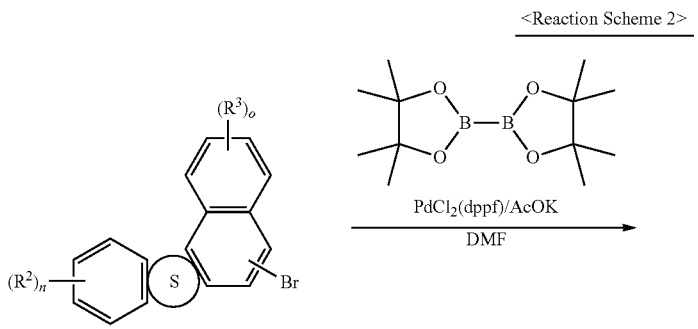

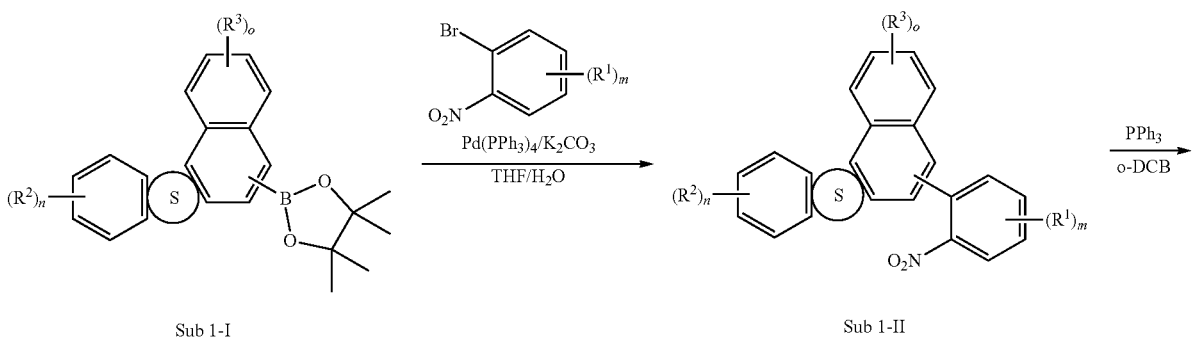

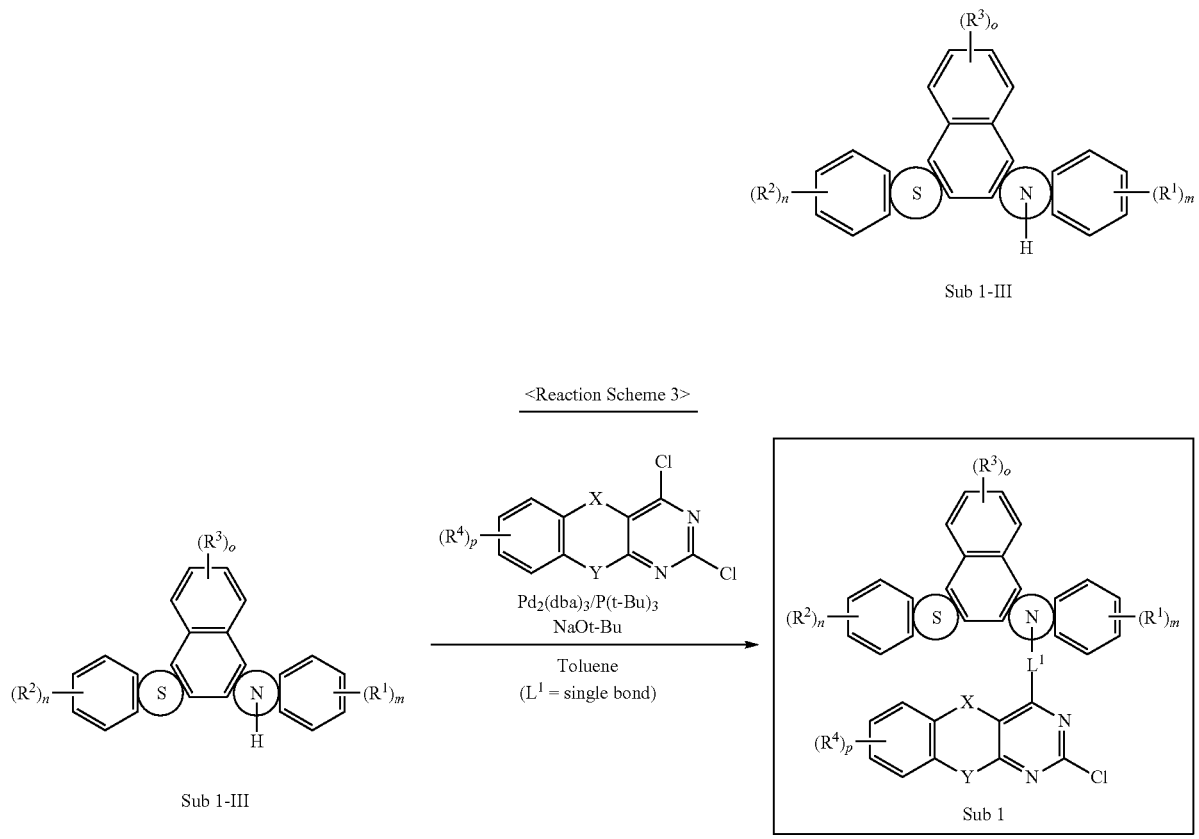
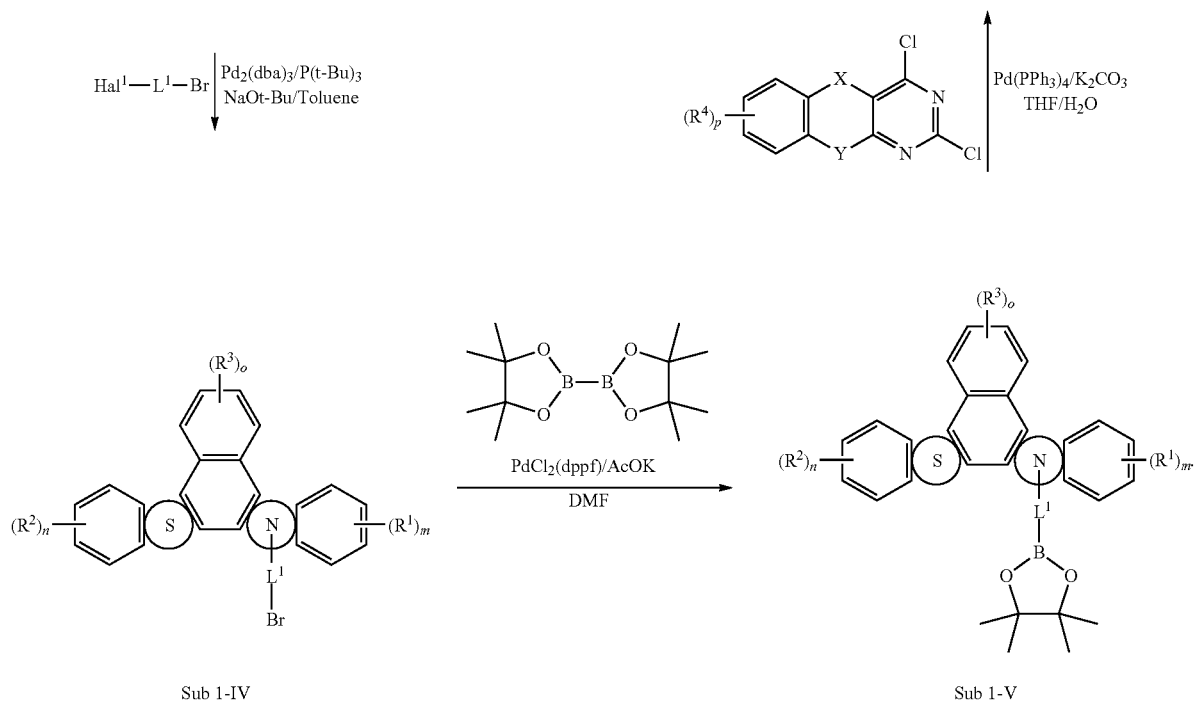
Hal[1] is I or Br

Synthesis Examples of compounds comprised in Sub 1 are as follows. Synthesis Example of Sub 1-1

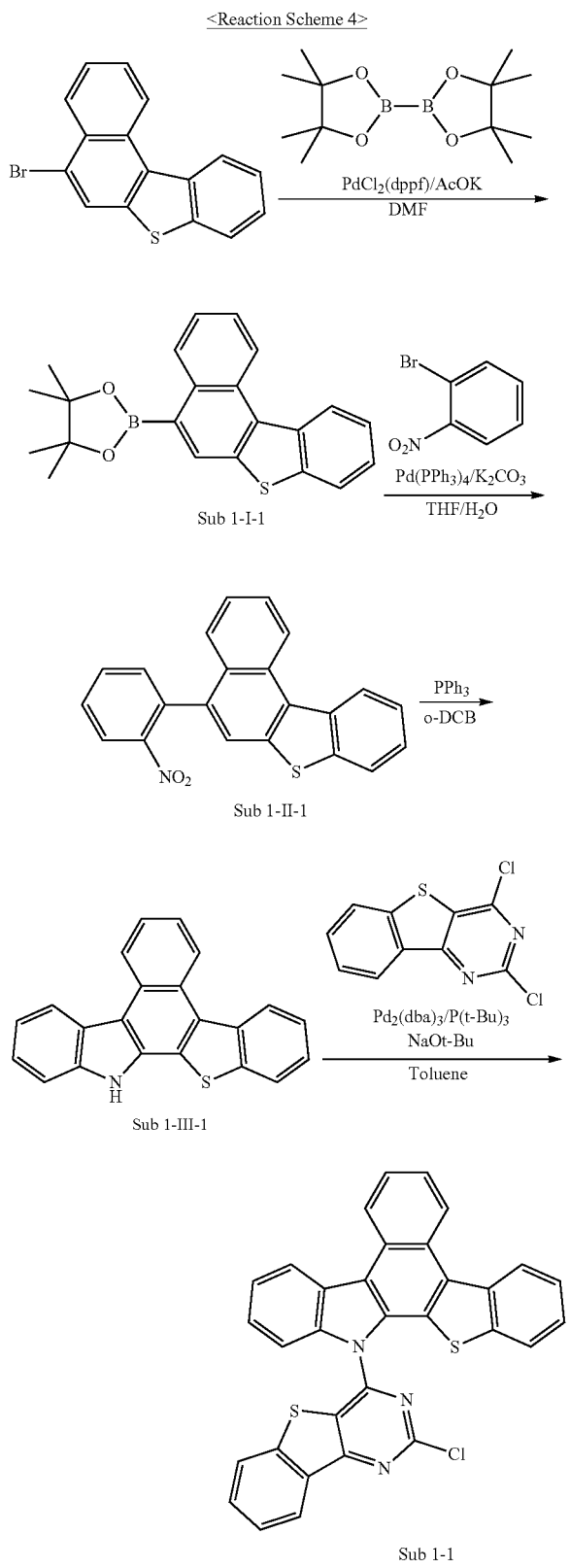

(1) Synthesis of Sub 1-I-1

After 5-bromobenzo[b]naphtho[1,2-d]thiophene (274.84 g, 877.49 mmol) was placed in a round bottom flask and was dissolved in DMF (2900 mL), Bis(pinacolato) diboron (245.11 g, 965.24 mmol), Pd(dppf)Cl$_2$ (21.50 g, 26.32 mmol) and KOAc (258.35 g, 2632.48 mmol) were added. Then, the mixture was stirred at 90° C. When the reaction was completed, DMF was removed by vacuum distillation and the resultant was extracted with CH$_2$Cl$_2$ and water. The organic layer was dried with MgSO$_4$ and concentrated. The concentrate was applied to silica gel column and recrystallized to obtain 256.08 g (yield: 81%) of the product.

(2) Synthesis of Sub 1-II-1

After Sub 1-I-1 (234.68 g, 651.28 mmol) obtained in the above synthesis was placed in a round bottom flask and was dissolved in THF (2400 mL), 1-bromo-2-nitrobenzene (157.90 g, 781.66 mmol), Pd(PPh$_3$)$_4$ (30.11 g, 26.06 mmol), K$_2$CO$_3$ (270.08 g, 1954.15 mmol) and water (1200 mL) were added and the mixture was stirred at 80° C. When the reaction was completed, the resultant was extracted with CH$_2$Cl$_2$ and water. The organic layer was dried with MgSO$_4$ and concentrated. The concentrate was applied to silica gel column and recrystallized to obtain 166.69 g (yield: 72%) of the product.

(3) Synthesis of Sub 1-III-1

After Sub 1-II-1 (166.69 g, 469.01 mmol) obtained in the above synthesis was placed in a round bottom flask and was dissolved in o-dichlorobenzene (4100 mL), triphenylphosphine (307.54 g, 1172.52 mmol) was added and the mixture was stirred at 200° C. When the reaction was completed, o-dichlorobenzene was removed by distillation and the resultant was extracted with CH$_2$Cl$_2$ and water. The organic layer was dried with MgSO$_4$ and concentrated. The concentrate was applied to silica gel column and recrystallized to obtain 115.28 g (yield: 76%) of the product.

(4) Synthesis of Sub 1-1

After Sub 1-III-1 (20.36 g, 62.95 mmol) obtained in the above synthesis was placed in a round bottom flask and was dissolved in toluene (690 mL), 2,4-dichlorobenzo[4,5]thieno[3,2-d]pyrimidine (19.27 g, 75.54 mmol), Pd$_2$(dba)$_3$ (1.73 g, 1.89 mmol), 50% P(t-Bu)$_3$ (1.8 ml, 3.78 mmol) and NaOt-Bu (18.15 g, 188.86 mmol) were added and the mixture was stirred at 100° C. When the reaction was completed, the resultant was extracted with CH$_2$Cl$_2$ and water. The organic layer was dried with MgSO$_4$ and concentrated. The concentrate was applied to silica gel column and recrystallized to obtain 18.09 g (yield: 53%) of the product.

2. Synthesis Example of Sub 1-3
<Reaction Scheme 5>
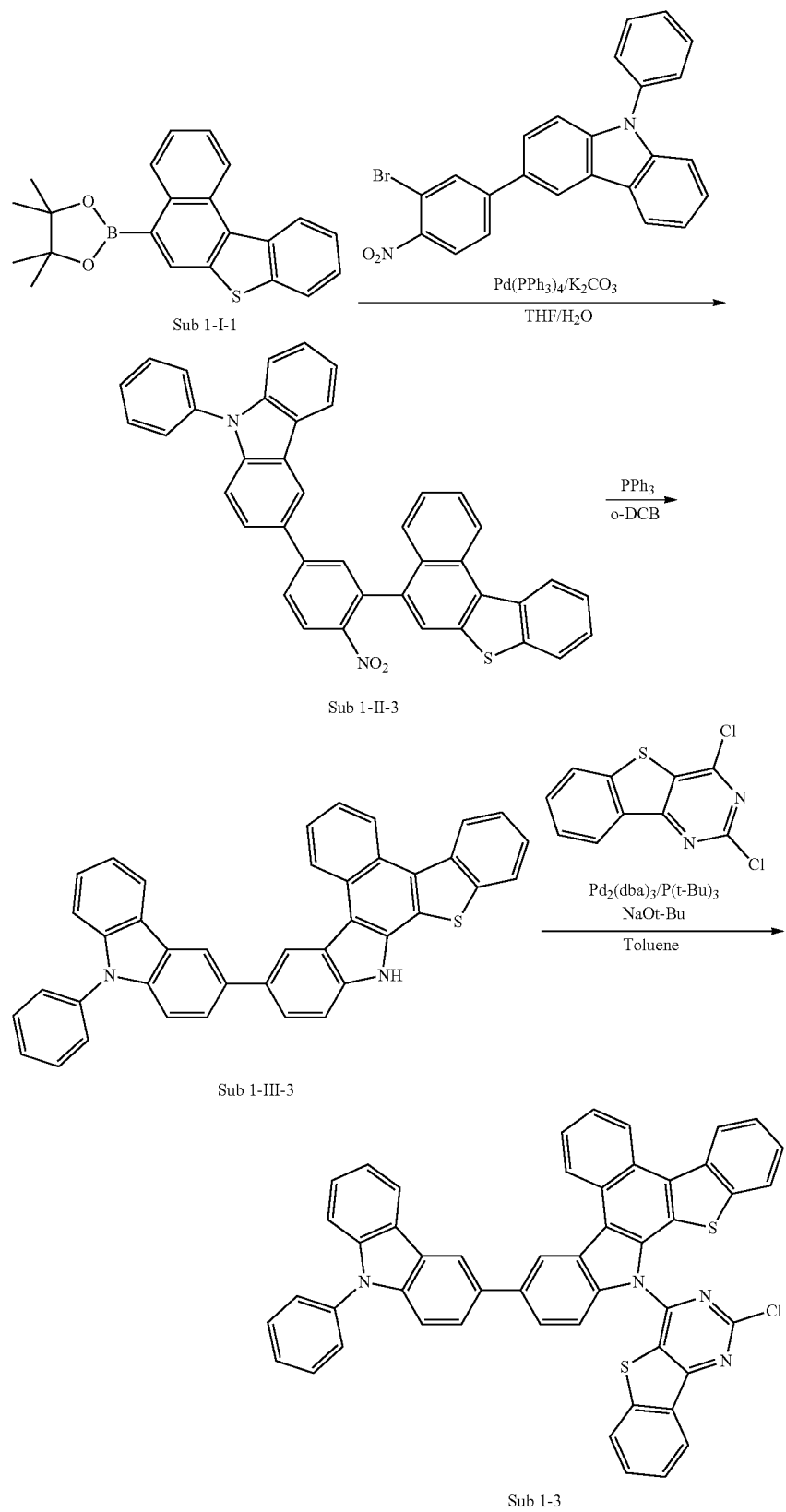
Sub 1-3

(1) Synthesis of Sub 1-II-3

3-(3-bromo-4-nitrophenyl)-9-phenyl-9H-carbazole (31.17 g, 70.31 mmol), Pd(PPh$_3$)$_4$ (2.71 g, 2.34 mmol), K$_2$CO$_3$ (24.29 g, 175.78 mmol), THF (210 mL) and water (105 mL) were added to Sub 1-I-1 (21.11 g, 58.59 mmol) obtained in the above synthesis. Then, 30.42 g (yield: 87%) of the product was obtained by the same method as in synthesis of Sub 1-II-1.

(2) Synthesis of Sub 1-III-3

Triphenylphosphine (33.43 g, 127.45 mmol) and o-dichlorobenzene (445 mL) were added to Sub 1-II-3 (30.42 g, 50.98 mmol) obtained in the above synthesis. Then, 18.43 g (yield: 64%) of the product was obtained by the same method as in synthesis of Sub 1-III-1.

(3) Synthesis of Sub 1-3

2,4-dichlorobenzo[4,5]thieno[3,2-d]pyrimidine (9.99 g, 39.16 mmol), Pd$_2$(dba)$_3$ (0.90 g, 0.98 mmol), 50% P(t-Bu)$_3$ (1.0 ml, 1.96 mmol), NaOt-Bu (9.41 g, 97.91 mmol) and toluene (360 ml) were added to Sub 1-III-3 (18.43 g, 32.64 mmol) obtained in the above synthesis. Then, 12.78 g (yield: 50%) of the product was obtained by the same method as in synthesis of Sub 1-1.

3. Synthesis Example of Sub 1-6

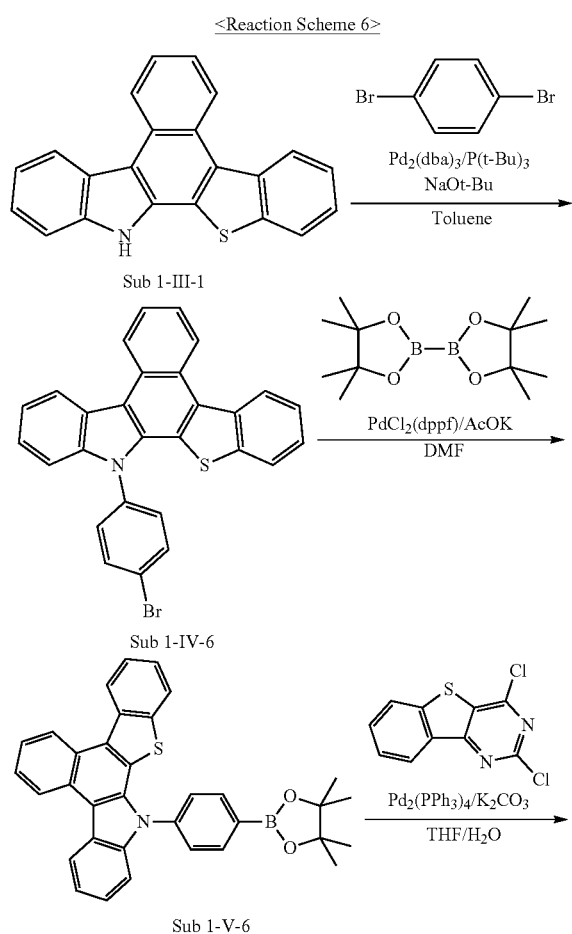

<Reaction Scheme 6>

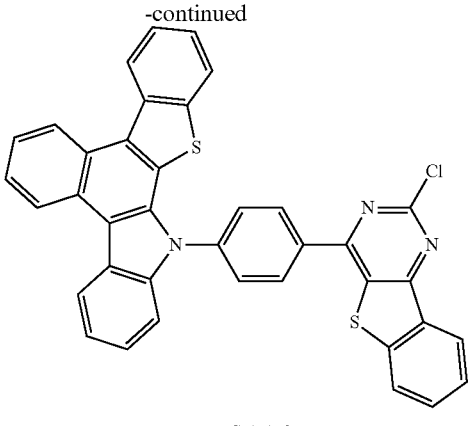

Sub 1-6

(1) Synthesis of Sub 1-IV-6

After Sub 1-III-1 (54.26 g, 167.77 mmol) obtained in the above synthesis was placed in a round bottom flask and was dissolved in toluene (1845 mL), 1,4-dibromobenzene (47.50 g, 201.33 mmol), Pd$_2$(dba)$_3$ (4.61 g, 5.03 mmol), 50% P(t-Bu)$_3$ (4.9 mL, 10.07 mmol) and NaOt-Bu (48.37 g, 503.32 mmol) were added and the mixture was stirred at 100° C. When the reaction was completed, the resultant was extracted with CH$_2$Cl$_2$ and water. The organic layer was dried with MgSO$_4$ and concentrated. The concentrate was applied to silica gel column and recrystallized to obtain 54.58 g (yield: 68%) of the product.

(2) Synthesis of Sub 1-V-6

After Sub 1-IV-6 (54.58 g, 114.09 mmol) was placed in a round bottom flask and was dissolved in DMF (570 mL), Bis(pinacolato)diboron (34.77 g, 136.90 mmol), Pd(dppf)Cl$_2$ (2.80 g, 3.42 mmol) and KOAc (33.59 g, 342.26 mmol) were added. Then, the mixture was stirred at 120° C. When the reaction was completed, DMF was removed by distillation and the resultant was extracted with CH$_2$Cl$_2$ and water. The organic layer was dried with MgSO$_4$ and concentrated. The concentrate was applied to silica gel column and recrystallized to obtain 43.76 g (yield: 73%) of the product.

(3) Synthesis of Sub 1-6

After Sub 1-V-6 (21.61 g, 41.13 mmol) obtained in the above synthesis was placed in a round bottom flask and was dissolved in THF (150 mL), 1-2,4-dichlorobenzo[4,5]thieno[3,2-d]pyrimidine (12.59 g, 49.35 mmol), Pd(PPh$_3$)$_4$ (1.90 g, 1.65 mmol), K$_2$CO$_3$ (17.05 g, 123.38 mmol) and water (75 mL) were added and the mixture was stirred at 80° C. When the reaction was completed, the resultant was extracted with CH$_2$Cl$_2$ and water. The organic layer was dried with MgSO$_4$ and concentrated. The concentrate was applied to silica gel column and recrystallized to obtain 11.95 g (yield: 47%) of the product.

4. Synthesis Example of Sub 1-12

<Reaction Scheme 7>

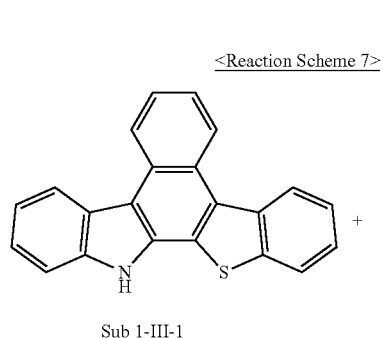

Sub 1-III-1

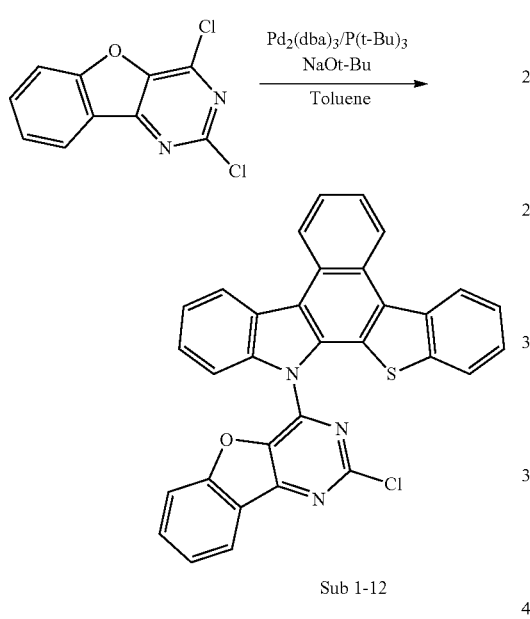

Sub 1-12

2,4-dichlorobenzofuro[3,2-d]pyrimidine (9.14 g, 38.22 mmol), Pd$_2$(dba)$_3$ (0.87 g, 0.96 mmol), 50% P(t-Bu)$_3$ (0.9 mL, 1.91 mmol), NaOt-Bu (9.18 g, 95.54 mmol) and toluene (350 mL) were added to Sub 1-III-1 (10.30 g, 31.85 mmol) obtained in the above synthesis. Then, 9.05 g (yield: 54%) of the product was obtained by the same method as in synthesis of Sub 1-1.

5. Synthesis Example of Sub 1-20

<Reaction Scheme 8>

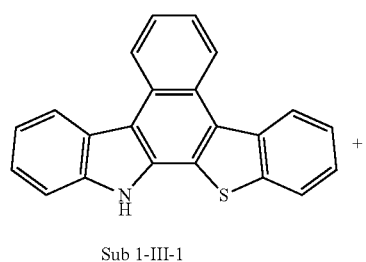

Sub 1-III-1

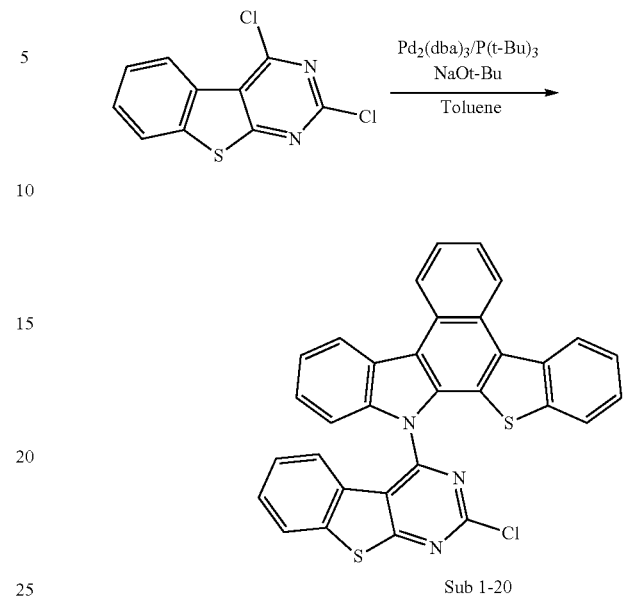

Sub 1-20

2,4-dichlorobenzo[4,5]thieno[2,3-d]pyrimidine (11.27 g, 44.19 mmol), Pd$_2$(dba)$_3$ (1.01 g, 1.10 mmol), 50% P(t-Bu)$_3$ (1.1 mL, 2.21 mmol), NaOt-Bu (10.62 g, 110.48 mmol) and toluene (405 mL) were added to Sub 1-III-1 (11.91 g, 36.83 mmol) obtained in the above synthesis. Then, 10.18 g (yield: 51%) of the product was obtained by the same method as in synthesis of Sub 1-1.

6. Synthesis Example of Sub 1-36

<Reaction Scheme 9>

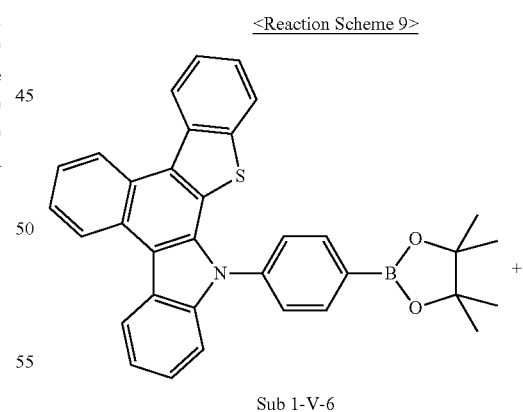

Sub 1-V-6

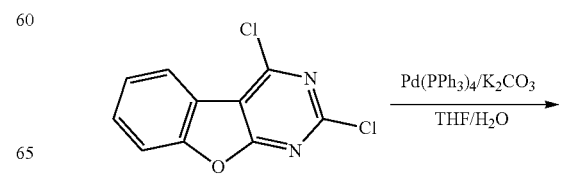

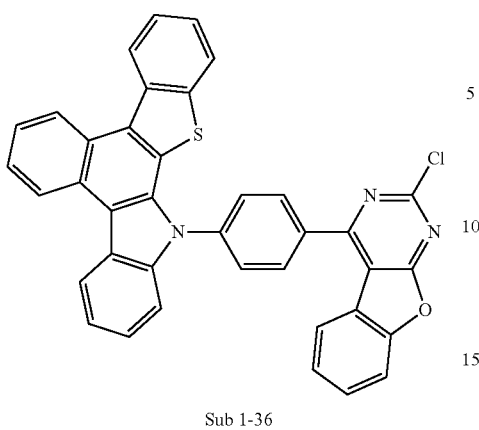

Sub 1-36

2,4-dichlorobenzofuro[2,3-d]pyrimidine (1.87 g, 49.67 mmol), Pd(PPh₃)₄ (1.91 g, 1.66 mmol), K₂CO₃ (17.16 g, 124.17 mmol), THF (150 mL) and water (75 mL) were added to Sub 1-V-6 (21.75 g, 41.39 mmol) obtained in the above synthesis. Then, 11.22 g (yield: 45%) of the product was obtained by the same method as in synthesis of Sub 1-6.

7. Synthesis Example of Sub 1-38

<Reaction Scheme 10>

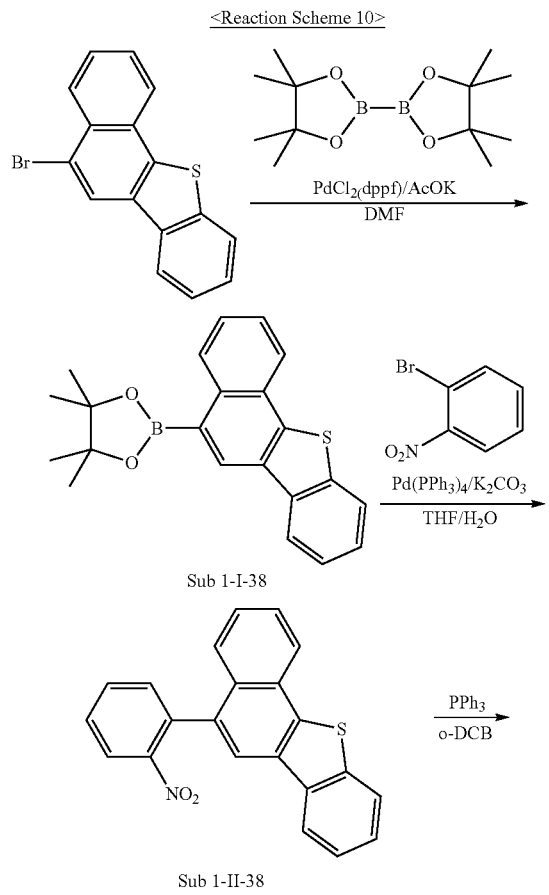

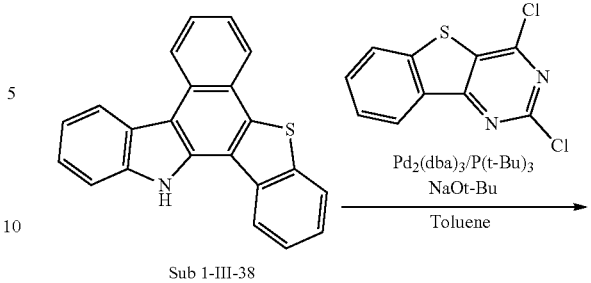

Sub 1-III-38

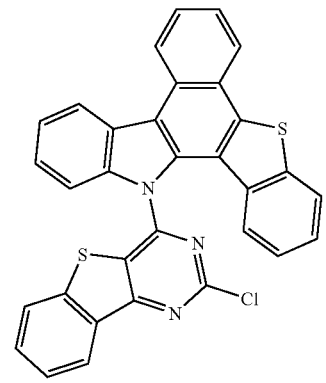

Sub 1-38

(1) Synthesis of Sub 1-I-38

Bis(pinacolato)diboron (171.88 g, 676.84 mmol), Pd(dppf)Cl₂ (15.07 g, 18.46 mmol), KOAc (181.16 g, 1845.92 mmol) and DMF (2000 mL) were added to the starting material 5-bromobenzo[b]naphtho[2,1-d]thiophene (192.72 g, 615.31 mmol). Then, 190.65 g (yield: 86%) of the product was obtained by the same method as in synthesis of Sub 1-I-1.

(2) Synthesis of Sub 1-II-38

1-bromo-2-nitrobenzene (128.28 g, 635.01 mmol), Pd(PPh₃)₄ (24.46 g, 21.17 mmol), K₂CO₃ (219.41 g, 1587.52 mmol), THF (1940 mL) and water (970 mL) were added to Sub 1-I-38 (190.65 g, 529.17 mmol) obtained in the above synthesis. Then, 144.82 g (yield: 77%) of the product was obtained by the same method as in synthesis of Sub 1-II-1.

(3) Synthesis of Sub 1-III-38

Triphenylphosphine (267.19 g, 1018.68 mmol) and o-dichlorobenzene (3560 mL) were added to Sub 1-II-38 (144.82 g, 407.47 mmol) obtained in the above synthesis. Then, 89.61 g (yield: 68%) of the product was obtained by the same method as in synthesis of Sub 1-III-1.

(4) Synthesis of Sub 1-38

2,4-dichlorobenzo[4,5]thieno[3,2-d]pyrimidine (12.10 g, 47.42 mmol), Pd₂(dba)₃ (1.09 g, 1.19 mmol), 50% P(t-Bu)₃ (1.2 mL, 2.37 mmol), NaOt-Bu (11.39 g, 118.55 mmol) and toluene (435 mL) were added to Sub 1-III-38 (12.78 g, 39.52 mmol) obtained in the above synthesis. Then, 9.85 g (yield: 46%) of the product was obtained by the same method as in synthesis of Sub 1-1.

8. Synthesis Example of Sub 1-44

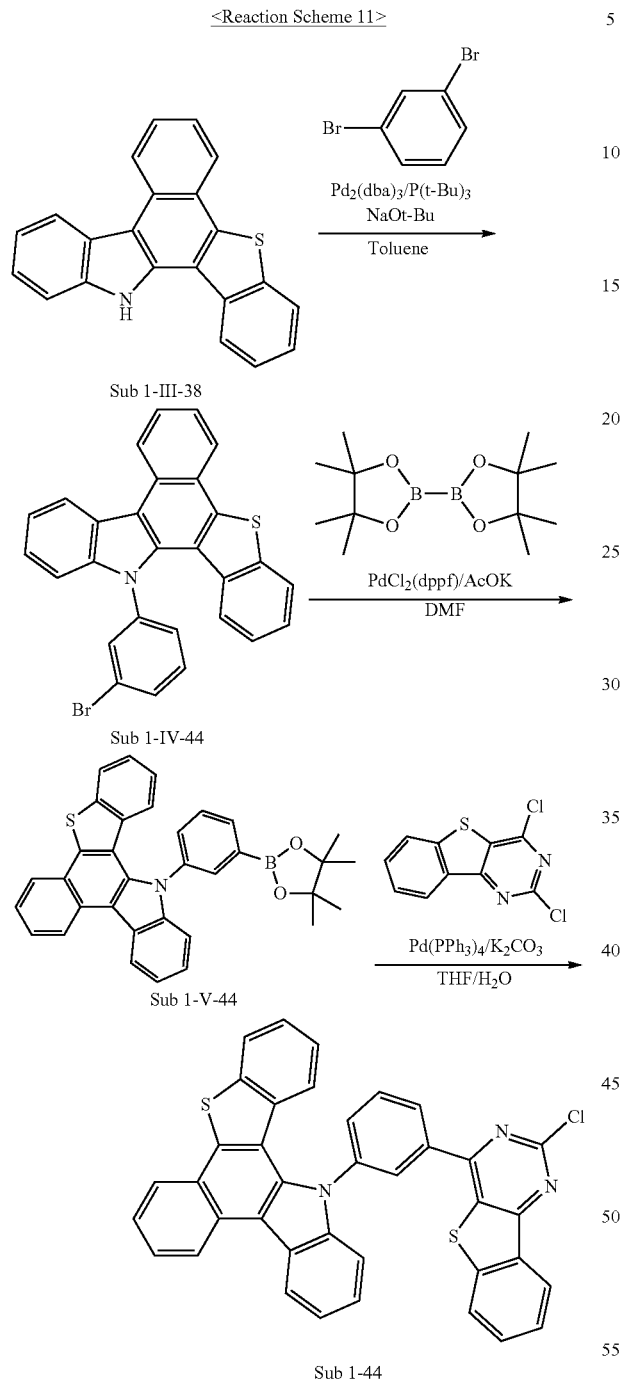

<Reaction Scheme 11>

Sub 1-III-38

Sub 1-IV-44

Sub 1-V-44

Sub 1-44

(1) Synthesis of Sub 1-IV-44

1,3-dibromobenzene (42.30 g, 179.33 mmol), Pd$_2$(dba)$_3$ (4.11 g, 4.48 mmol), 50% P(t-Bu)$_3$ (4.4 mL, 8.97 mmol), NaOt-Bu (43.09 g, 448.32 mmol) and toluene (1640 mL) were added to Sub 1-III-38 (48.33 g, 149.44 mmol) obtained in the above synthesis. Then, 48.62 g (yield: 68%) of the product was obtained by the same method as in synthesis of Sub 1-IV-6.

(2) Synthesis of Sub 1-V-44

Bis(pinacolato)diboron (30.97 g, 121.95 mmol), Pd(dppf)Cl$_2$ (2.49 g, 3.05 mmol), KOAc (29.92 g, 304.88 mmol) and DMF (500 mL) were added to Sub 1-IV-44 (48.62 g, 101.63 mmol) obtained in the above synthesis. Then, 37.38 g (yield: 70%) of the product was obtained by the same method as in synthesis of Sub 1-V-6.

(3) Synthesis of Sub 1-44

2,4-dichlorobenzo[4,5]thieno[3,2-d]pyrimidine (10.93 g, 42.84 mmol), Pd(PPh$_3$)$_4$ (1.65 g, 1.43 mmol), K$_2$CO$_3$ (14.80 g, 107.10 mmol), THF (130 mL) and water (65 mL) were added to Sub 1-V-44 (18.76 g, 35.70 mmol) obtained in the above synthesis. Then, 10.81 g (yield: 49%) of the product was obtained by the same method as in synthesis of Sub 1-6.

9. Synthesis Example of Sub 1-50

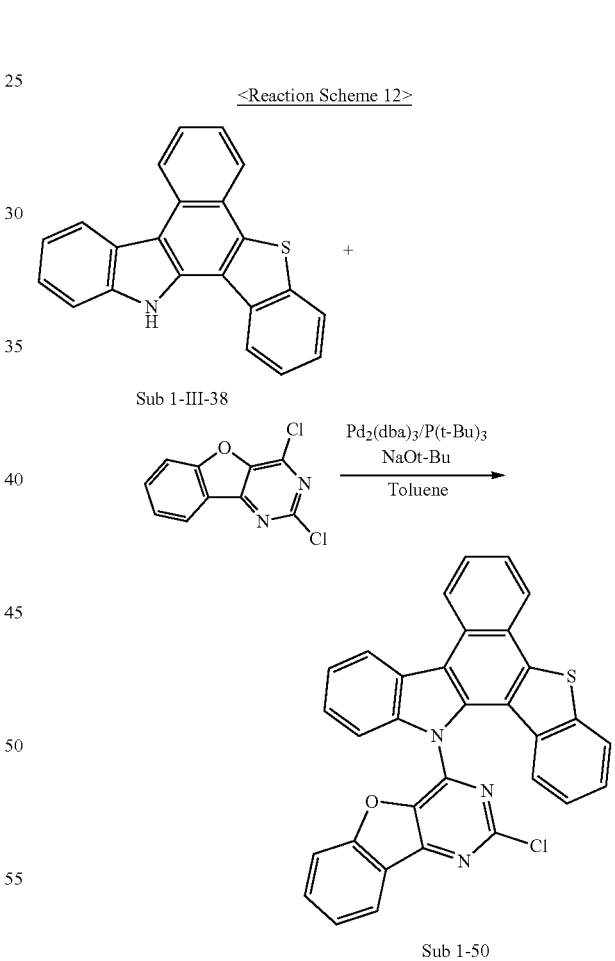

<Reaction Scheme 12>

Sub 1-III-38

Sub 1-50

2,4-dichlorobenzofuro[3,2-d]pyrimidine (11.63 g, 48.64 mmol), Pd$_2$(dba)$_3$ (1.11 g, 1.22 mmol), 50% P(t-Bu)$_3$ (1.2 mL, 2.43 mmol), NaOt-Bu (11.69 g, 121.61 mmol) and toluene (445 mL) were added to Sub 1-III-38 (13.11 g, 40.54 mmol) obtained in the above synthesis. Then, 9.17 g (yield: 43%) of the product was obtained by the same method as in synthesis of Sub 1-1.

10. Synthesis Example of Sub 1-62

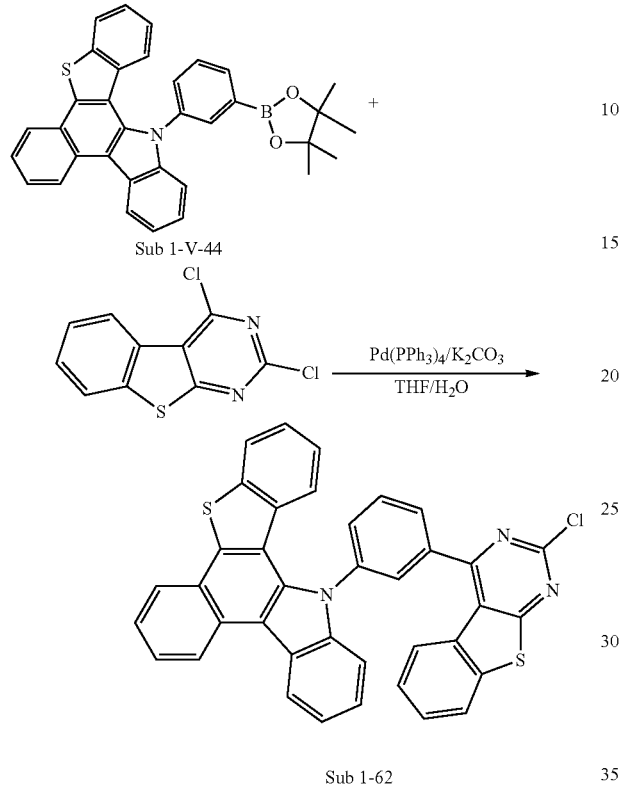

<Reaction Scheme 13>

Sub 1-V-44

Pd(PPh₃)₄/K₂CO₃
THF/H₂O

Sub 1-62

2,4-dichlorobenzo[4,5]thieno[2,3-d]pyrimidine (10.82 g, 42.41 mmol), Pd(PPh₃)₄ (1.63 g, 1.41 mmol), K₂CO₃ (14.65 g, 106.02 mmol), THF (130 mL) and water (65 mL) were added to Sub 1-V-44 (18.57 g, 35.34 mmol) obtained in the above synthesis. Then, 10.27 g (yield: 47%) of the product was obtained by the same method as in synthesis of Sub 1-6.

11. Synthesis Example of Sub 1-64

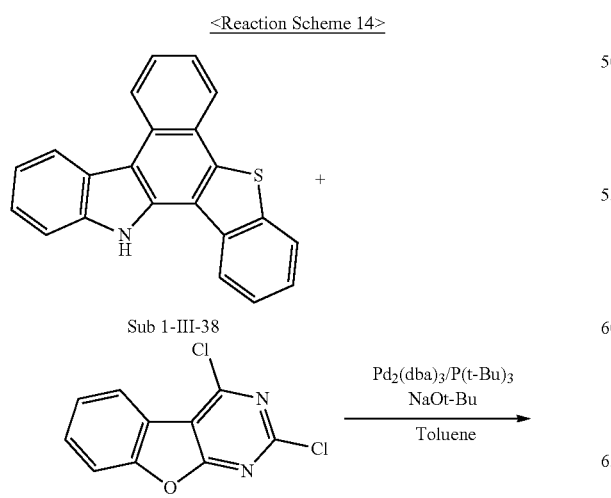

<Reaction Scheme 14>

Sub 1-III-38

Pd₂(dba)₃/P(t-Bu)₃
NaOt-Bu
Toluene

Sub 1-64

2,4-dichlorobenzofuro[2,3-d]pyrimidine (13.65 g, 57.10 mmol), Pd₂(dba)₃ (1.31 g, 1.43 mmol), 50% P(t-Bu)₃ (1.4 mL, 2.86 mmol), NaOt-Bu (13.72 g, 142.76 mmol) and toluene (520 mL) were added to Sub 1-III-38 (15.39 g, 47.59 mmol) obtained in the above synthesis. Then, 11.26 g (yield: 45%) of the product was obtained by the same method as in synthesis of Sub 1-1.

12. Synthesis Example of Sub 1-68

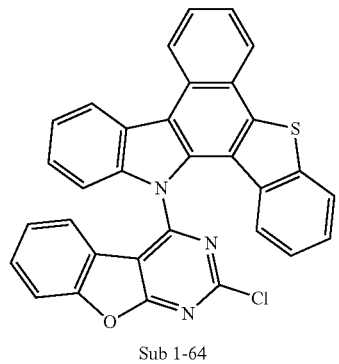

<Reaction Scheme 15>

PdCl₂(dppf)/AcOK
DMF

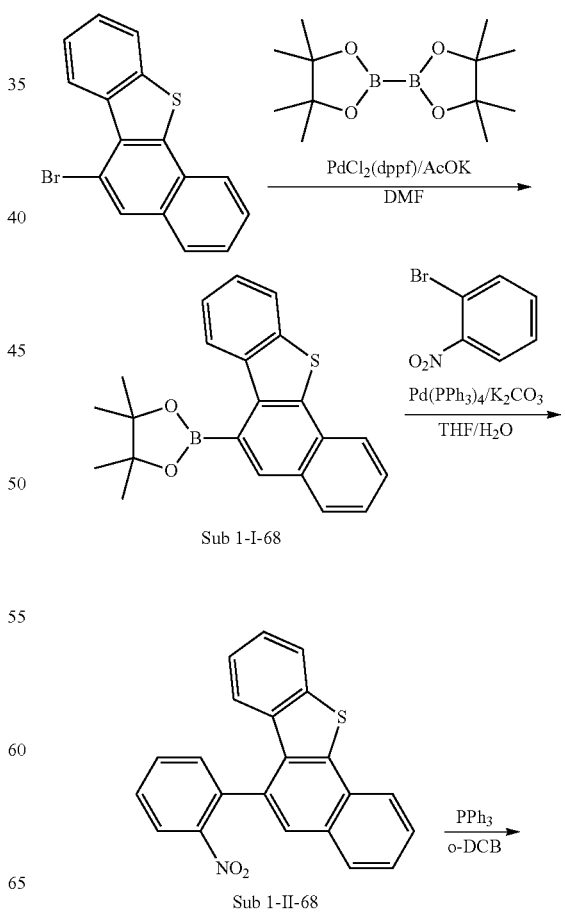

Pd(PPh₃)₄/K₂CO₃
THF/H₂O

Sub 1-I-68

Sub 1-II-68

PPh₃
o-DCB

-continued

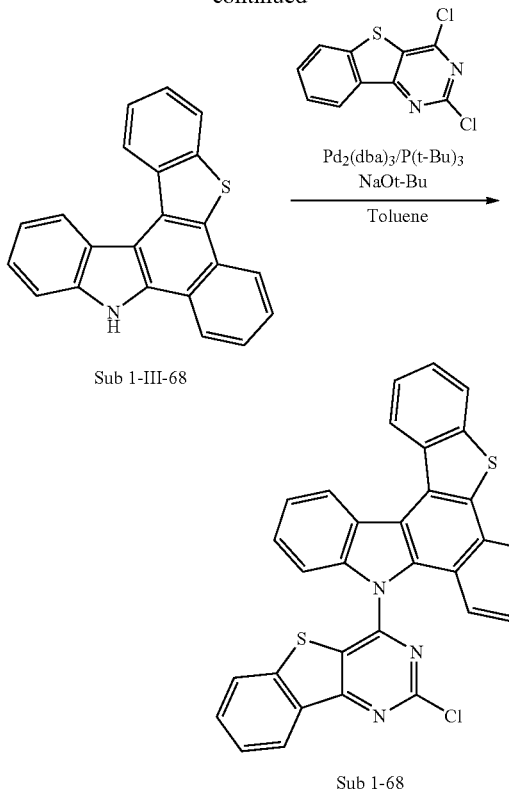

(1) Synthesis of Sub 1-I-68

Bis(pinacolato)diboron (246.36 g, 970.16 mmol), Pd(dppf)Cl$_2$ (21.61 g, 26.46 mmol), KOAc (259.67 g, 2645.89 mmol) and DMF (2900 mL) were added to the starting material 6-bromobenzo[b]naphtho[2,1-d]thiophene (276.24 g, 881.96 mmol). Then, 193.83 g (yield: 61%) of the product was obtained by the same method as in synthesis of Sub 1-I-1.

(2) Synthesis of Sub 1-II-68

1-bromo-2-nitrobenzene (130.42 g, 645.60 mmol), Pd(PPh$_3$)$_4$ (24.87 g, 21.52 mmol), K$_2$CO$_3$ (223.07 g, 1613.99 mmol), THF (1970 mL) and water (985 mL) were added to Sub 1-I-68 (193.83 g, 538.00 mmol) obtained in the above synthesis. Then, 110.90 g (yield: 58%) of the product was obtained by the same method as in synthesis of Sub 1-II-1.

(3) Synthesis of Sub 1-III-68

Triphenylphosphine (204.61 g, 780.08 mmol) and o-dichlorobenzene (2730 ml) were added to Sub 1-II-68 (110.90 g, 312.03 mmol) obtained in the above synthesis. Then, 74.68 g (yield: 74%) of the product was obtained by the same method as in synthesis of Sub 1-III-1.

(4) Synthesis of Sub 1-68

2,4-dichlorobenzo[4,5]thieno[3,2-d]pyrimidine (11.49 g, 45.04 mmol), Pd$_2$(dba)$_3$ (1.03 g, 1.13 mmol), 50% P(t-Bu)$_3$ (1.1 mL, 2.25 mmol), NaOt-Bu (10.82 g, 112.61 mmol) and toluene (410 mL) were added to Sub 1-III-68 (12.14 g, 37.54 mmol) obtained in the above synthesis. Then, 8.95 g (yield: 44%) of the product was obtained by the same method as in synthesis of Sub 1-1.

13. Synthesis Example of Sub 1-78

<Reaction Scheme 16>

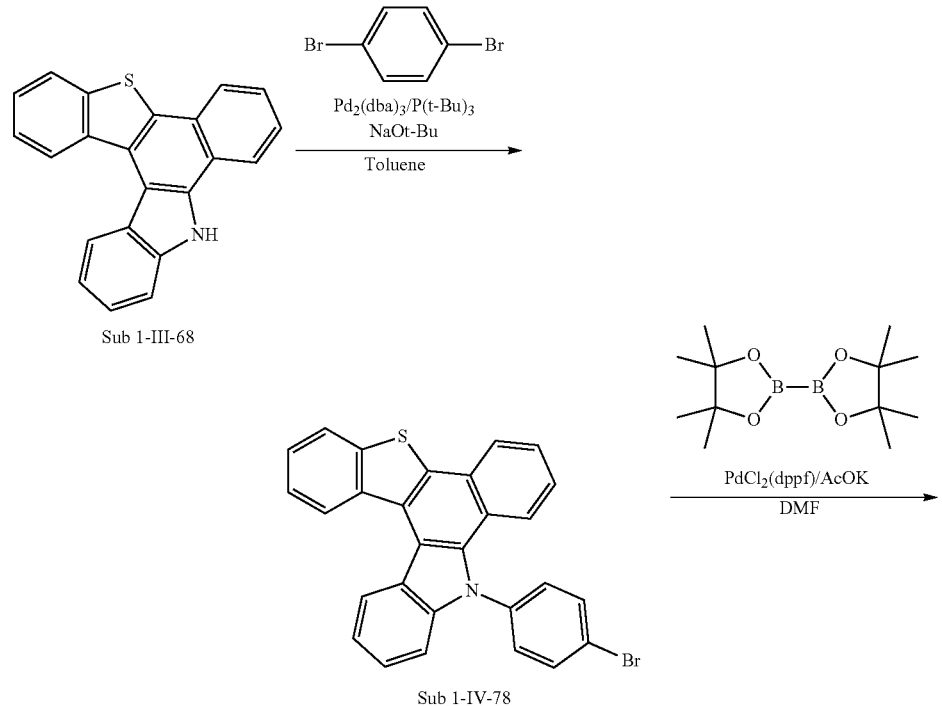

-continued

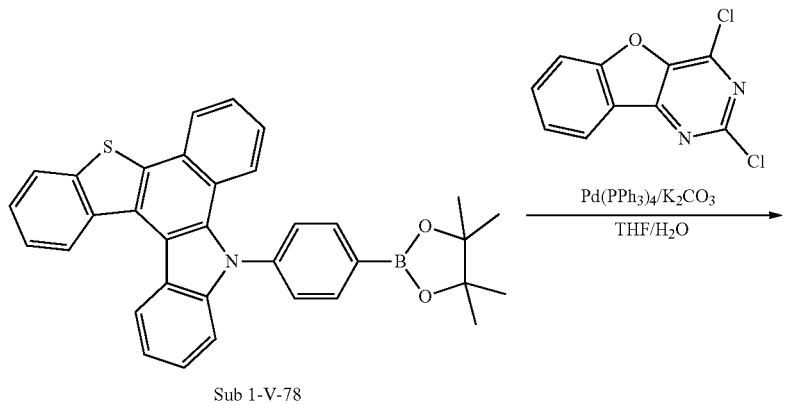

Sub 1-V-78

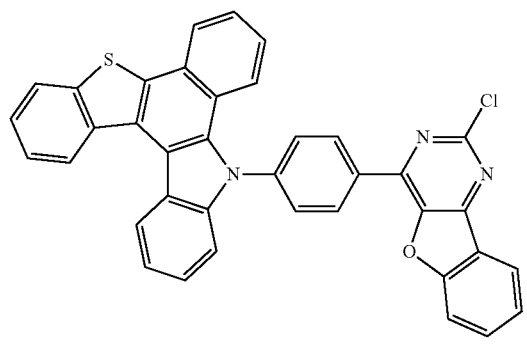

Sub 1-78

(1) Synthesis of Sub 1-IV-78

1,4-dibromobenzene (25.77 g, 109.24 mmol), Pd$_2$(dba)$_3$ (2.50 g, 2.73 mmol), 50% P(t-Bu)$_3$ (2.7 mL, 5.46 mmol), NaOt-Bu (26.25 g, 273.09 mmol) and toluene (1000 mL) were added to Sub 1-III-68 (29.44 g, 91.03 mmol) obtained in the above synthesis. Then, 28.31 g (yield: 65%) of the product was obtained by the same method as in synthesis of Sub 1-IV-6.

(2) Synthesis of Sub 1-V-78

Bis(pinacolato)diboron (18.03 g, 71.01 mmol), Pd(dppf)Cl$_2$ (1.45 g, 1.78 mmol), KOAc (17.42 g, 177.53 mmol) and DMF (296 mL) were added to Sub 1-IV-78 (28.31 g, 59.18 mmol) obtained in the above synthesis. Then, 23.32 g (yield: 75%) of the product was obtained by the same method as in synthesis of Sub 1-V-6.

(3) Synthesis of Sub 1-78

2,4-dichlorobenzofuro[3,2-d]pyrimidine (12.73 g, 53.26 mmol), Pd(PPh$_3$)$_4$ (2.05 g, 1.78 mmol), K$_2$CO$_3$ (18.40 g, 133.14 mmol), THF (160 mL) and water (80 mL) were added to Sub 1-V-78 (23.32 g, 44.38 mmol) obtained in the above synthesis. Then, 11.22 g (yield: 42%) of the product was obtained by the same method as in synthesis of Sub 1-6.

14. Synthesis Example of Sub 1-79

<Reaction Scheme 17>

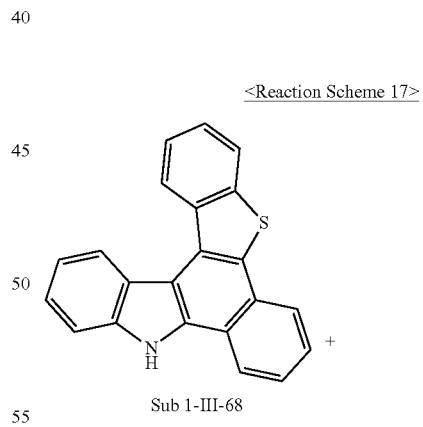

Sub 1-III-68

+

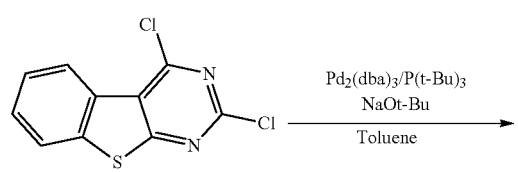

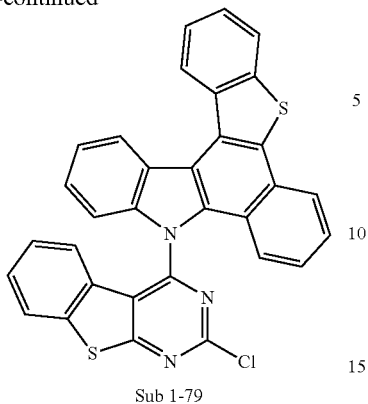

Sub 1-79

2,4-dichlorobenzo[4,5]thieno[2,3-d]pyrimidine (16.73 g, 65.56 mmol), Pd$_2$(dba)$_3$ (1.50 g, 1.64 mmol), 50% P(t-Bu)$_3$ (1.6 mL, 3.28 mmol), NaOt-Bu (15.75 g, 163.91 mmol) and toluene (600 mL) were added to Sub 1-III-68 (17.67 g, 54.64 mmol) obtained in the above synthesis. Then, 11.85 g (yield: 40%) of the product was obtained by the same method as in synthesis of Sub 1-1.

15. Synthesis Example of Sub 1-90

<Reaction Scheme 18>

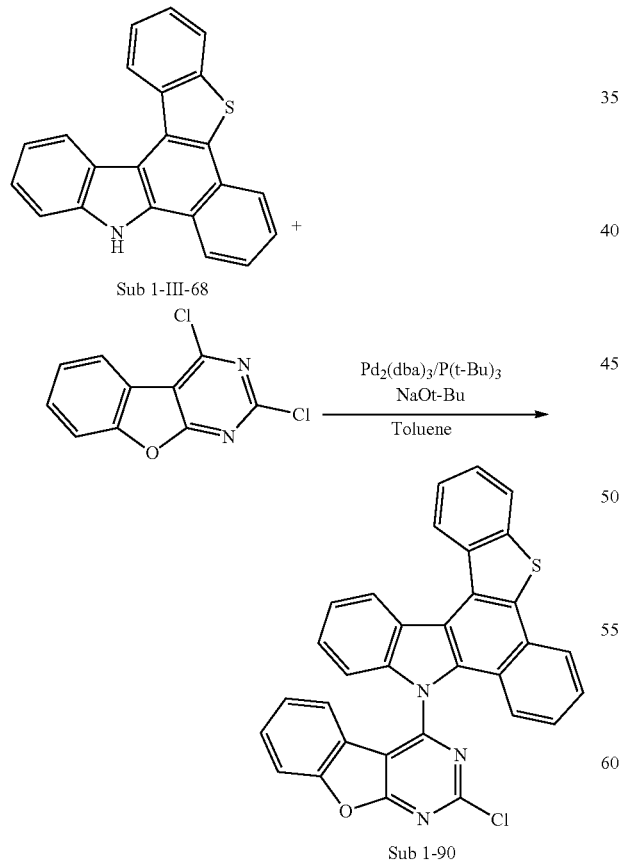

Sub 1-90

2,4-dichlorobenzofuro[2,3-d]pyrimidine (14.69 g, 61.45 mmol), Pd$_2$(dba)$_3$ (1.41 g, 1.54 mmol), 50% P(t-Bu)$_3$ (1.5 mL, 3.07 mmol), NaOt-Bu (14.76 g, 153.61 mmol) and toluene (560 mL) were added to Sub 1-III-68 (16.56 g, 51.20 mmol) obtained in the above synthesis. Then, 11.58 g (yield: 43%) of the product was obtained by the same method as in synthesis of Sub 1-1.

16. Synthesis Example of Sub 1-97

<Reaction Scheme 19>

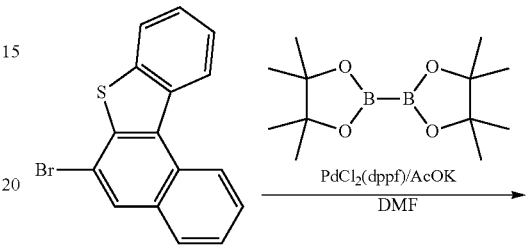

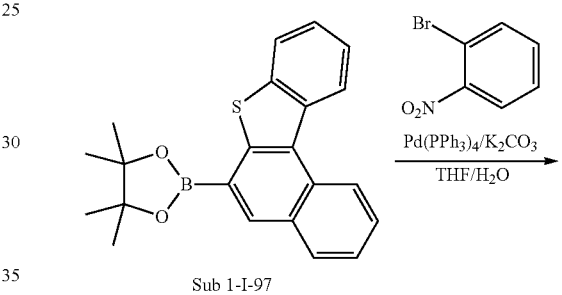

Sub 1-I-97

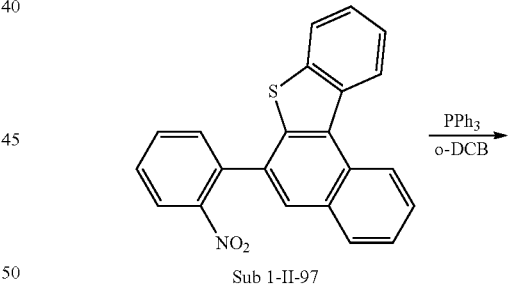

Sub 1-II-97

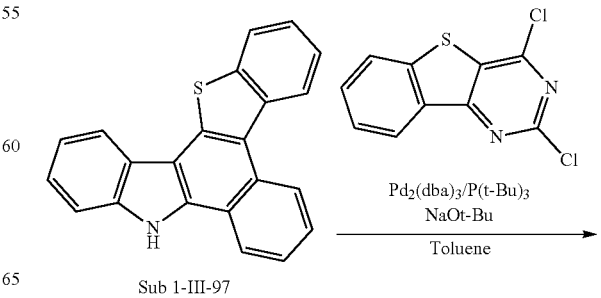

Sub 1-III-97

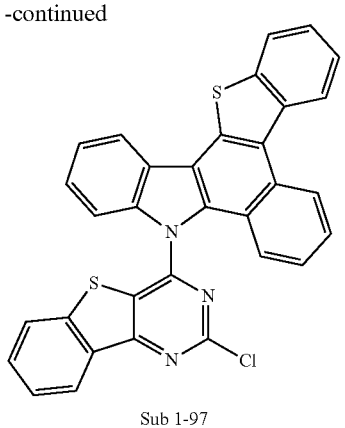

Sub 1-97

(1) Synthesis of Sub 1-I-97

Bis(pinacolato)diboron (187.22 g, 737.24 mmol), Pd(dppf)Cl$_2$ (16.42 g, 20.11 mmol), KOAc (197.33 g, 2010.66 mmol) and DMF (2230 mL) were added to the starting material 6-bromobenzo[b]naphtho[1,2-d]thiophene (209.92 g, 670.22 mmol). Then, 164.20 g (yield: 68%) of the product was obtained by the same method as in synthesis of Sub 1-I-1.

(2) Synthesis of Sub 1-II-97

1-bromo-2-nitrobenzene (110.48 g, 546.91 mmol), Pd(PPh$_3$)$_4$ (21.07 g, 18.23 mmol), K$_2$CO$_3$ (188.97 g, 1367.27 mmol), THF (1670 mL) and water (835 mL) were added to Sub 1-I-97 (164.20 g, 455.76 mmol) obtained in the above synthesis. Then, 106.91 g (yield: 66%) of the product was obtained by the same method as in synthesis of Sub 1-II-1.

(3) Synthesis of Sub 1-III-97

Triphenylphosphine (197.25 g, 752.02 mmol) and o-dichlorobenzene (2630 ml) were added to Sub 1-II-97 (106.91 g, 300.81 mmol) obtained in the above synthesis. Then, 70.04 g (yield: 72%) of the product was obtained by the same method as in synthesis of Sub 1-III-1.

(4) Synthesis of Sub 1-97

2,4-dichlorobenzo[4,5]thieno[3,2-d]pyrimidine (13.61 g, 53.36 mmol), Pd$_2$(dba)$_3$ (1.22 g, 1.33 mmol), 50% P(t-Bu)$_3$ (1.3 mL, 2.67 mmol), NaOt-Bu (12.82 g, 133.39 mmol) and toluene (490 mL) were added to Sub 1-III-97 (14.38 g, 44.46 mmol) obtained in the above synthesis. Then, 11.09 g (yield: 46%) of the product was obtained by the same method as in synthesis of Sub 1-1.

17. Synthesis Example of Sub 1-109

<Reaction Scheme 20>

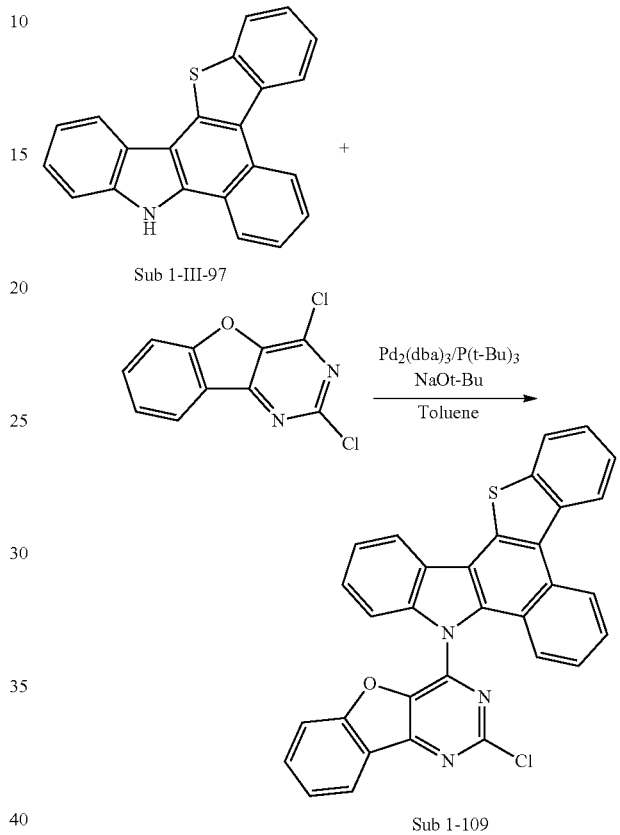

Sub 1-109

2,4-dichlorobenzofuro[3,2-d]pyrimidine (14.80 g, 61.93 mmol), Pd$_2$(dba)$_3$ (1.42 g, 1.55 mmol), 50% P(t-Bu)$_3$ (1.5 mL, 3.10 mmol), NaOt-Bu (14.88 g, 154.82 mmol) and toluene (570 mL) were added to Sub 1-III-97 (16.69 g, 51.61 mmol) obtained in the above synthesis. Then, 11.40 g (yield: 42%) of the product was obtained by the same method as in synthesis of Sub 1-1.

18. Synthesis Example of Sub 1-120

<Reaction Scheme 21>

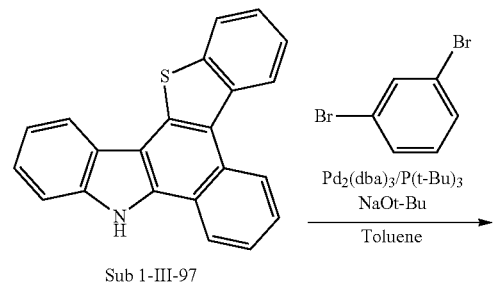

Sub 1-III-97

-continued

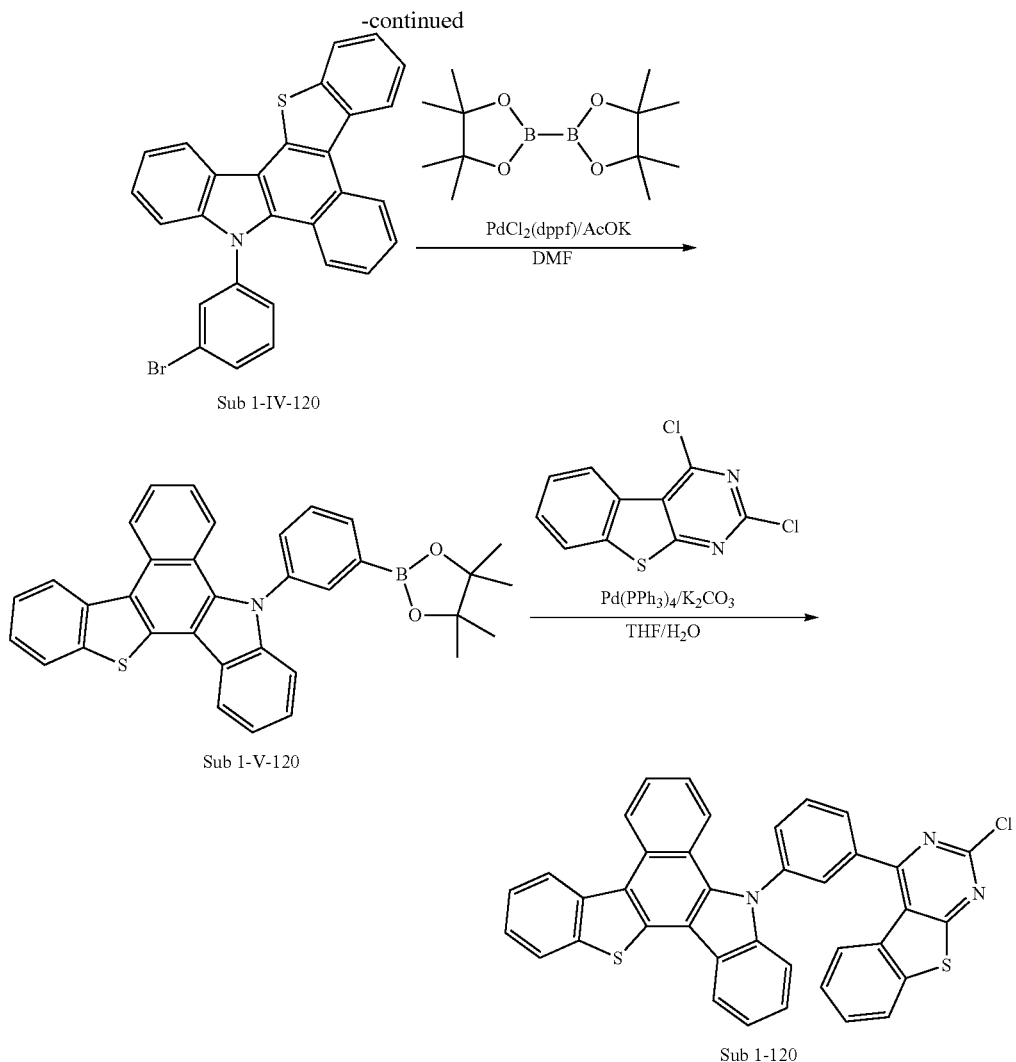

Sub 1-IV-120

Sub 1-V-120

Sub 1-120

(1) Synthesis of Sub 1-IV-120

1,3-dibromobenzene (21.76 g, 92.24 mmol), Pd$_2$(dba)$_3$ (2.11 g, 2.31 mmol), 50% P(t-Bu)$_3$ (2.2 mL, 4.61 mmol), NaOt-Bu (22.16 g, 230.61 mmol) and toluene (845 mL) were added to Sub 1-III-97 (24.86 g, 76.87 mmol) obtained in the above synthesis. Then, 25.01 g (yield: 68%) of the product was obtained by the same method as in synthesis of Sub 1-IV-6.

(2) Synthesis of Sub 1-V-120

Bis(pinacolato)diboron (15.93 g, 62.73 mmol), Pd(dppf)Cl$_2$ (1.28 g, 1.57 mmol), KOAc (15.39 g, 156.83 mmol) and DMF (260 mL) were added to Sub 1-IV-120 (25.01 g, 52.28 mmol) obtained in the above synthesis. Then, 20.33 g (yield: 74%) of the product was obtained by the same method as in synthesis of Sub 1-V-6.

(3) Synthesis of Sub 1-120

2,4-dichlorobenzo[4,5]thieno[2,3-d]pyrimidine (11.84 g, 46.43 mmol), Pd(PPh$_3$)$_4$ (1.79 g, 1.55 mmol), K$_2$CO$_3$ (16.04 g, 116.07 mmol), THF (140 mL) and water (70 mL) were added to Sub 1-V-120 (20.33 g, 38.69 mmol) obtained in the above synthesis. Then, 11.96 g (yield: 50%) of the product was obtained by the same method as in synthesis of Sub 1-6.

19. Synthesis Example of Sub 1-122

<Reaction Scheme 22>

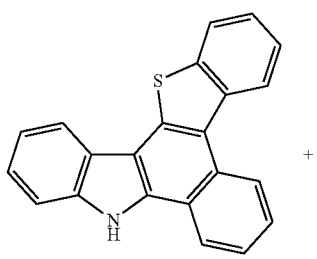

Sub 1-III-97
+

-continued

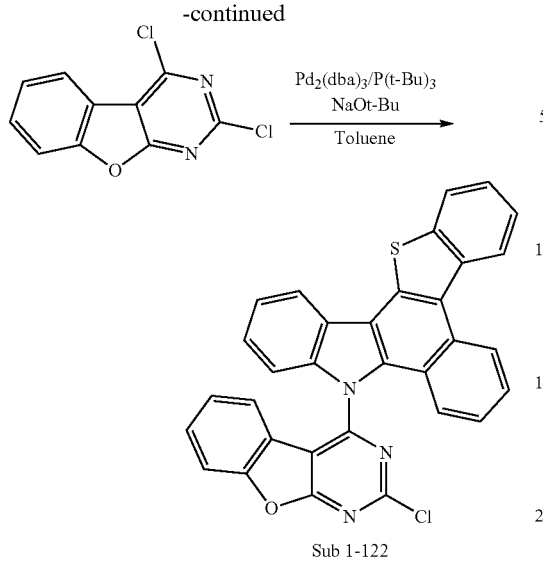
Sub 1-122

2,4-dichlorobenzofuro[2,3-d]pyrimidine (12.43 g, 51.98 mmol), Pd$_2$(dba)$_3$ (1.19 g, 1.30 mmol), 50% P(t-Bu)$_3$ (1.3 mL, 2.60 mmol), NaOt-Bu (12.49 g, 129.96 mmol) and toluene (475 mL) were added to Sub 1-III-97 (14.01 g, 43.32 mmol) obtained in the above synthesis. Then, 10.25 g (yield: 45%) of the product was obtained by the same method as in synthesis of Sub 1-1.

The compound belonging to Sub 1 may be, but not limited to, the following compounds, and Table 1 shows FD-MS (Field Desorption-Mass Spectrometry) values of some compounds belonging to Sub 1.

Sub 1-1

-continued

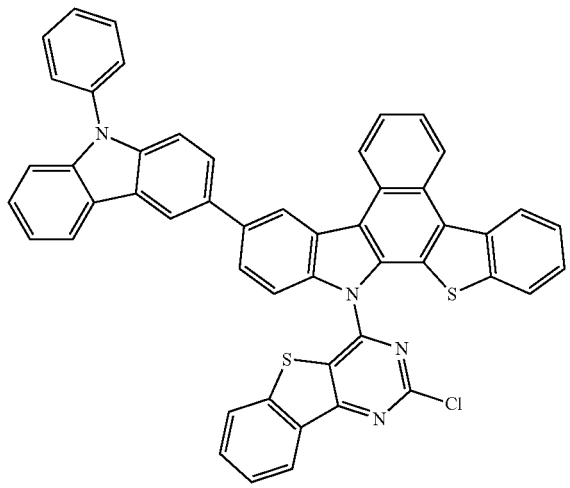
Sub 1-3

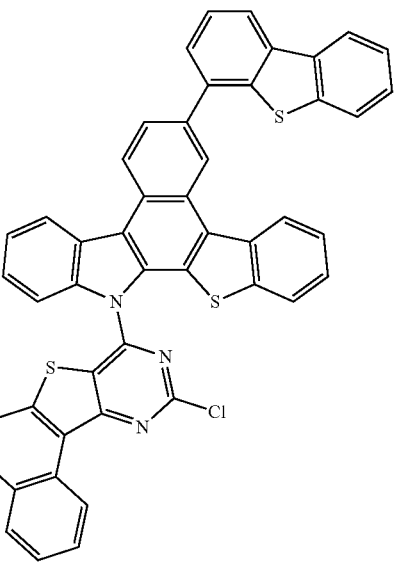
Sub 1-4

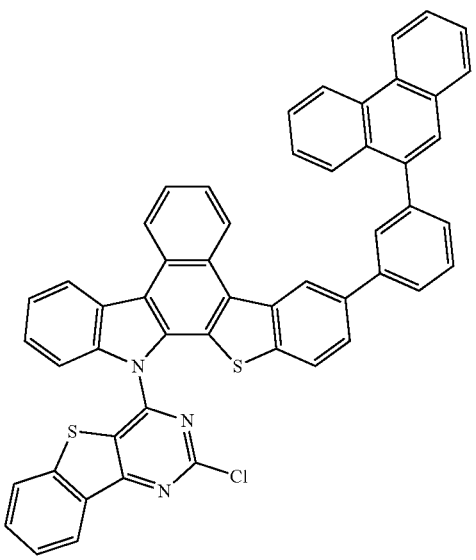
Sub 1-5

Sub 1-2

Sub 1-6
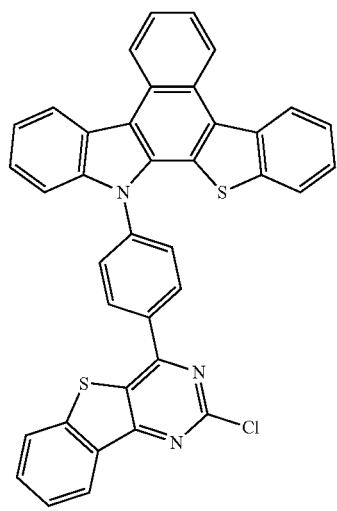
Sub 1-7
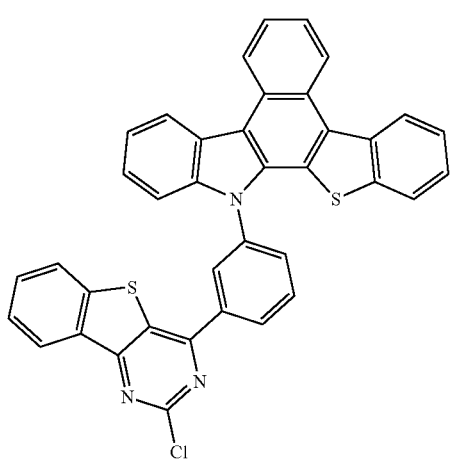
Sub 1-8
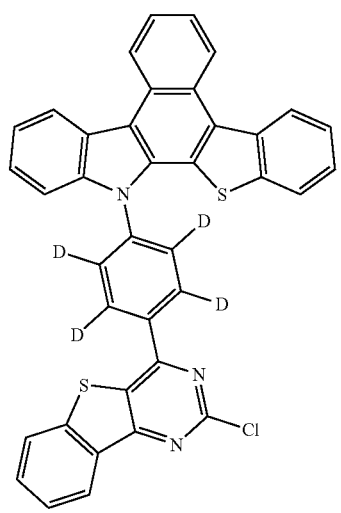
Sub 1-9
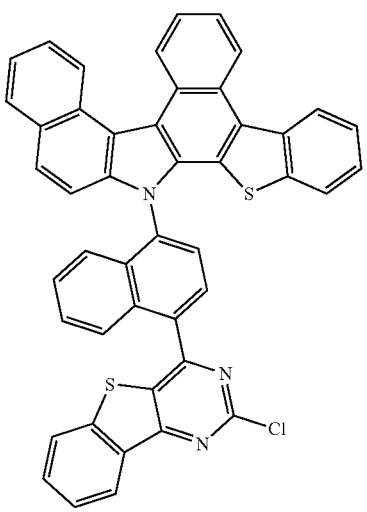
Sub 1-10
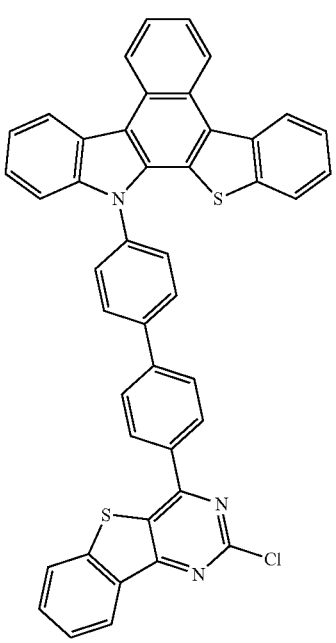

Sub 1-11
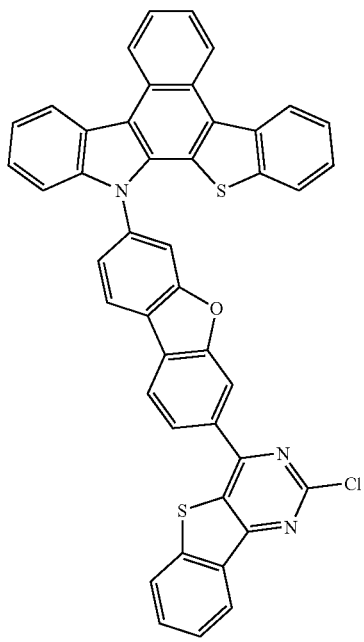
Sub 1-12
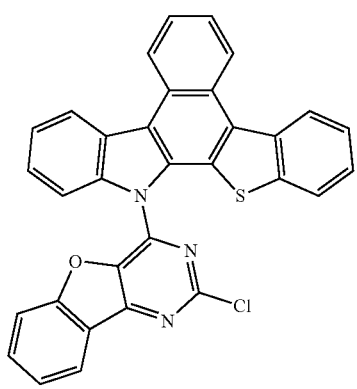
Sub 1-13
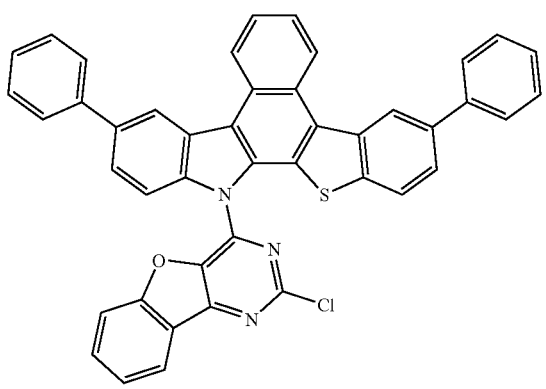
Sub 1-14
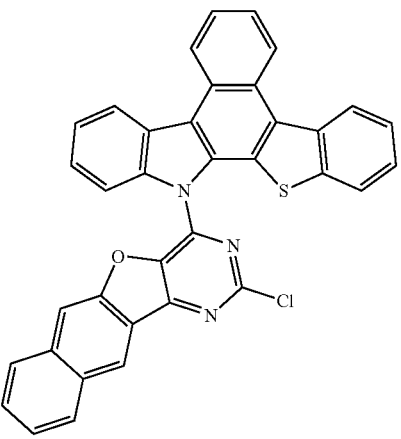
Sub 1-15
Sub 1-16
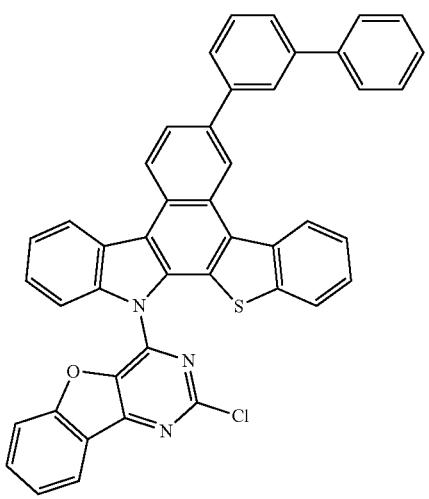

-continued
Sub 1-17
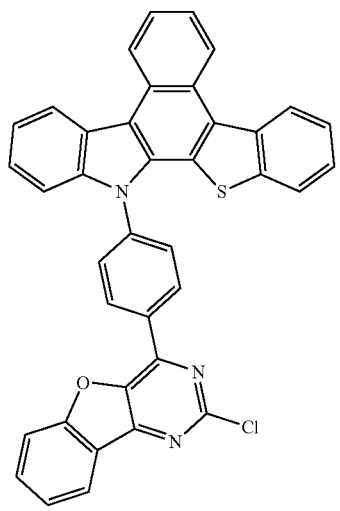
Sub 1-20
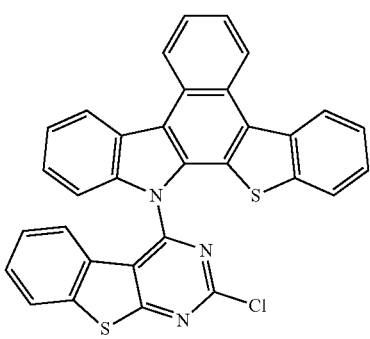
Sub 1-21
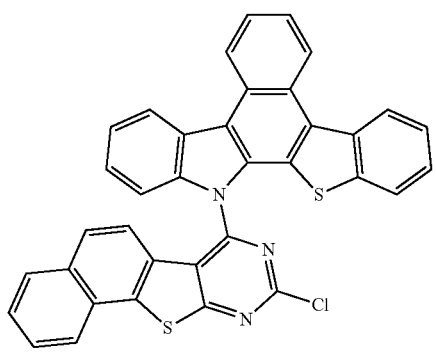
Sub 1-18
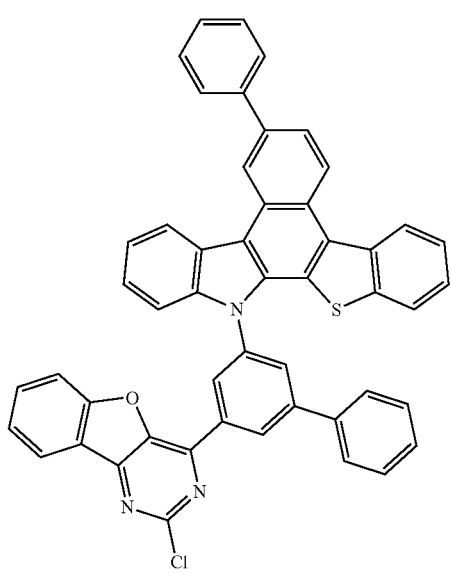
Sub 1-22
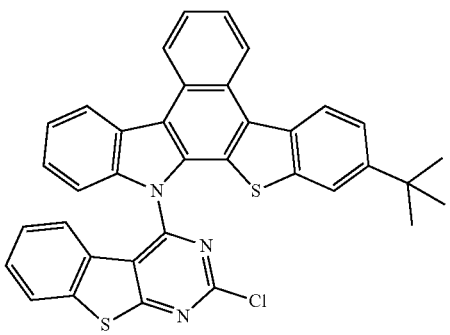
Sub 1-19
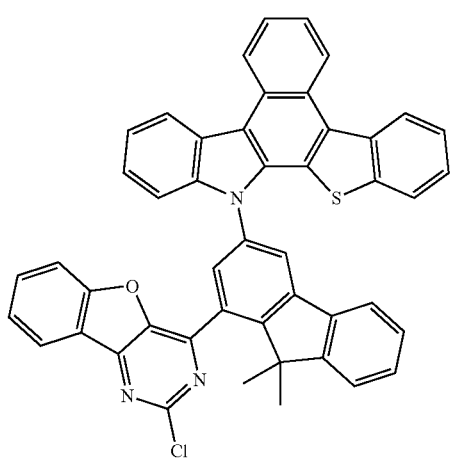
Sub 1-23
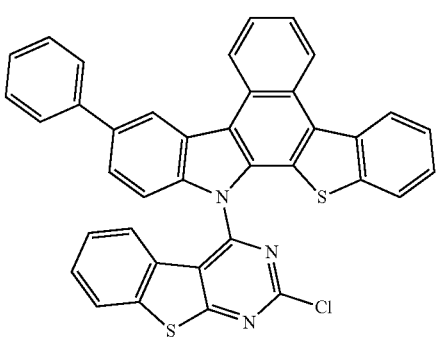

129
-continued
Sub 1-24
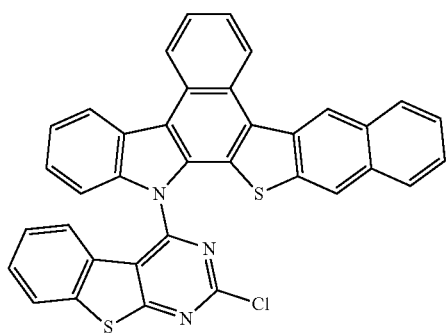
Sub 1-25
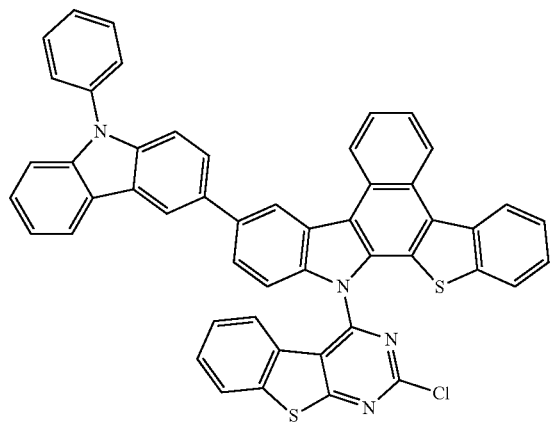
Sub 1-26
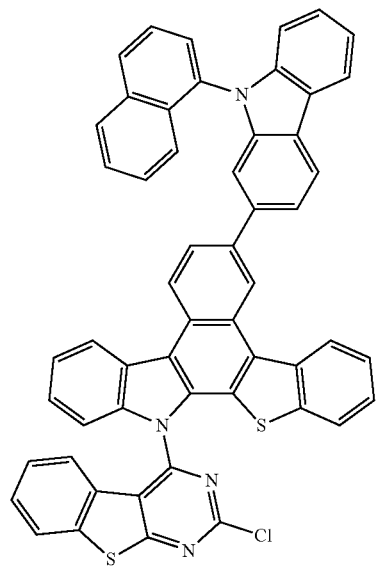
130
-continued
Sub 1-27
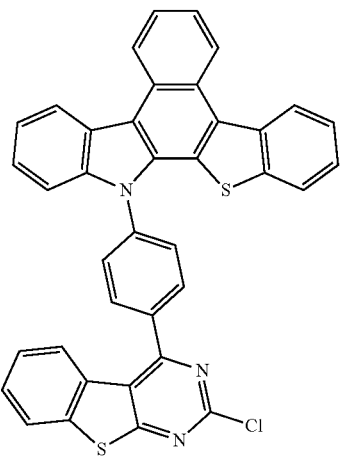
Sub 1-28
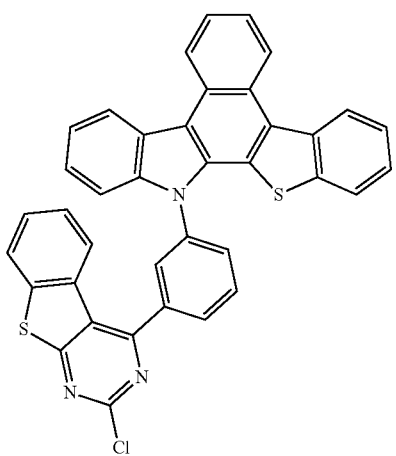
Sub 1-29
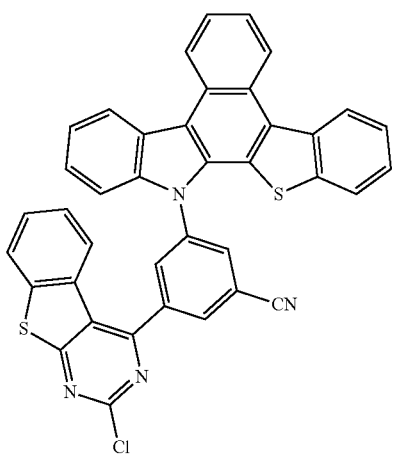

-continued
Sub 1-30
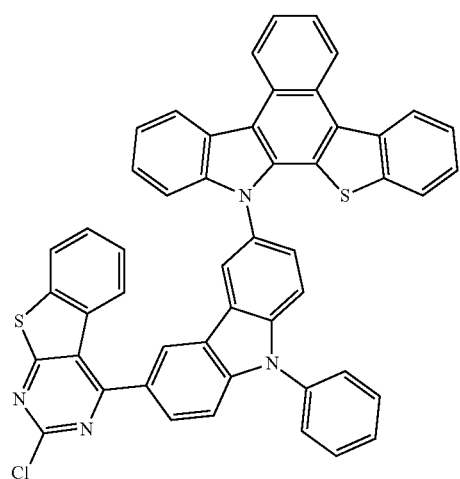
Sub 1-31
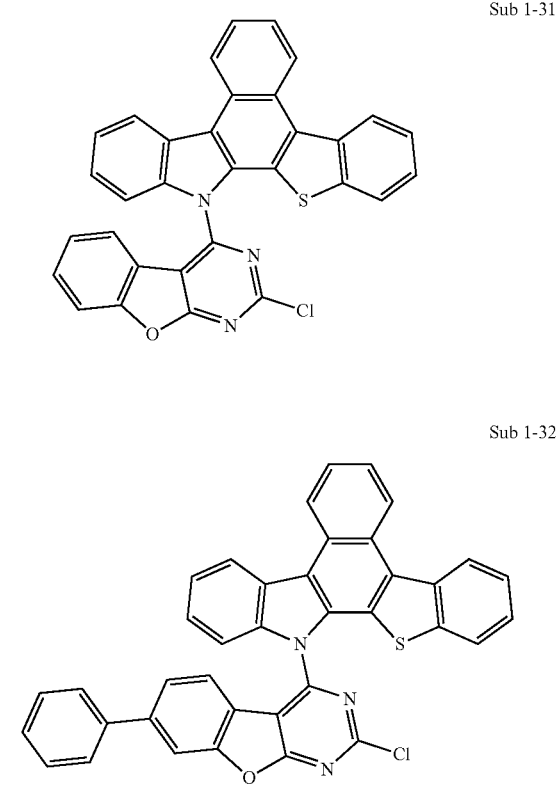
Sub 1-32
Sub 1-33
Sub 1-34
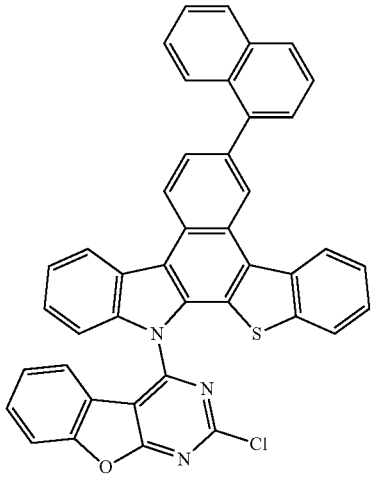
Sub 1-35
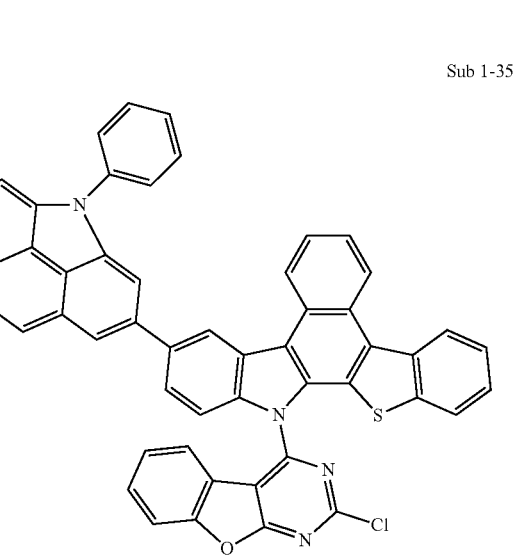
Sub 1-36
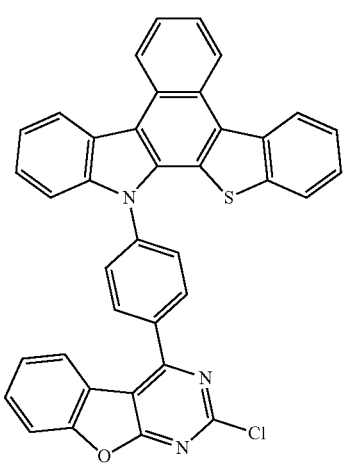

Sub 1-37
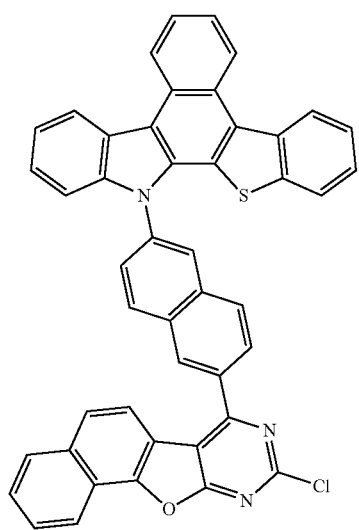
Sub 1-38
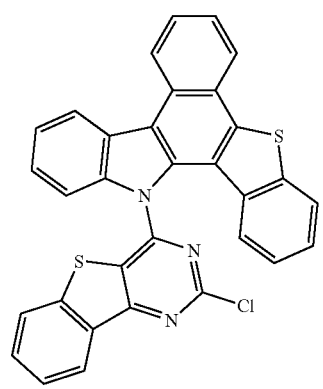
Sub 1-39
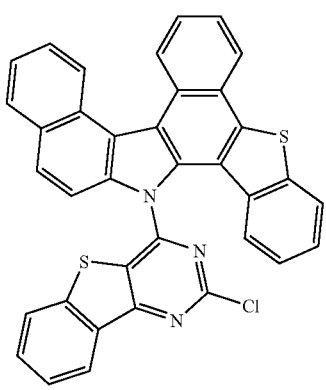
Sub 1-40
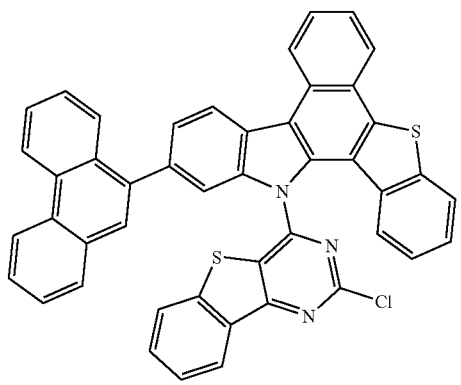
Sub 1-41
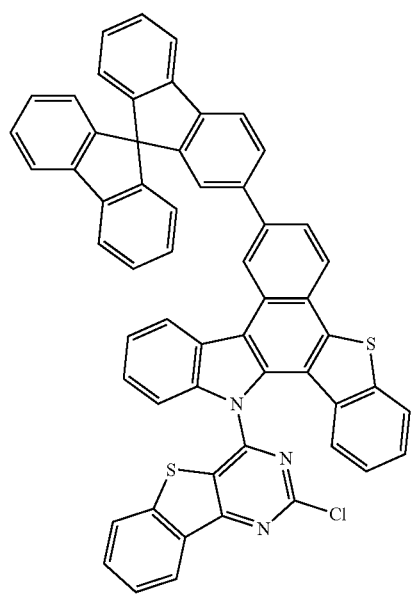
Sub 1-42
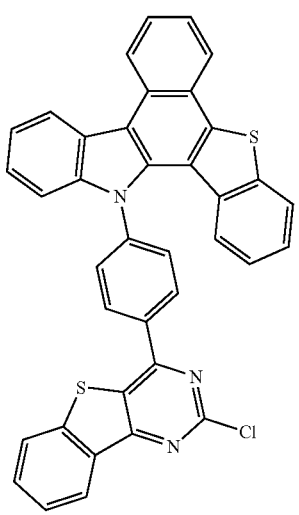

-continued
Sub 1-43
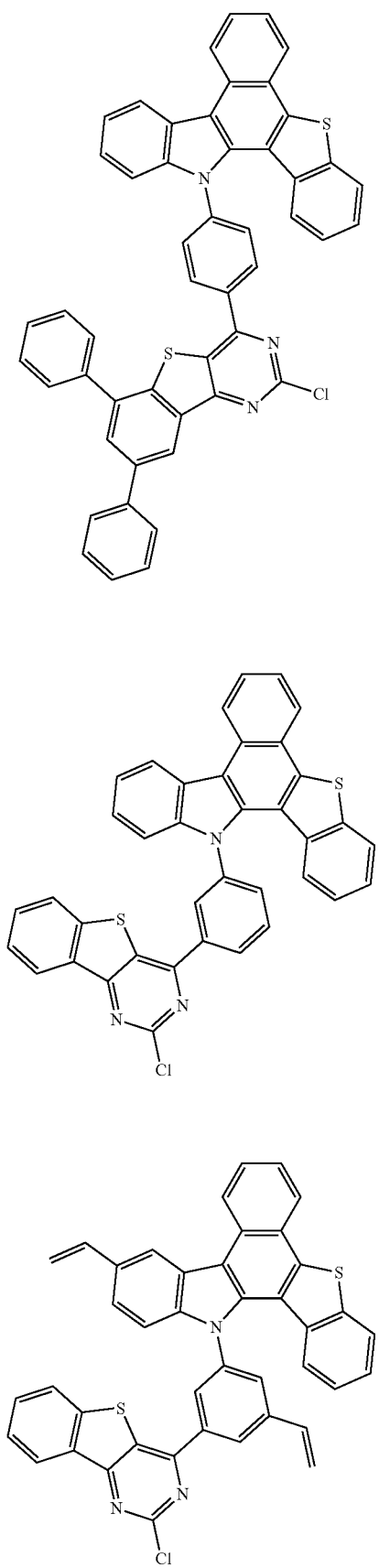
Sub 1-44
Sub 1-45
-continued
Sub 1-46
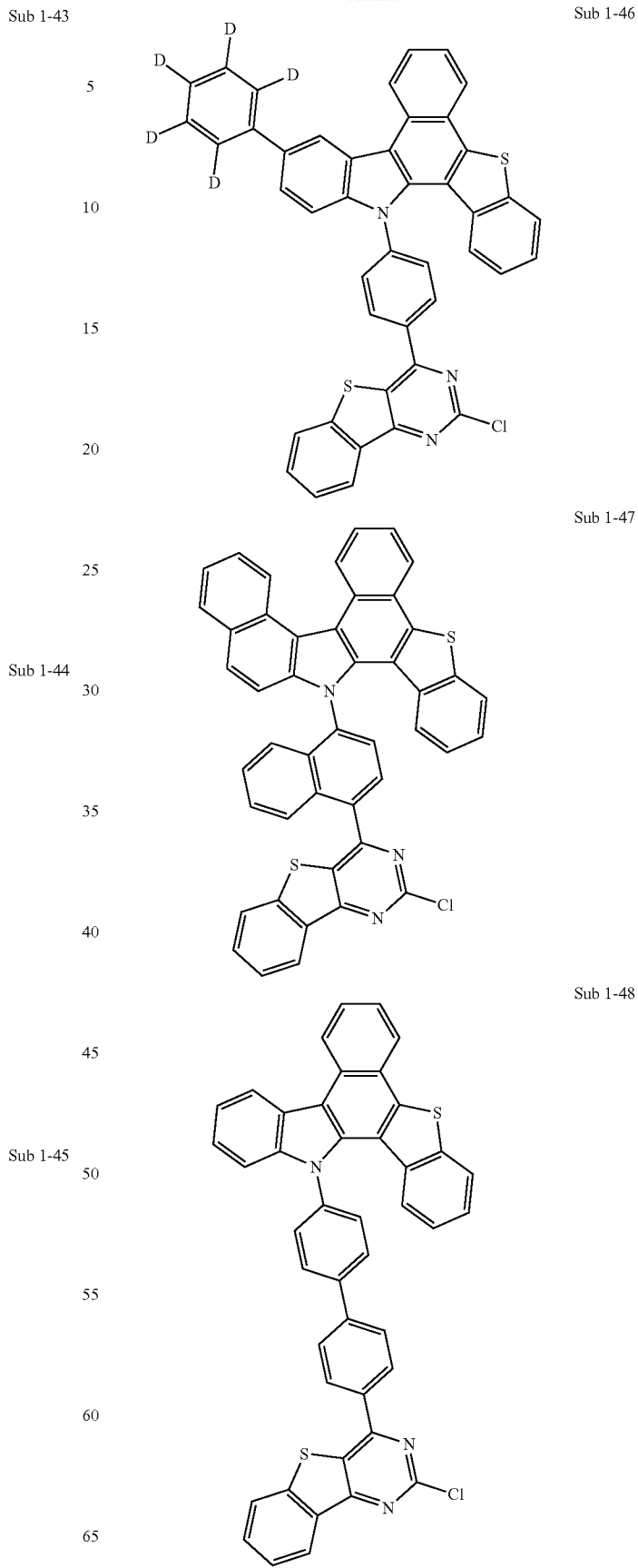
Sub 1-47
Sub 1-48

Sub 1-49
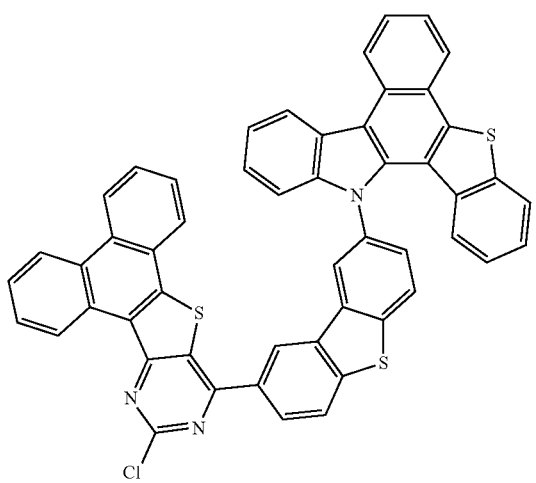
Sub 1-50
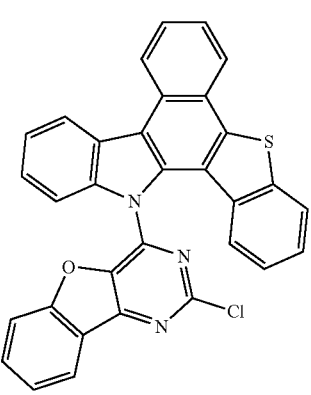
Sub 1-51
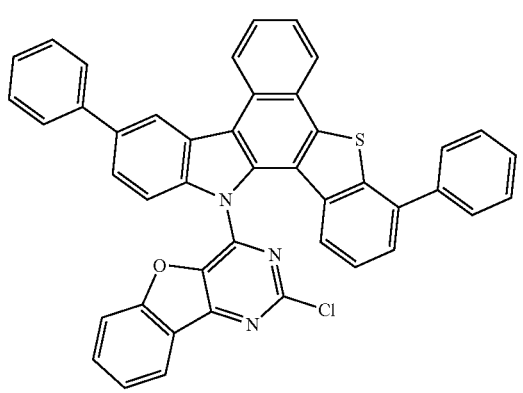
Sub 1-52
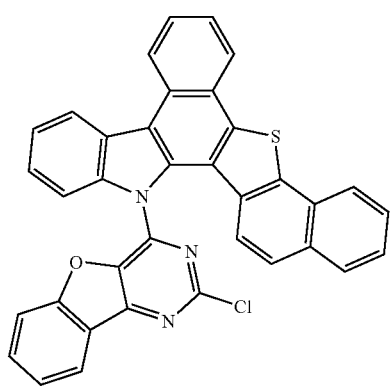
Sub 1-53
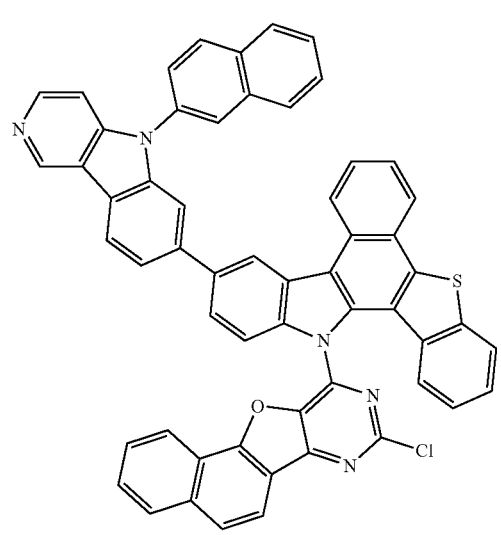
Sub 1-54
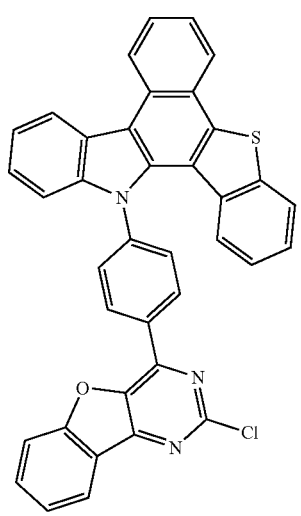
Sub 1-55
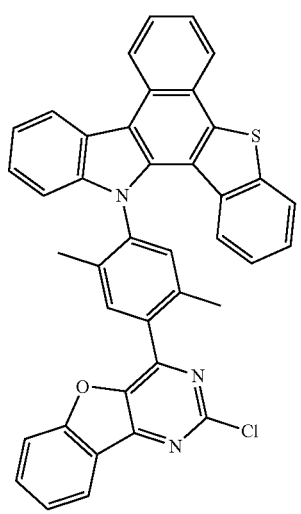

Sub 1-56
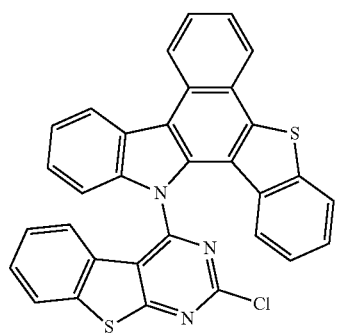
Sub 1-57
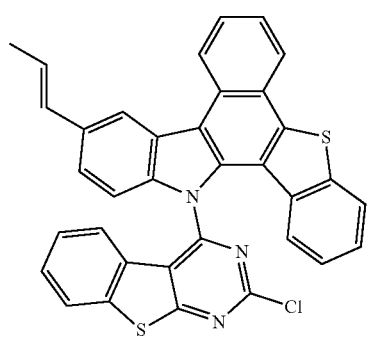
Sub 1-58
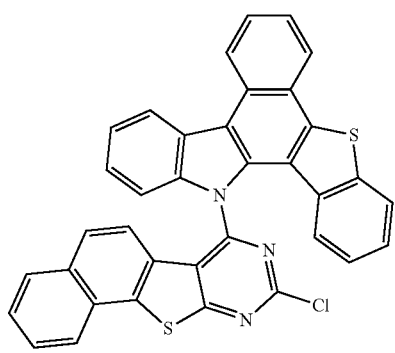
Sub 1-59
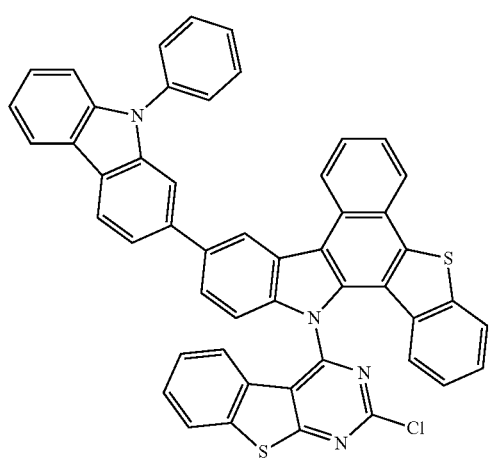
Sub 1-60
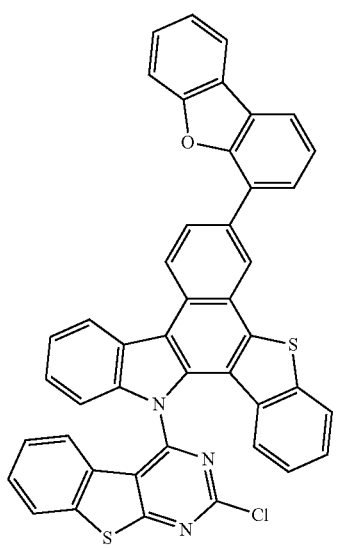
Sub 1-61
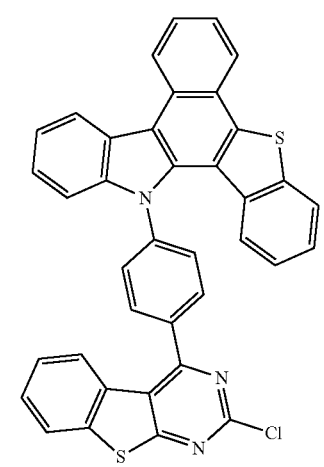
Sub 1-62
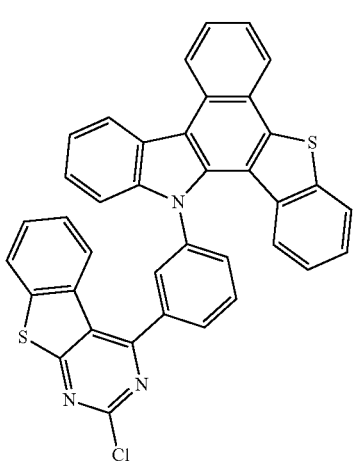

Sub 1-63
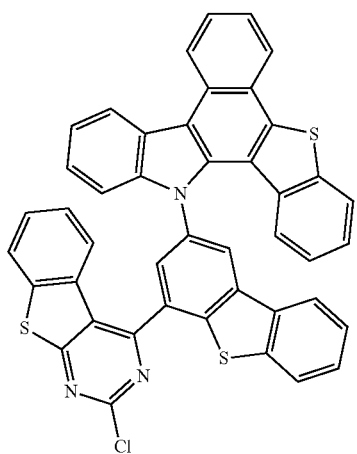
Sub 1-64
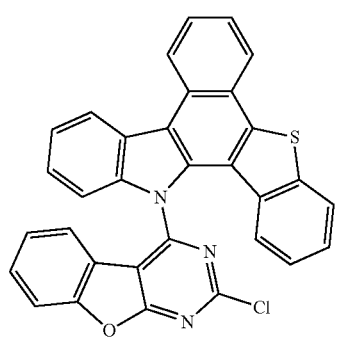
Sub 1-65
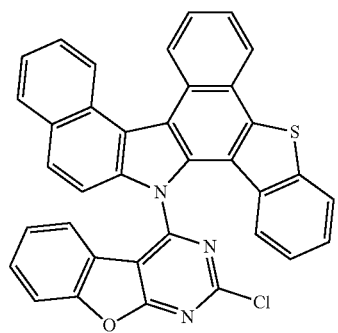
Sub 1-66
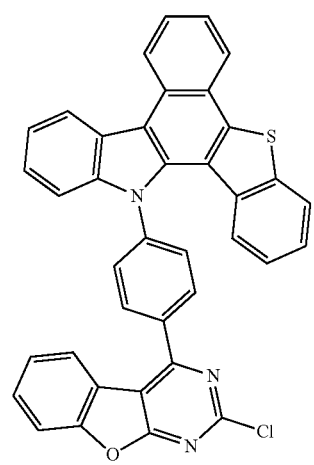
Sub 1-67
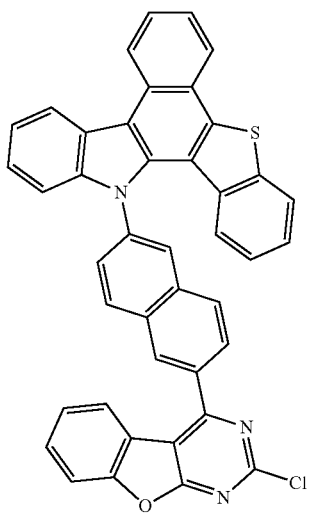
Sub 1-68
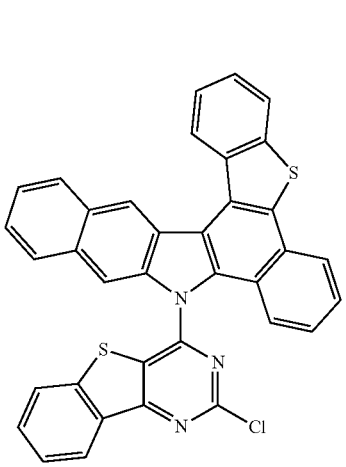
Sub 1-69
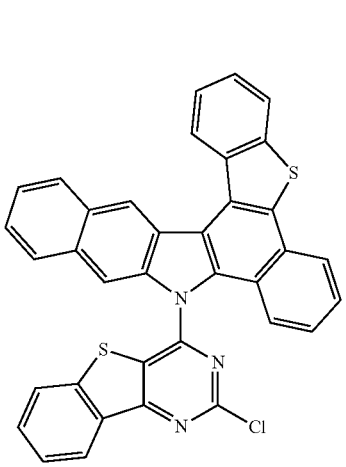

Sub 1-70
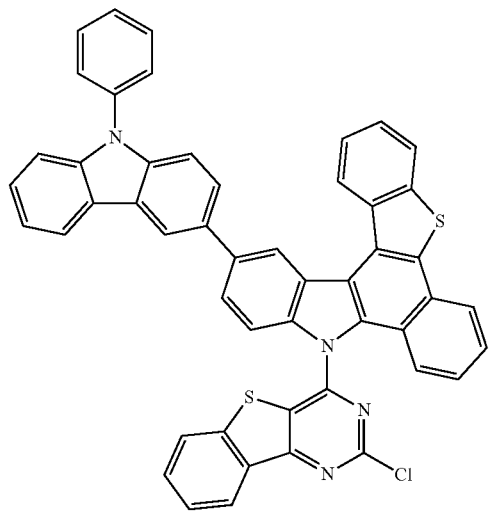
Sub 1-71
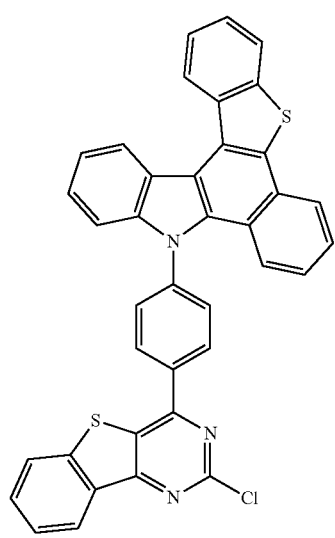
Sub 1-72
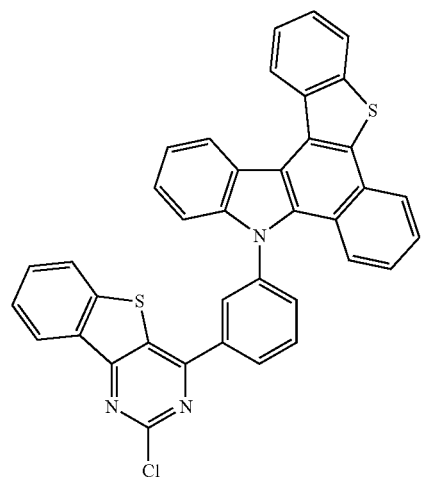
Sub 1-73
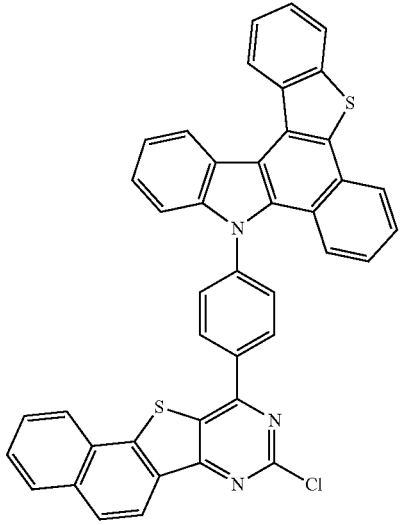
Sub 1-74
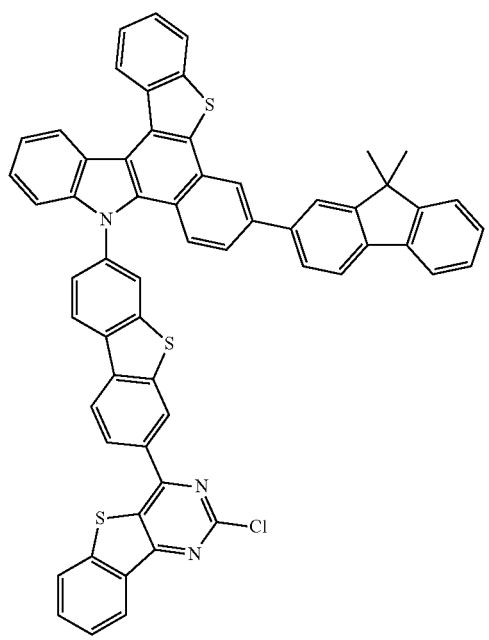
Sub 1-75
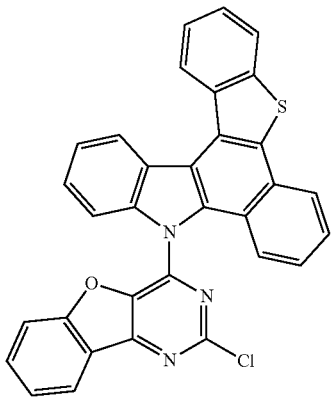

145
-continued
Sub 1-76
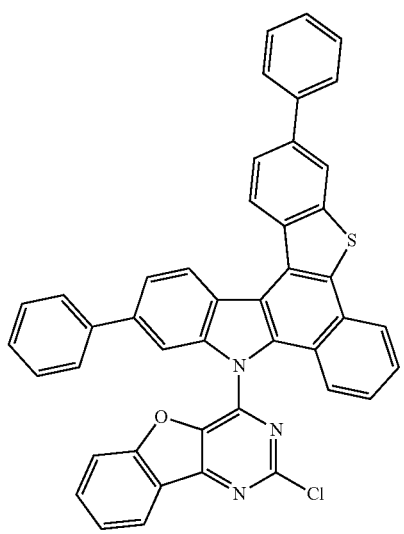
Sub 1-77
Sub 1-78
146
-continued
Sub 1-79
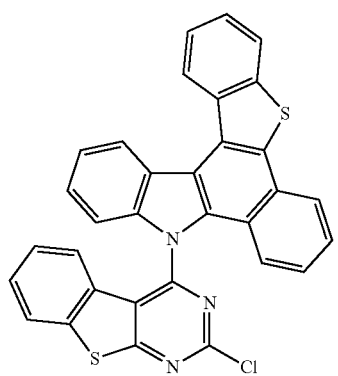
Sub 1-80
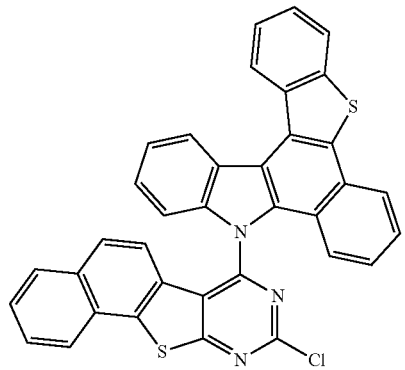
Sub 1-81
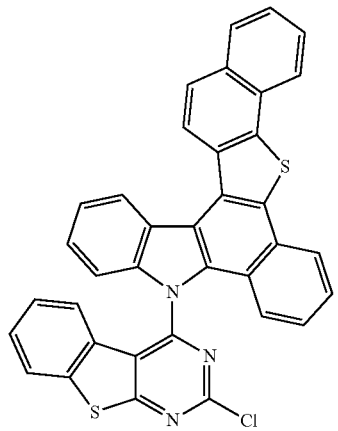
Sub 1-82
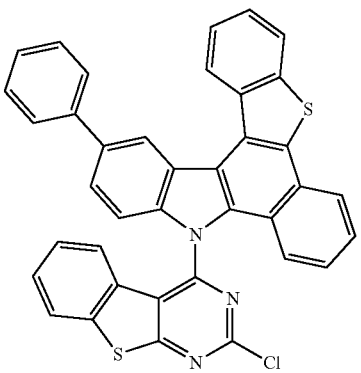

Sub 1-83
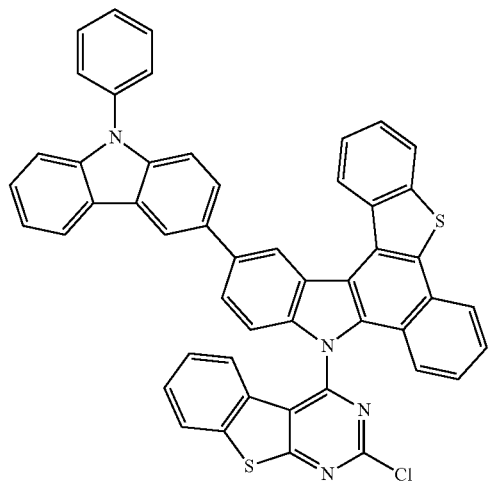
Sub 1-84
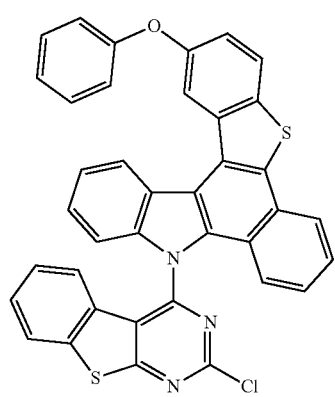
Sub 1-85
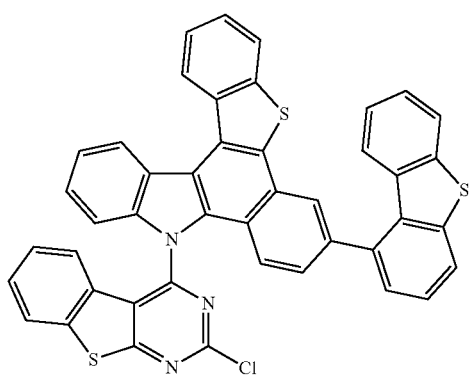
Sub 1-86
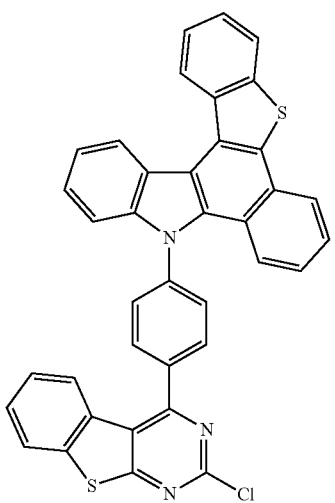
Sub 1-87
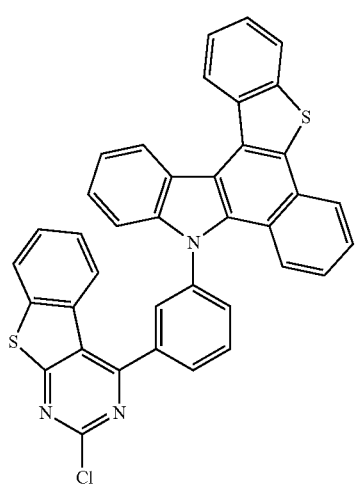
Sub 1-88
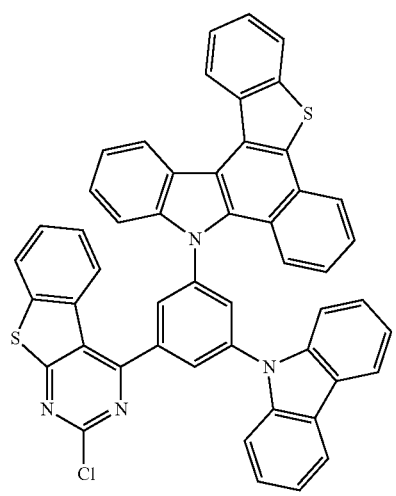

Sub 1-89
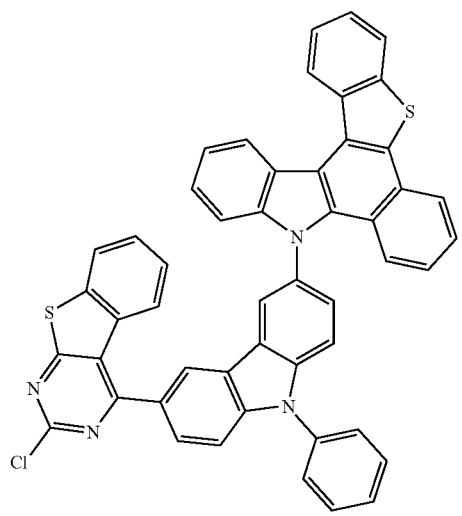
Sub 1-90
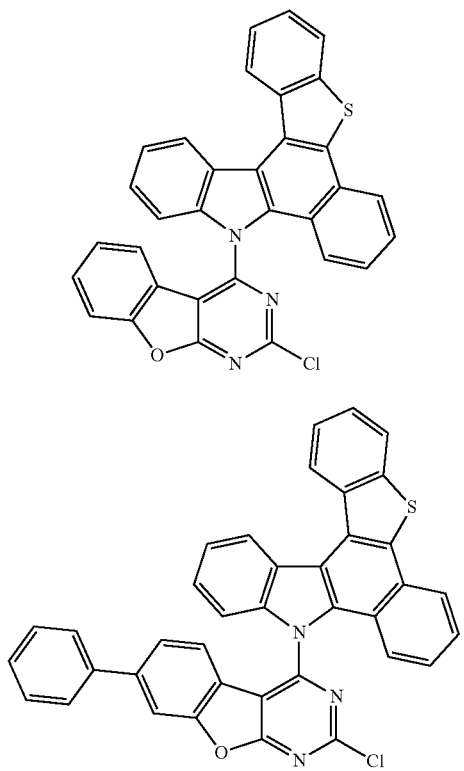
Sub 1-91
Sub 1-92
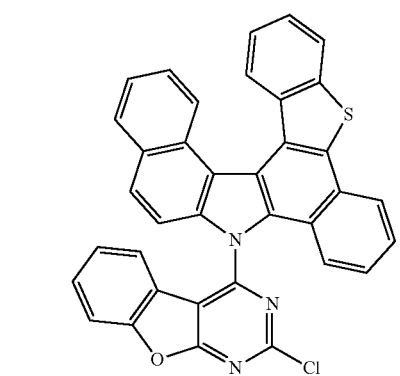
Sub 1-93
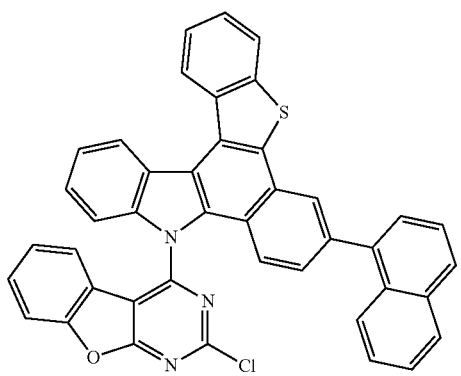
Sub 1-94
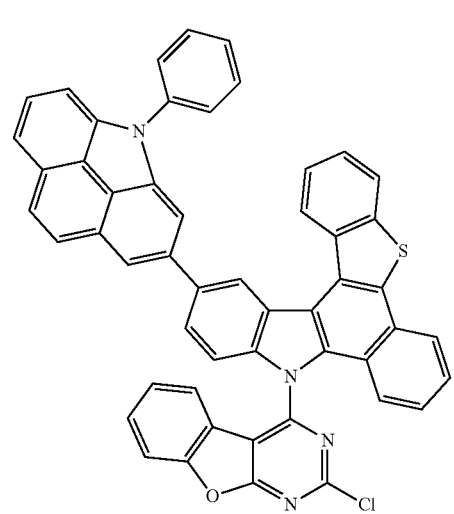
Sub 1-95
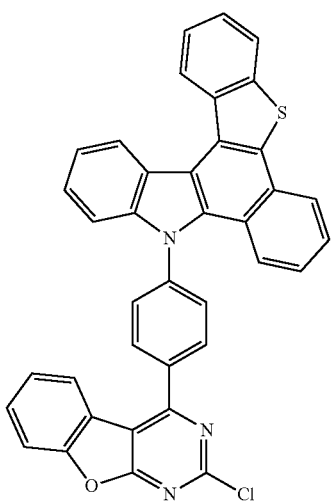

Sub 1-96
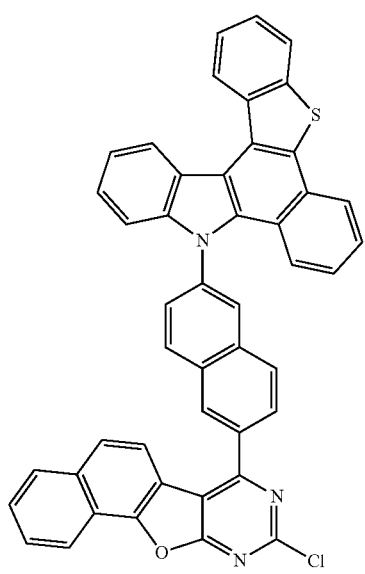
Sub 1-97
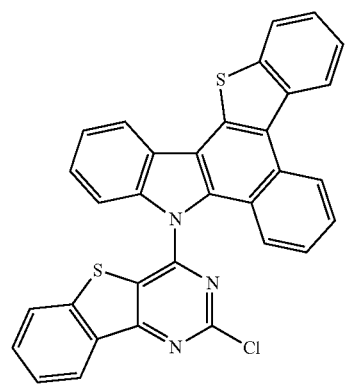
Sub 1-98
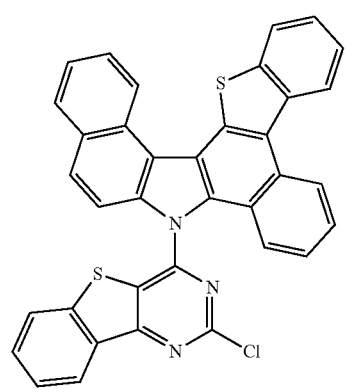
Sub 1-99
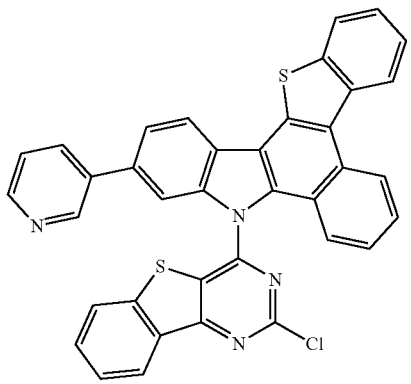
Sub 1-100
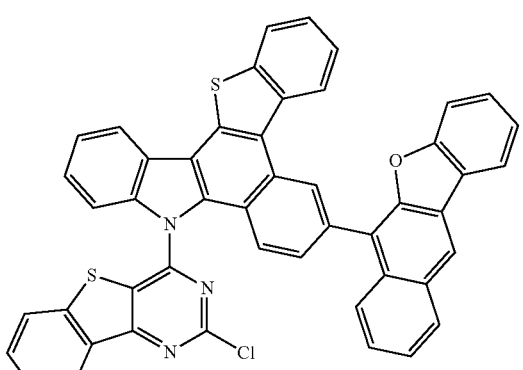
Sub 1-101
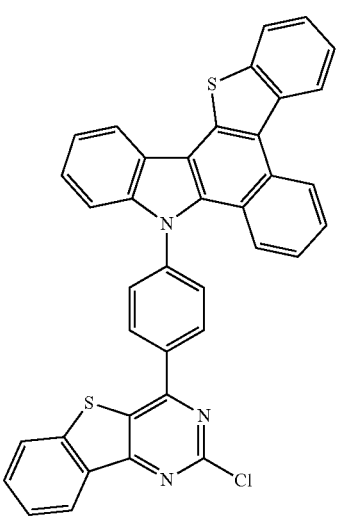

Sub 1-102
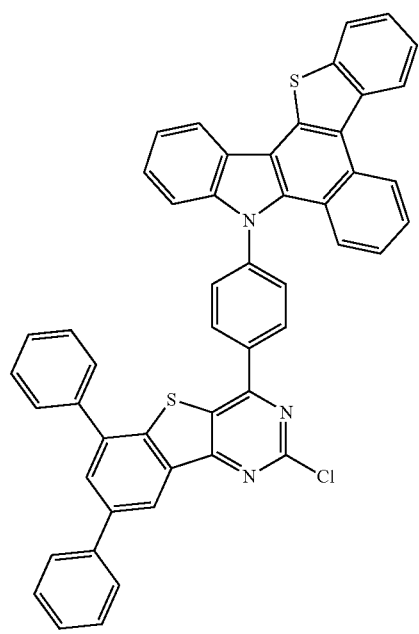
Sub 1-103
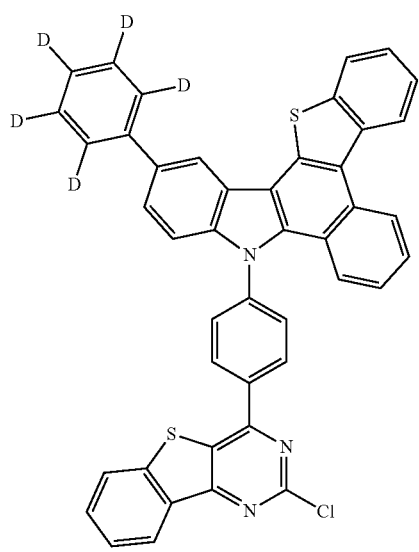
Sub 1-104
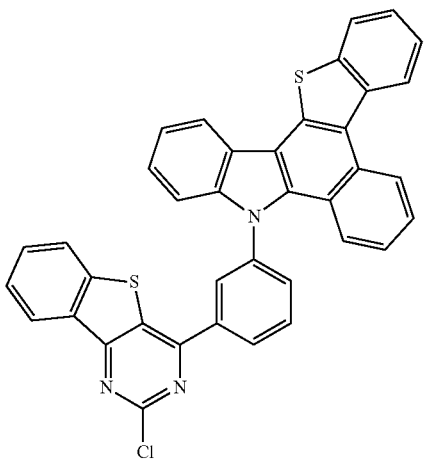
Sub 1-105
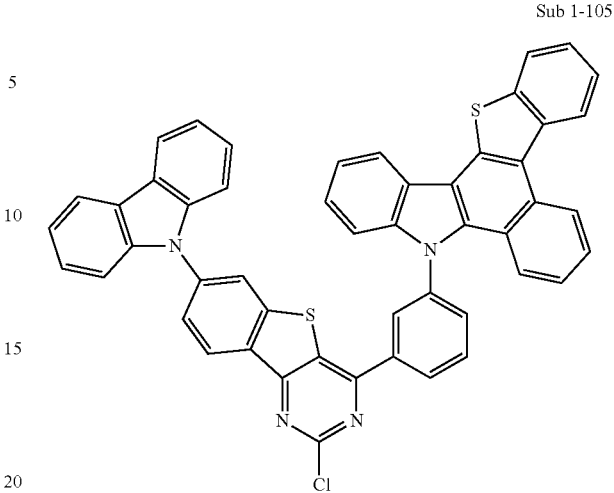
Sub 1-106
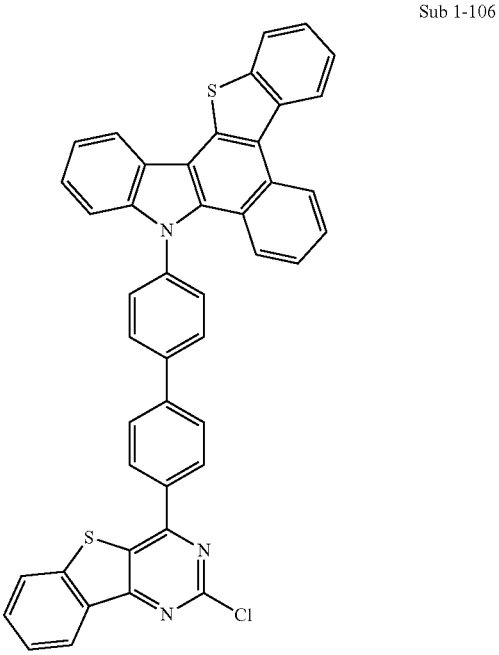
Sub 1-107
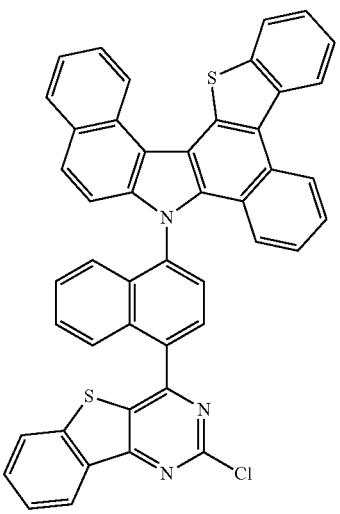

Sub 1-108
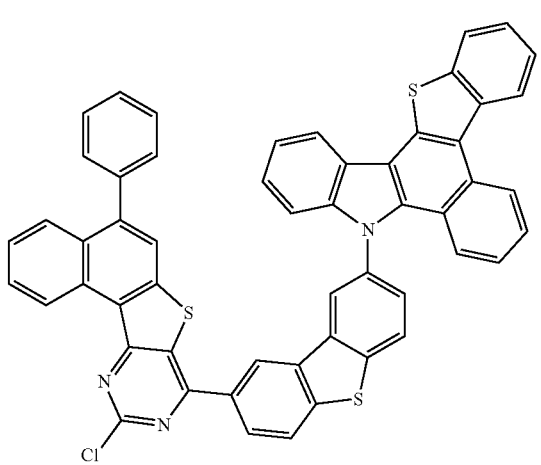
Sub 1-109
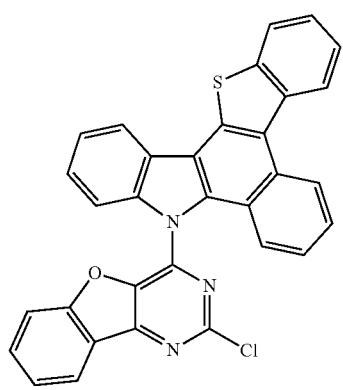
Sub 1-110
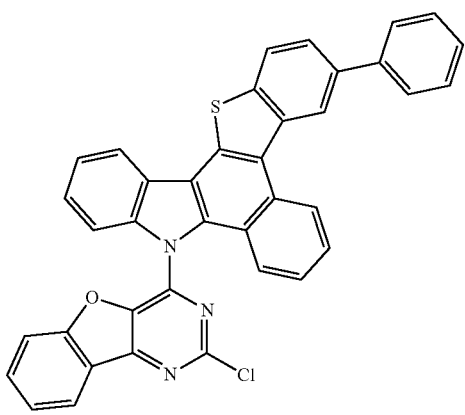
Sub 1-111
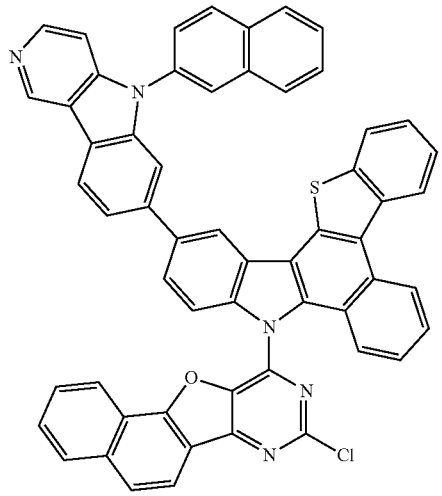
Sub 1-112
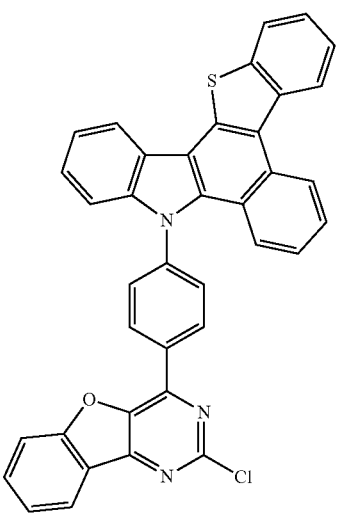
Sub 1-113
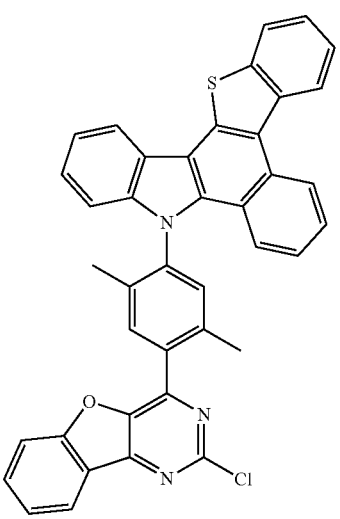

Sub 1-114
Sub 1-115
Sub 1-116
Sub 1-117
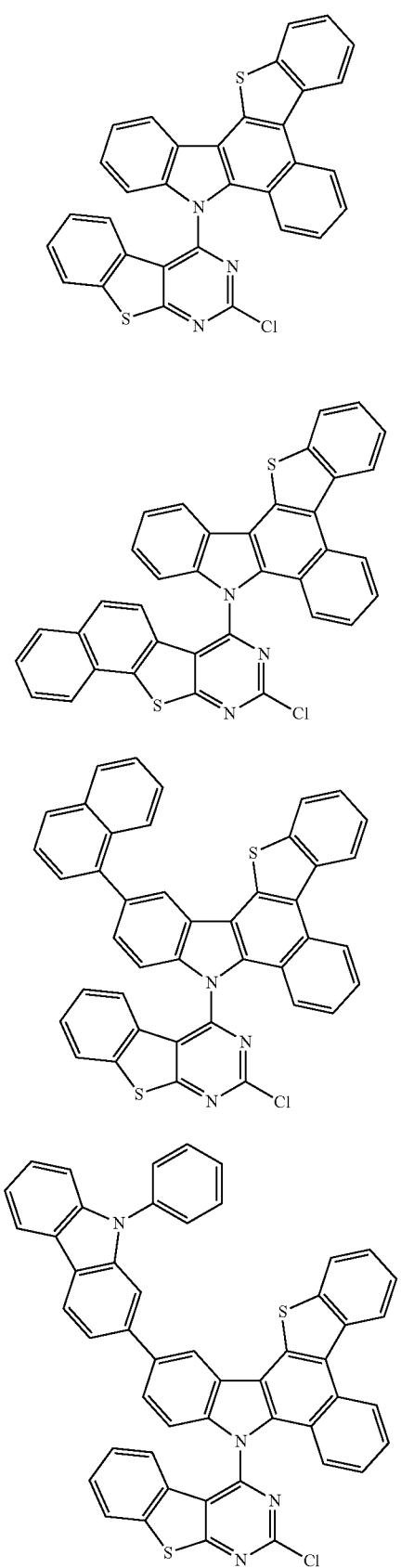
Sub 1-118
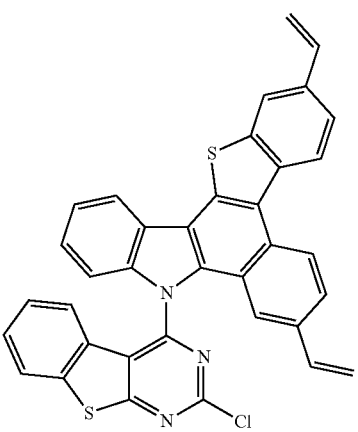
Sub 1-119
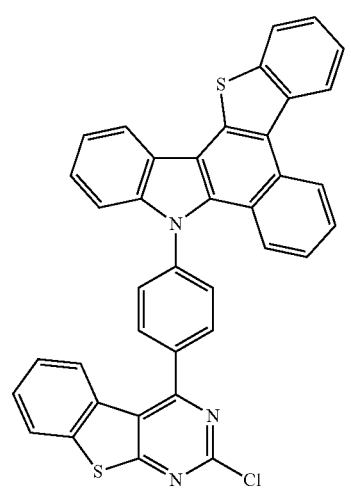
Sub 1-120
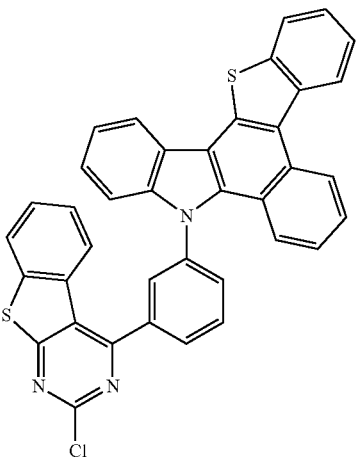

-continued

Sub 1-121

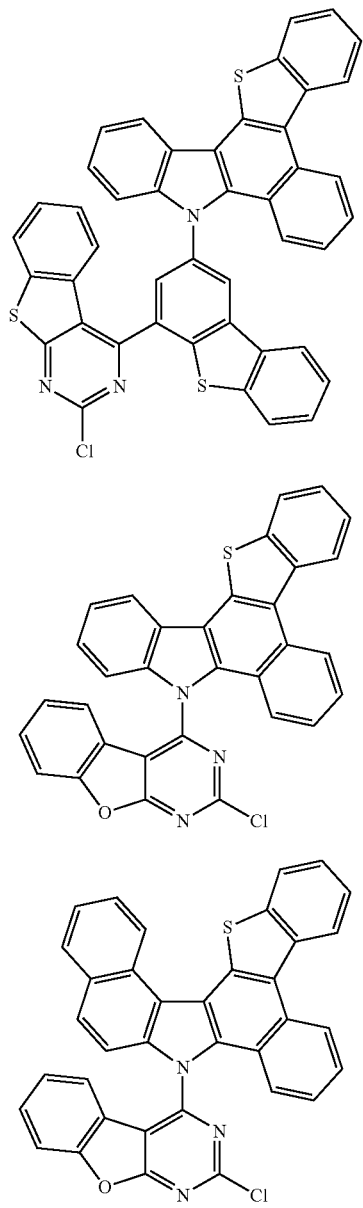

Sub 1-122

Sub 1-123

-continued

Sub 1-124

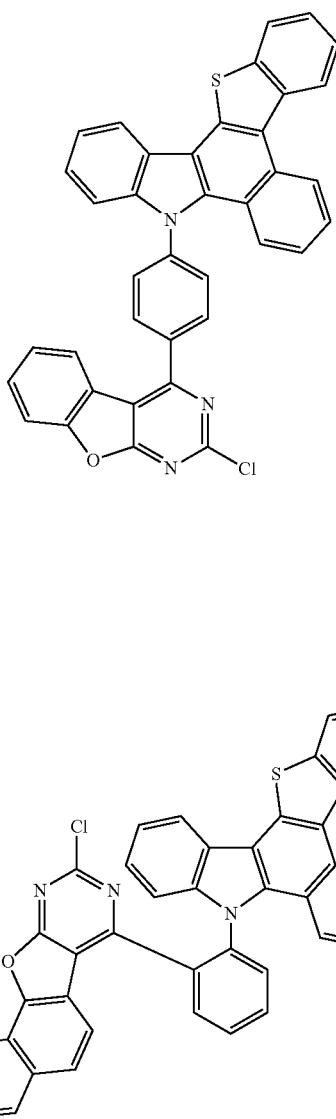

Sub 1-125

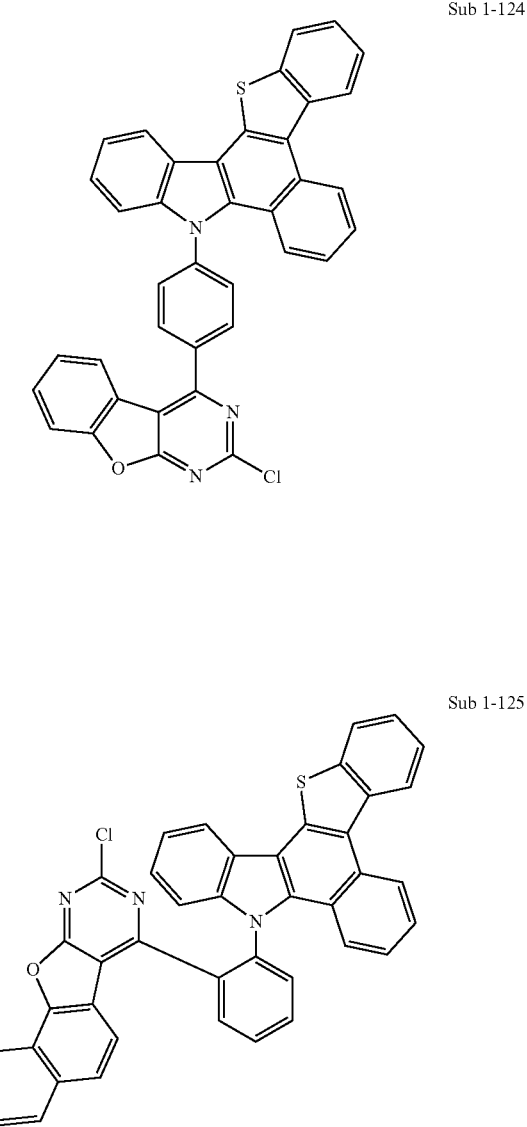

TABLE 1

| Compound | FD-MS | Compound | FD-MS |
| --- | --- | --- | --- |
| Sub 1-1 | m/z = 541.05($C_{32}H_{16}ClN_3S_2$ = 542.07) | Sub 1-3 | m/z = 782.14($C_{50}H_{27}ClN_4S_2$ = 783.36) |
| Sub 1-6 | m/z = 617.08($C_{38}H_{20}ClN_3S_2$ = 618.17) | Sub 1-12 | m/z = 525.07($C_{32}H_{16}ClN_3OS$ = 526.01) |
| Sub 1-20 | m/z = 541.05($C_{32}H_{16}ClN_3S_2$ = 542.07) | Sub 1-36 | m/z = 601.10($C_{38}H_{20}ClN_3OS$ = 602.11) |
| Sub 1-38 | m/z = 541.05($C_{32}H_{16}ClN_3S_2$ = 542.07) | Sub 1-44 | m/z = 617.08($C_{38}H_{20}ClN_3S_2$ = 618.17) |
| Sub 1-50 | m/z = 525.07($C_{32}H_{16}ClN_3OS$ = 526.01) | Sub 1-62 | m/z = 617.08($C_{38}H_{20}ClN_3S_2$ = 618.17) |
| Sub 1-64 | m/z = 525.07($C_{32}H_{16}ClN_3OS$ = 526.01) | Sub 1-68 | m/z = 541.05($C_{32}H_{16}ClN_3S_2$ = 542.07) |
| Sub 1-78 | m/z = 601.10($C_{38}H_{20}ClN_3OS$ = 602.11) | Sub 1-79 | m/z = 541.05($C_{32}H_{16}ClN_3S_2$ = 542.07) |
| Sub 1-90 | m/z = 525.07($C_{32}H_{16}ClN_3OS$ = 526.01) | Sub 1-97 | m/z = 541.05($C_{32}H_{16}ClN_3S_2$ = 542.07) |
| Sub 1-109 | m/z = 525.07($C_{32}H_{16}ClN_3OS$ = 526.01) | Sub 1-120 | m/z = 617.08($C_{38}H_{20}ClN_3S_2$ = 618.17) |
| Sub 1-122 | m/z = 525.07($C_{32}H_{16}ClN_3OS$ = 526.01) | | |

II. Synthesis of Sub 2

Sub 2 of the Reaction Scheme 1 can be synthesized according to, but not limited to, the reaction route of the following Reaction Scheme 23.

<Reaction Scheme 23>

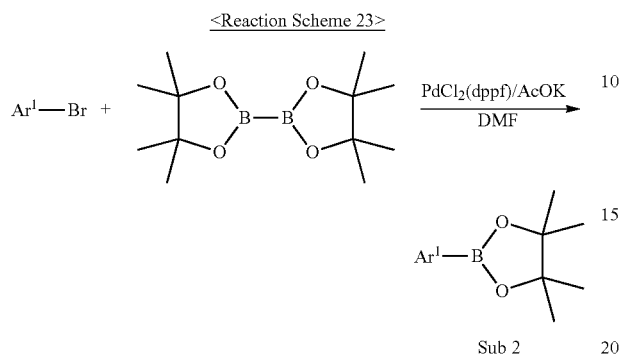

Synthesis Examples of compounds comprised in Sub 2 are as follows.

1. Synthesis Example of Sub 2-1

<Reaction Scheme 24>

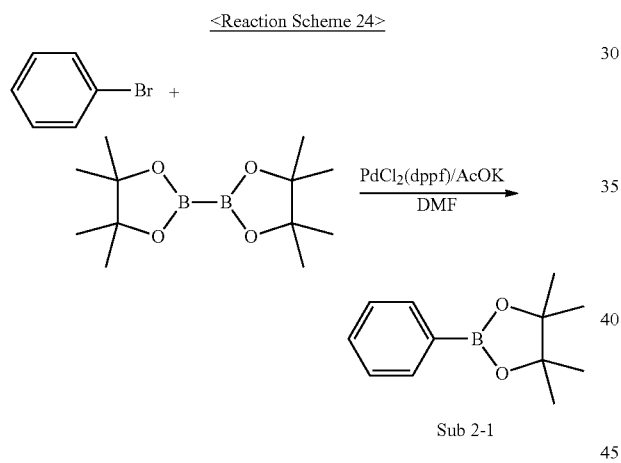

After bromobenzene (29.16 g, 185.72 mmol) was placed in a round bottom flask and was dissolved in DMF (930 mL), Bis(pinacolato)diboron (51.88 g, 204.29 mmol), Pd(dppf)Cl$_2$ (4.55 g, 5.57 mmol) and KOAc (54.68 g, 557.16 mmol) were added and the mixture was stirred at 90° C. When the reaction was completed, DMF was removed by distillation and the resultant was extracted with CH$_2$Cl$_2$ and water. The organic layer was dried with MgSO$_4$ and concentrated. The concentrate was applied to silica gel column and recrystallized to obtain 31.84 g (yield: 84%) of the product.

2. Synthesis Example of Sub 2-3

<Reaction Scheme 25>

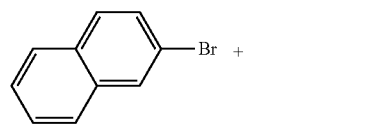

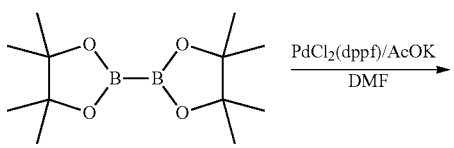

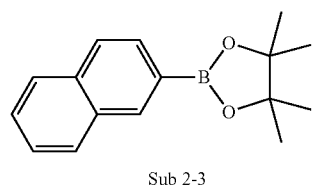

Bis(pinacolato)diboron (29.04 g, 114.37 mmol), Pd(dppf)Cl$_2$ (2.55 g, 3.12 mmol), KOAc (30.61 g, 311.92 mmol) and DMF (520 mL) were added to the starting material 2-bromonaphthalene (21.53 g, 103.97 mmol). Then, 21.14 g (yield: 80%) of the product was obtained by the same method as in synthesis of Sub 2-1.

3. Synthesis Example of Sub 2-5

<Reaction Scheme 26>

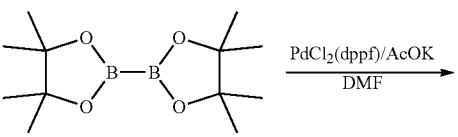

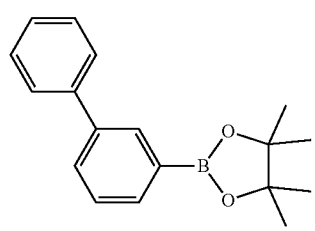

Bis(pinacolato)diboron (19.46 g, 76.63 mmol), Pd(dppf)Cl$_2$ (1.71 g, 2.09 mmol), KOAc (20.51 g, 209.00 mmol) and DMF (350 mL) were added to the starting material 3-bromo-1,1'-biphenyl(16.24 g, 69.67 mmol). Then, 15.81 g (yield: 81%) of the product was obtained by the same method as in synthesis of Sub 2-1.

4. Synthesis Example of Sub 2-19

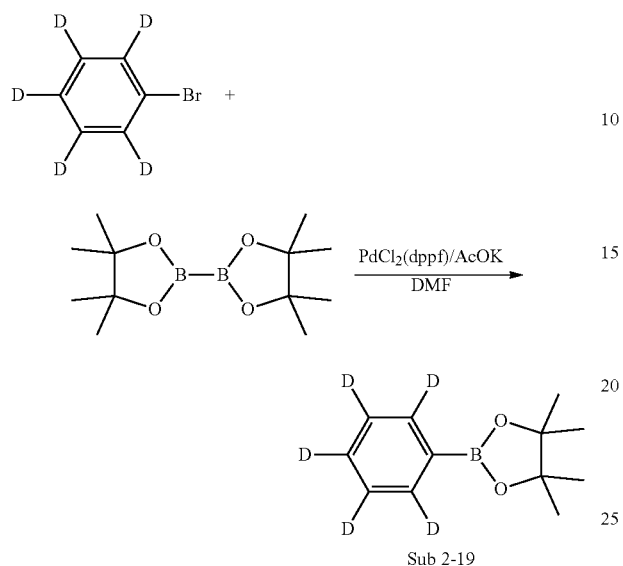

Bis(pinacolato)diboron (18.70 g, 73.65 mmol), Pd(dppf)Cl$_2$ (1.64 g, 2.01 mmol), KOAc (19.71 g, 200.88 mmol) and DMF (335 mL) were added to the starting material 1-bromobenzene-2,3,4,5,6-d5 (10.85 g, 66.96 mmol). Then, 10.22 g (yield: 73%) of the product was obtained by the same method as in synthesis of Sub 2-1.

5. Synthesis Example of Sub 2-34

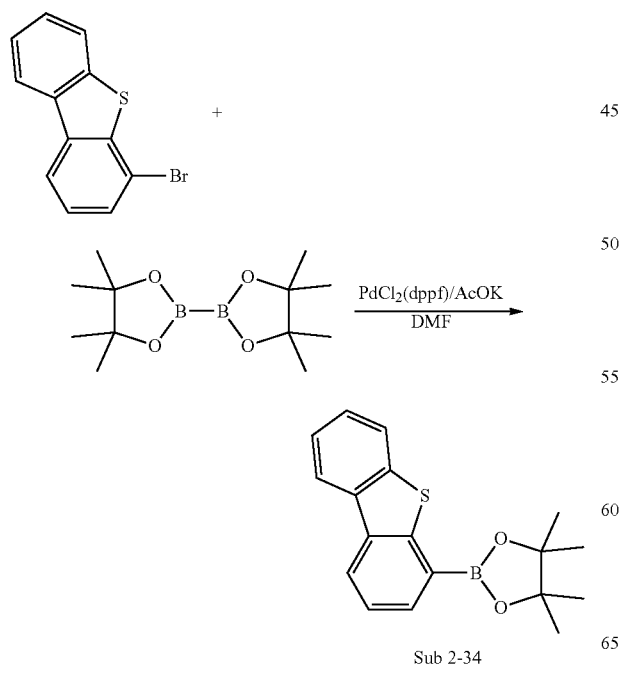

Bis(pinacolato)diboron (15.11 g, 59.48 mmol), Pd(dppf)Cl$_2$ (1.32 g, 1.62 mmol), KOAc (15.92 g, 162.23 mmol) and DMF (270 mL) were added to the starting material 4-bromodibenzo[b,d]thiophene (14.23 g, 54.08 mmol). Then, 13.76 g (yield: 82%) of the product was obtained by the same method as in synthesis of Sub 2-1.

6. Synthesis Example of Sub 2-43

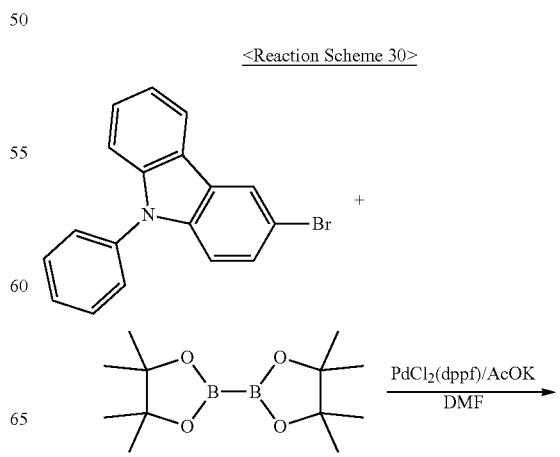

Bis(pinacolato)diboron (18.48 g, 72.79 mmol), Pd(dppf)Cl$_2$ (1.62 g, 1.99 mmol), KOAc (19.48 g, 198.51 mmol) and DMF (330 mL) were added to the starting material 2-bromodibenzo[b,d]furan (16.35 g, 66.17 mmol). Then, 16.74 g (yield: 86%) of the product was obtained by the same method as in synthesis of Sub 2-1.

7. Synthesis Example of Sub 2-44

-continued

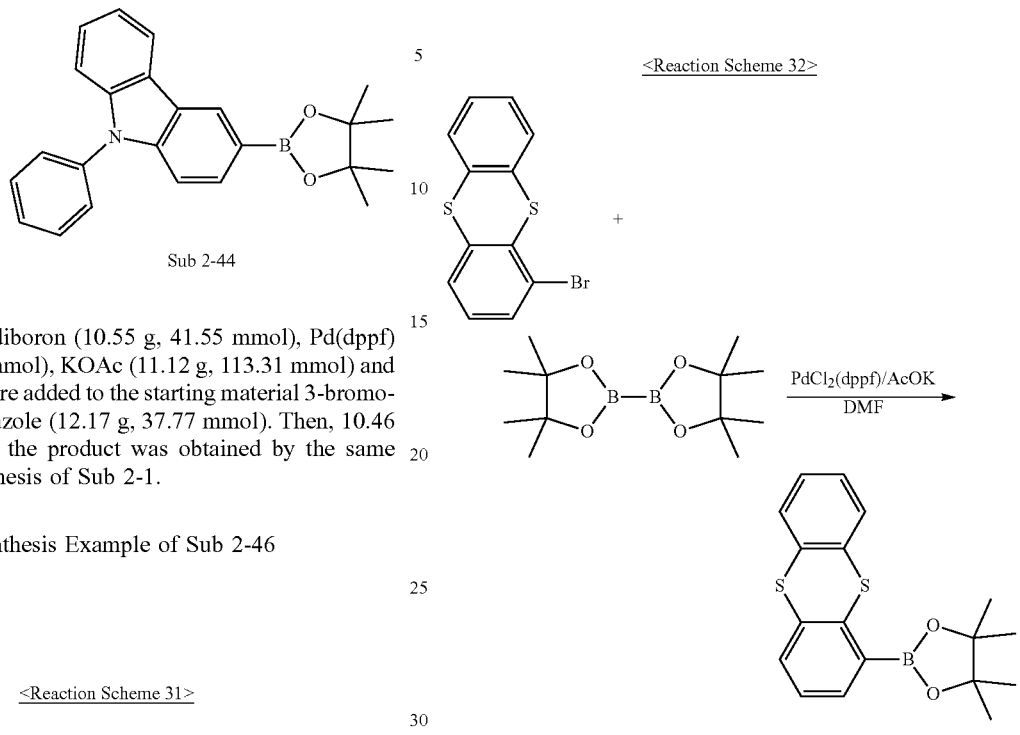

Sub 2-44

Bis(pinacolato)diboron (10.55 g, 41.55 mmol), Pd(dppf)Cl₂ (0.93 g, 1.13 mmol), KOAc (11.12 g, 113.31 mmol) and DMF (190 mL) were added to the starting material 3-bromo-9-phenyl-9H-carbazole (12.17 g, 37.77 mmol). Then, 10.46 g (yield: 75%) of the product was obtained by the same method as in synthesis of Sub 2-1.

8. Synthesis Example of Sub 2-46

<Reaction Scheme 31>

Sub 2-46

Bis(pinacolato)diboron (18.97 g, 74.70 mmol), Pd(dppf)Cl₂ (1.66 g, 2.04 mmol), KOAc (19.99 g, 203.73 mmol) and DMF 340 mL) were added to the starting material 1-bromodibenzo[b,d]furan (16.78 g, 67.91 mmol). Then, 15.98 g (yield: 80%) of the product was obtained by the same method as in synthesis of Sub 2-1.

9. Synthesis Example of Sub 2-51

<Reaction Scheme 32>

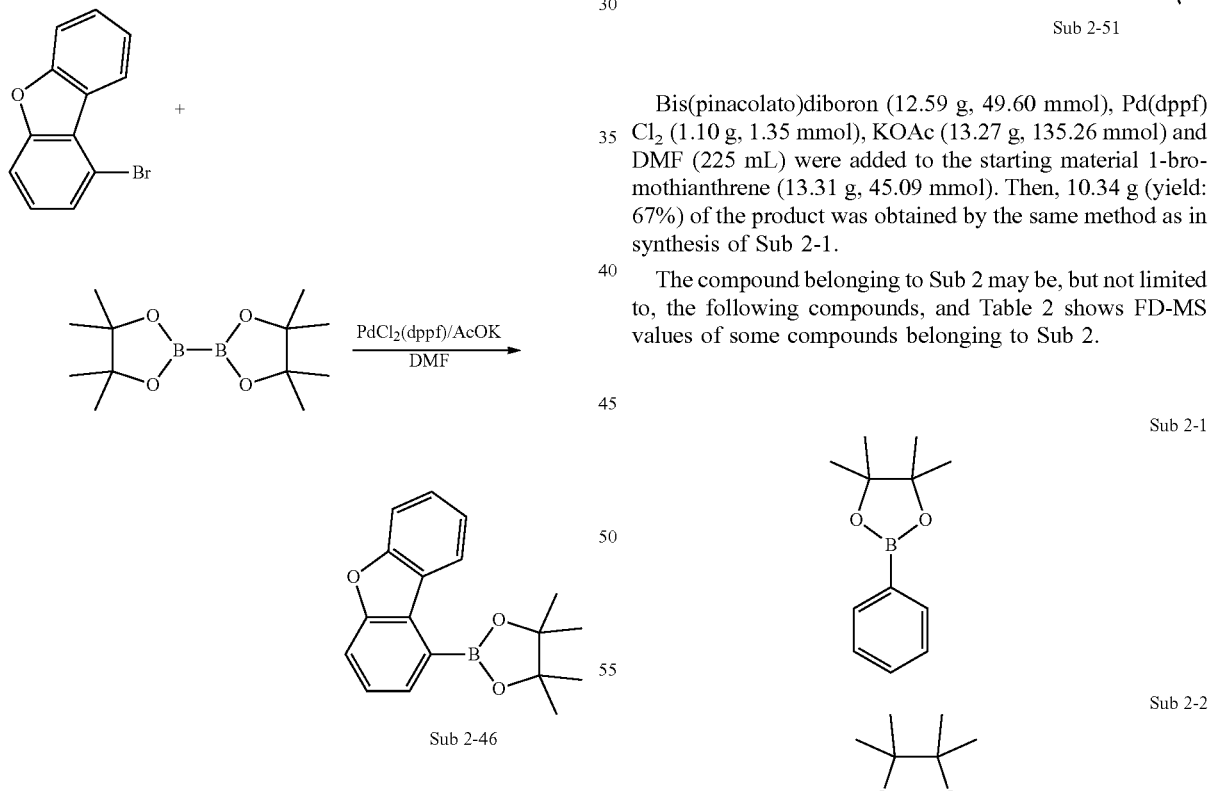

Sub 2-51

Bis(pinacolato)diboron (12.59 g, 49.60 mmol), Pd(dppf)Cl₂ (1.10 g, 1.35 mmol), KOAc (13.27 g, 135.26 mmol) and DMF (225 mL) were added to the starting material 1-bromothianthrene (13.31 g, 45.09 mmol). Then, 10.34 g (yield: 67%) of the product was obtained by the same method as in synthesis of Sub 2-1.

The compound belonging to Sub 2 may be, but not limited to, the following compounds, and Table 2 shows FD-MS values of some compounds belonging to Sub 2.

Sub 2-1

Sub 2-2

-continued
Sub 2-3
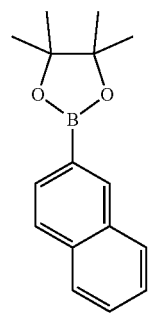
Sub 2-4
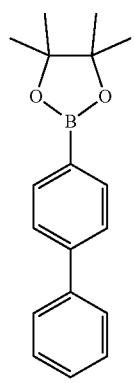
Sub 2-5
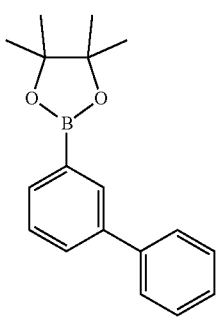
Sub 2-6
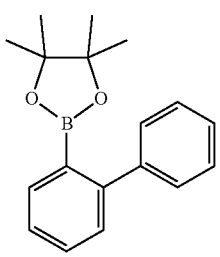
Sub 2-7
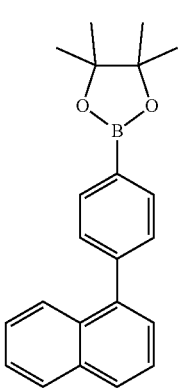
-continued
Sub 2-8
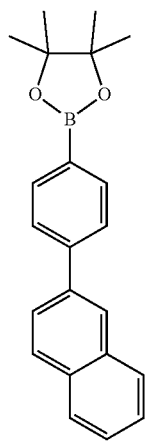
Sub 2-9
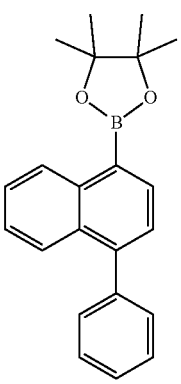
Sub 2-10
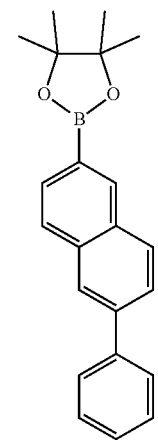
Sub 2-11
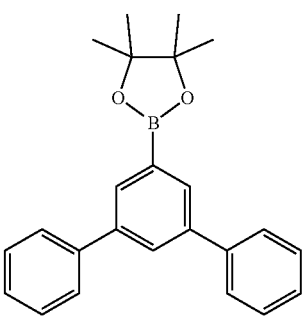

Sub 2-12
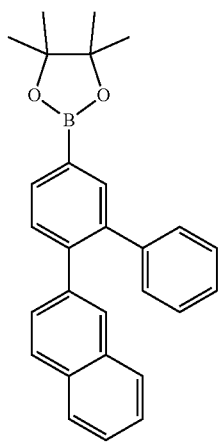
Sub 2-13
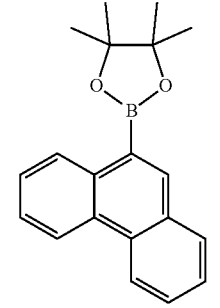
Sub 2-14
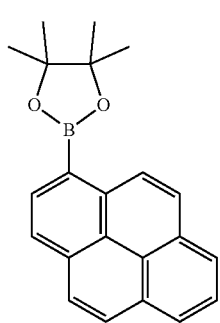
Sub 2-15
Sub 2-16
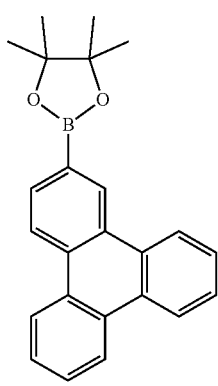
Sub 2-17
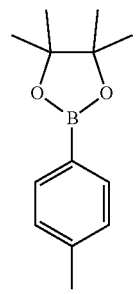
Sub 2-18
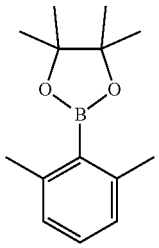
Sub 2-19
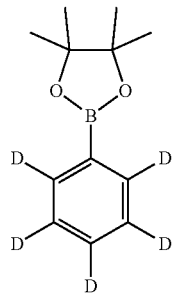
Sub 2-20
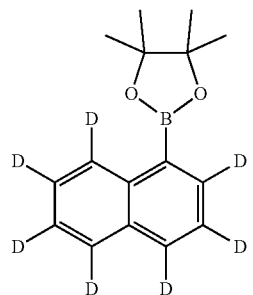

Sub 2-21
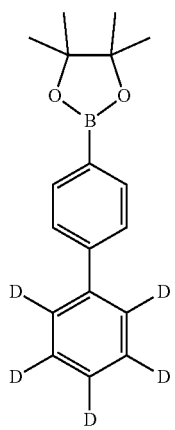
Sub 2-22
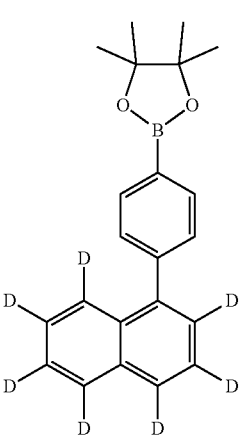
Sub 2-23
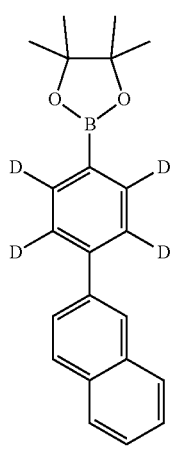
Sub 2-24
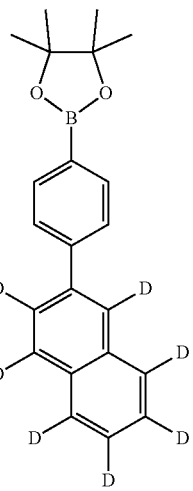
Sub 2-25
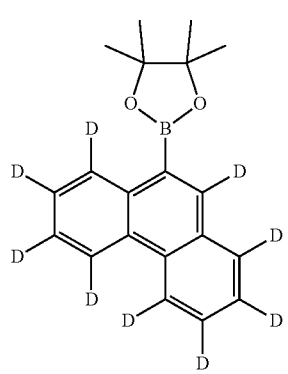
Sub 2-26
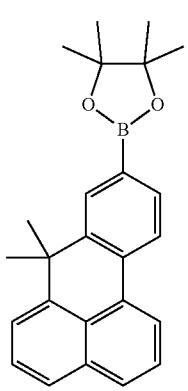
Sub 2-27
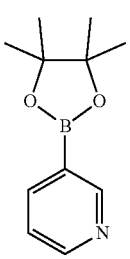

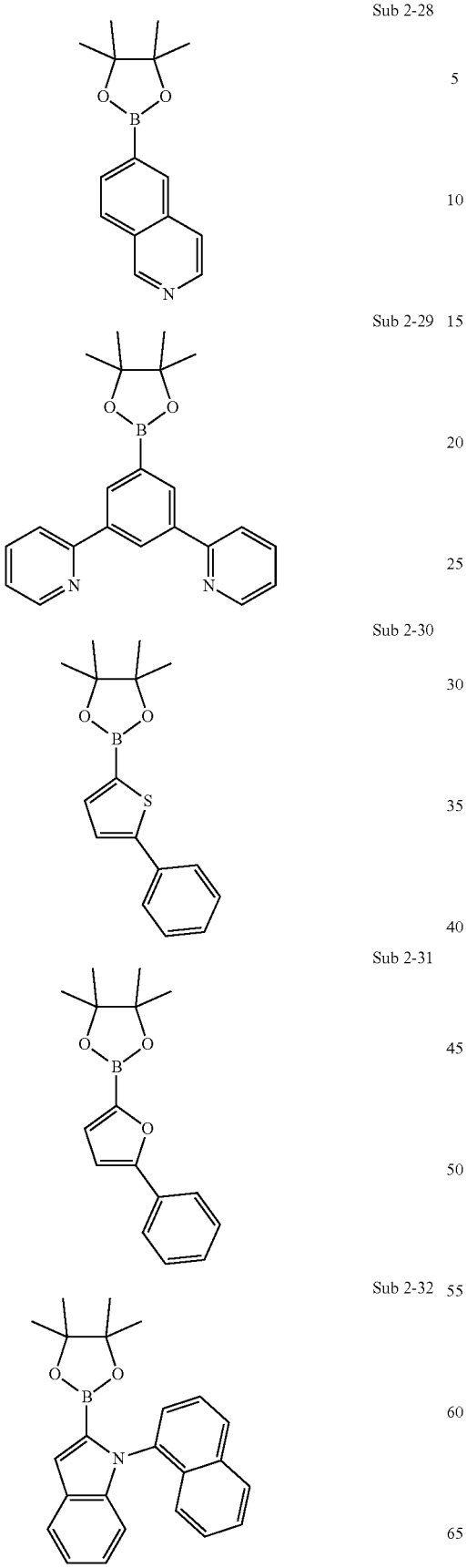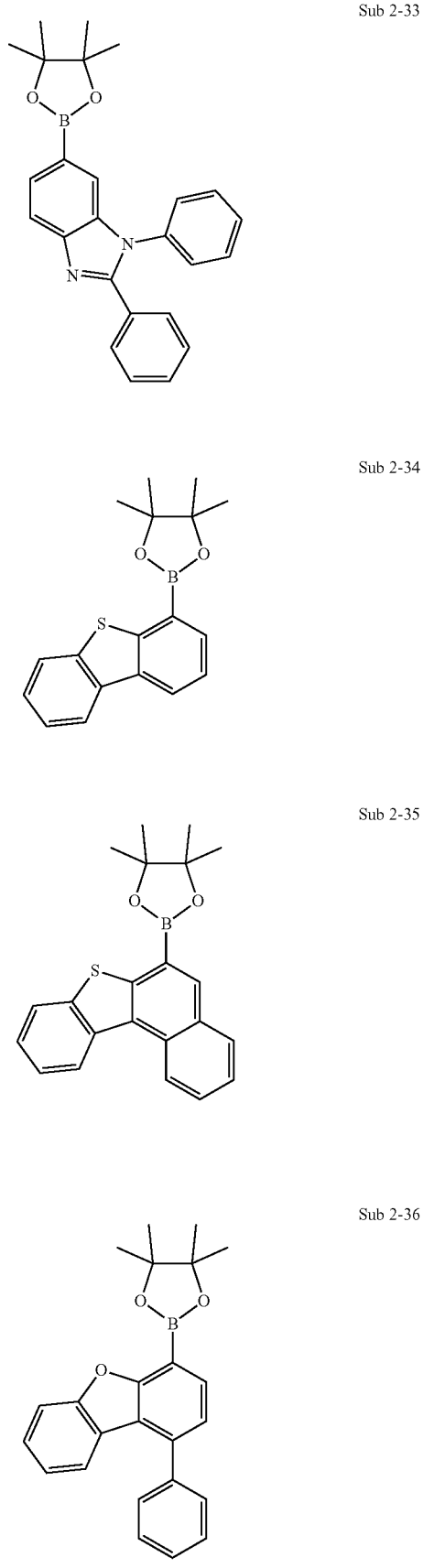

Sub 2-37
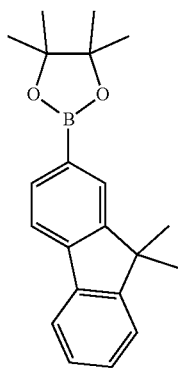
Sub 2-38
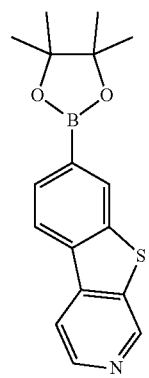
Sub 2-39
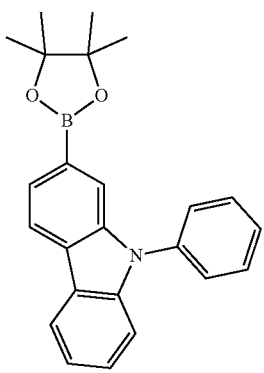
Sub 2-40
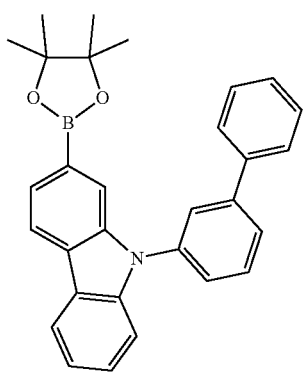
Sub 2-41
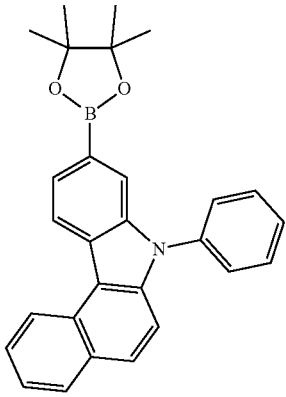
Sub 2-42
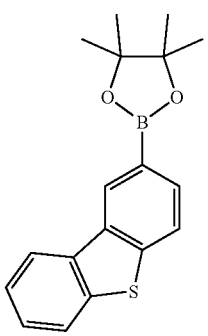
Sub 2-43
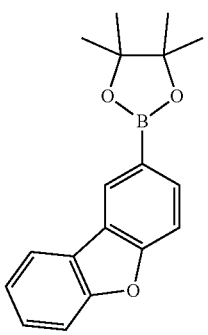
Sub 2-44
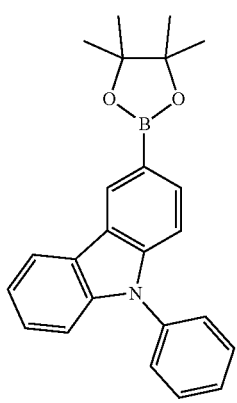

Sub 2-45
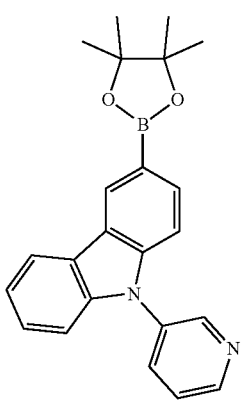
Sub 2-46
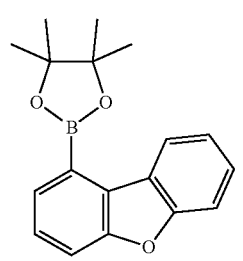
Sub 2-47
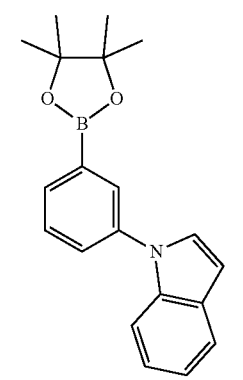
Sub 2-48
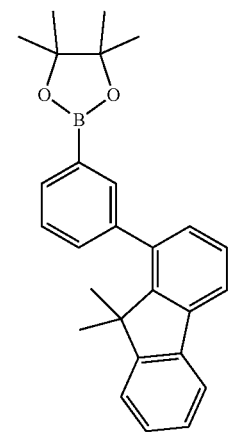
Sub 2-49
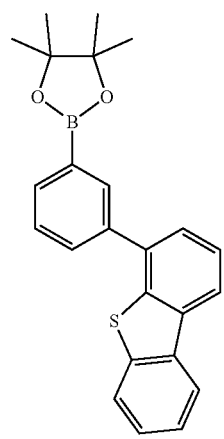
Sub 2-50
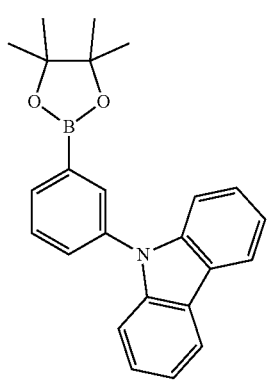
Sub 2-51
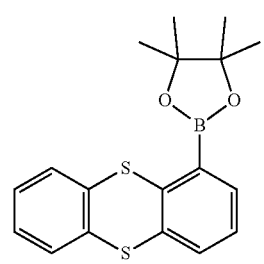
Sub 2-52
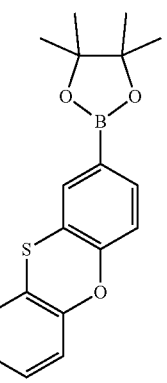

-continued

Sub 2-53

Sub 2-54

Sub 2-55

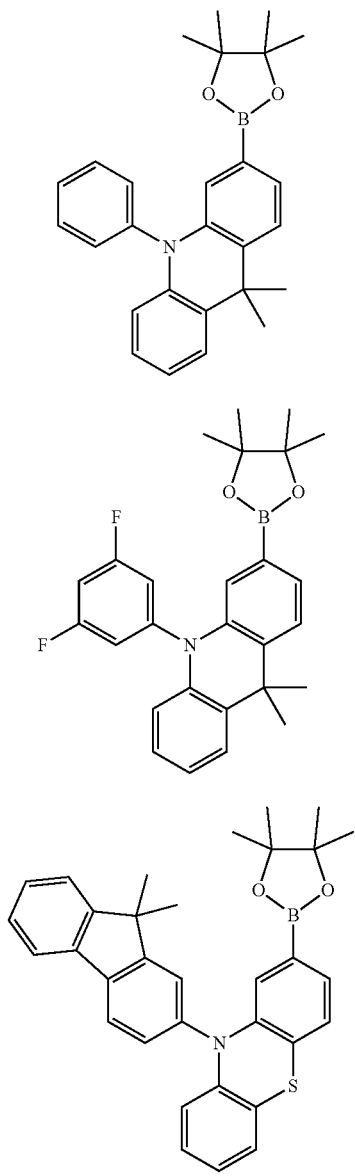

-continued

Sub 2-56

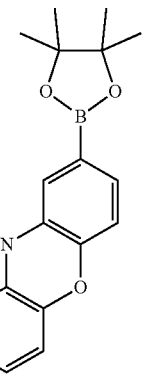

Sub 2-57

Sub 2-58

TABLE 2

| Compound | FD-MS | Compound | FD-MS |
|---|---|---|---|
| Sub 2-1 | m/z = 204.13($C_{12}H_{17}BO_2$ = 204.08) | Sub 2-3 | m/z = 254.15($C_{16}H_{19}BO_2$ = 254.14) |
| Sub 2-5 | m/z = 280.16($C_{18}H_{21}BO_2$ = 280.17) | Sub 2-19 | m/z = 209.16($C_{12}H_{12}D_5BO_2$ = 209.11) |
| Sub 2-34 | m/z = 310.12($C_{18}H_{19}BO_2S$ = 310.22) | Sub 2-43 | m/z = 294.14($C_{18}H_{19}BO_3$ = 294.16) |
| Sub 2-44 | m/z = 369.19($C_{24}H_{24}BNO_2$ = 369.27) | Sub 2-46 | m/z = 294.14($C_{18}H_{19}BO_3$ = 294.16) |
| Sub 2-51 | m/z = 342.09($C_{18}H_{19}BO_2S_2$ = 342.28) | | |

III. Synthesis of Product

After Sub 1 (1 eq.) was placed in a round bottom flask and was dissolved in THF, Sub 2 (1 eq.), Pd(PPh$_3$)$_4$ (0.04 eq.), NaOH (3 eq.) and water were added and the mixture was stirred at 70□. When the reaction was completed, the resultant was extracted with CH$_2$Cl$_2$ and water. The organic layer was dried with MgSO$_4$ and concentrated. The concentrate was applied to silica gel column and recrystallized to obtain a final product.

1. Synthesis Example of P 1-2

<Reaction Scheme 33>

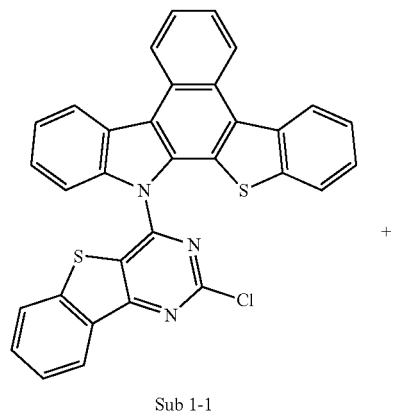

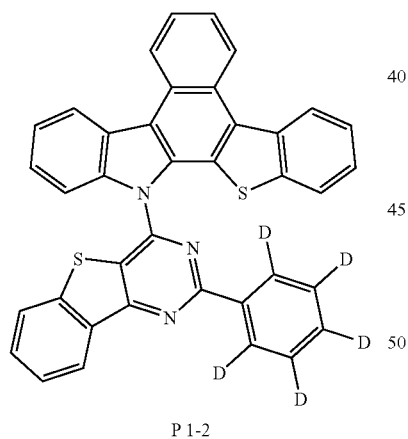

After Sub 1-1 (9.63 g, 17.77 mmol) obtained in the above synthesis was placed in a round bottom flask and was dissolved in THF (60 ml), Sub 2-19 (3.71 g, 17.77 mmol), Pd(PPh₃)₄ (0.82 g, 0.71 mmol), NaOH (2.13 g, 53.30 mmol) and water (30 mL) were added and the mixture was stirred at 70° C. When the reaction was completed, the resultant was extracted with CH₂Cl₂ and water. The organic layer was dried with MgSO₄ and concentrated. The concentrate was applied to silica gel column and recrystallized to obtain 7.53 g (yield: 72%) of the product.

2. Synthesis Example of P 1-5

<Reaction Scheme 34>

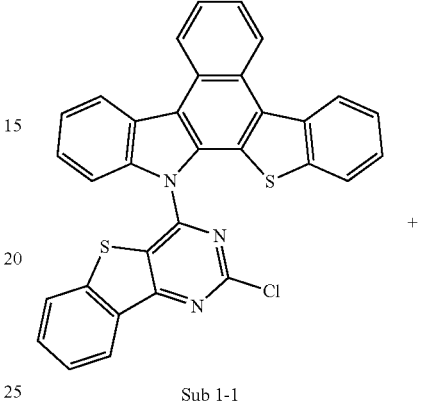

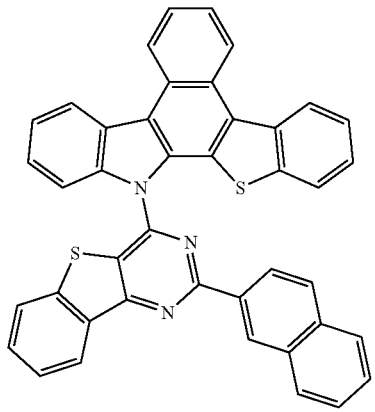

Sub 2-3 (3.84 g, 15.09 mmol), Pd(PPh₃)₄ (0.70 g, 0.60 mmol), NaOH (1.81 g, 45.27 mmol), THF (50 mL) and water (25 mL) were added to Sub 1-1 (8.18 g, 15.09 mmol) obtained in the above synthesis. Then, 7.17 g (yield: 75%) of the product was obtained by the same method as in synthesis of P 1-2.

3. Synthesis Example of P 1-11

<Reaction Scheme 35>

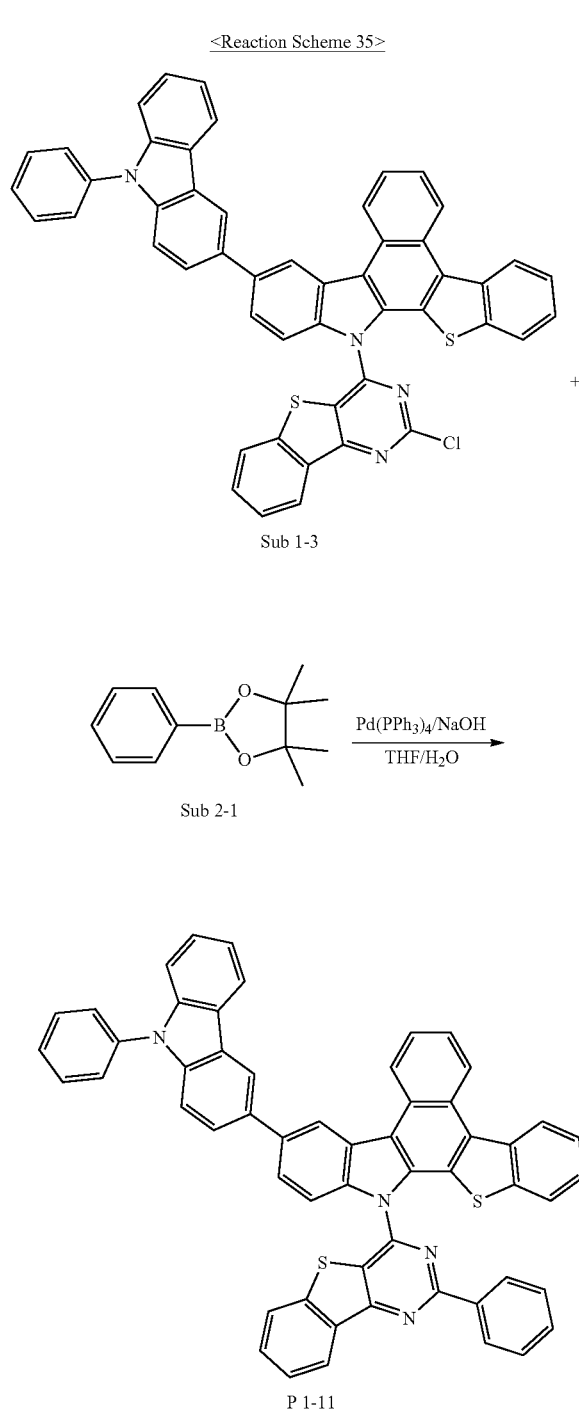

P 1-11

Sub 2-1 (3.06 g, 14.99 mmol), Pd(PPh₃)₄ (0.69 g, 0.60 mmol), NaOH (1.80 g, 44.96 mmol), THF (50 mL) and water (25 mL) were added to Sub 1-3 (11.74 g, 14.99 mmol) obtained in the above synthesis. Then, 7.54 g (yield: 61%) of the product was obtained by the same method as in synthesis of P 1-2.

4. Synthesis Example of P 1-14

<Reaction Scheme 36>

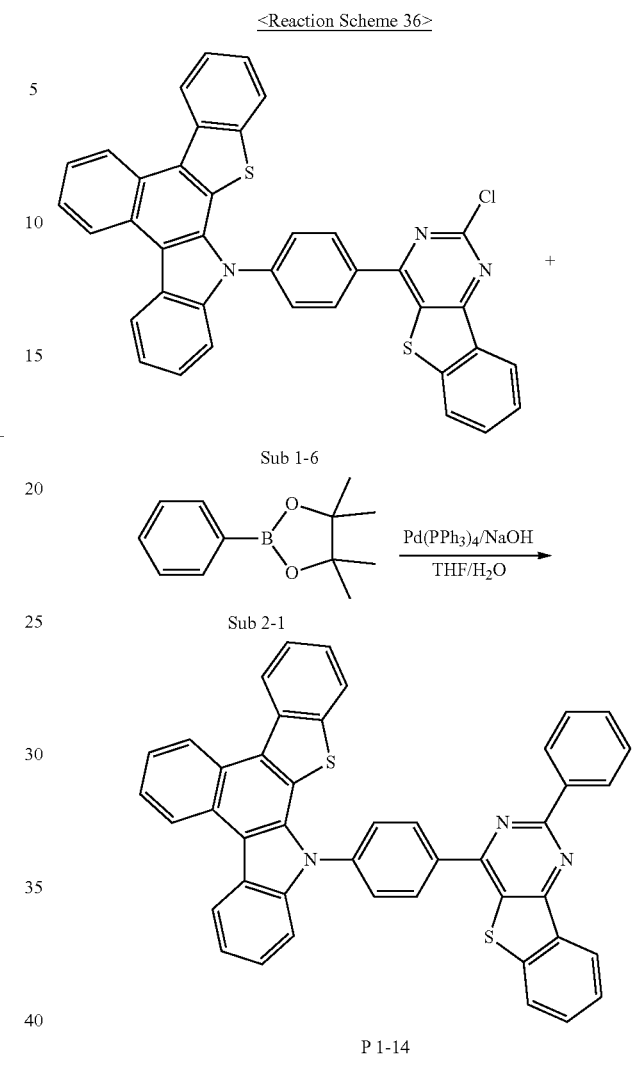

P 1-14

Sub 2-1 (3.71 g, 18.20 mmol), Pd(PPh₃)₄ (0.84 g, 0.73 mmol), NaOH (2.18 g, 54.60 mmol), THF (60 mL) and water (30 mL) were added to Sub 1-6 (11.25 g, 18.20 mmol) obtained in the above synthesis. Then, 7.69 g (yield: 64%) of the product was obtained by the same method as in synthesis of P 1-2.

5. Synthesis Example of P 1-28

<Reaction Scheme 37>

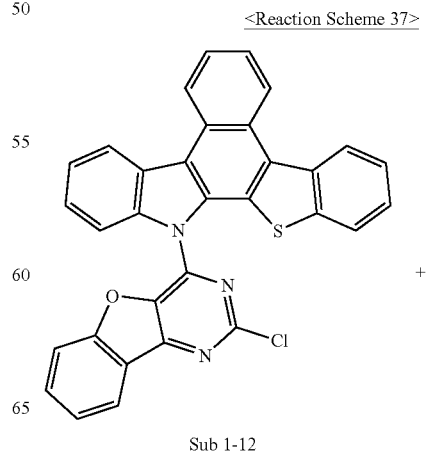

Sub 1-12

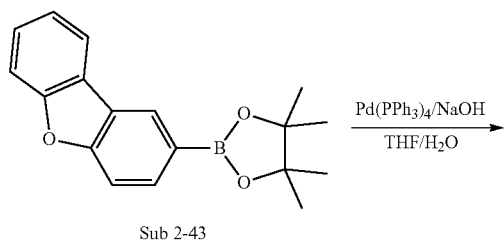

Sub 2-43

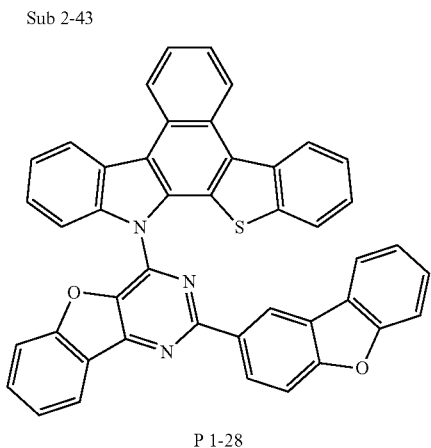

P 1-28

Sub 2-43 (4.52 g, 15.38 mmol), Pd(PPh$_3$)$_4$ (0.71 g, 0.62 mmol), NaOH (1.85 g, 46.14 mmol), THF (50 mL) and water (25 mL) were added to Sub 1-12 (8.09 g, 15.38 mmol) obtained in the above synthesis. Then, 6.88 g (yield: 68%) of the product was obtained by the same method as in synthesis of P 1-2.

6. Synthesis Example of P 1-38

<Reaction Scheme 38>

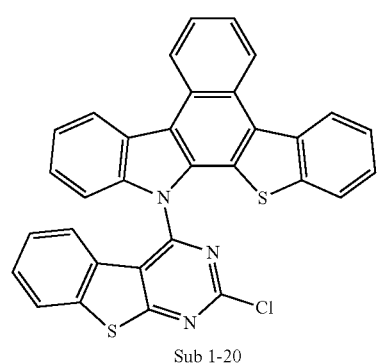

Sub 1-20

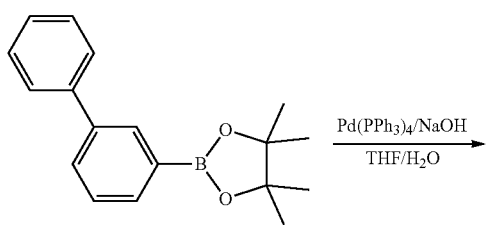

Sub 2-5

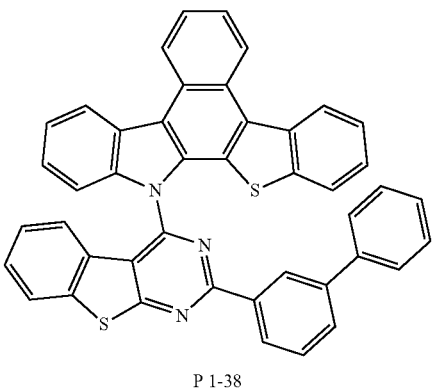

P 1-38

Sub 2-5 (4.26 g, 15.20 mmol), Pd(PPh$_3$)$_4$ (0.70 g, 0.61 mmol), NaOH (1.82 g, 45.60 mmol), THF (50 mL) and water (25 mL) were added to Sub 1-20 (8.24 g, 15.20 mmol) obtained in the above synthesis. Then, 7.32 g (yield: 73%) of the product was obtained by the same method as in synthesis of P 1-2.

7. Synthesis Example of P 1-59

<Reaction Scheme 39>

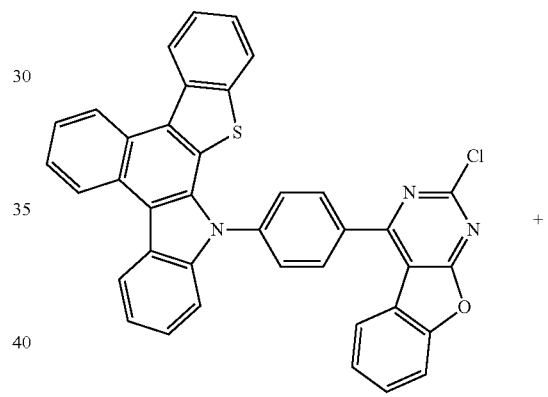

Sub 1-36

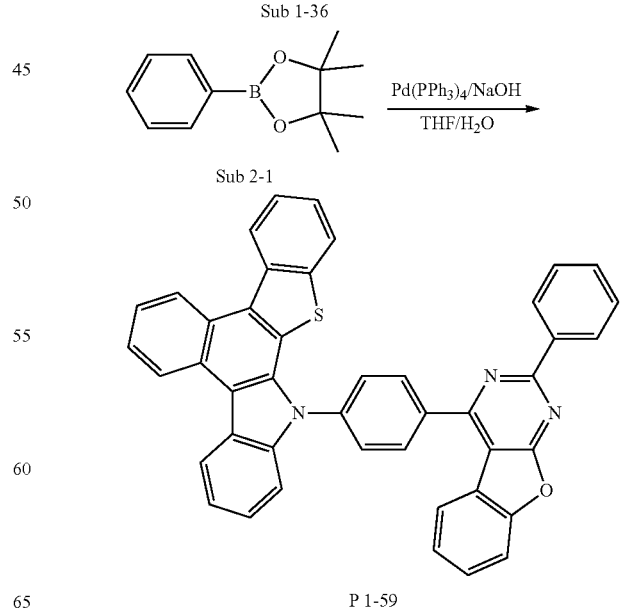

Sub 2-1

P 1-59

Sub 2-1 (3.60 g, 17.64 mmol), Pd(PPh₃)₄ (0.82 g, 0.71 mmol), NaOH (2.12 g, 52.91 mmol), THF (60 mL) and water (30 mL) were added to Sub 1-36 (10.62 g, 17.64 mmol) obtained in the above synthesis. Then, 7.38 g (yield: 65%) of the product was obtained by the same method as in synthesis of P 1-2.

8. Synthesis Example of P 2-3

<Reaction Scheme 40>

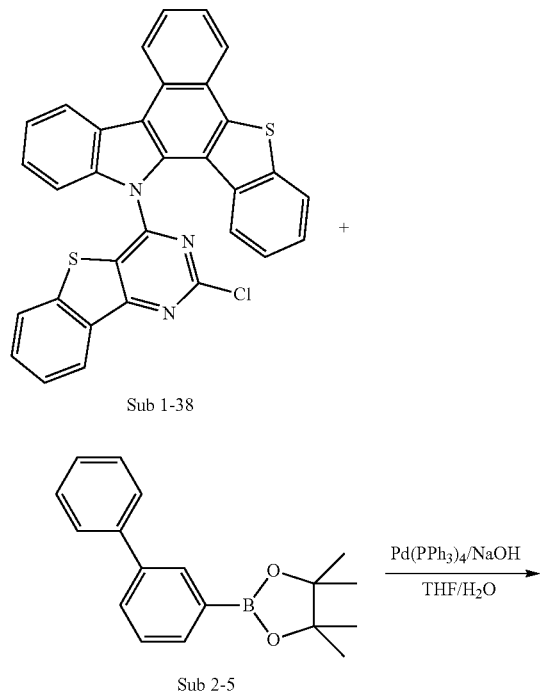

Sub 1-38

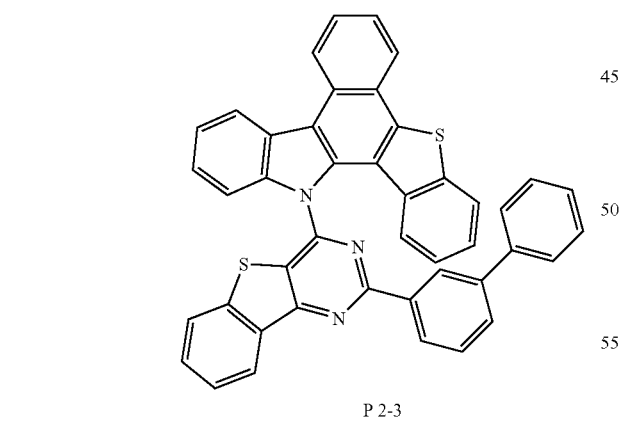

Sub 2-5

P 2-3

Sub 2-5 (4.96 g, 17.69 mmol), Pd(PPh₃)₄ (0.82 g, 0.71 mmol), NaOH (2.12 g, 53.07 mmol), THF (60 mL) and water (30 mL) were added to Sub 1-38 (9.59 g, 17.69 mmol) obtained in the above synthesis. Then, 7.24 g (yield: 62%) of the product was obtained by the same method as in synthesis of P 1-2.

9. Synthesis Example of P 2-14

<Reaction Scheme 41>

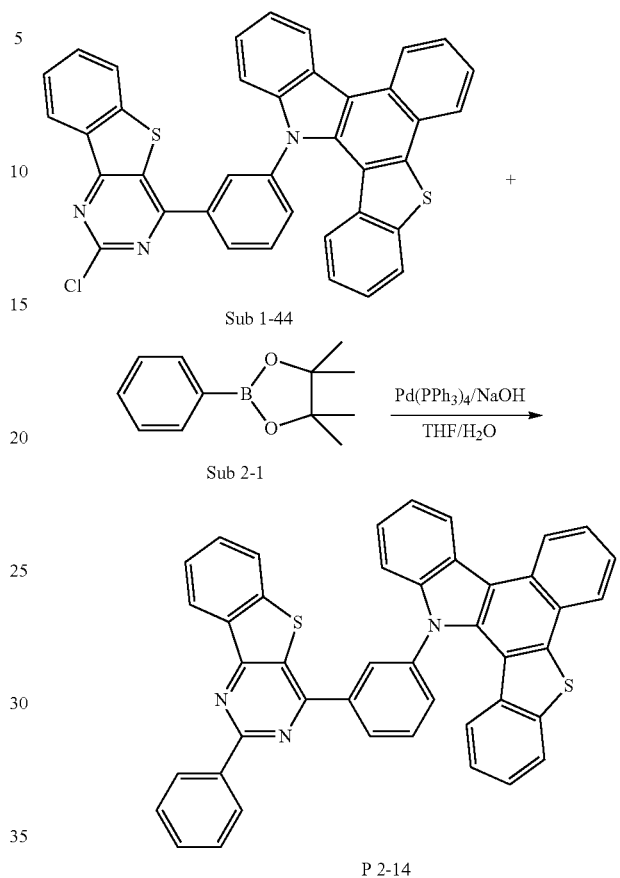

Sub 1-44

Sub 2-1

P 2-14

Sub 2-1 (3.43 g, 16.79 mmol), Pd(PPh₃)₄ (0.78 g, 0.67 mmol), NaOH (2.01 g, 50.37 mmol), THF (56 mL) and water (28 mL) were added to Sub 1-44 (10.38 g, 16.79 mmol) obtained in the above synthesis. Then, 7.09 g (yield: 64%) of the product was obtained by the same method as in synthesis of P 1-2.

10. Synthesis Example of P 2-26

<Reaction Scheme 42>

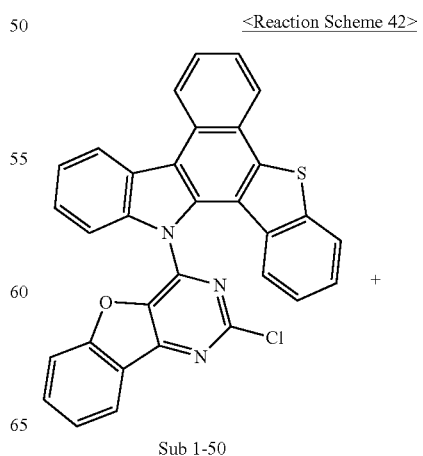

Sub 1-50

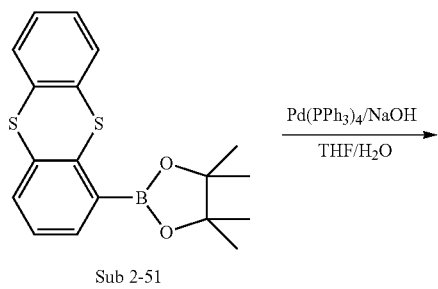

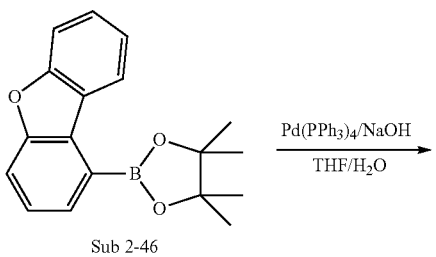

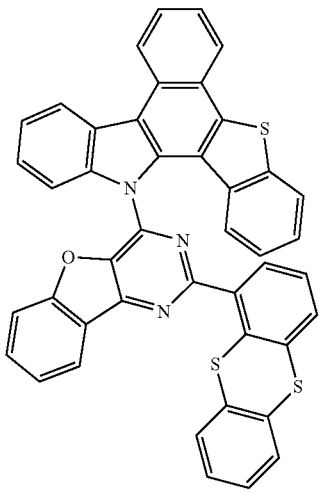

P 2-26

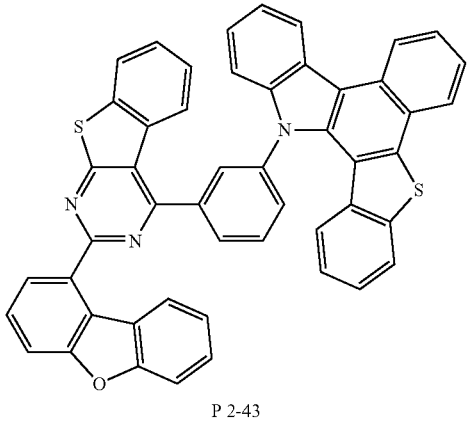

P 2-43

Sub 2-51 (5.84 g, 17.05 mmol), Pd(PPh₃)₄ (0.79 g, 0.68 mmol), NaOH (2.05 g, 51.16 mmol), THF (60 mL) and water (30 mL) were added to Sub 1-50 (8.97 g, 17.05 mmol) obtained in the above synthesis. Then, 6.98 g (yield: 58%) of the product was obtained by the same method as in synthesis of P 1-2.

11. Synthesis Example of P 2-43

<Reaction Scheme 43>

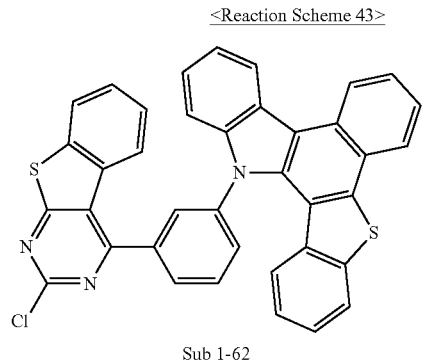

Sub 2-46 (4.77 g, 16.21 mmol), Pd(PPh₃)₄ (0.75 g, 0.65 mmol), NaOH (1.95 g, 48.63 mmol), THF (54 mL) and water (27 mL) were added to Sub 1-62 (10.02 g, 16.21 mmol) obtained in the above synthesis. Then, 6.81 g (yield: 56%) of the product was obtained by the same method as in synthesis of P 1-2.

12. Synthesis Example of P 2-45

<Reaction Scheme 44>

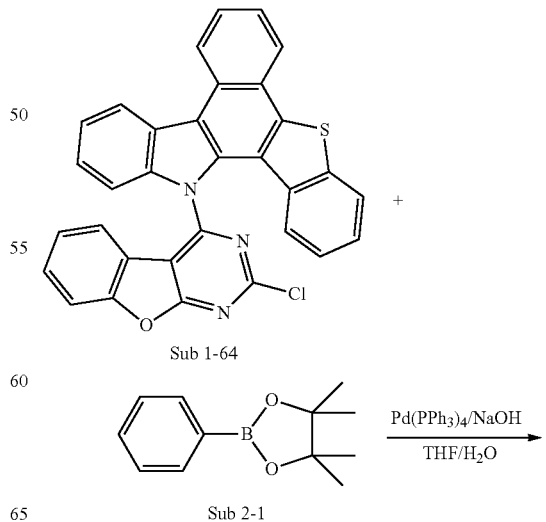

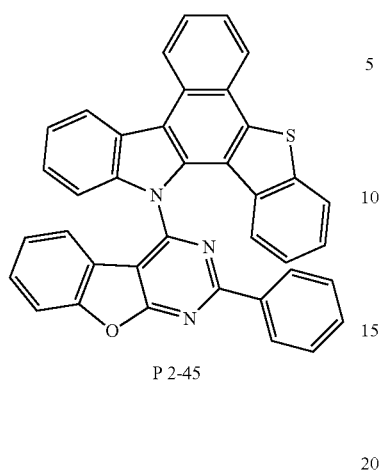

P 2-45

Sub 2-1 (4.30 g, 21.08 mmol), Pd(PPh₃)₄ (0.97 g, 0.84 mmol), NaOH (2.53 g, 63.25 mmol), THF (70 mL) and water (35 mL) were added to Sub 1-64 (11.09 g, 21.08 mmol) obtained in the above synthesis. Then, 7.54 g (yield: 63%) of the product was obtained by the same method as in synthesis of P 1-2.

13. Synthesis Example of P 3-7

<Reaction Scheme 45>

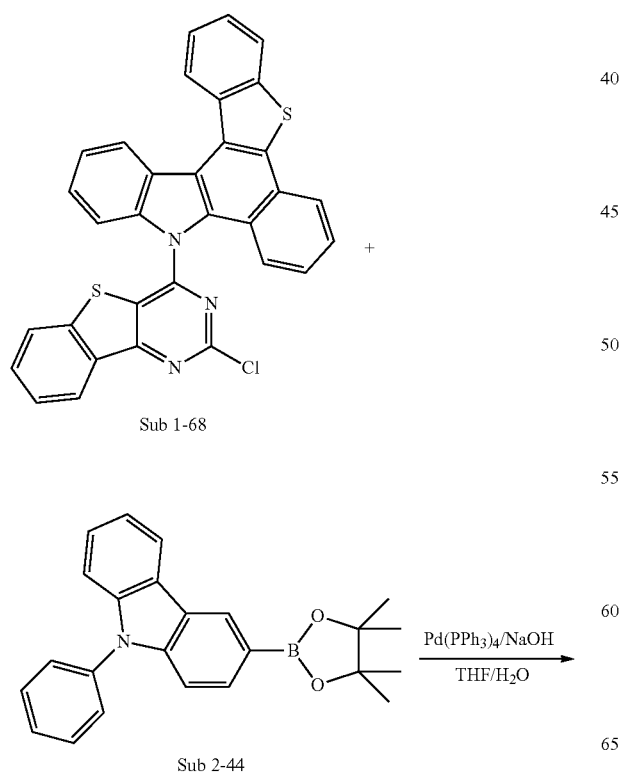

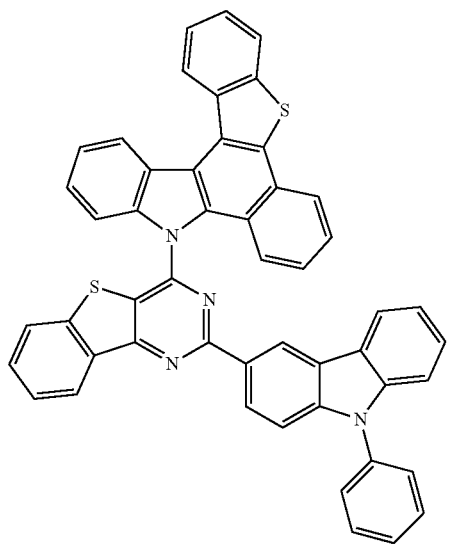

P 3-7

Sub 2-44 (6.04 g, 16.34 mmol), Pd(PPh₃)₄ (0.76 g, 0.65 mmol), NaOH (1.96 g, 49.03 mmol), THF (54 mL) and water (27 mL) were added to Sub 1-68 (8.86 g, 16.34 mmol) obtained in the above synthesis. Then, 7.22 g (yield: 59%) of the product was obtained by the same method as in synthesis of P 1-2.

14. Synthesis Example of P 3-24

<Reaction Scheme 46>

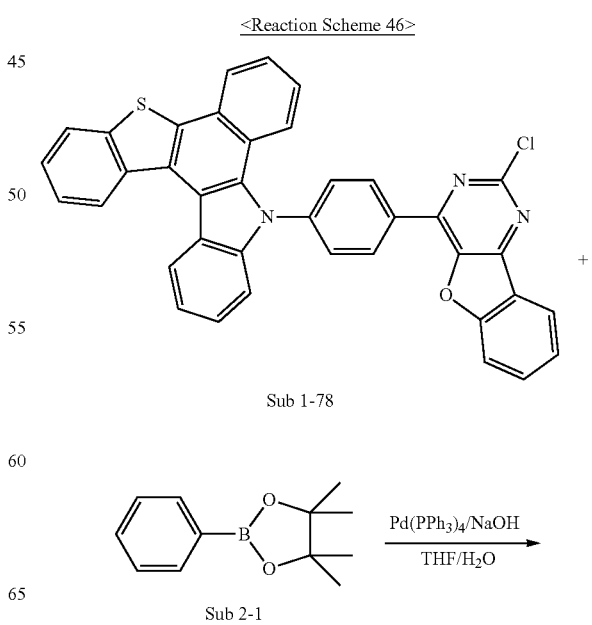

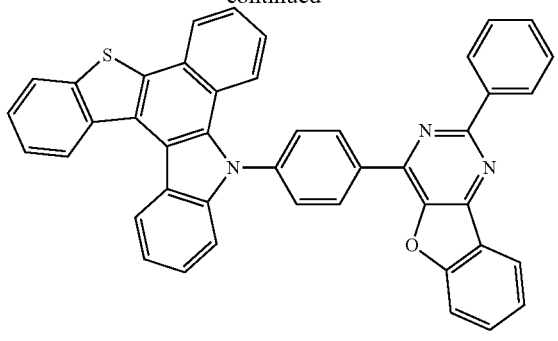

P 3-24

Sub 2-1 (3.79 g, 18.57 mmol), Pd(PPh₃)₄ (0.86 g, 0.74 mmol), NaOH (2.23 g, 55.70 mmol), THF (60 mL) and water (30 mL) were added to Sub 1-78 (11.18 g, 18.57 mmol) obtained in the above synthesis. Then, 7.53 g (yield: 63%) of the product was obtained by the same method as in synthesis of P 1-2.

15. Synthesis Example of P 3-26

<Reaction Scheme 47>

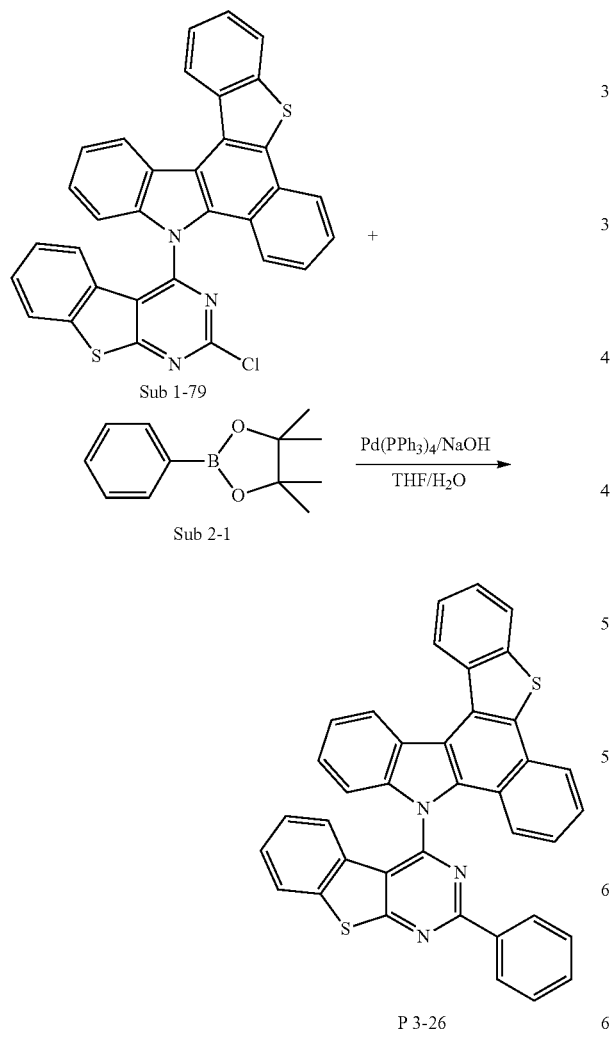

P 3-26

Sub 2-1 (4.27 g, 20.90 mmol), Pd(PPh₃)₄ (0.97 g, 0.84 mmol), NaOH (2.51 g, 62.70 mmol), THF (70 mL) and water (35 mL) were added to Sub 1-79 (11.33 g, 20.90 mmol) obtained in the above synthesis. Then, 7.32 g (yield: 60%) of the product was obtained by the same method as in synthesis of P 1-2.

16. Synthesis Example of P 3-43

<Reaction Scheme 48>

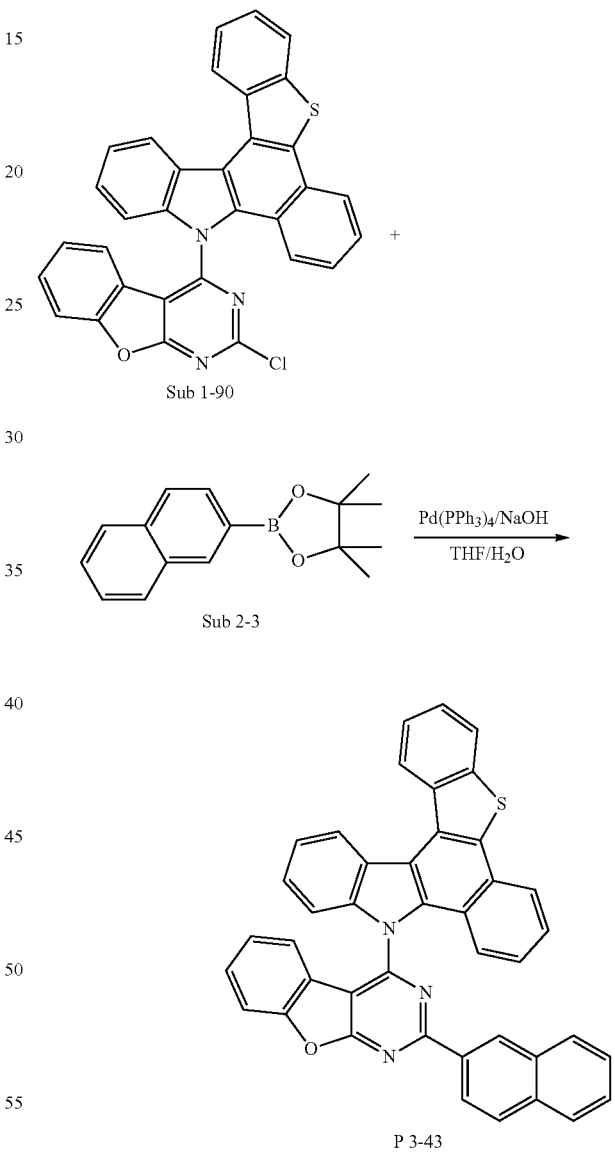

P 3-43

Sub 2-3 (5.45 g, 21.43 mmol), Pd(PPh₃)₄ (0.99 g, 0.86 mmol), NaOH (2.57 g, 64.28 mmol), THF (70 mL) and water (35 mL) were added to Sub 1-90 (11.27 g, 21.43 mmol) obtained in the above synthesis. Then, 7.54 g (yield: 57%) of the product was obtained by the same method as in synthesis of P 1-2.

17. Synthesis Example of P 4-7

<Reaction Scheme 49>

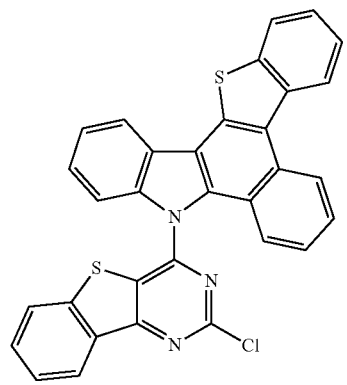

Sub 1-97

+

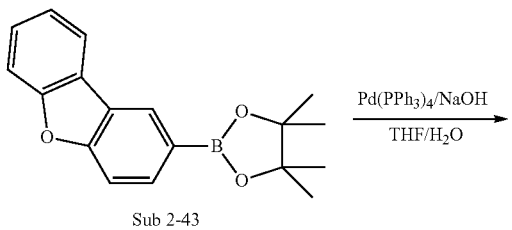

Sub 2-43

Pd(PPh$_3$)$_4$/NaOH
THF/H$_2$O
→

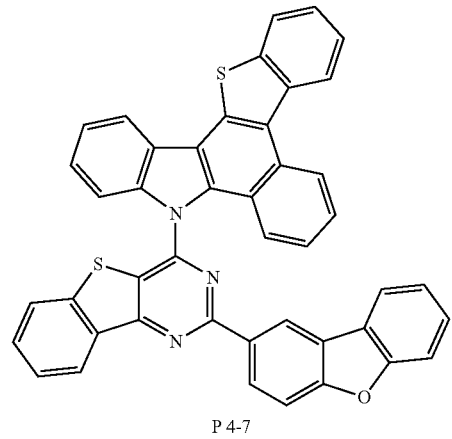

P 4-7

Sub 2-43 (5.94 g, 20.20 mmol), Pd(PPh$_3$)$_4$ (0.93 g, 0.81 mmol), NaOH (2.42 g, 60.60 mmol), THF (70 mL) and water (35 mL) were added to Sub 1-97 (10.95 g, 20.20 mmol) obtained in the above synthesis. Then, 7.21 g (yield: 53%) of the product was obtained by the same method as in synthesis of P 1-2.

18. Synthesis Example of P 4-25

<Reaction Scheme 50>

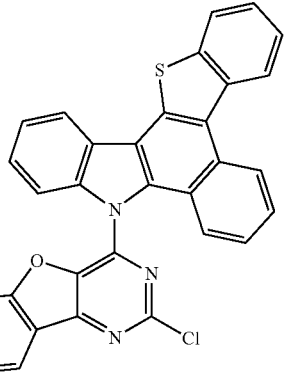

Sub 1-109

+

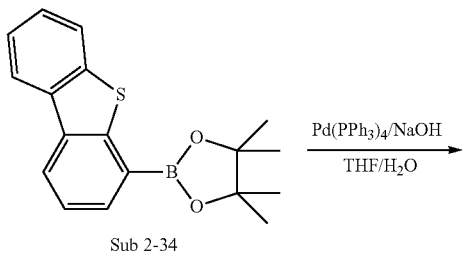

Sub 2-34

Pd(PPh$_3$)$_4$/NaOH
THF/H$_2$O
→

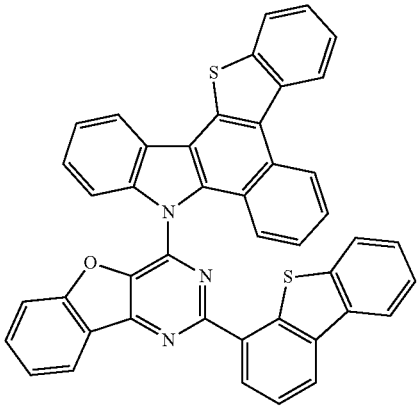

P 4-25

Sub 2-34 (6.63 g, 21.37 mmol), Pd(PPh$_3$)$_4$ (0.99 g, 0.85 mmol), NaOH (2.56 g, 64.11 mmol), THF (70 mL) and water (35 mL) were added to Sub 1-109 (11.24 g, 21.37 mmol) obtained in the above synthesis. Then, 7.92 g (yield: 55%) of the product was obtained by the same method as in synthesis of P 1-2.

19. Synthesis Example of P 4-43

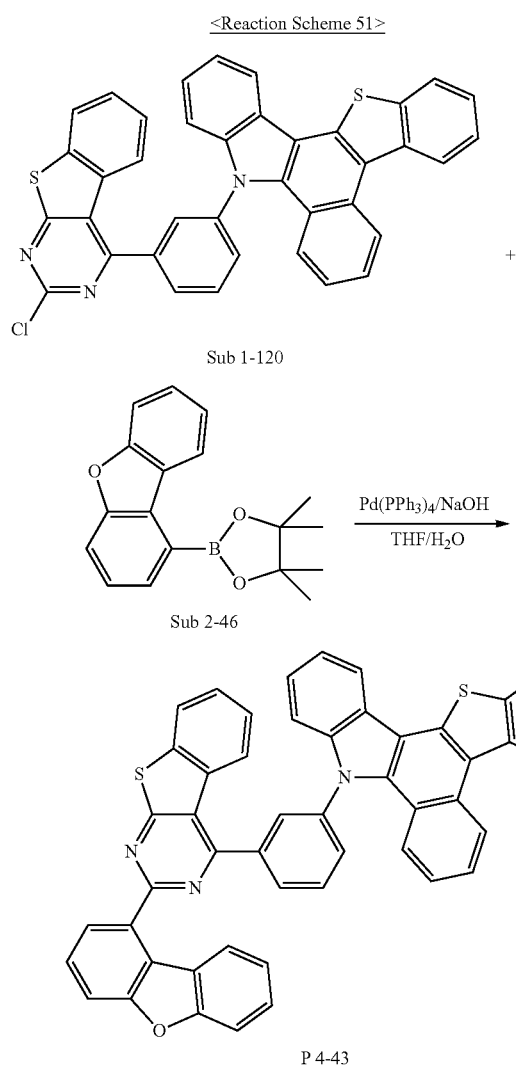

<Reaction Scheme 51>

Sub 2-46 (5.58 g, 18.96 mmol), Pd(PPh₃)₄ (0.88 g, 0.76 mmol), NaOH (2.28 g, 56.88 mmol), THF (60 mL) and water (30 mL) were added to Sub 1-120 (11.72 g, 18.96 mmol) obtained in the above synthesis. Then, 7.39 g (yield: 52%) of the product was obtained by the same method as in synthesis of P 1-2.

20. Synthesis Example of P 4-46

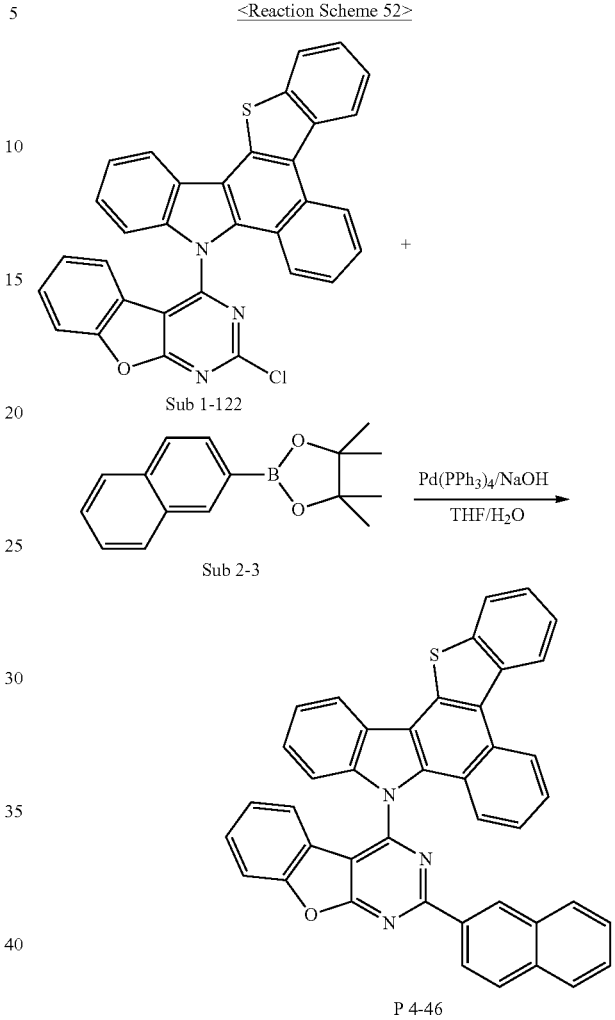

<Reaction Scheme 52>

Sub 2-3 (4.80 g, 18.88 mmol), Pd(PPh₃)₄ (0.87 g, 0.76 mmol), NaOH (2.27 g, 56.63 mmol), THF (60 mL) and water (30 mL) were added to Sub 1-122 (9.93 g, 18.88 mmol) obtained in the above synthesis. Then, 7.46 g (yield: 64%) of the product was obtained by the same method as in synthesis of P 1-2.

The FD-MS values of some compounds of the present invention prepared according to the above synthesis examples are shown in Table 3 below.

TABLE 3

| Compound | FD-MS | Compound | FD-MS |
| --- | --- | --- | --- |
| P 1-2 | m/z = 588.15($C_{38}H_{16}D_5N_3S_2$ = 588.76) | P 1-5 | m/z = 633.13($C_{42}H_{23}N_3S_2$ = 633.79) |
| P 1-11 | m/z = 824.21($C_{56}H_{32}N_4S$ = 825.02) | P 1-14 | m/z = 659.15($C_{44}H_{25}N_3S_2$ = 659.83) |
| P1-28 | m/z = 657.15($C_{44}H_{23}N_3O_2S$ = 657.75) | P 1-38 | m/z = 659.15($C_{44}H_{25}N_3S_2$ = 659.83) |
| P1-59 | m/z = 643.17($C_{44}H_{25}N_3OS$ = 643.76) | P 2-3 | m/z = 659.15($C_{44}H_{25}N_3S_2$ = 659.83) |
| P 2-14 | m/z = 659.15($C_{44}H_{25}N_3S_2$ = 659.83) | P 2-26 | m/z = 705.10($C_{44}H_{23}N_3OS_3$ = 705.87) |
| P 2-43 | m/z = 749.16($C_{50}H_{27}N_3OS_2$ = 749.91) | P 2-45 | m/z = 567.14($C_{38}H_{21}N_3OS$ = 567.67) |
| P 3-7 | m/z = 748.18($C_{50}H_{28}N_4S_2$ = 748.92) | P 3-24 | m/z = 643.17($C_{44}H_{25}N_3OS$ = 643.76) |
| P 3-26 | m/z = 583.12($C_{38}H_{21}N_3S_2$ = 583.73) | P 3-43 | m/z = 617.16($C_{42}H_{23}N_3OS$ = 617.73) |
| P 4-7 | m/z = 673.13($C_{44}H_{23}N_3OS_2$ = 673.81) | P 4-25 | m/z = 673.13($C_{44}H_{23}N_3OS_2$ = 673.81) |
| P 4-43 | m/z = 749.16($C_{50}H_{27}N_3OS_2$ = 749.91) | P 4-46 | m/z = 617.16($C_{42}H_{23}N_3OS$ = 617.73) |

In the above, even though an exemplary synthesis example of the present invention represented by the Formula 1 are described, all of them are based on Suzuki cross-coupling reaction, Miyaura boration reaction, PPh₃-mediated reductive cyclization reaction (J. Org. Chem. 2005, 70, 5014), Buchwald-Hartwig cross coupling reaction and the like. It will be understood by those skilled in the art that the above reaction proceeds even when other substituents (substituents of X, Y, $R^1$ to $R^4$, $L^1$, $Ar^1$, m, n, o and p and the like) defined in Formula 1 are bonded, in addition to the substituents described in the specific synthesis example.

For example, the reaction of Sub 1 and Sub 2→Final Product in Reaction Scheme 1, the reaction of Sub 1-I→Sub 1-II in Reaction Scheme 2, and the reaction of Sub 1-V→Sub 1 in Reaction Scheme 3 are based on Suzuki cross-coupling reaction, the reaction of the starting material→Sub 1-I in Reaction Scheme 2, the reaction of Sub 1-IV→Sub 1-V in Reaction Scheme 3, and the reaction of the starting material→Sub 2 in Reaction Scheme 23 are based on Miyaura boration reaction, and the reaction of Sub 1-II→Sub 1-III in Reaction Scheme 2 is based on PPh₃-mediated reductive cyclization reaction (J. Org. Chem. 2005, 70, 5014). Further, the reactions of Sub 1-III→Sub 1-IV and Sub 1-III→Sub 1 are based on Buchwald-Hartwig cross coupling reaction. The above reactions will proceed even if a substituent not specifically mentioned is attached.

Fabrication and Evaluation of Organic Electronic Element

[Example 1] Red OLED (Phosphorescent Host)

Organic light emitting diodes (OLEDs) were fabricated according to a conventional method by using a compound of the present invention as a host material of a light emitting layer.

First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm.

Subsequently, 4,4'-bis[N-(1-naphthyl)-N-phenylamino] biphenyl(hereinafter, "NPD") was vacuum-deposited with a thickness of 60 nm on the hole injection layer to form a hole transport layer.

Subsequently, a light emitting layer with a thickness of 30 nm was formed on the hole transport layer by using compound P-1 of the present invention as a host material and bis-(1-phenylisoquinoline)iridium(III)acetylacetonate (hereinafter, "(piq)₂Ir(acac)") as a dopant material in a weight ratio of 95:5.

Next, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "Alq₃") was formed with a thickness of 40 nm to form an electron transport layer.

Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 70] Red OLED

The OLEDs were fabricated in the same manner as described in Example 1 except that the compounds of the present invention described in Table 4, instead of the compound P 1-1 according to Example 1 of the present invention, were used as as a host material of a light emitting layer.

[Comparative Example 1] to [Comparative Example 6]

The OLEDs were fabricated in the same manner as described in Example 1 except that any one of the following Comparative Compounds 1 to 6 described in Table 4, instead of the compound P 1-1 according to Example 1 of the present invention, was used as as a host material of a light emitting layer.

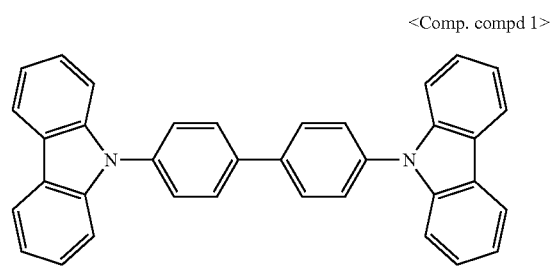

<Comp. compd 1>

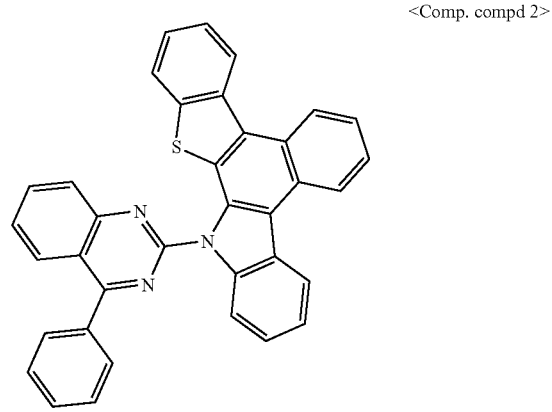

<Comp. compd 2>

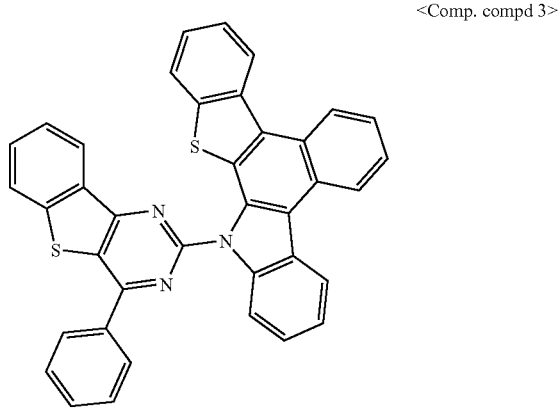

<Comp. compd 3>

<Comp. compd 4>

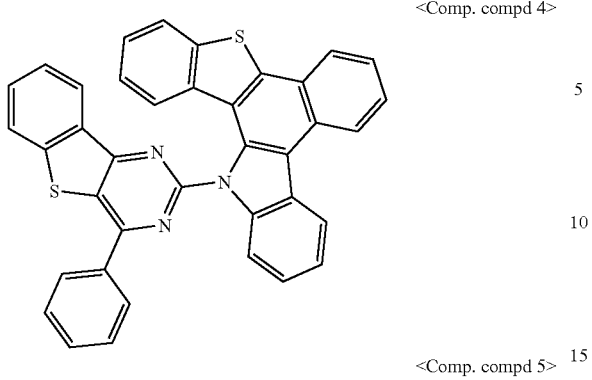

<Comp. compd 5>

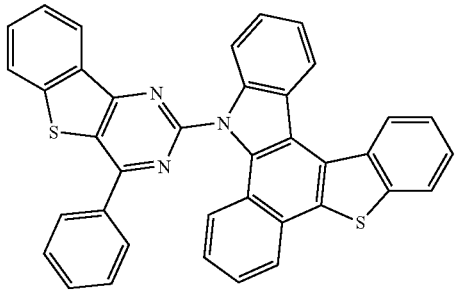

<Comp. compd 6>

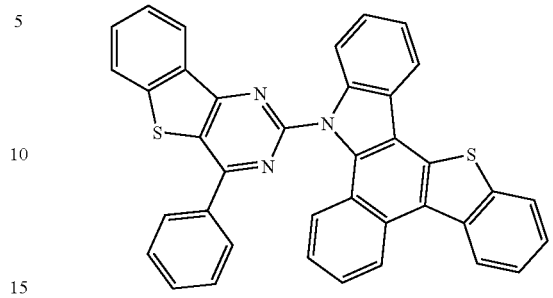

Electroluminescence (EL) characteristics were measured with a PR-650 (Photoresearch) by applying a forward bias DC voltage to the OLEDs prepared in Examples 1 to 70 of the present invention and Comparative Examples 1 to 6. And, the T95 life time was measured using a life time measuring apparatus manufactured by Macscience Inc. at reference brightness of 2500 cd/m$^2$. The measurement results are shown in Table 4 below.

TABLE 4

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(1) | comp. Com 1 | 6.6 | 35.2 | 2500 | 7.1 | 63.5 | 0.65 | 0.31 |
| comp. Ex(2) | comp. Com 2 | 6.1 | 21.4 | 2500 | 11.7 | 167.8 | 0.67 | 0.62 |
| comp. Ex(3) | comp. Com 3 | 5.9 | 15.7 | 2500 | 15.9 | 161.0 | 0.66 | 0.32 |
| comp. Ex(4) | comp. Com 4 | 5.9 | 17.7 | 2500 | 14.1 | 150.2 | 0.66 | 0.32 |
| comp. Ex(5) | comp. Com 5 | 5.9 | 16.2 | 2500 | 15.4 | 159.5 | 0.66 | 0.32 |
| comp. Ex(6) | comp. Com 6 | 6.0 | 17.5 | 2500 | 14.3 | 146.9 | 0.66 | 0.32 |
| Ex. (1) | Com. (P 1-1) | 5.8 | 12.2 | 2500 | 20.5 | 182.7 | 0.66 | 0.31 |
| Ex. (2) | Com. (P 1-2) | 5.9 | 12.4 | 2500 | 20.2 | 181.7 | 0.66 | 0.32 |
| Ex. (3) | Com. (P 1-4) | 5.7 | 12.0 | 2500 | 20.8 | 190.9 | 0.66 | 0.32 |
| Ex. (4) | Com. (P 1-5) | 5.7 | 12.1 | 2500 | 20.7 | 188.2 | 0.66 | 0.32 |
| Ex. (5) | Com. (P 1-9) | 5.9 | 12.7 | 2500 | 19.7 | 173.4 | 0.66 | 0.32 |
| Ex. (6) | Com. (P 1-11) | 5.9 | 12.6 | 2500 | 19.9 | 173.2 | 0.66 | 0.31 |
| Ex. (7) | Com. (P 1-14) | 5.9 | 13.1 | 2500 | 19.1 | 167.1 | 0.66 | 0.31 |
| Ex. (8) | Com. (P 1-16) | 5.9 | 13.2 | 2500 | 18.9 | 159.9 | 0.66 | 0.32 |
| Ex. (9) | Com. (P 1-21) | 5.8 | 12.9 | 2500 | 19.4 | 170.5 | 0.66 | 0.31 |
| Ex. (10) | Com. (P 1-24) | 5.9 | 12.9 | 2500 | 19.4 | 173.5 | 0.66 | 0.32 |
| Ex. (11) | Com. (P 1-32) | 5.9 | 13.6 | 2500 | 18.4 | 154.5 | 0.66 | 0.31 |
| Ex. (12) | Com. (P 1-36) | 5.8 | 12.3 | 2500 | 20.3 | 184.6 | 0.66 | 0.31 |
| Ex. (13) | Com. (P 1-39) | 5.8 | 12.1 | 2500 | 20.7 | 189.2 | 0.66 | 0.32 |
| Ex. (14) | Com. (P 1-46) | 5.8 | 13.0 | 2500 | 19.2 | 166.7 | 0.66 | 0.31 |
| Ex. (15) | Com. (P 1-51) | 5.8 | 13.0 | 2500 | 19.2 | 171.9 | 0.66 | 0.32 |
| Ex. (16) | Com. (P 1-53) | 5.9 | 12.8 | 2500 | 19.5 | 174.5 | 0.66 | 0.31 |
| Ex. (17) | Com. (P 1-59) | 5.8 | 13.6 | 2500 | 18.4 | 153.7 | 0.66 | 0.32 |
| Ex. (18) | Com. (P 2-1) | 5.9 | 13.7 | 2500 | 18.2 | 163.0 | 0.66 | 0.32 |
| Ex. (19) | Com. (P 2-4) | 5.9 | 13.6 | 2500 | 18.4 | 164.8 | 0.66 | 0.31 |
| Ex. (20) | Com. (P 2-5) | 5.9 | 13.6 | 2500 | 18.4 | 164.8 | 0.66 | 0.32 |
| Ex. (21) | Com. (P 2-8) | 5.9 | 13.9 | 2500 | 18.0 | 154.0 | 0.66 | 0.31 |
| Ex. (22) | Com. (P 2-11) | 5.9 | 14.6 | 2500 | 17.2 | 151.1 | 0.66 | 0.32 |
| Ex. (23) | Com. (P 2-13) | 5.9 | 14.3 | 2500 | 17.4 | 150.1 | 0.66 | 0.31 |
| Ex. (24) | Com. (P 2-17) | 5.9 | 14.5 | 2500 | 17.2 | 145.8 | 0.66 | 0.32 |
| Ex. (25) | Com. (P 2-21) | 5.9 | 14.4 | 2500 | 17.3 | 150.6 | 0.66 | 0.31 |
| Ex. (26) | Com. (P 2-23) | 5.9 | 14.3 | 2500 | 17.4 | 154.5 | 0.66 | 0.31 |
| Ex. (27) | Com. (P 2-24) | 5.9 | 14.6 | 2500 | 17.1 | 150.4 | 0.66 | 0.31 |
| Ex. (28) | Com. (P 2-28) | 5.9 | 14.5 | 2500 | 17.2 | 145.3 | 0.66 | 0.32 |
| Ex. (29) | Com. (P 2-31) | 5.9 | 13.5 | 2500 | 18.5 | 161.4 | 0.66 | 0.32 |
| Ex. (30) | Com. (P 2-32) | 5.9 | 14.2 | 2500 | 17.6 | 153.2 | 0.66 | 0.31 |
| Ex. (31) | Com. (P 2-33) | 5.9 | 13.6 | 2500 | 18.3 | 163.2 | 0.66 | 0.31 |
| Ex. (32) | Com. (P 2-41) | 5.9 | 14.6 | 2500 | 17.1 | 150.9 | 0.66 | 0.31 |
| Ex. (33) | Com. (P 2-45) | 5.9 | 14.4 | 2500 | 17.3 | 152.1 | 0.66 | 0.31 |

TABLE 4-continued

| Compound | | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (34) | Com. (P 2-46) | 5.9 | 14.4 | 2500 | 17.3 | 153.2 | 0.66 | 0.31 |
| Ex. (35) | Com. (P 2-49) | 5.9 | 14.6 | 2500 | 17.1 | 146.6 | 0.66 | 0.31 |
| Ex. (36) | Com. (P 3-1) | 5.8 | 12.9 | 2500 | 19.4 | 171.4 | 0.66 | 0.31 |
| Ex. (37) | Com. (P 3-2) | 5.9 | 12.9 | 2500 | 19.3 | 170.9 | 0.66 | 0.32 |
| Ex. (38) | Com. (P 3-3) | 5.9 | 12.9 | 2500 | 19.4 | 174.3 | 0.66 | 0.32 |
| Ex. (39) | Com. (P 3-4) | 5.9 | 12.9 | 2500 | 19.4 | 174.2 | 0.66 | 0.31 |
| Ex. (40) | Com. (P 3-11) | 5.9 | 13.6 | 2500 | 18.3 | 155.1 | 0.66 | 0.31 |
| Ex. (41) | Com. (P 3-16) | 5.9 | 13.6 | 2500 | 18.4 | 163.2 | 0.66 | 0.32 |
| Ex. (42) | Com. (P 3-19) | 5.9 | 13.5 | 2500 | 18.5 | 164.8 | 0.66 | 0.31 |
| Ex. (43) | Com. (P 3-24) | 5.9 | 14.6 | 2500 | 17.2 | 150.3 | 0.66 | 0.31 |
| Ex. (44) | Com. (P 3-26) | 5.8 | 12.9 | 2500 | 19.4 | 171.7 | 0.66 | 0.32 |
| Ex. (45) | Com. (P 3-27) | 5.8 | 12.9 | 2500 | 19.4 | 172.4 | 0.66 | 0.31 |
| Ex. (46) | Com. (P 3-28) | 5.8 | 13.2 | 2500 | 19.0 | 164.4 | 0.66 | 0.32 |
| Ex. (47) | Com. (P 3-29) | 5.8 | 12.8 | 2500 | 19.5 | 174.2 | 0.66 | 0.32 |
| Ex. (48) | Com. (P 3-36) | 5.8 | 13.6 | 2500 | 18.4 | 153.6 | 0.66 | 0.32 |
| Ex. (49) | Com. (P 3-38) | 5.9 | 14.0 | 2500 | 17.9 | 151.1 | 0.66 | 0.31 |
| Ex. (50) | Com. (P 3-41) | 5.9 | 13.6 | 2500 | 18.3 | 162.3 | 0.66 | 0.31 |
| Ex. (51) | Com. (P 3-43) | 5.9 | 13.5 | 2500 | 18.5 | 163.5 | 0.66 | 0.31 |
| Ex. (52) | Com. (P 3-49) | 5.9 | 14.3 | 2500 | 17.5 | 150.2 | 0.66 | 0.31 |
| Ex. (53) | Com. (P 4-1) | 5.9 | 13.7 | 2500 | 18.3 | 162.7 | 0.66 | 0.31 |
| Ex. (54) | Com. (P 4-3) | 5.9 | 13.6 | 2500 | 18.3 | 163.8 | 0.66 | 0.32 |
| Ex. (55) | Com. (P 4-4) | 5.9 | 13.6 | 2500 | 18.3 | 163.4 | 0.66 | 0.32 |
| Ex. (56) | Com. (P 4-5) | 5.9 | 14.1 | 2500 | 17.7 | 152.6 | 0.66 | 0.32 |
| Ex. (57) | Com. (P 4-11) | 5.9 | 14.6 | 2500 | 17.2 | 151.2 | 0.66 | 0.31 |
| Ex. (58) | Com. (P 4-12) | 5.9 | 14.4 | 2500 | 17.4 | 145.7 | 0.66 | 0.31 |
| Ex. (59) | Com. (P 4-21) | 5.9 | 14.5 | 2500 | 17.3 | 153.4 | 0.66 | 0.32 |
| Ex. (60) | Com. (P 4-23) | 5.9 | 14.4 | 2500 | 17.3 | 154.8 | 0.66 | 0.32 |
| Ex. (61) | Com. (P 4-28) | 5.9 | 14.6 | 2500 | 17.1 | 146.0 | 0.66 | 0.31 |
| Ex. (62) | Com. (P 4-31) | 5.9 | 13.8 | 2500 | 18.1 | 160.8 | 0.66 | 0.32 |
| Ex. (63) | Com. (P 4-32) | 5.9 | 14.1 | 2500 | 17.7 | 152.5 | 0.66 | 0.31 |
| Ex. (64) | Com. (P 4-33) | 5.9 | 13.6 | 2500 | 18.4 | 164.8 | 0.66 | 0.32 |
| Ex. (65) | Com. (P 4-34) | 5.9 | 13.9 | 2500 | 17.9 | 155.0 | 0.66 | 0.32 |
| Ex. (66) | Com. (P 4-38) | 5.9 | 14.0 | 2500 | 17.9 | 153.8 | 0.66 | 0.32 |
| Ex. (67) | Com. (P 4-41) | 5.9 | 14.3 | 2500 | 17.5 | 148.3 | 0.66 | 0.32 |
| Ex. (68) | Com. (P 4-43) | 5.9 | 14.5 | 2500 | 17.3 | 146.2 | 0.66 | 0.31 |
| Ex. (69) | Com. (P 4-45) | 5.9 | 14.5 | 2500 | 17.3 | 151.6 | 0.66 | 0.31 |
| Ex. (70) | Com. (P 4-46) | 5.9 | 14.4 | 2500 | 17.3 | 153.9 | 0.66 | 0.31 |

From the measured results shown in Table 4 above, it is confirmed that OLED using the compound according to an embodiment of the present invention as a phosphorescent red host material of a light emitting layer showed the improved luminous efficiency and lifetime, particularly, remarkable luminous efficiency as compared with OLED using Comparative Compounds 1 to 6. First, when Comparative Compound 2 to Comparative Compound 6 were used as the phosphorescent host material, the driving voltage, the luminous efficiency, and the lifetime were remarkably improved, rather than the Comparative Compound 1 being CBP used as a common host material.

Further, comparing the compound of the present invention with the comparative compound 2 and the comparative compound 3, it can be seen that the characteristics of OLED vary depending on the kind of the substituent bonded to the N of the core and the bonding position of the substituent even though the core is the same.

Comparing the Comparative compounds 2 and 3 which have the same core but differ in substituent type, Comparative compound 3 shows a further improved luminous efficiency in comparison with the Comparative compound 2. This is because Comparative Compound 3 substituted with benzothienopyrimidine is more suitable for stably accepting both holes and electrons, comparing to Comparative compound 2 substituted with quinazoline.

Further, comparing the Comparative compounds 3 and the compound of the present invention which have the same core and substituent but differ in the bonding position, when the compound of the present invention is used, the luminous efficiency is remarkably higher than that in the case of using the Comparative compound 3. This is because the following reasons: The energy level of the compound changes depending on which position of the substituent is bonded to the N of the core. The compound of the present invention has a proper T1 value for facilitating the electron transfer from the host to the dopant and a deeper HOMO value than the Comparative compound 3. As a result, the movement of the holes is delayed and the charge balance in the light emitting layer is increased, thereby maximizing the luminous efficiency.

Furthermore, since it is necessary to grasp the correlation with the hole transport layer and the dopant in the case of the phosphorescent host, it is very difficult to infer the excellent electrical characteristics of the compound of the present invention exhibited in the phosphorescent host even though using the compound having the similar core.

Although the exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed herein is intended to illustrate the scope of the technical idea of the present invention, and the scope of the present invention is not limited by the embodiments. The scope of the present invention shall be construed on the basis of the accompanying claims, and it shall be

The invention claimed is:
1. A compound of Formula 1:

[Formula 1]

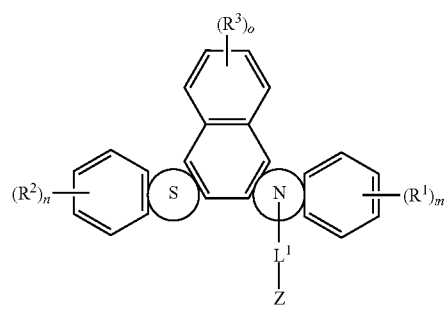

wherein,
S ring is a $C_4$ heterocyclic group comprising S,
N ring is a $C_4$ heterocyclic group comprising N,
$R^1$ to $R^3$ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-N($R^a$)($R^b$), a $C_1$-$C_{30}$ alkoxyl group and a $C_6$-$C_{30}$ aryloxy group, and neighboring groups are optionally linked to each other to form at least one ring,
m, n and o are each an integer of 0 to 4, and when each of them is an integer of 2 or more, each of the plurality of $R^1$ to $R^3$ may be the same or different from each other,
$L^1$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring,
Z is represented by the following formula,

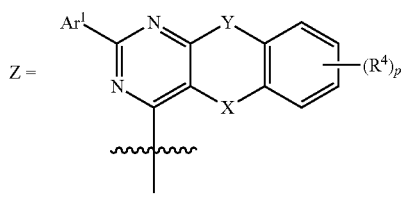

wherein,
X and Y are each independently a single bond, O or S, and one of X and Y is a a single bond and the other is O or S,
$R^4$ is selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-N($R^a$)($R^b$), a $C_1$-$C_{30}$ alkoxyl group and a $C_6$-$C_{30}$ aryloxy group,
p is an integer of 0 to 4, when p is an integer of 2 or more, the plurality of $R^4$ may be the same or different from each other, and neighboring groups are optionally linked to each other to form at least one ring,
$Ar^1$ is selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P,
$L^a$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring,
$R^a$ and $R^b$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, and a $C_2$-$C_{20}$ alkenyl group, and
the aryl group, arylene group, fluorenyl group, fluorenylene group, heterocyclic group, fused ring group, alkyl group, alkenyl group, alkynyl group, alkoxyl group and aryloxyl group are each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

2. The compound of claim 1 represented by one of the following Formulas 2 to 5:

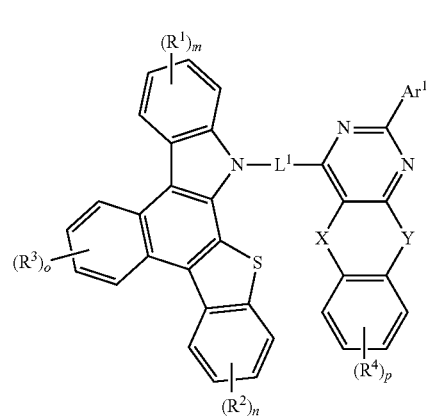

<Formula 2>

<Formula 3>
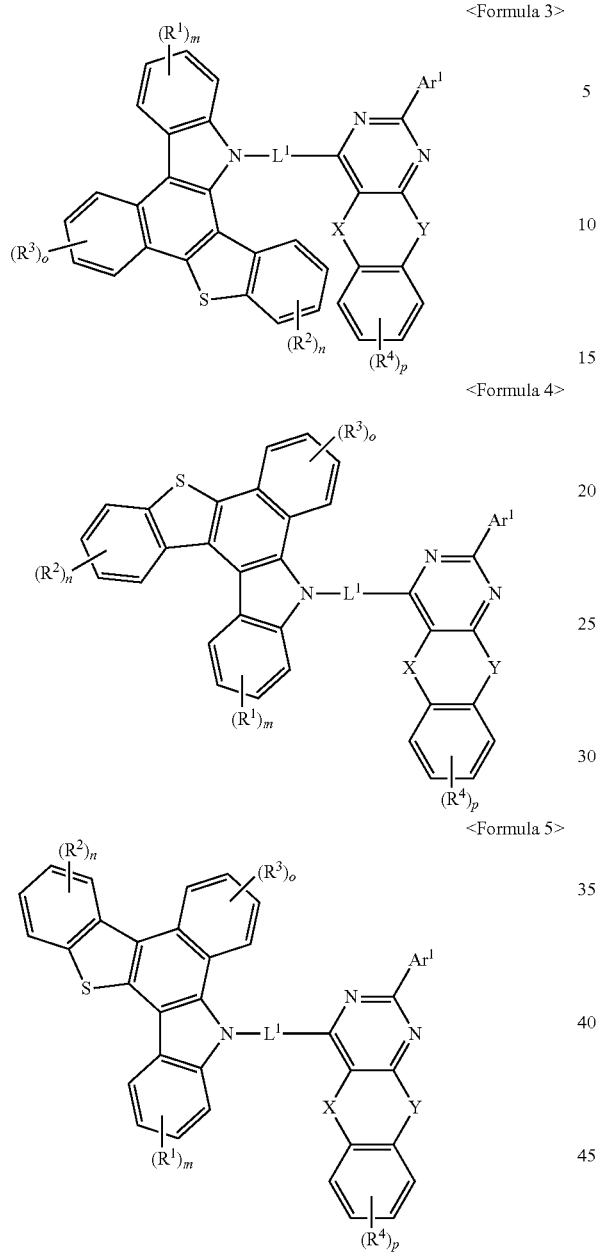
<Formula 4>
<Formula 5>
wherein X, Y, R¹~R⁴, L¹, Ar¹, m, n, o and p are the same as defined in claim 1.
3. The compound of claim 1, wherein Z is represented by one of the following formulas Z-1 to Z-8:
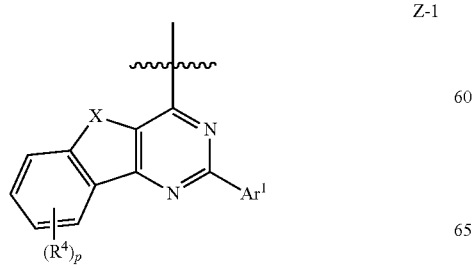
Z-1
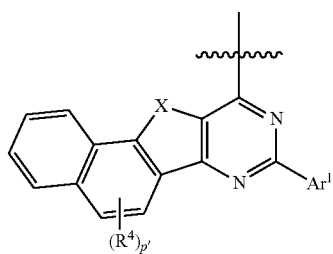
Z-2
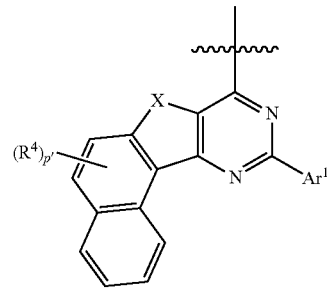
Z-3
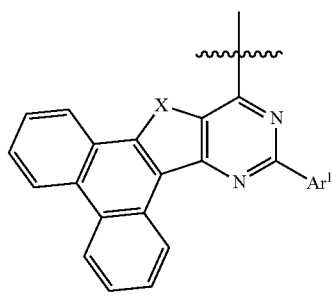
Z-4
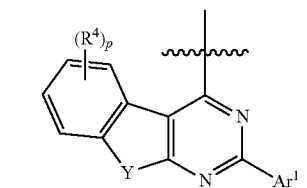
Z-5
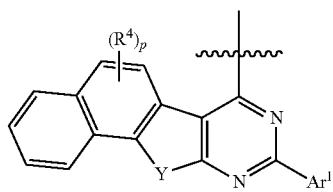
Z-6
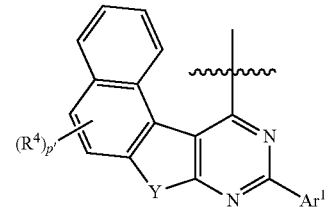
Z-7

Z-8
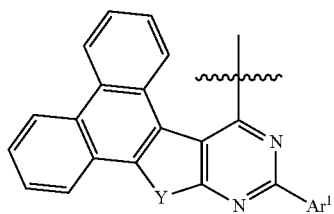
wherein X, Y, Ar¹, R⁴ and p are the same as defined in claim 1 and p' is an integer of 0 to 2.
4. The compound of claim 1 represented by one of the following Formulas 2-1 to 5-4:
<Formula 2-1>
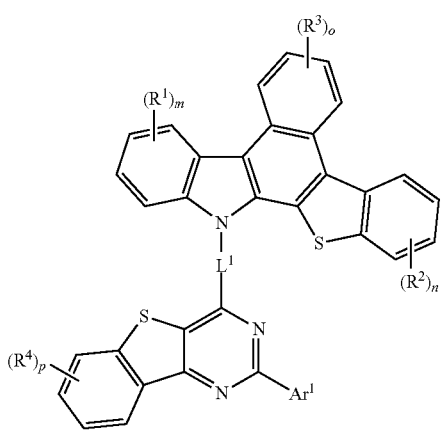
<Formula 2-2>
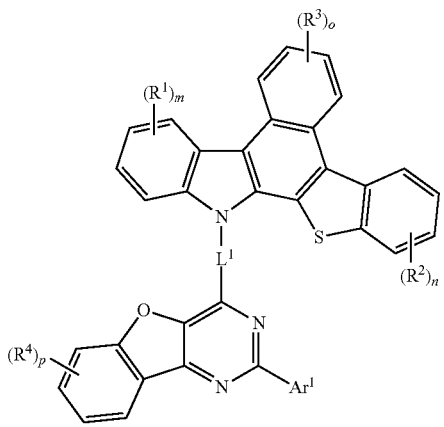
<Formula 2-3>
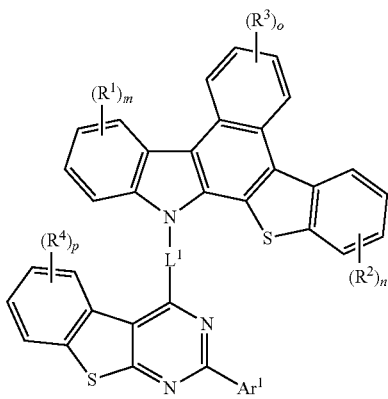
<Formula 2-4>
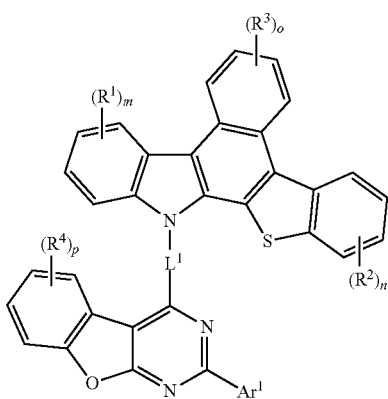
<Formula 3-1>
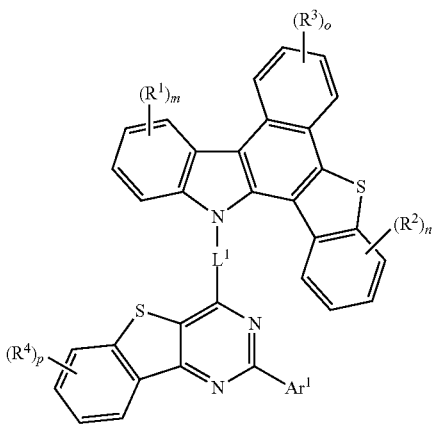

<Formula 3-2>
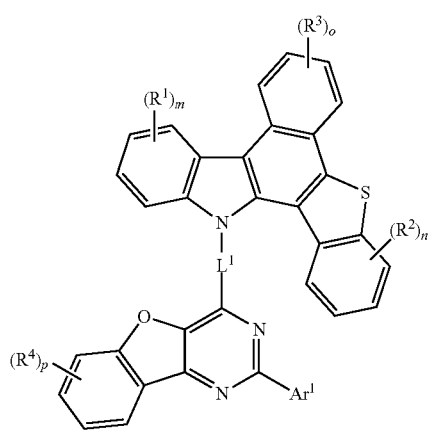
<Formula 4-1>
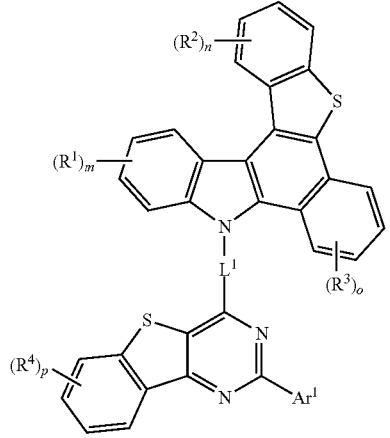
<Formula 3-3>
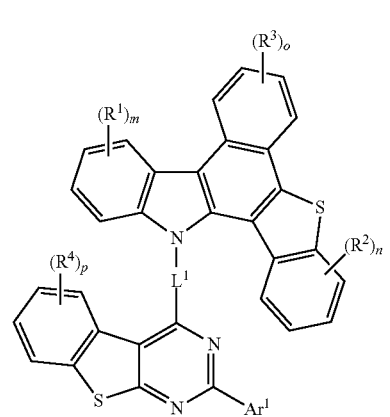
<Formula 4-2>
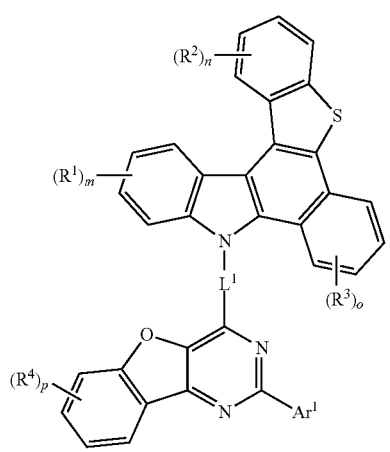
<Formula 3-4>
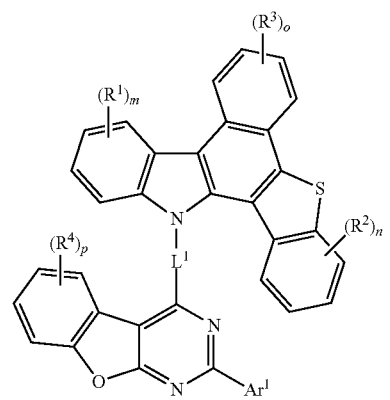
<Formula 4-3>
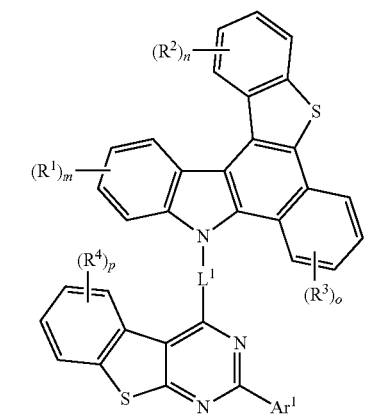

<Formula 4-4>
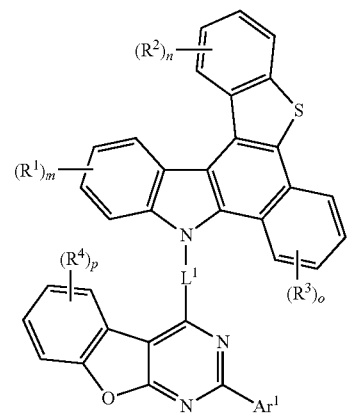
<Formula 5-1>
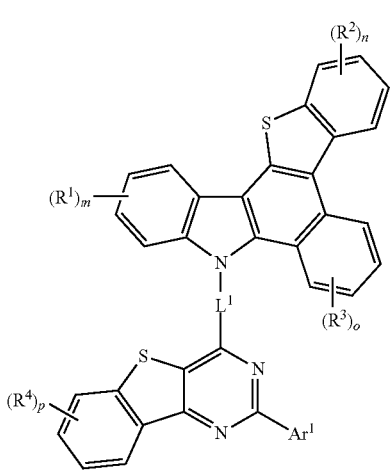
<Formula 5-2>
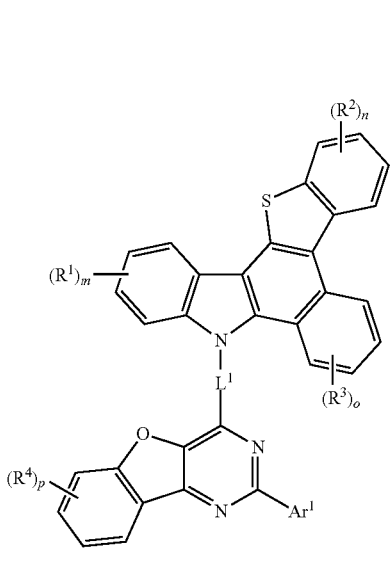
<Formula 5-3>
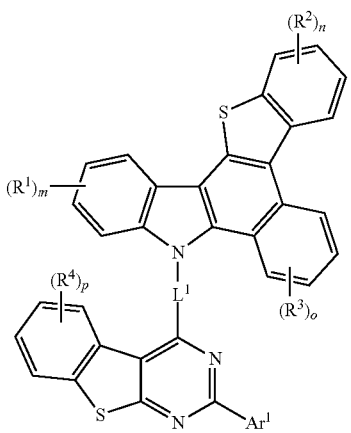
<Formula 5-4>
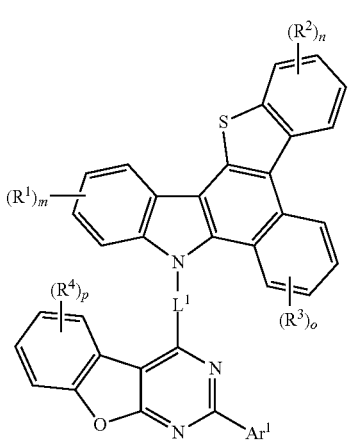
wherein $R^1$~$R^4$, $L^1$, $Ar^1$, m, n, o and p are the same as defined for Formula 1 in claim 1.
5. The compound of claim 1, wherein $Ar^1$ is represented by one of the following formulas Ar-1 to Ar-10:
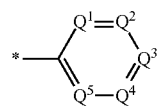
Ar-1
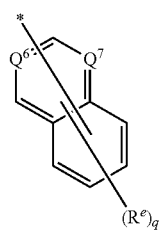
Ar-2
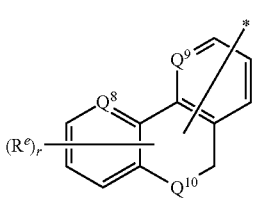
Ar-3

Ar-4

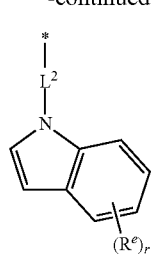

Ar-5

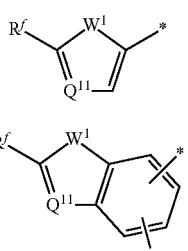

Ar-6

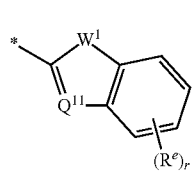

Ar-7

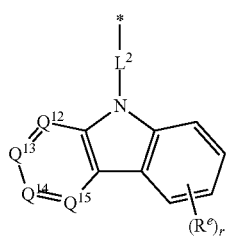

Ar-8

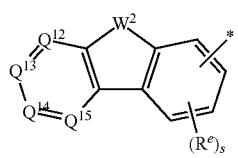

Ar-9

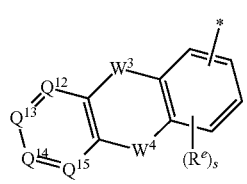

Ar-10 wherein $L^2$ is the same as $L^1$ defined in claim 1, $Q^1 \sim Q^{15}$ are each independently $C(R^g)$ or N, wherein $R^g$ is selected from the group consisting of hydrogen, deuterium, a $C_6$-$C_{20}$ aryl group, a fluorenyl group, a fused ring group of a $C_3$-$C_{20}$ aliphatic ring and a $C_6$-$C_{20}$ aromatic ring, a $C_2$-$C_{20}$ heterocyclic group containing at least one heteroatom selected from the group consisting of O, N, S, Si, and P, a $C_1$-$C_{20}$ alkyl group, a $C_2$-$C_{20}$ alkenyl group, a $C_2$-$C_{20}$ alkynyl group, and a $C_1$-$C_{30}$ alkoxyl group, $W^1$ is S, O or $N(R^h)$, and $W^2 \sim W^4$ are each independently S, O, $N(R^h)$ or $C(R^i)(R^j)$, wherein $R^h \sim R^j$ are each independently selected from the group consisting of a $C_6$-$C_{20}$ aryl group, a $C_2$-$C_{20}$ heterocyclic group containing at least one heteroatom selected from the group consisting of O, N, S, Si, and P, a $C_1$-$C_{20}$ alkyl group, a $C_2$-$C_{20}$ alkenyl group, a $C_1$-$C_{30}$ alkoxyl group, and a fluorenyl group, $R^e$ is selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group, and neighboring $R^e$ groups are optionally linked to each other to form a ring, q is an integer of 0 to 5, r is an integer of 0 to 4, s is an integer of 0 to 3, and when each of them is an integer of 2 or more, each of the plurality of $R^e$s may be the same or different from each other, $R^f$ is selected from the group consisting of hydrogen, deuterium, a $C_6$-$C_{20}$ aryl group, a fluorenyl group, a fused ring group of a $C_3$-$C_{20}$ aliphatic ring and a $C_6$-$C_{20}$ aromatic ring, a $C_2$-$C_{20}$ heterocyclic group containing at least one heteroatom selected from the group consisting of O, N, S, Si, and P, a $C_1$-$C_{20}$ alkyl group, a $C_2$-$C_{20}$ alkenyl group, a $C_2$-$C_{20}$ alkynyl group, and a $C_1$-$C_{30}$ alkoxyl group.

6. The compound of claim 1, wherein Formula 1 is any one of the following compounds P 1-1 to P 4-50:

P 1-1

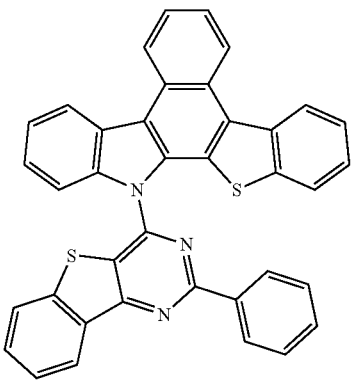

P 1-2

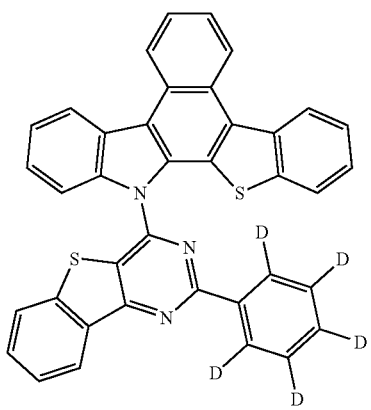

-continued
P 1-3
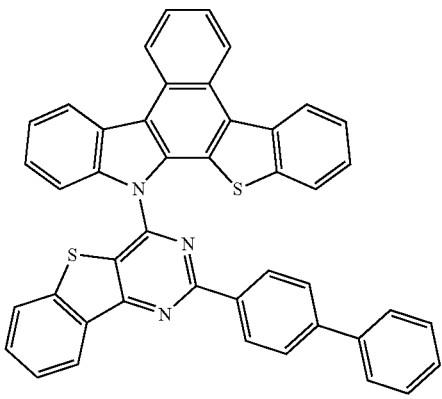
P 1-4
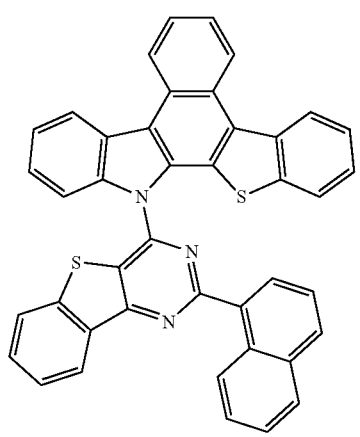
P 1-5
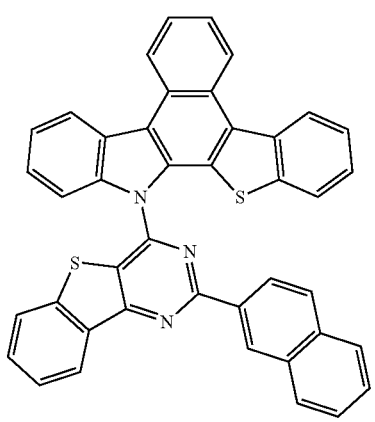
-continued
P 1-6
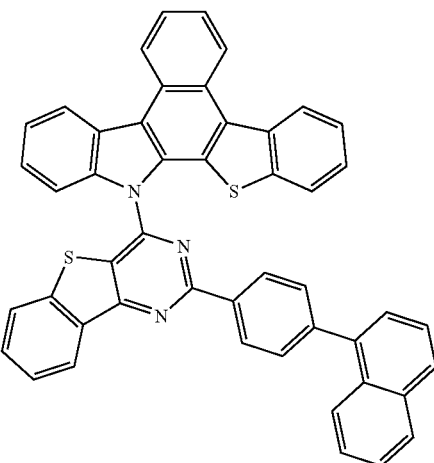
P 1-7
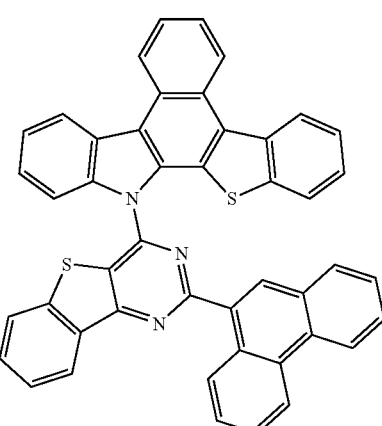
P 1-8
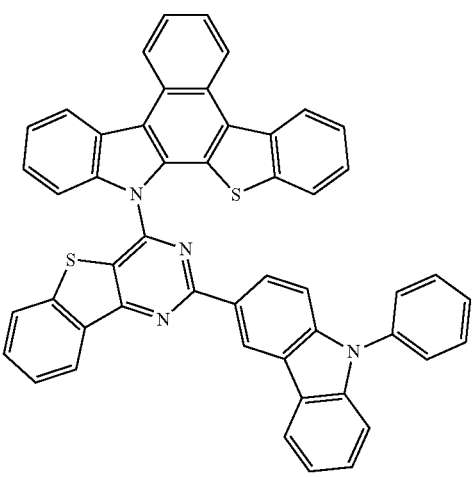

P 1-9
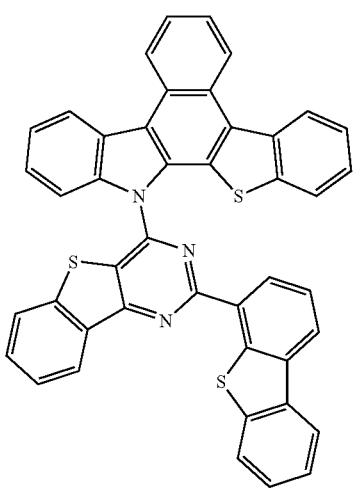
P 1-10
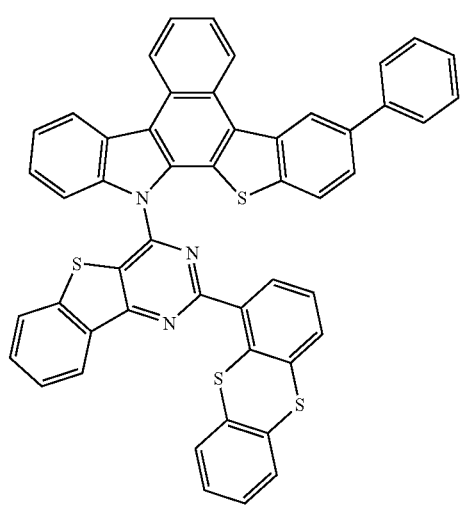
P 1-11
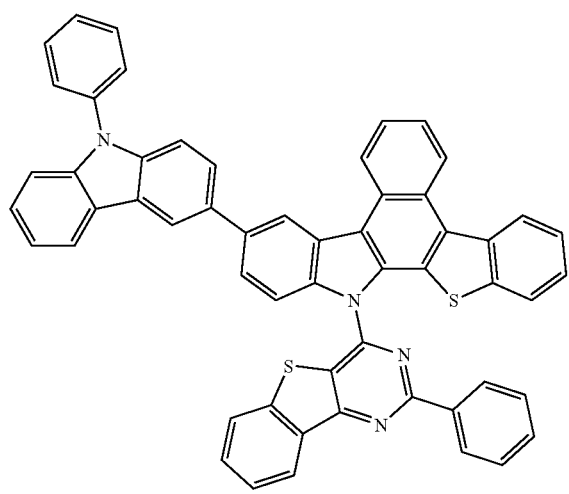
P 1-12
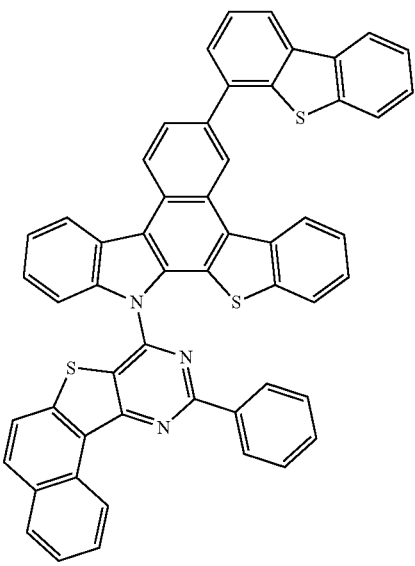
P 1-13
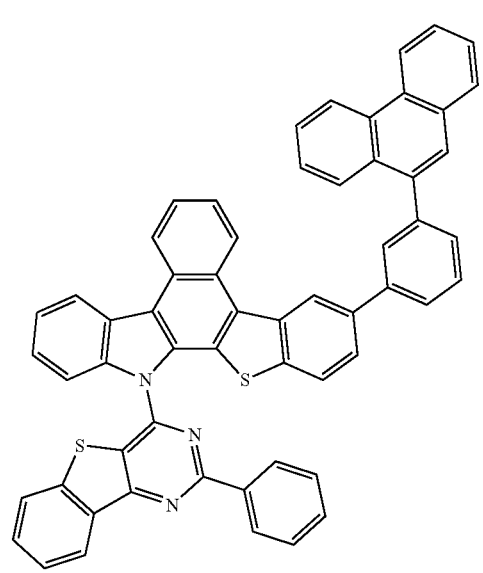
P 1-14
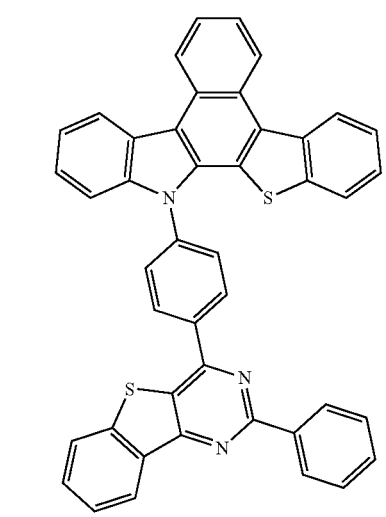

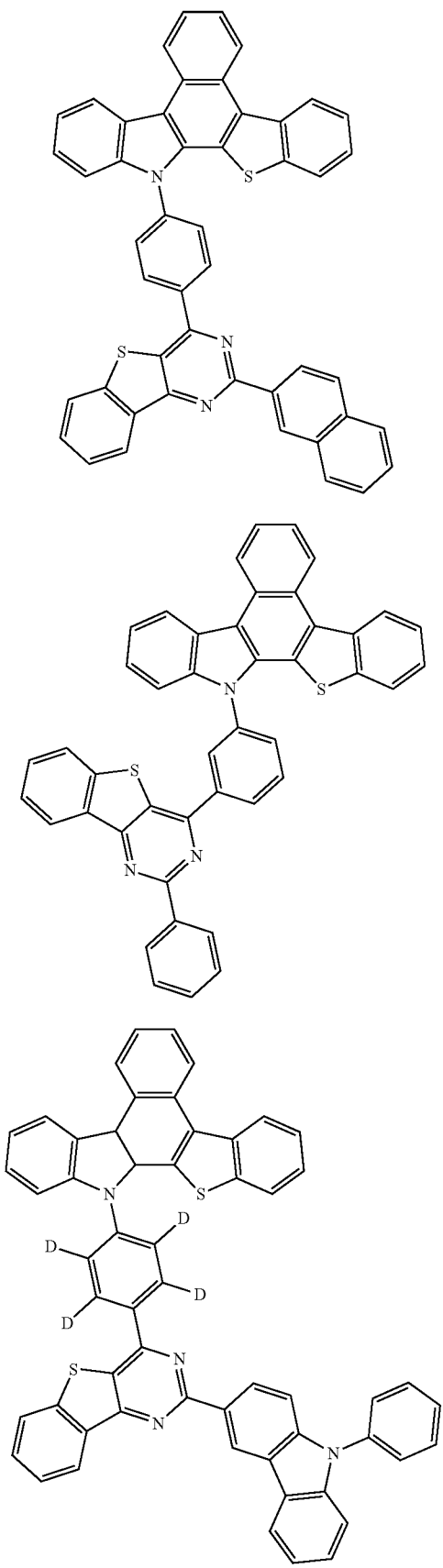
P 1-15
P 1-16
P 1-17
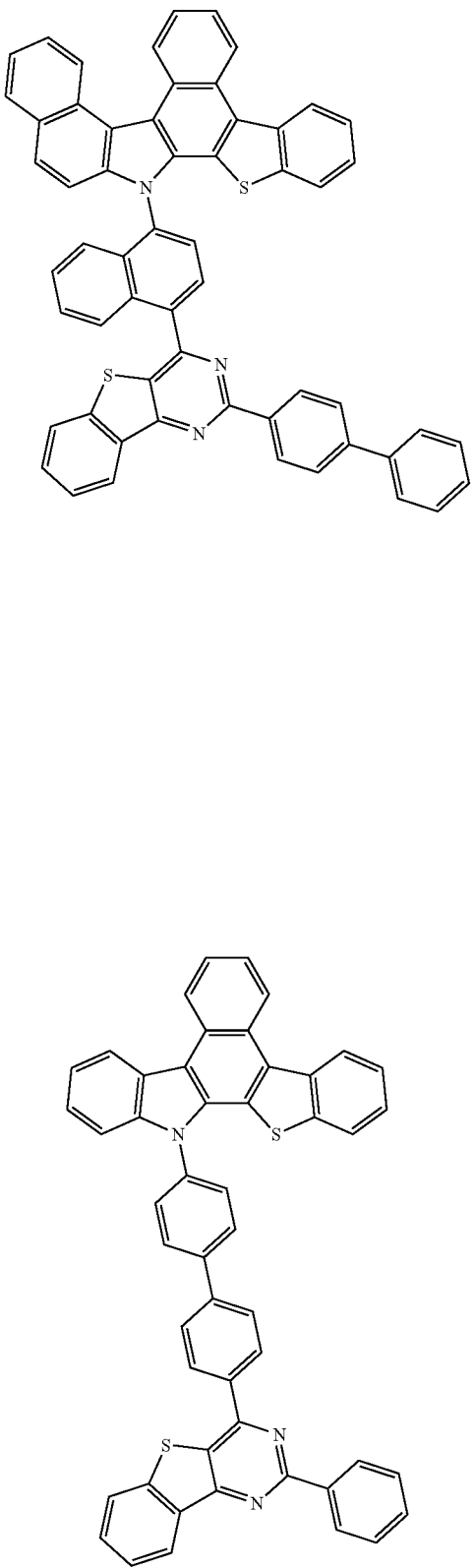
P 1-18
P 1-19

P 1-20
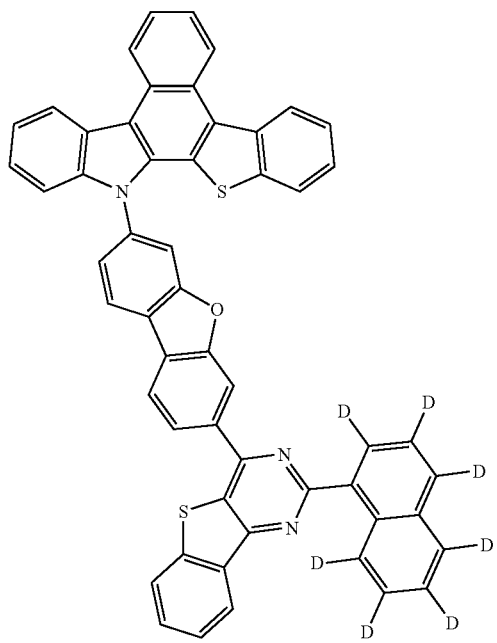
P 1-21
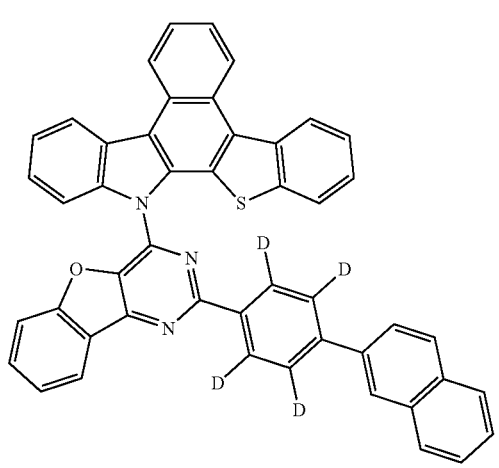
P 1-22
P 1-23
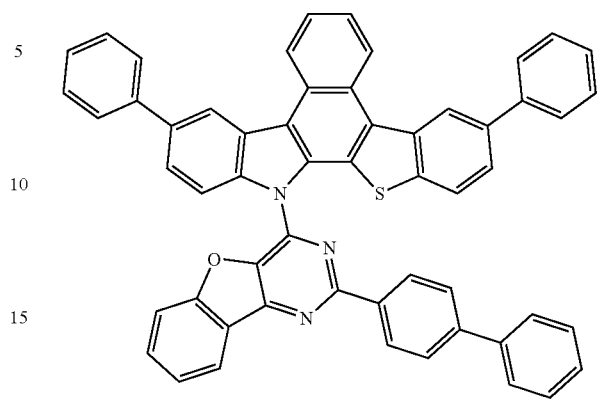
P 1-24
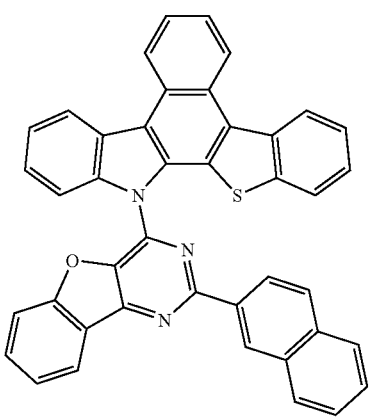
P 1-25
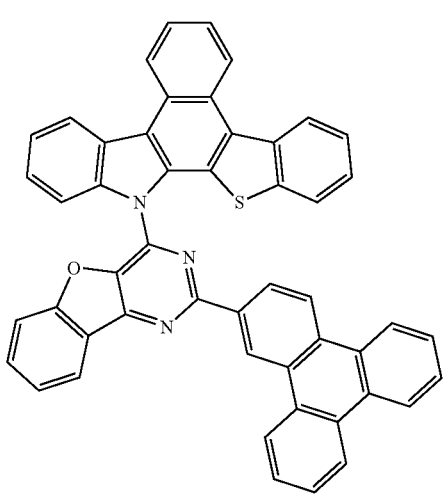

P 1-26
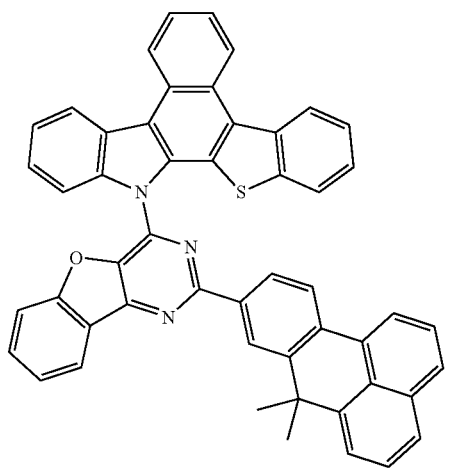
P 1-27
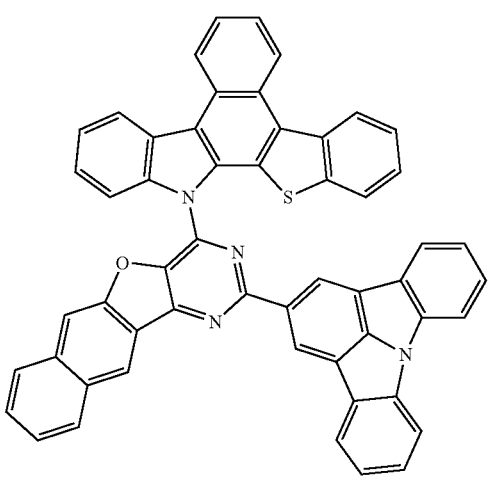
P 1-28
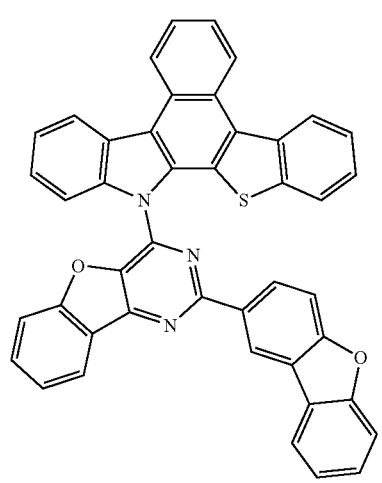
P 1-29
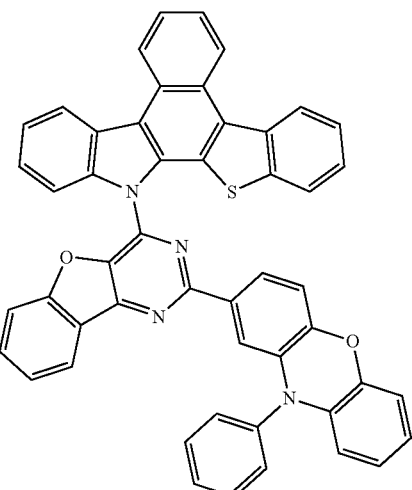
P 1-30
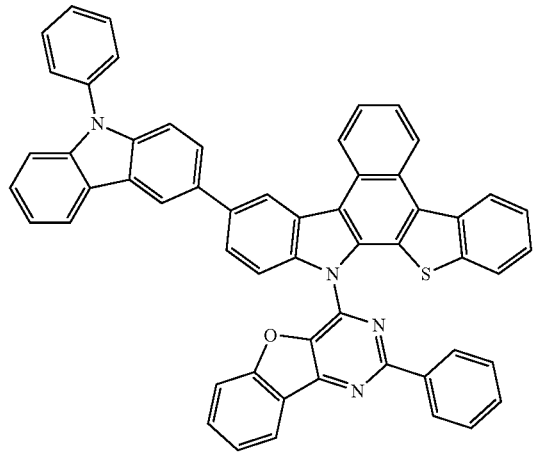
P 1-31

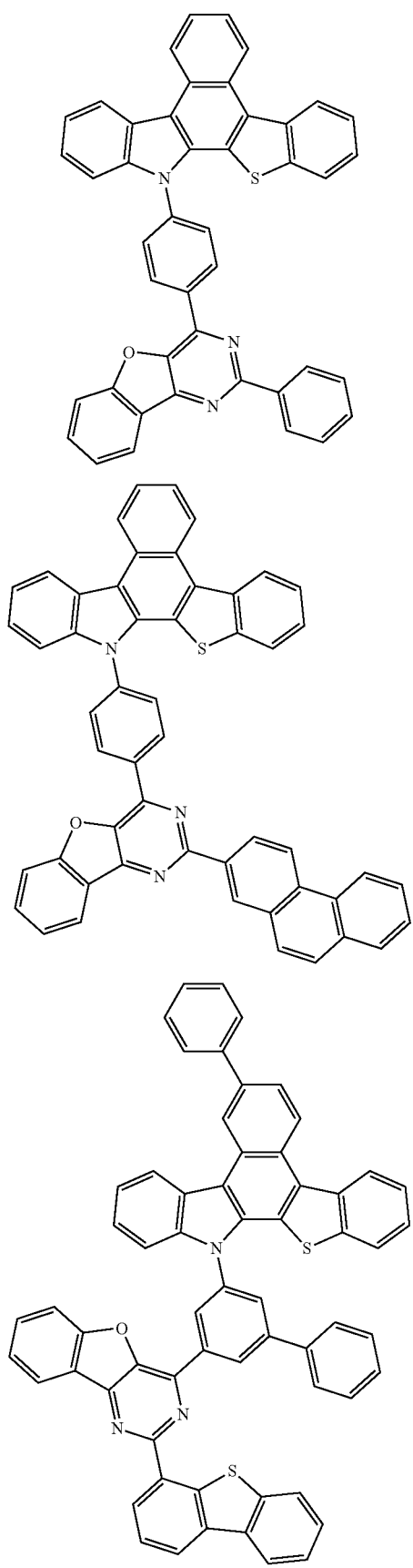
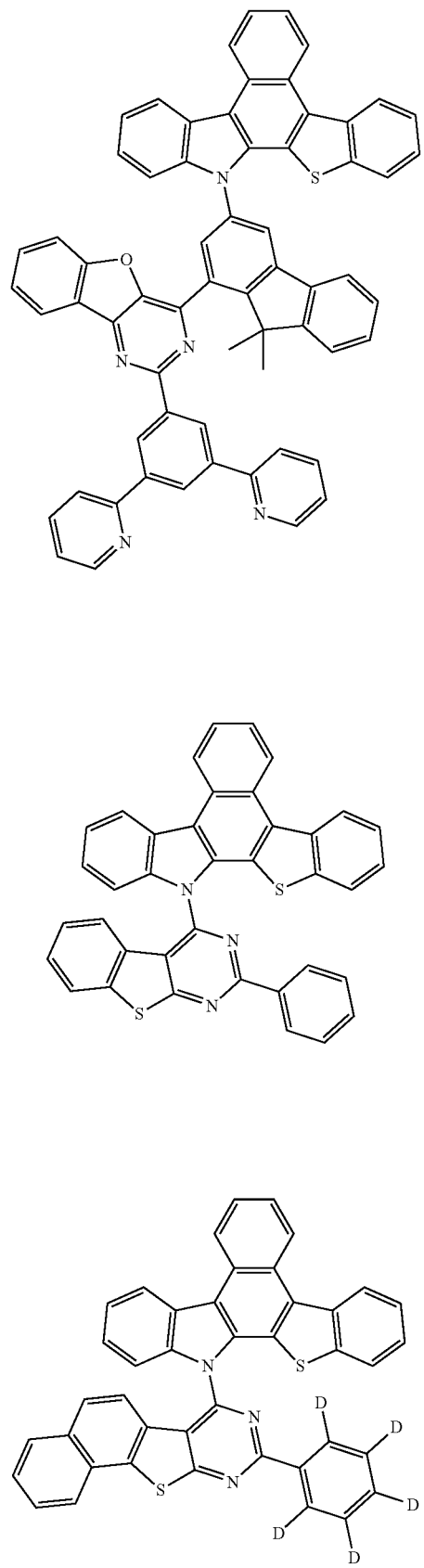

P 1-38
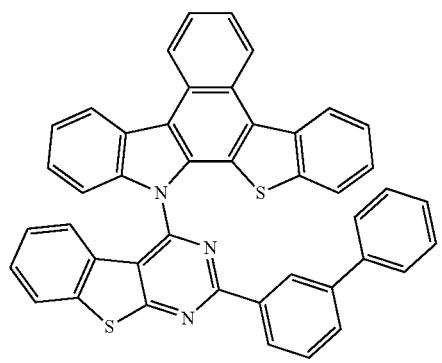
P 1-41
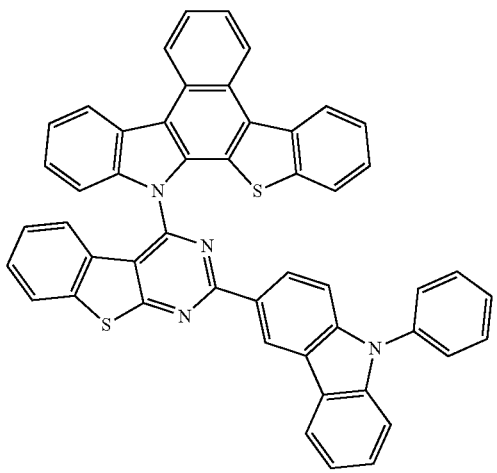
P 1-39
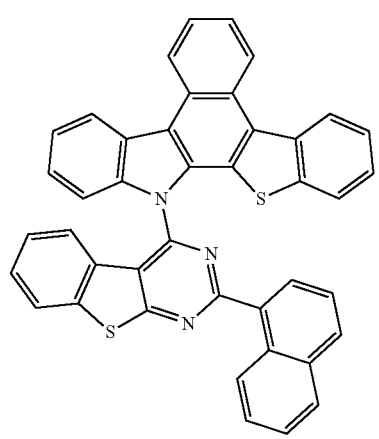
P 1-42
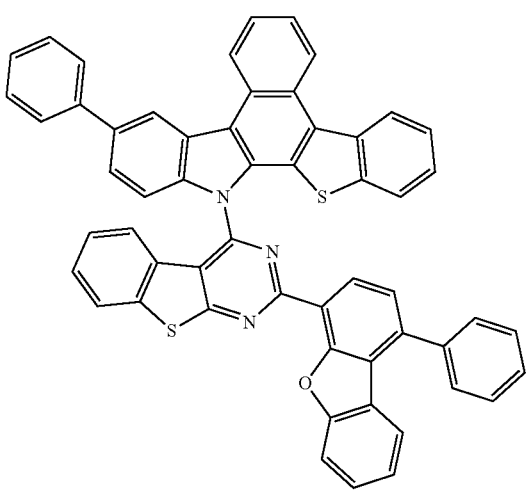
P 1-40
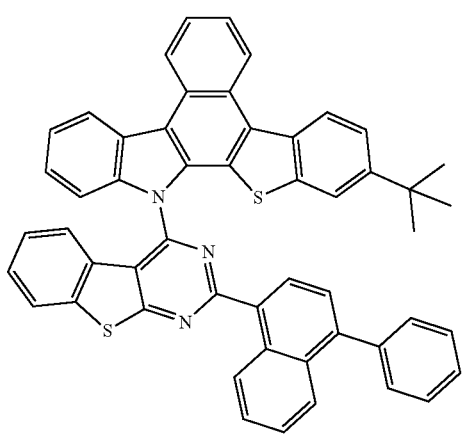
P 1-43
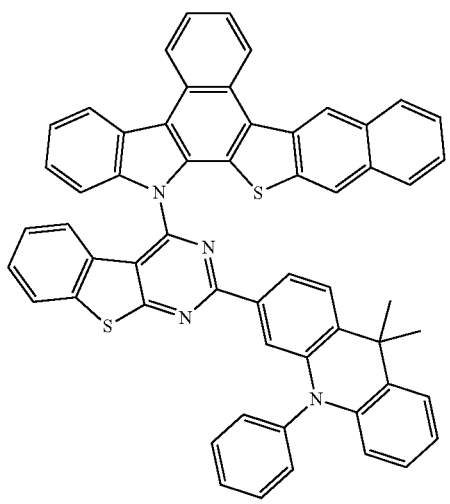

P 1-44
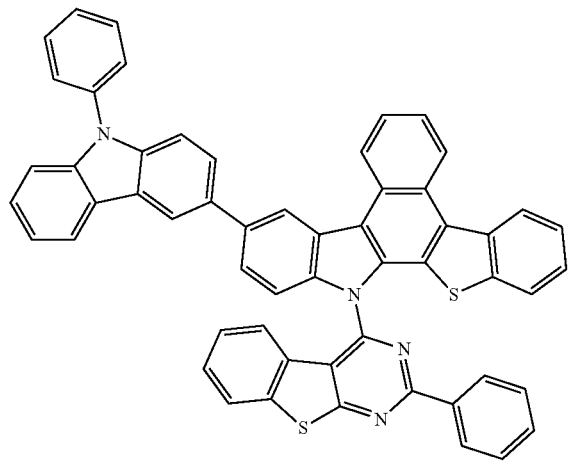
P 1-45
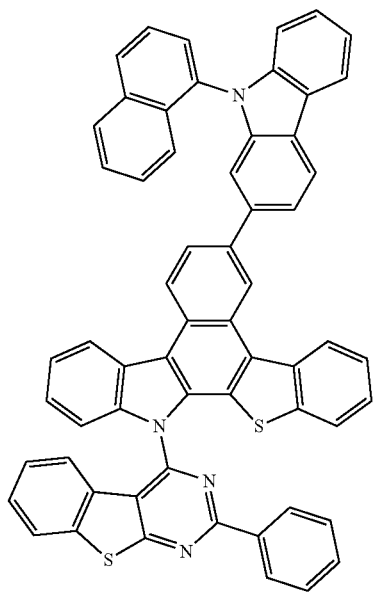
P 1-46
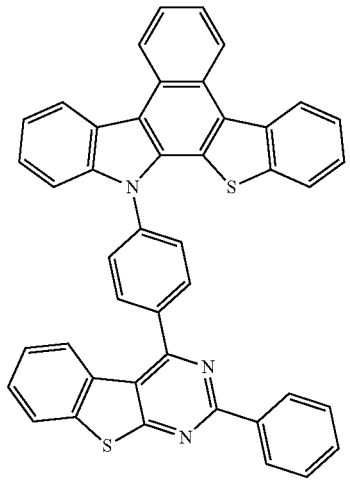
P 1-47
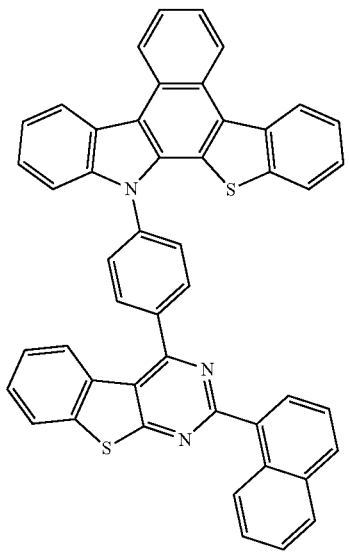
P 1-48
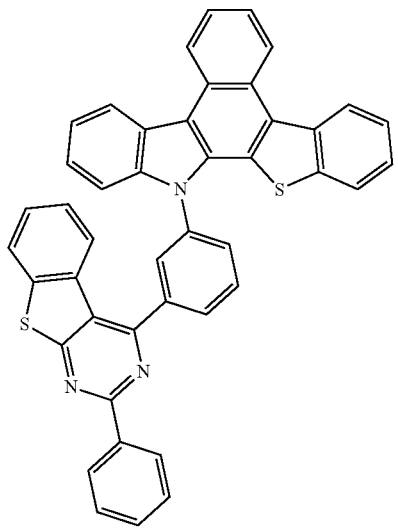
P 1-49
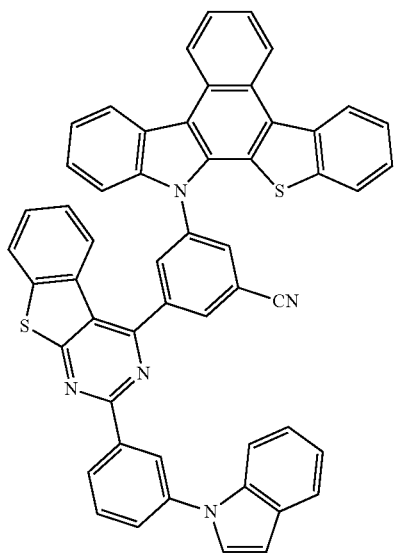

P 1-50
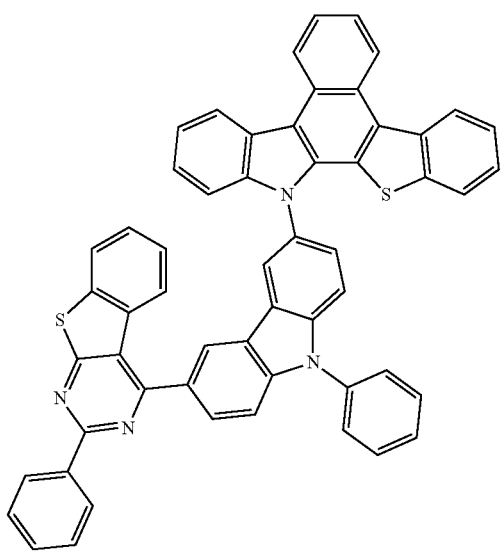
P 1-51
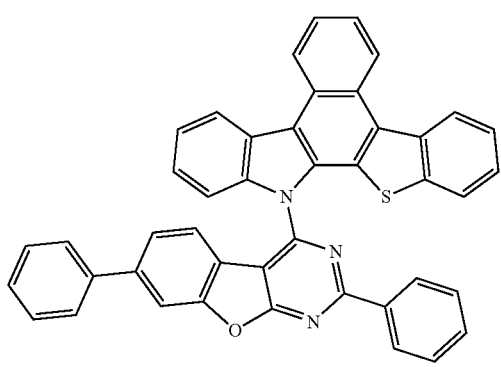
P 1-52
P 1-53
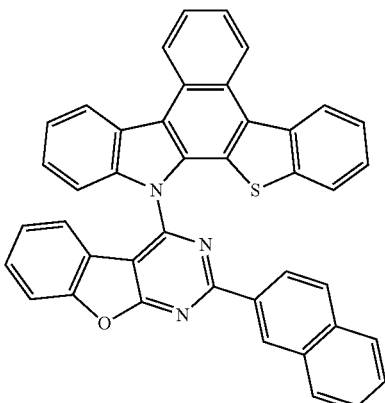
P 1-54
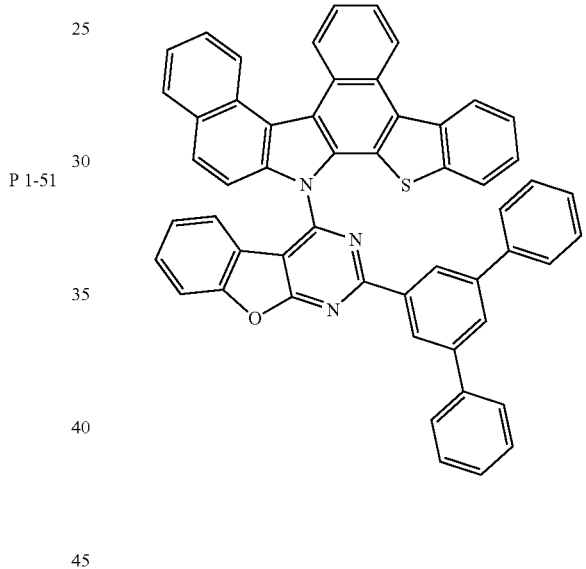
P 1-55
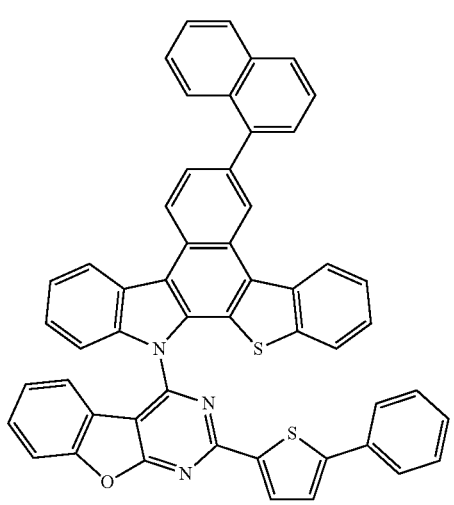

P 1-56
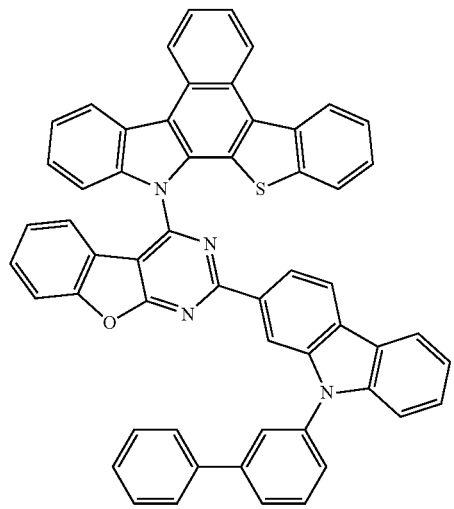
P 1-57
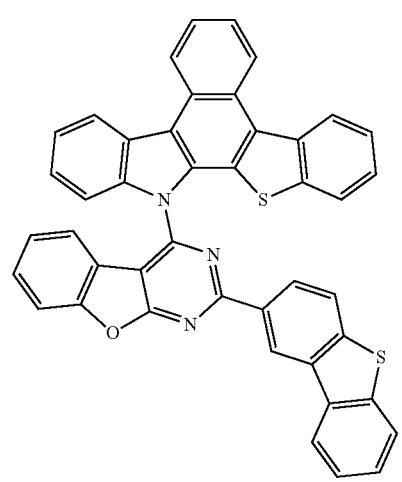
P 1-58
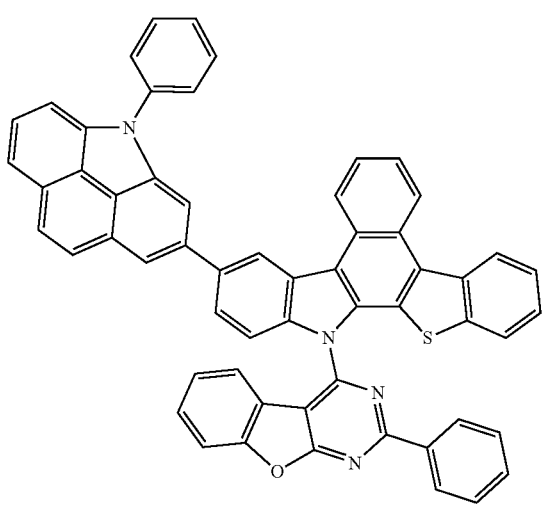
P 1-59
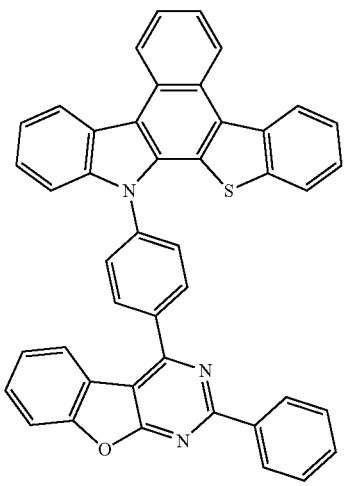
P 1-60
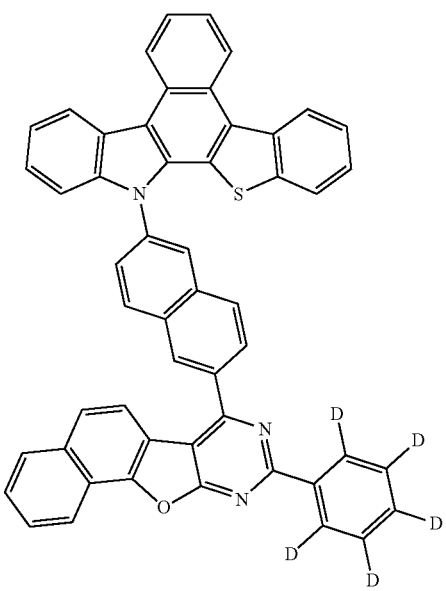
P 2-1
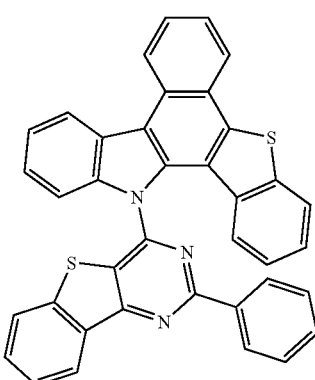

-continued
P 2-2
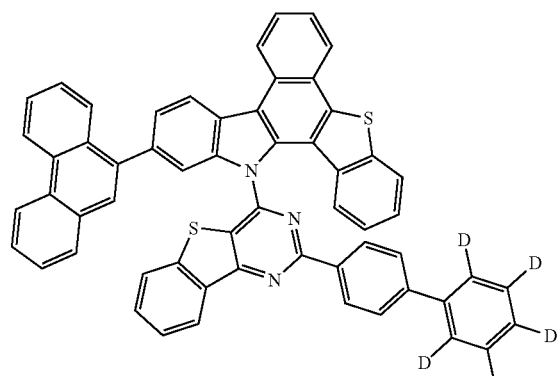
P 2-3
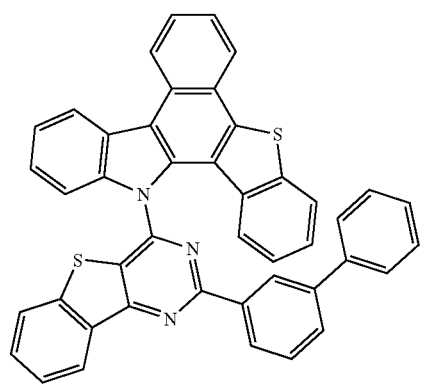
P 2-4
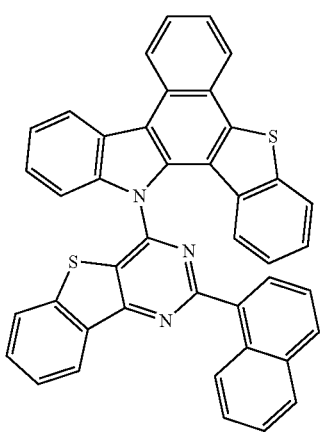
P 2-5
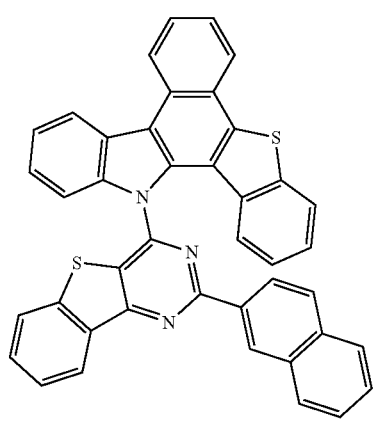
-continued
P 2-6
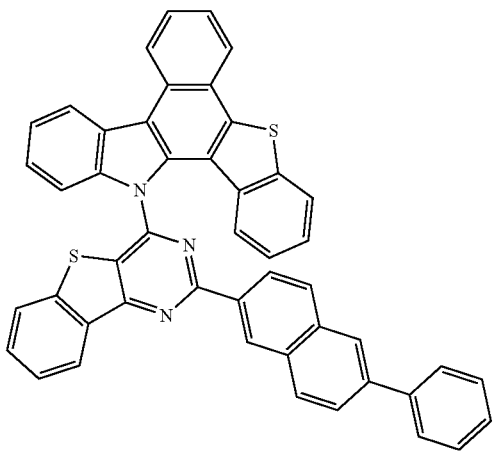
P 2-7
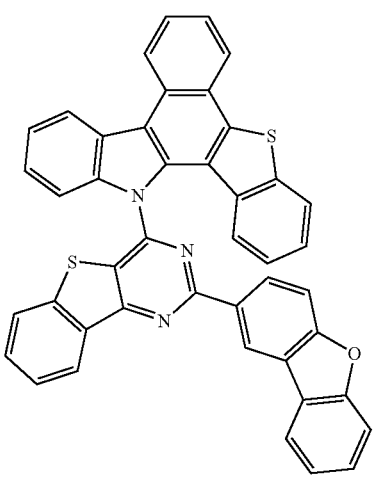
P 2-8
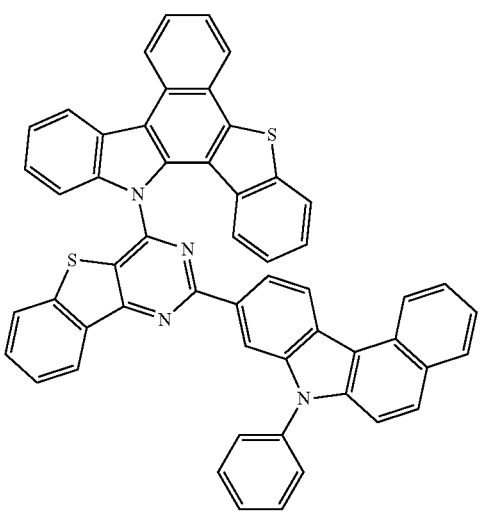

P 2-9
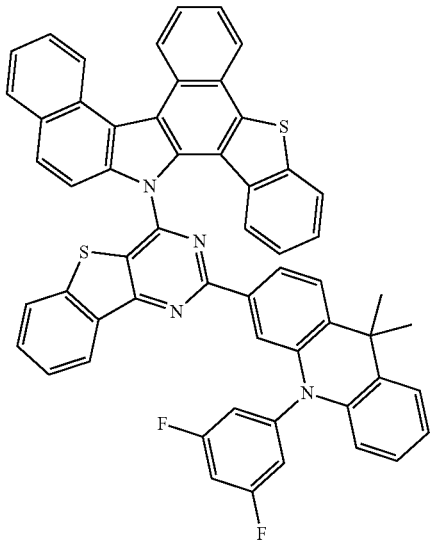
P 2-10
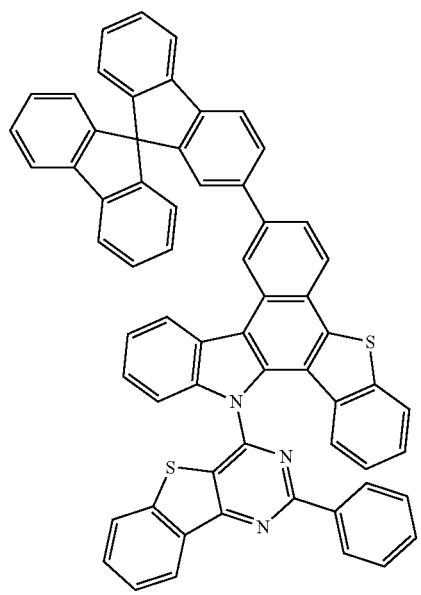
P 2-11
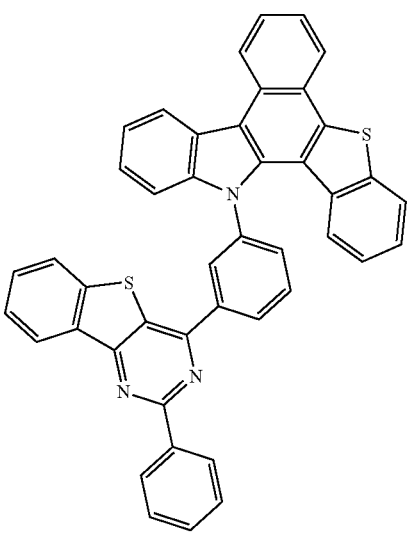
P 2-12
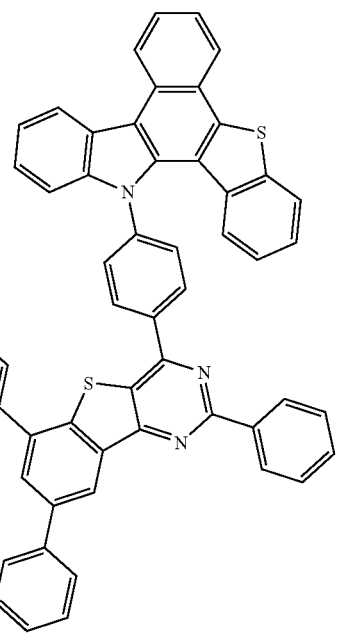
P 2-13
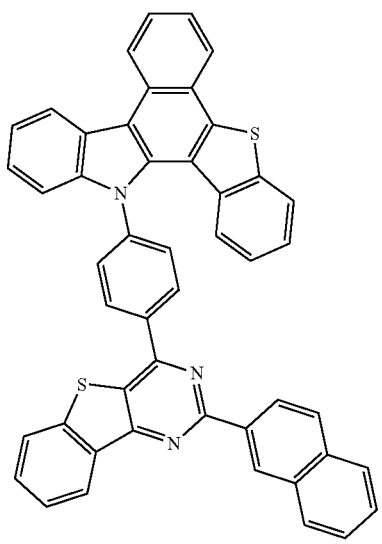
P 2-14
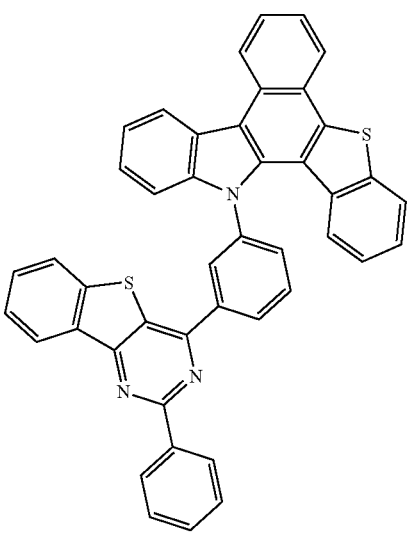

P 2-15
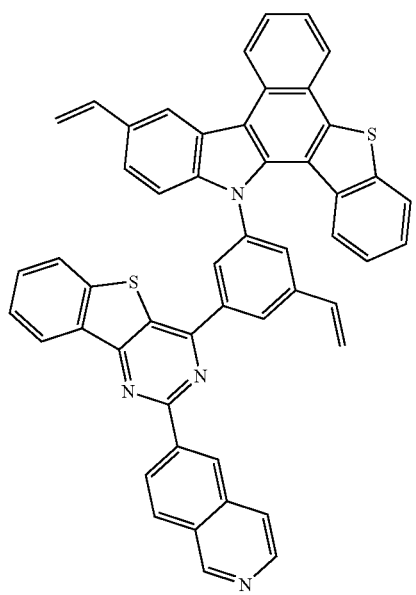
P 2-16
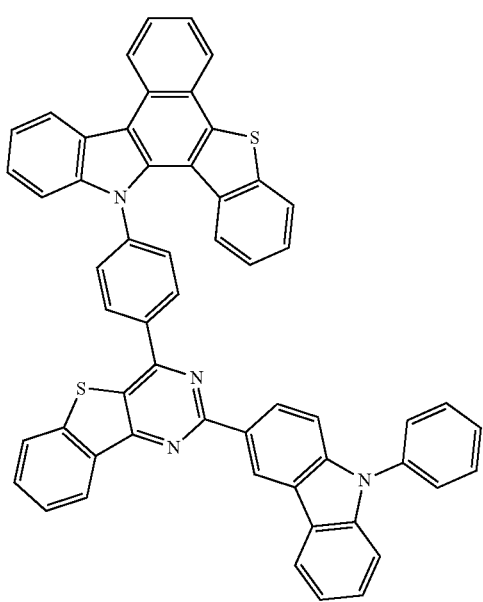
P 2-17
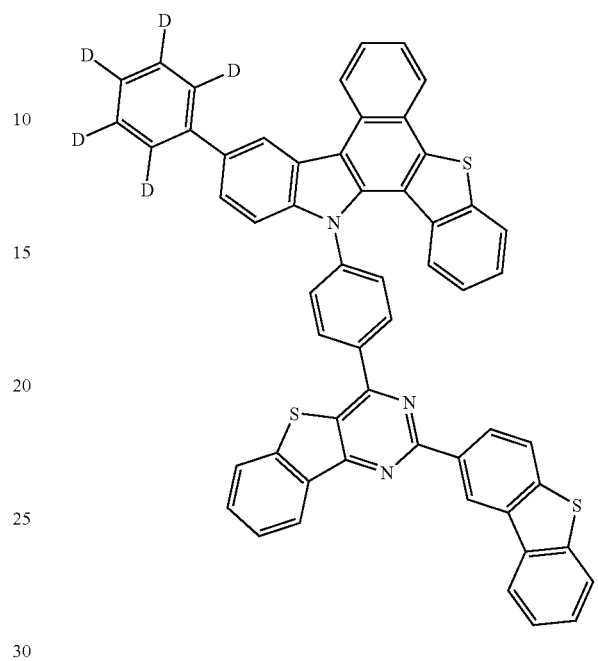
P 2-18
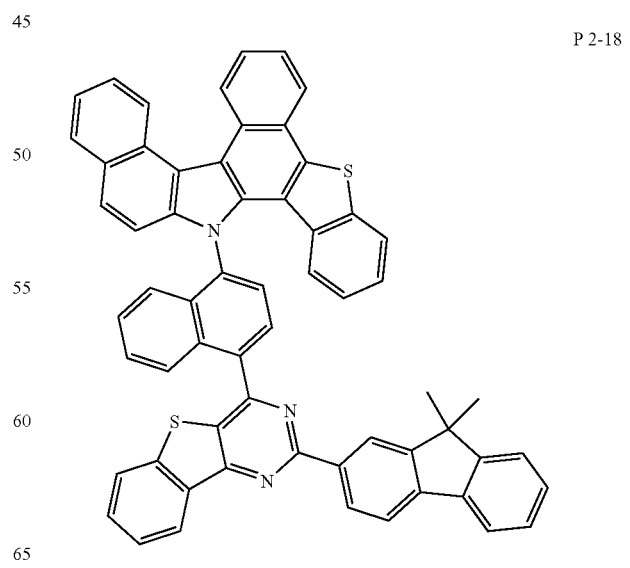

-continued
P 2-19
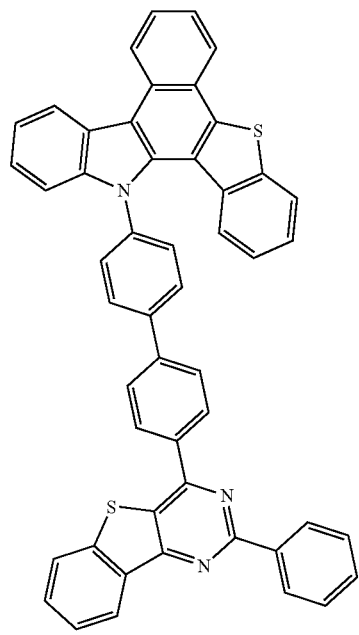
P 2-20
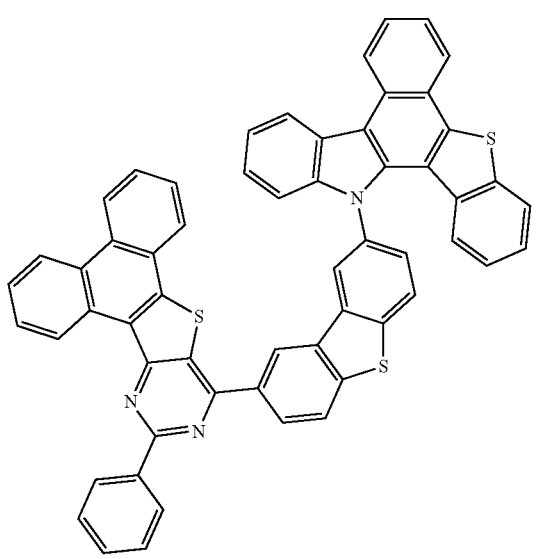
P 2-21
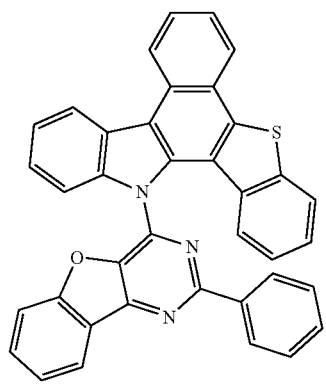
-continued
P 2-22
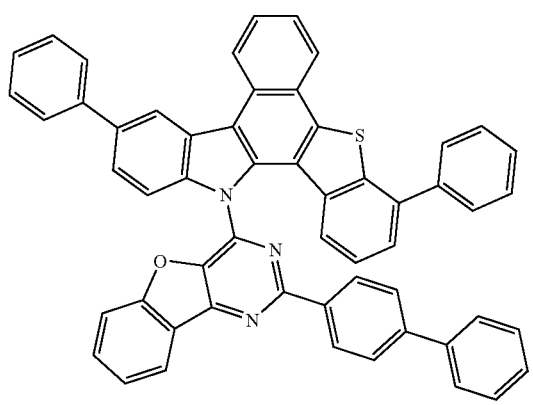
P 2-23
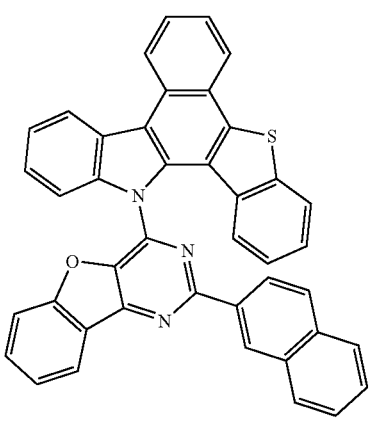
P 2-24
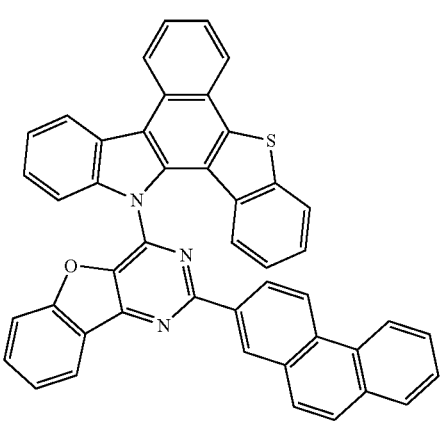

P 2-25
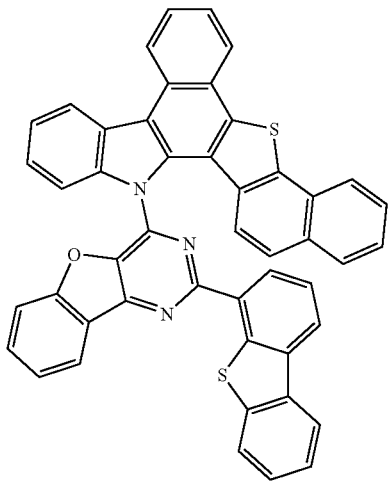
P 2-26
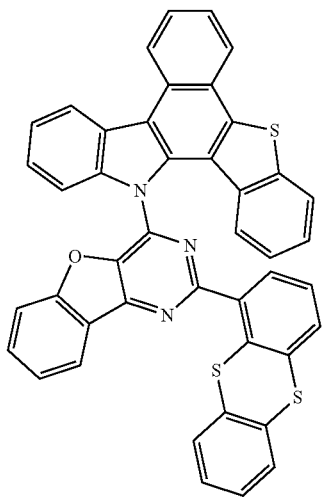
P 2-27
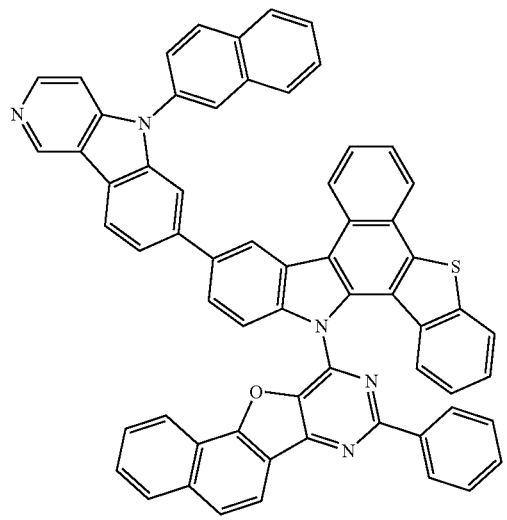
P 2-28
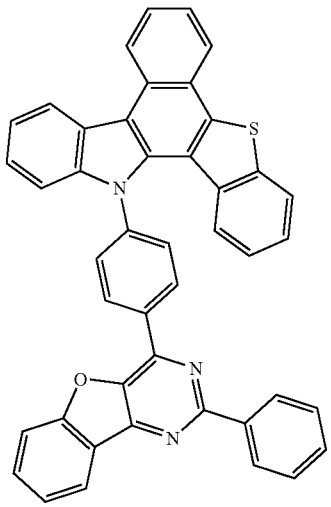
P 2-29
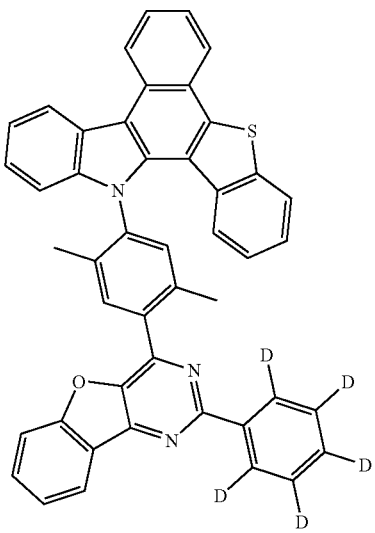
P 2-30
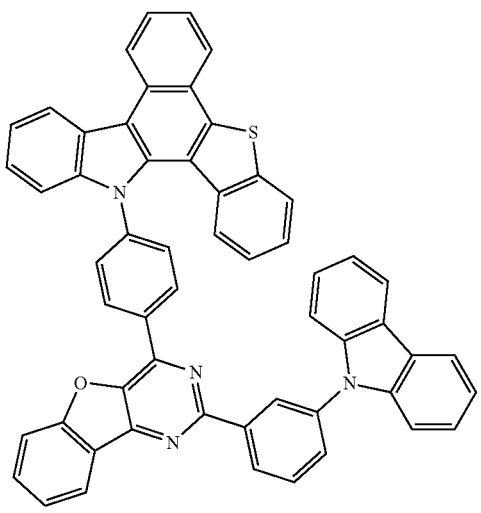

P 2-31
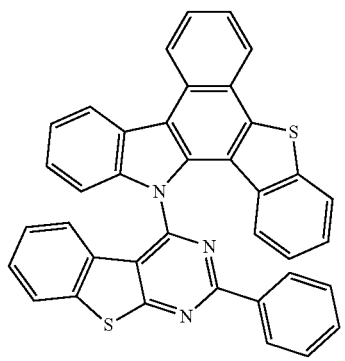
P 2-34
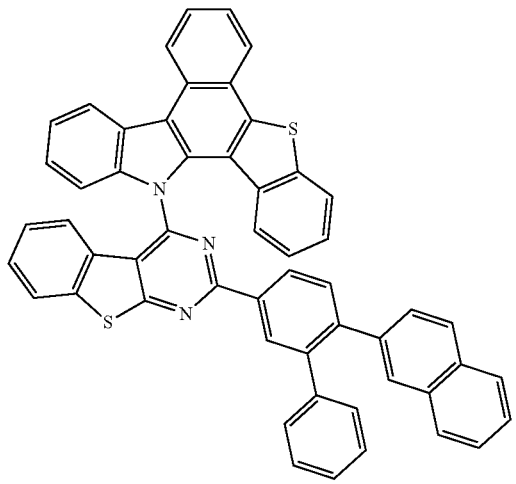
P 2-32
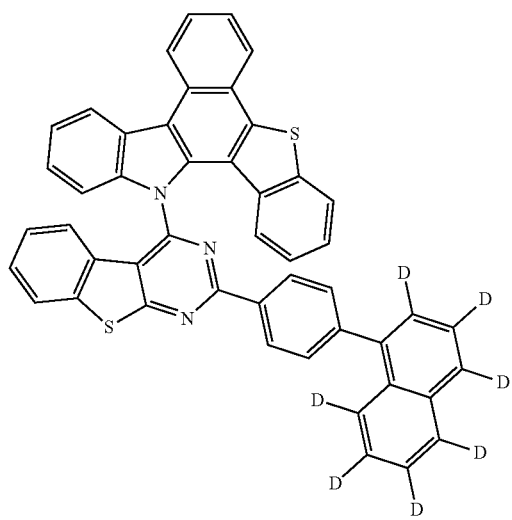
P 2-35
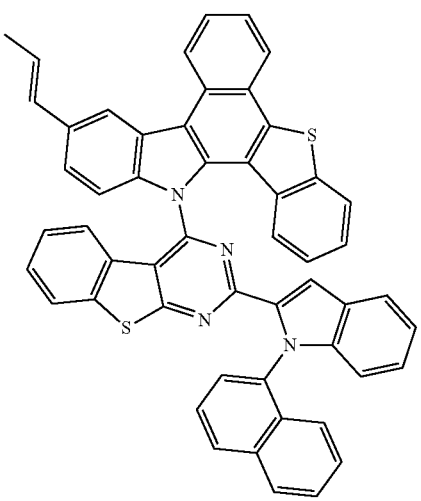
P 2-33
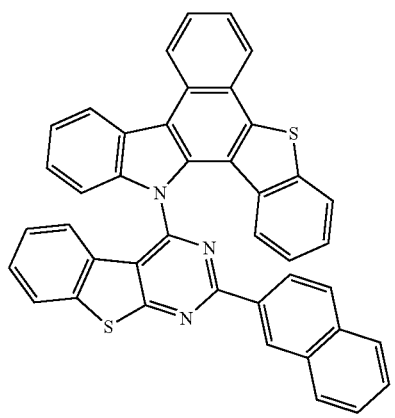
P 2-36
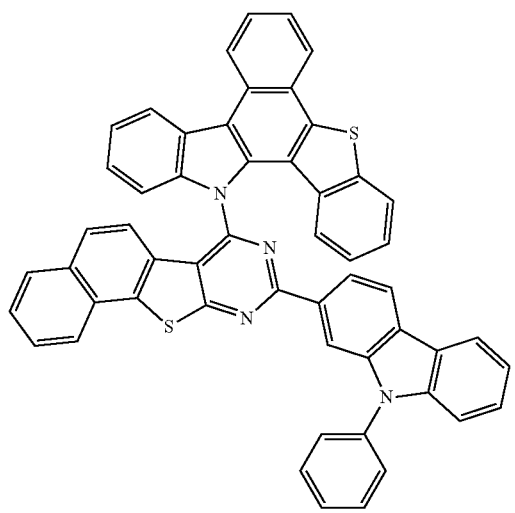

-continued
P 2-37
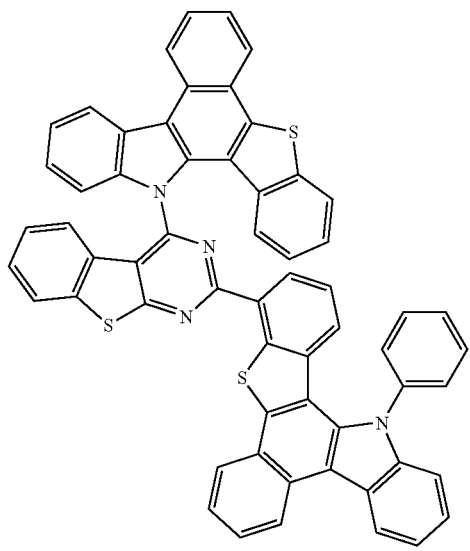
P 2-38
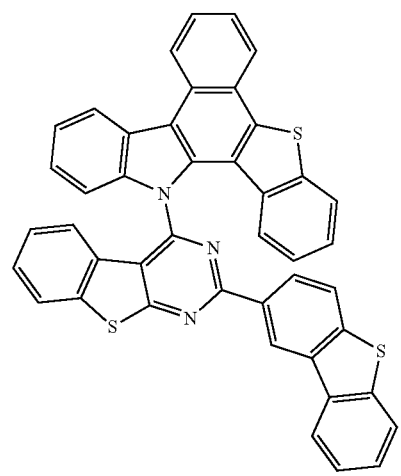
P 2-39
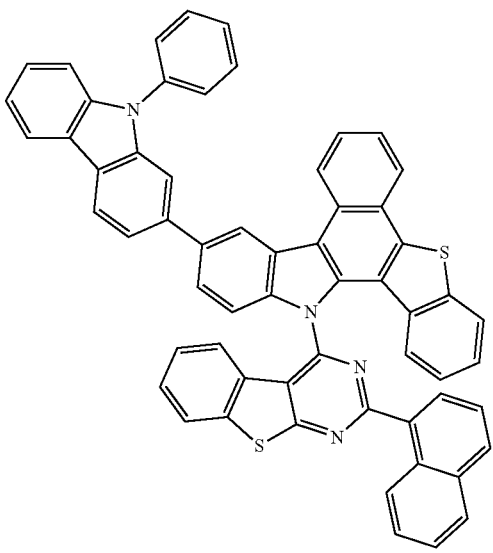
-continued
P 2-40
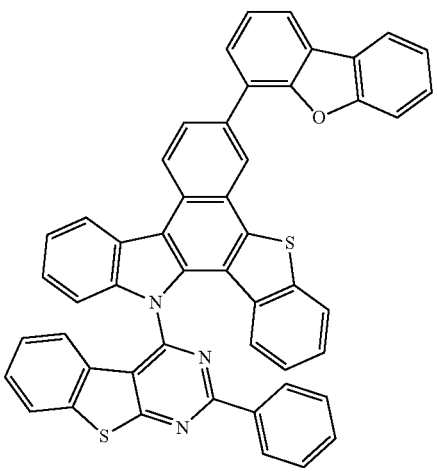
P 2-41
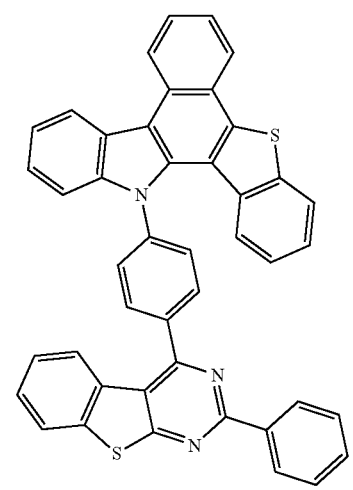
P 2-42
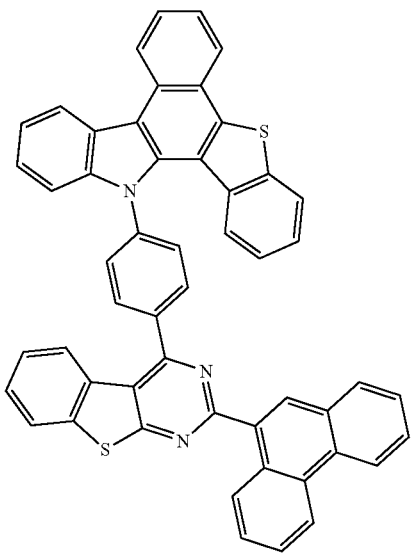

P 2-43
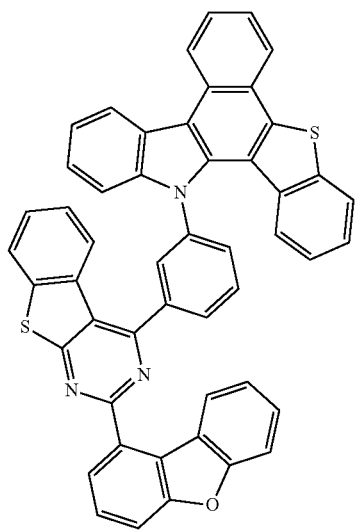
P 2-44
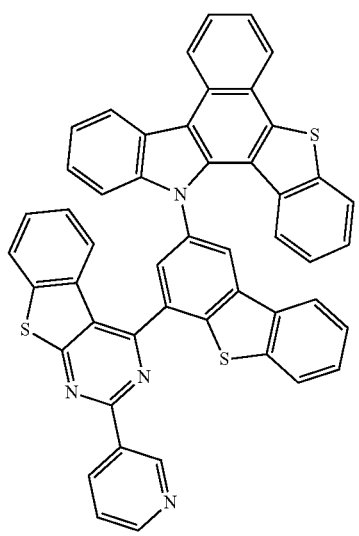
P 2-45
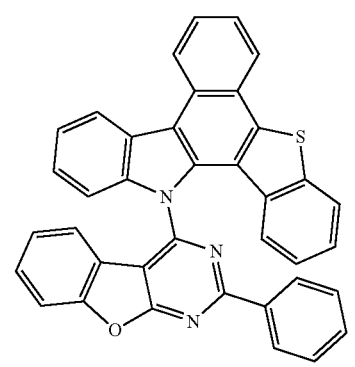
P 2-46
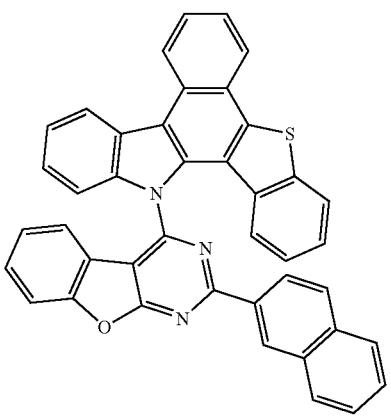
P 2-47
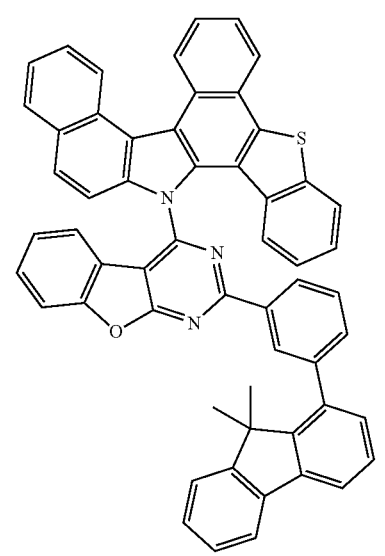
P 2-48
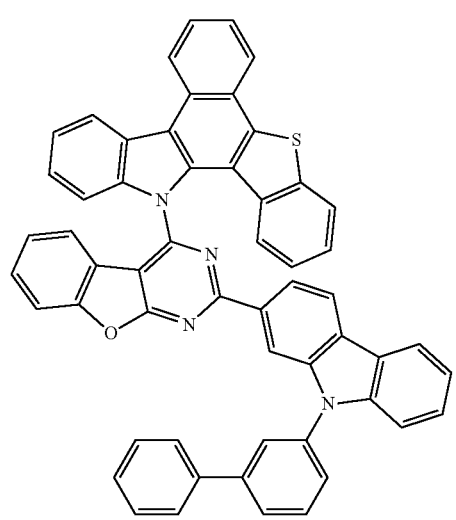

P 2-49
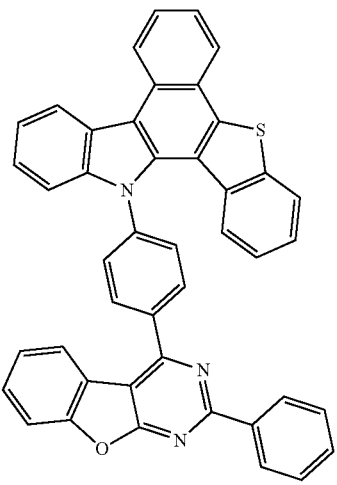
P 3-2
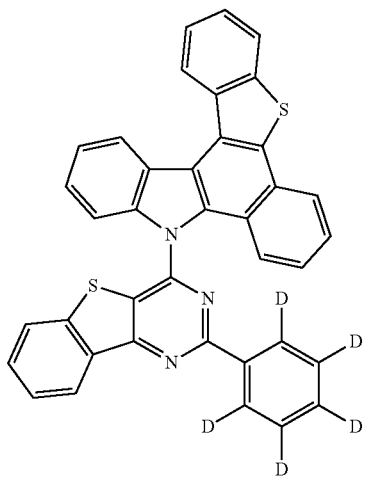
P 2-50
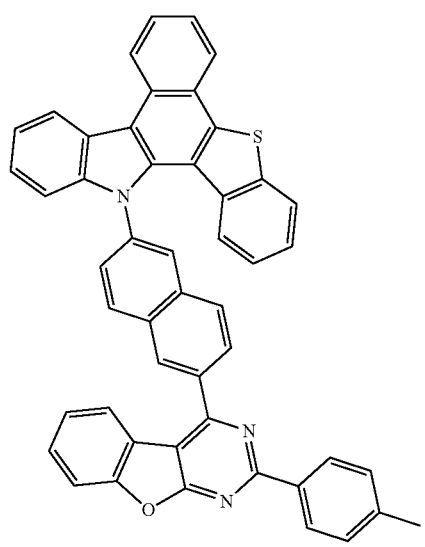
P 3-3
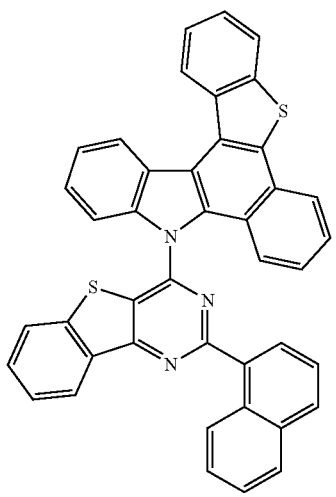
P 3-1
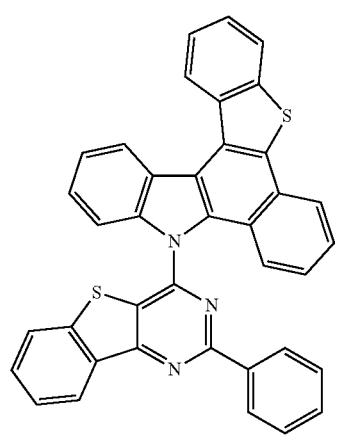
P 3-4
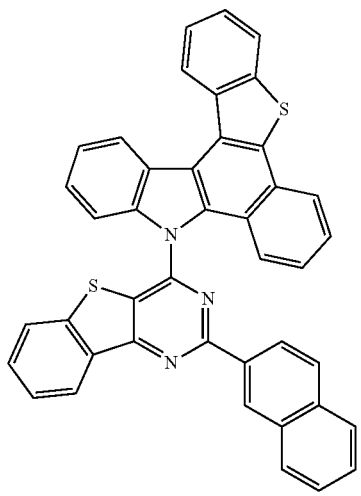

P 3-5
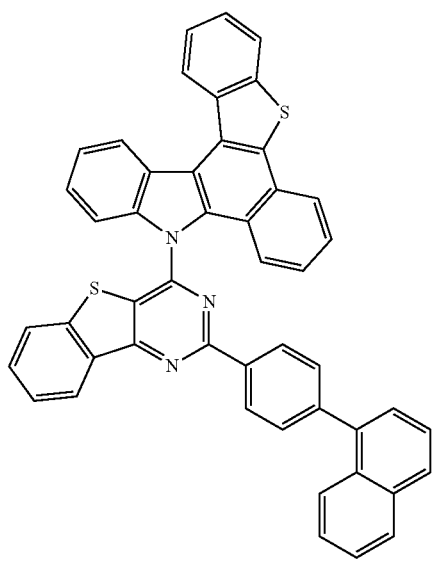
P 3-6
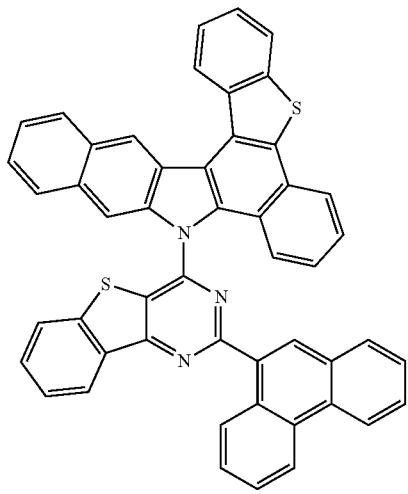
P 3-7
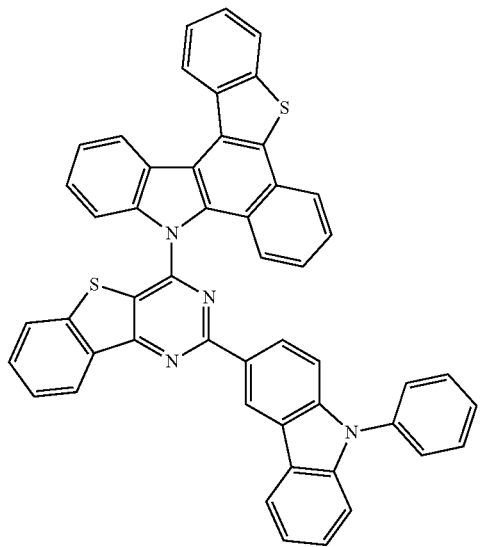
P 3-8
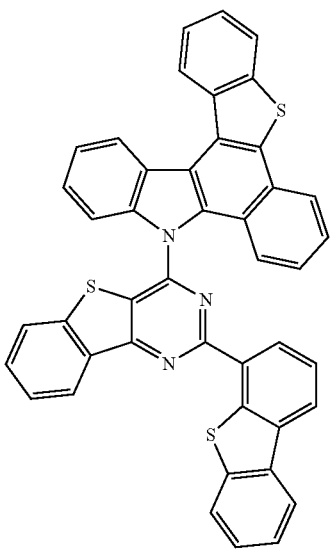
P 3-9
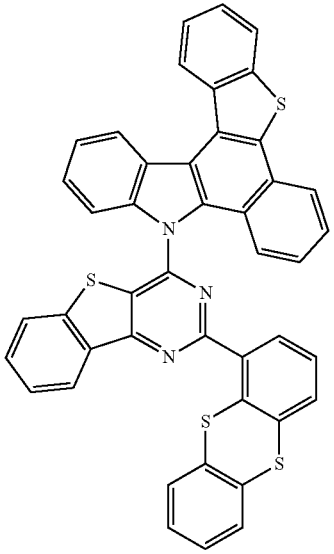
P 3-10
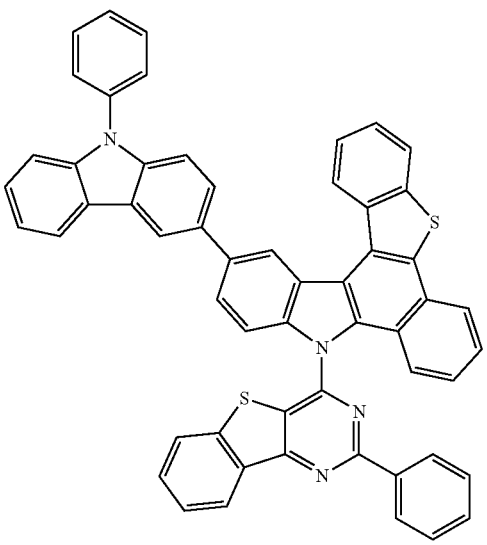

P 3-11
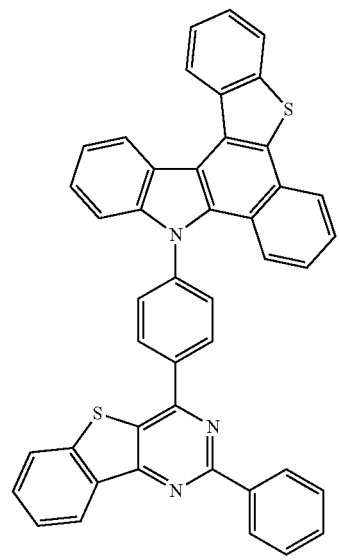
P 3-13
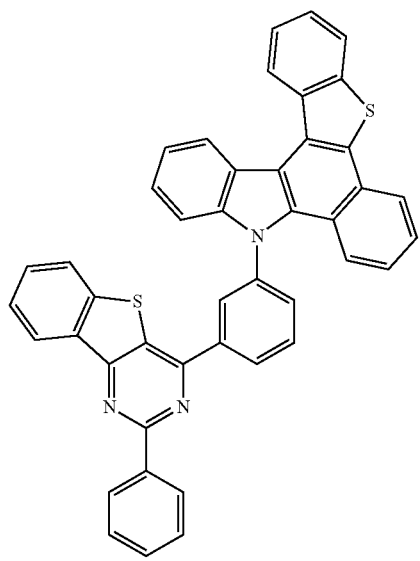
P 3-12
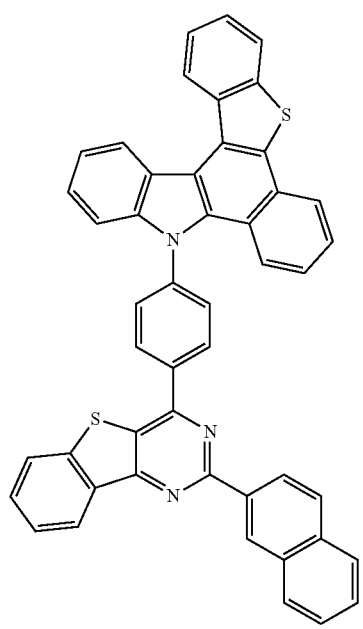
P 3-14
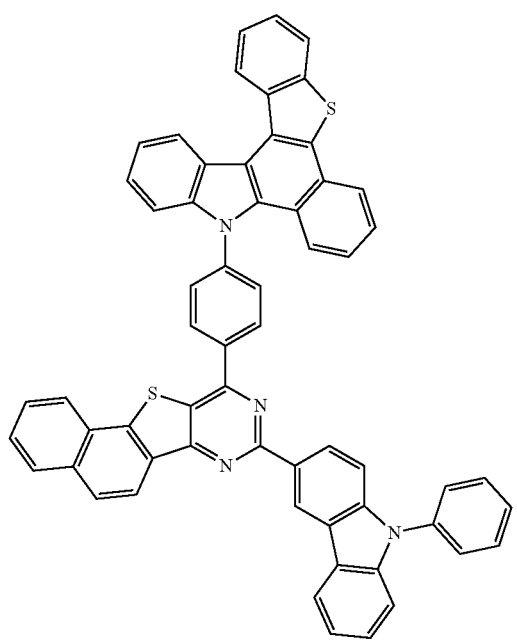

259
-continued
P 3-15
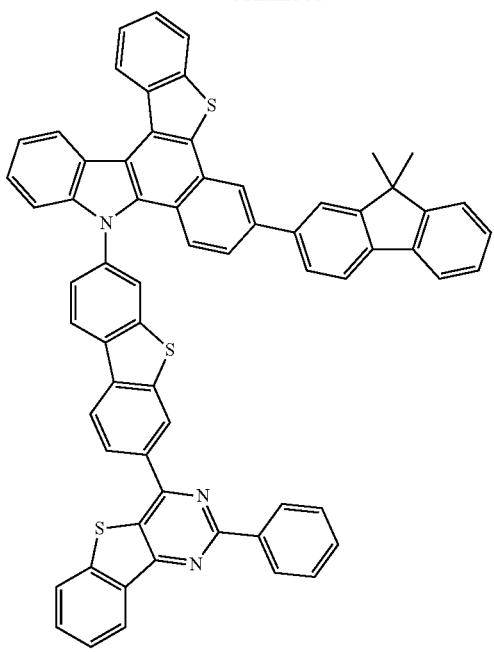
P 3-16
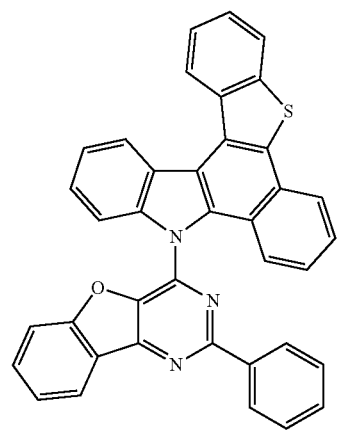
P 3-17
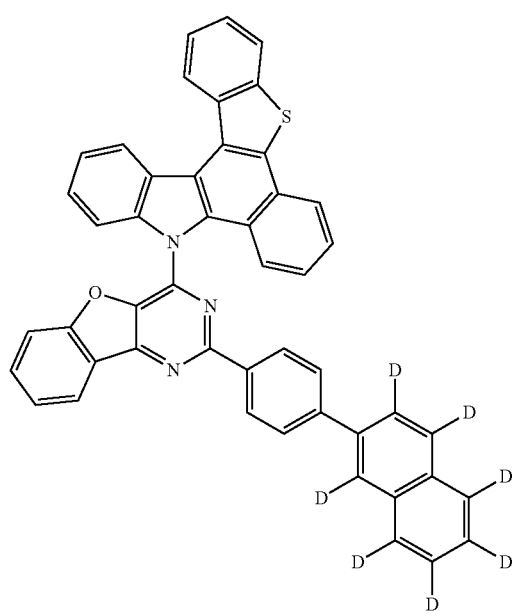
260
-continued
P 3-18
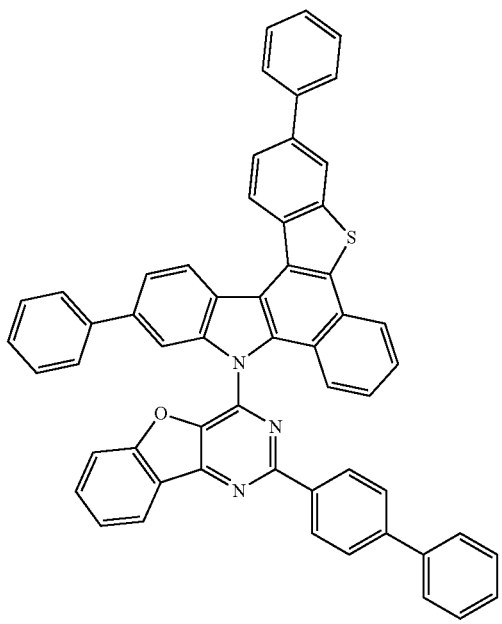
P 3-19
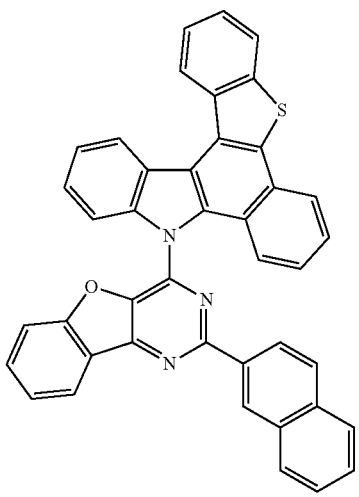
P 3-20
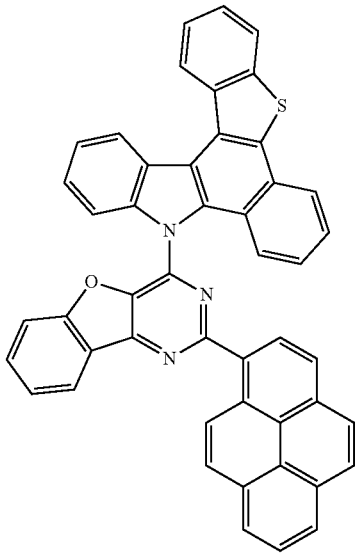

P 3-21
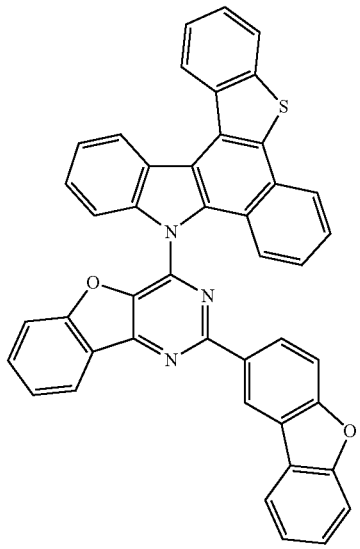
P 3-22
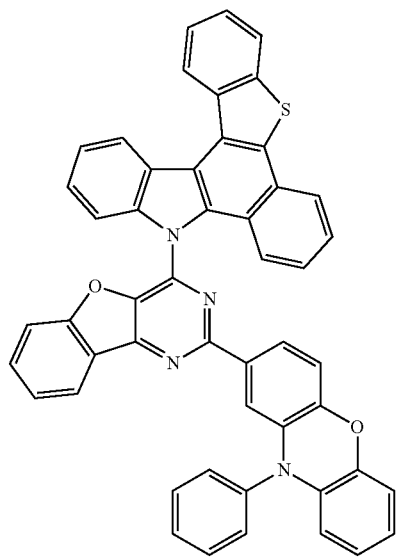
P 3-23
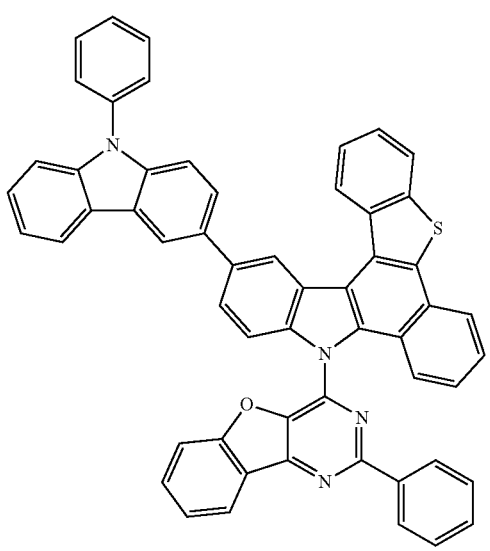
P 3-24
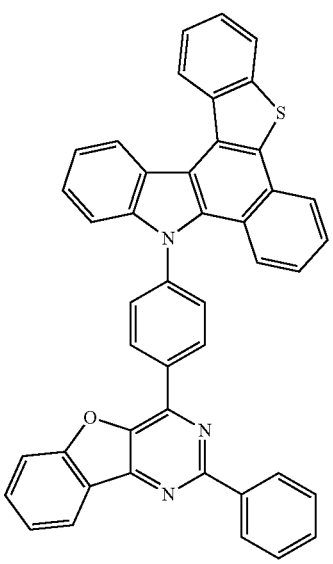
P 3-25
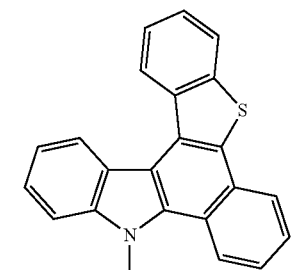
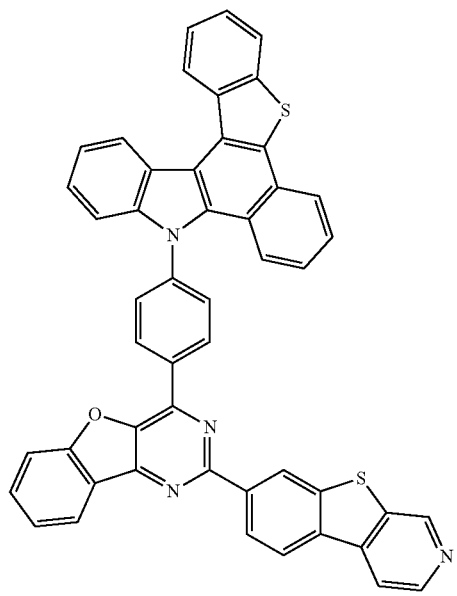
P 3-26

-continued
P 3-27
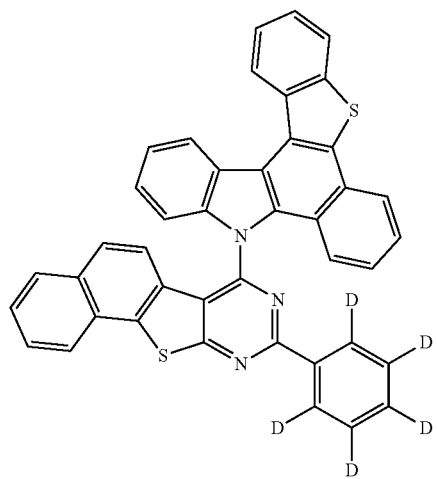
P 3-28
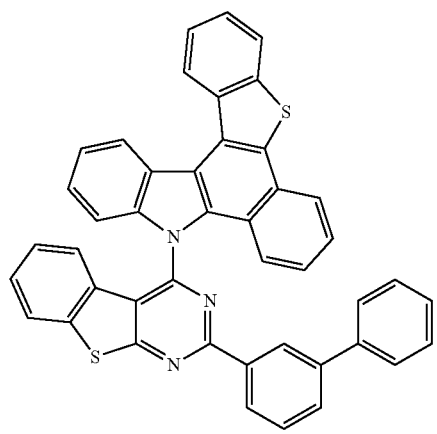
P 3-29
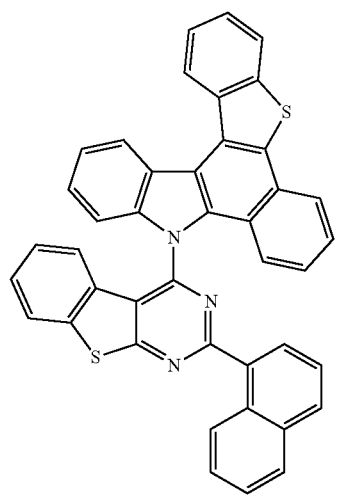
-continued
P 3-30
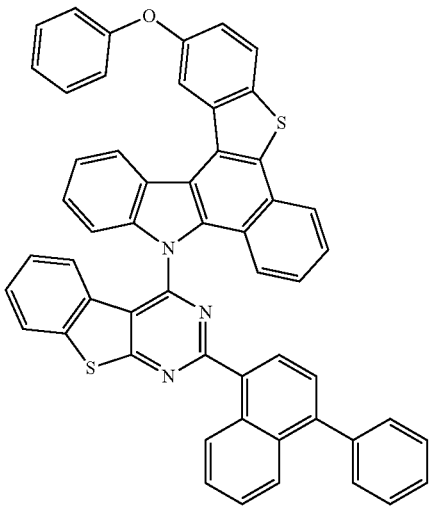
P 3-31
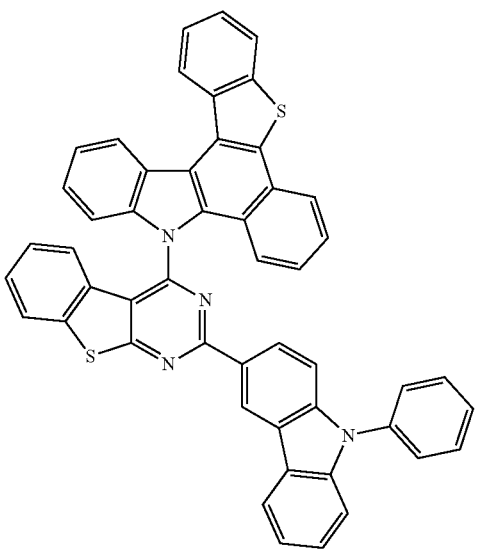
P 3-32
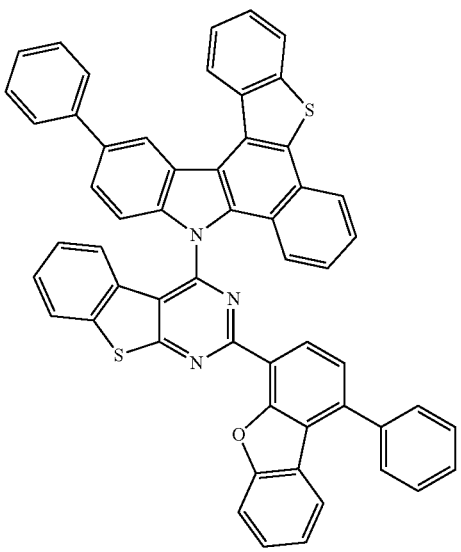

P 3-33
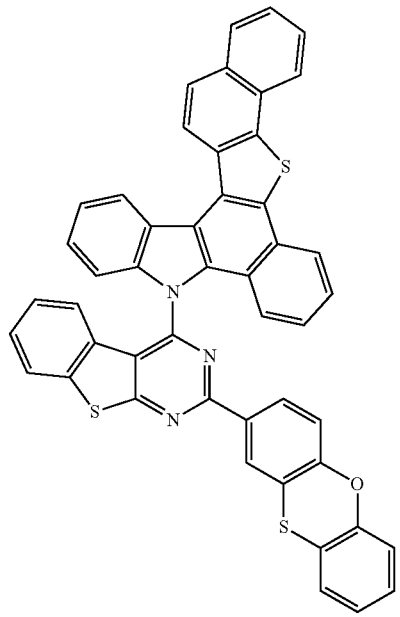
P 3-34
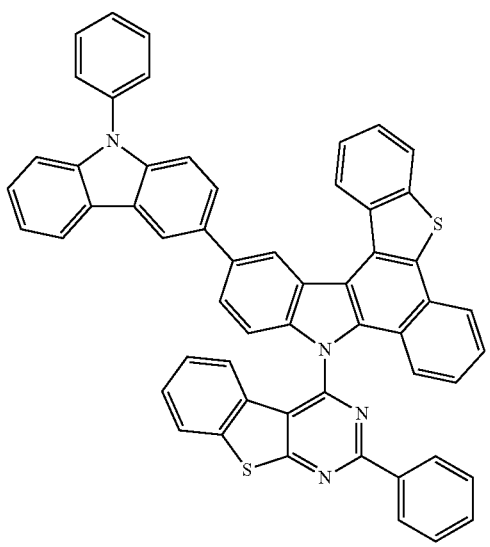
P 3-35
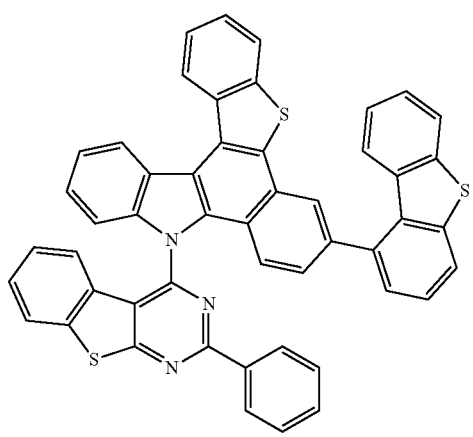
P 3-36
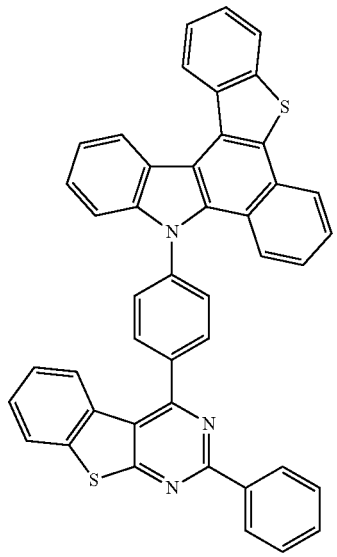
P 3-37
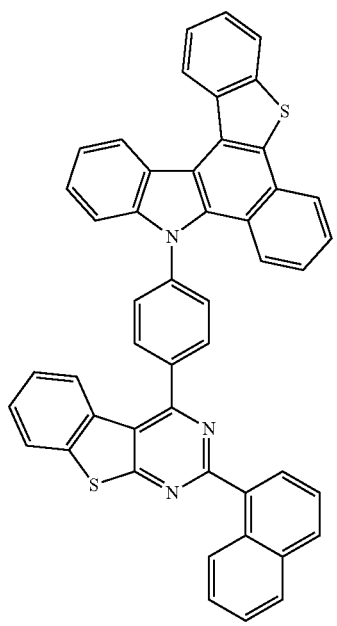

P 3-38
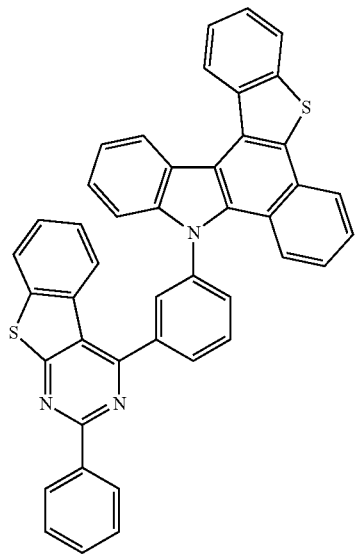
P 3-39
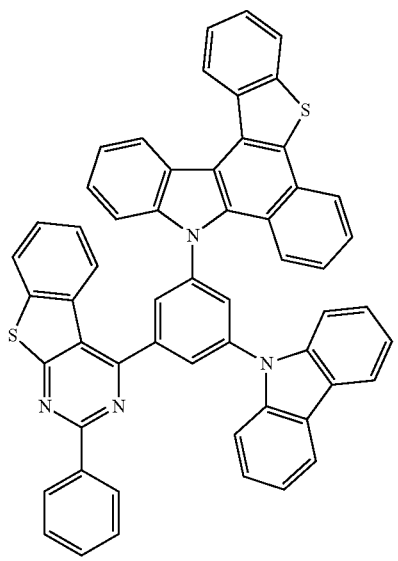
P 3-40
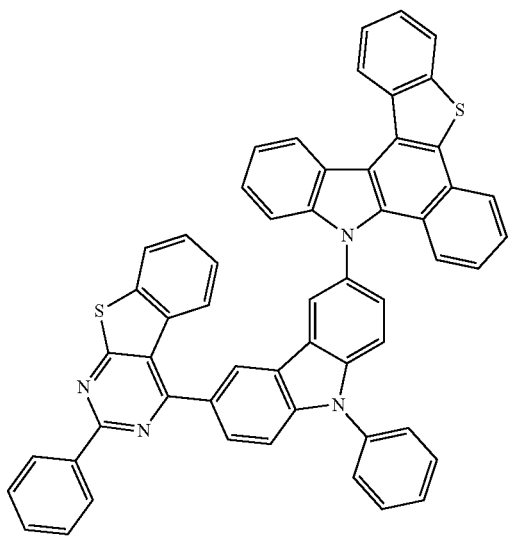
P 3-41
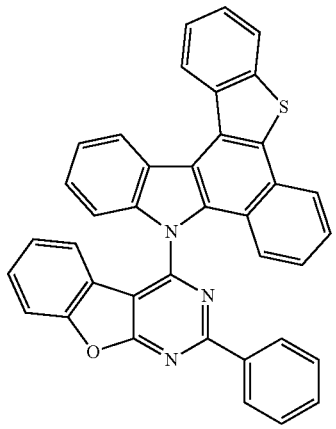
P 3-42
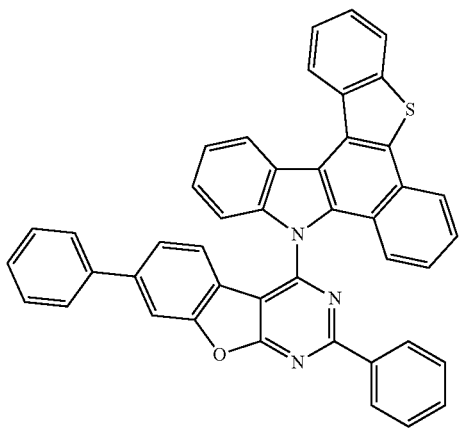
P 3-43
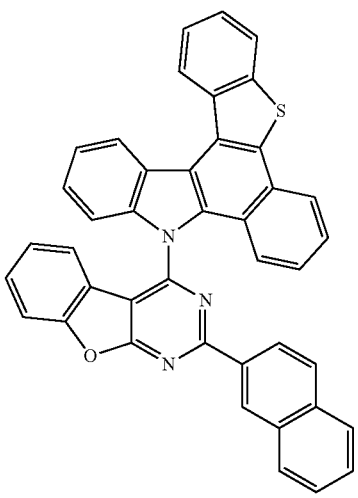

-continued
P 3-44
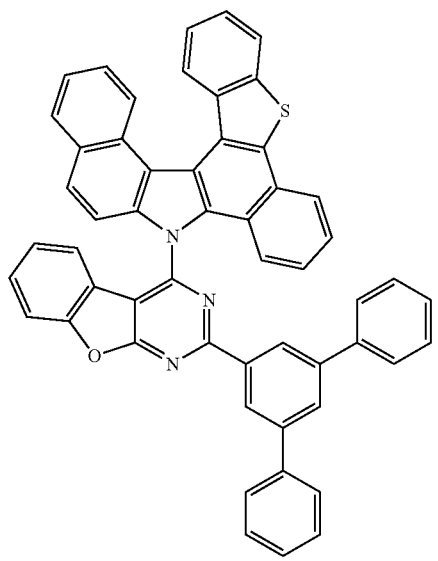
P 3-45
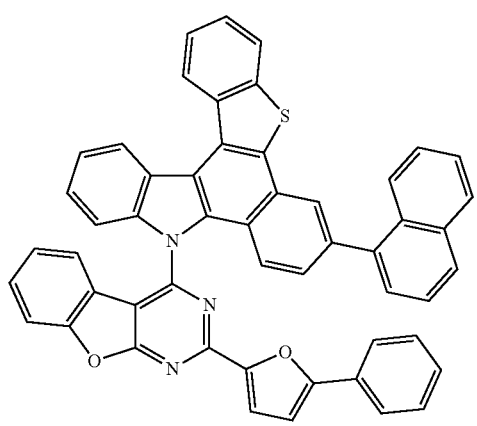
P 3-46
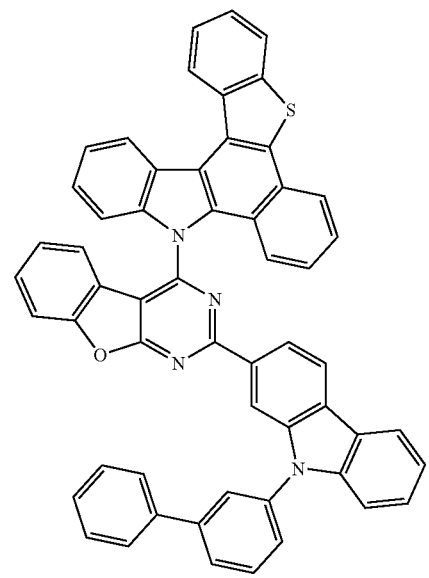
-continued
P 3-47
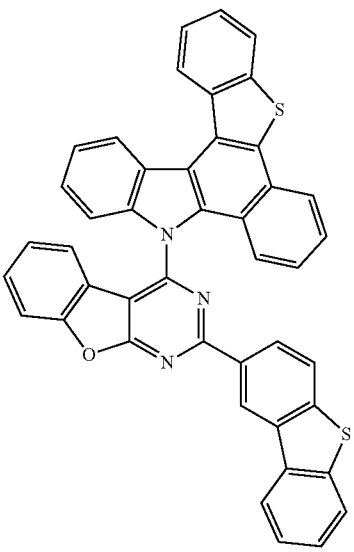
P 3-48
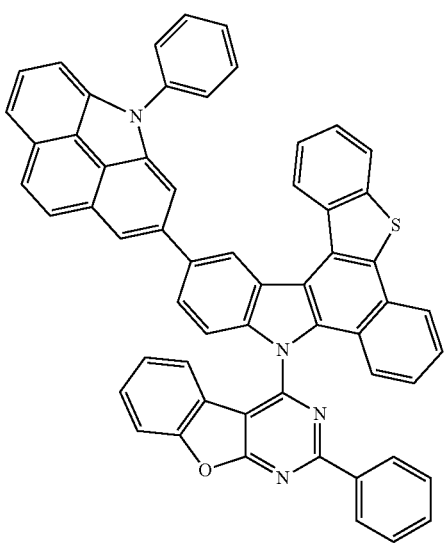
P 3-49
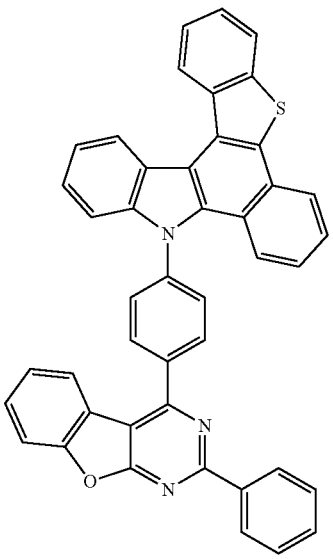

P 3-50
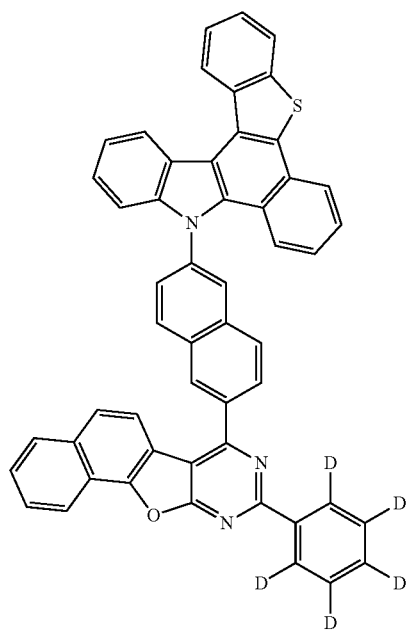
P 4-1
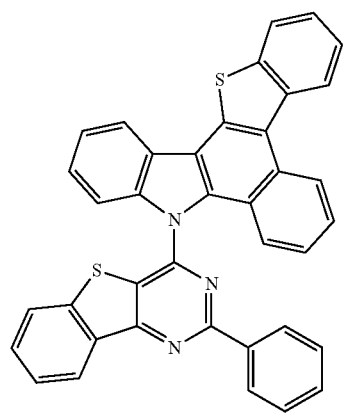
P 4-2
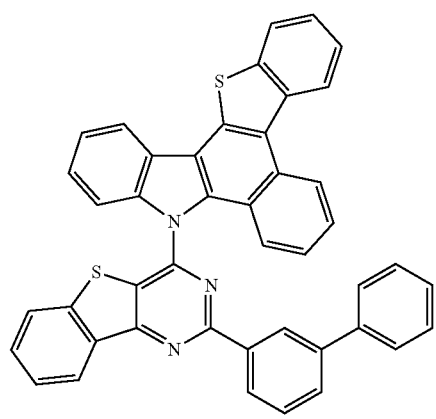
P 4-3
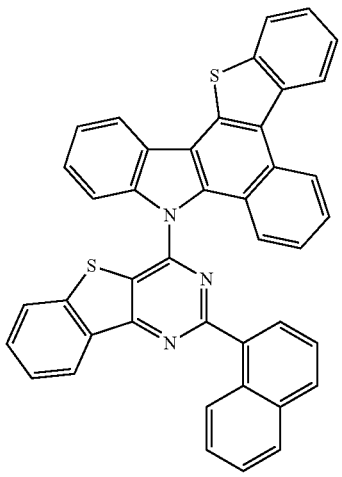
P 4-4
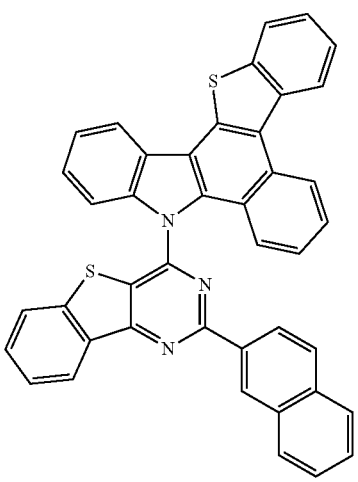
P 4-5
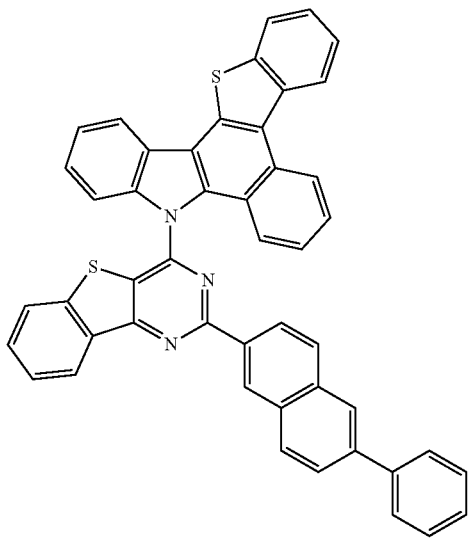

-continued
P 4-6
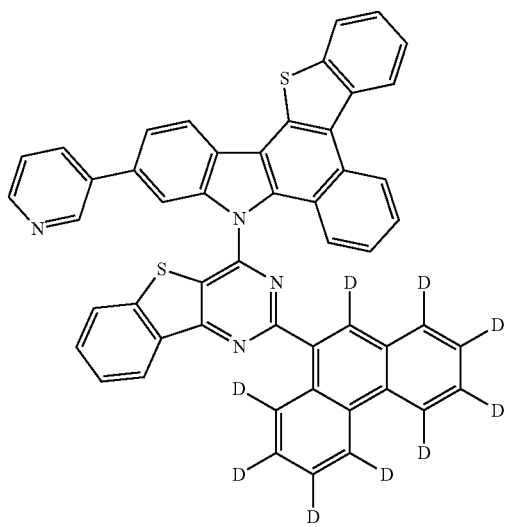
P 4-7
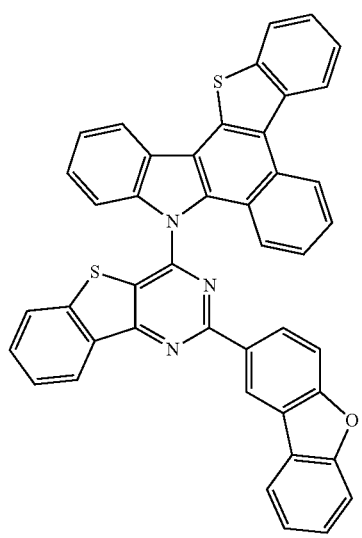
P 4-8
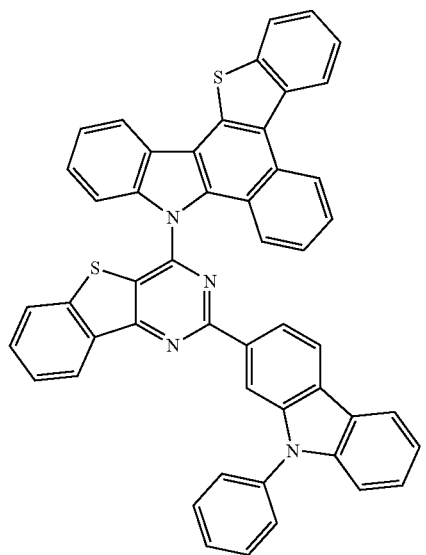
-continued
P 4-9
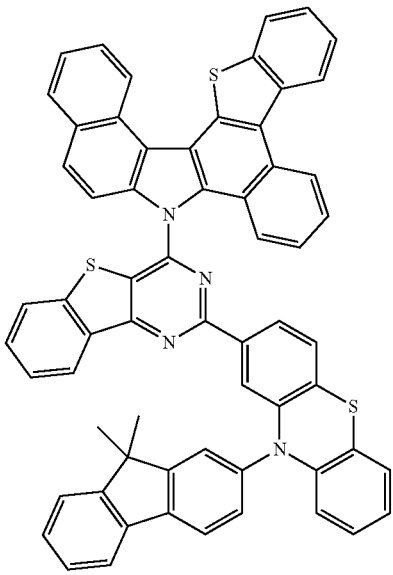
P 4-10
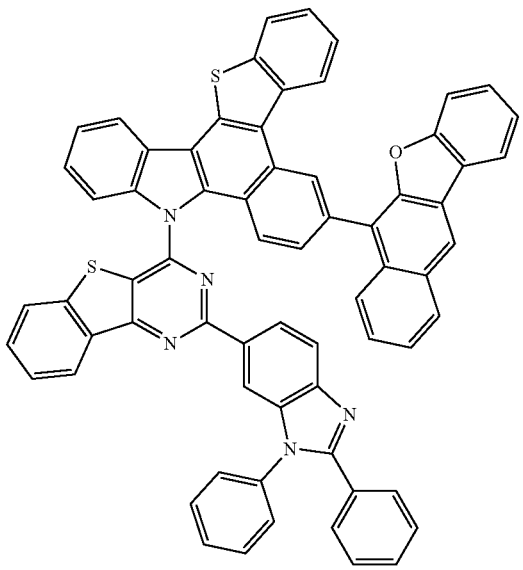
P 4-11
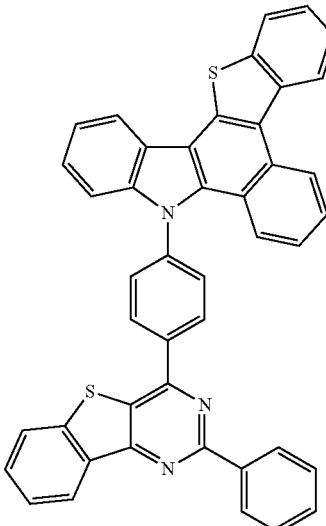

P 4-12
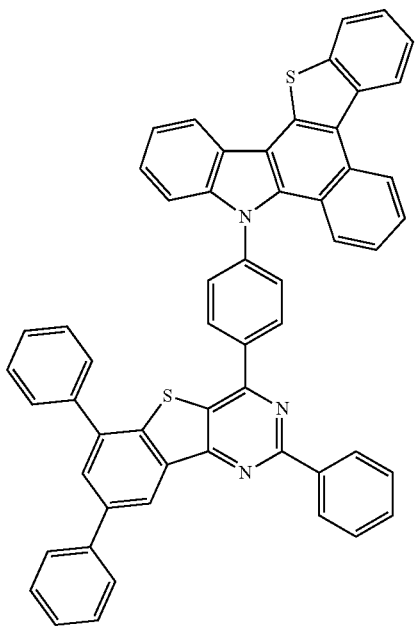
P 4-13
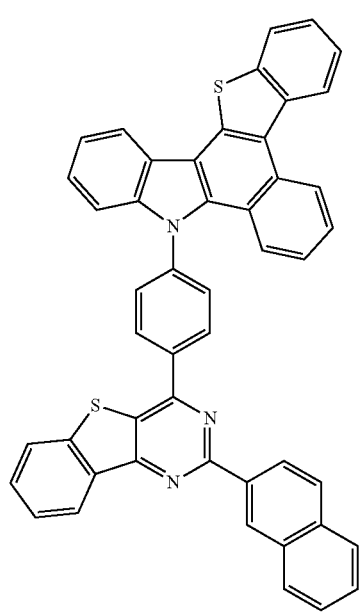
P 4-14
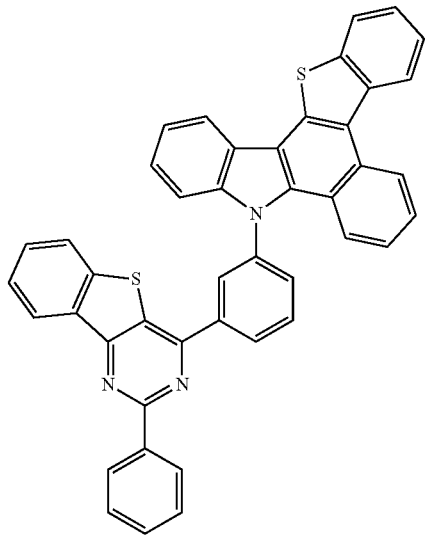
P 4-15
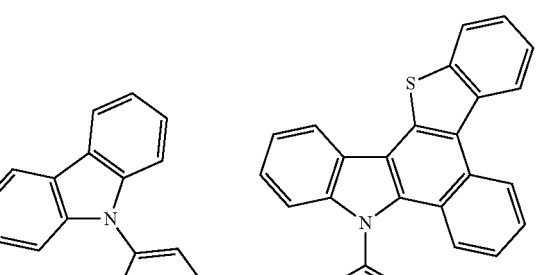
P 4-16
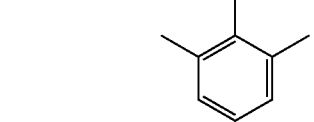

P 4-17
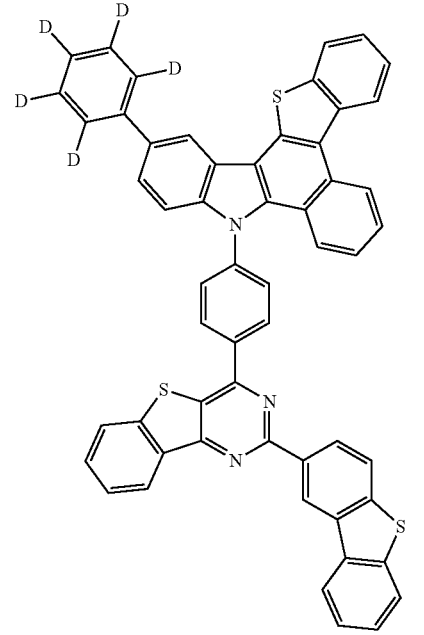
P 4-18
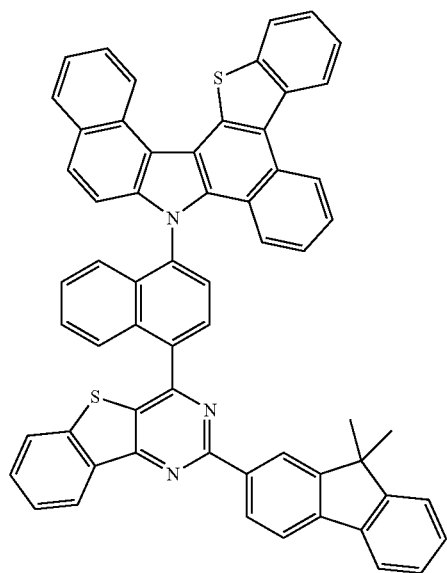
P 4-19
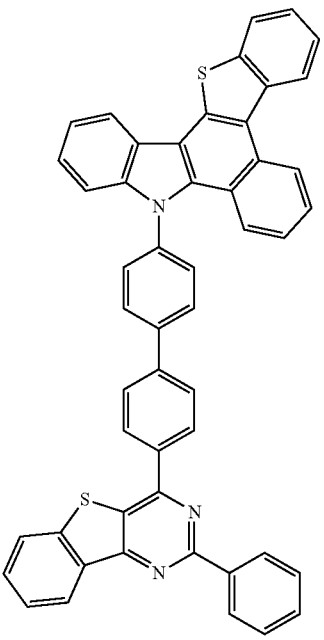
P 4-20
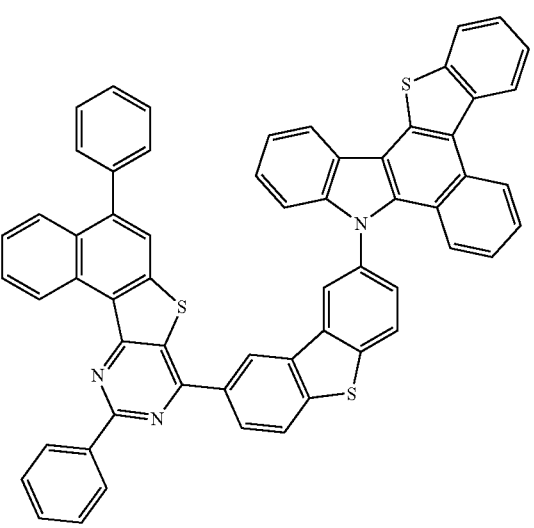
P 4-21
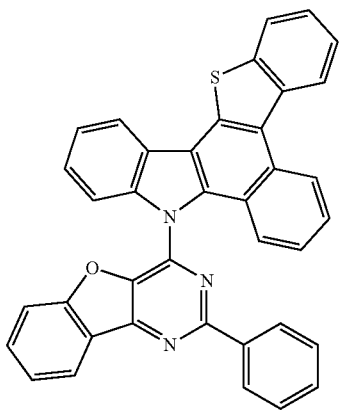

-continued
P 4-22
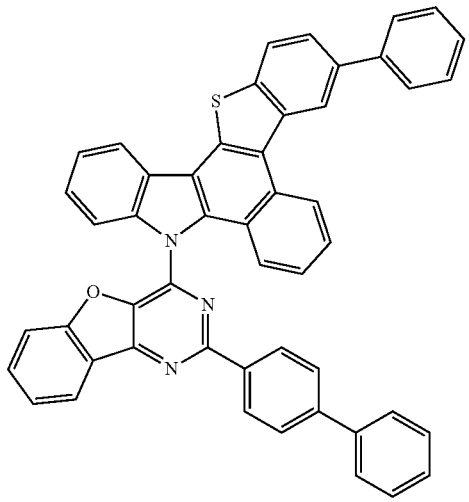
P 4-23
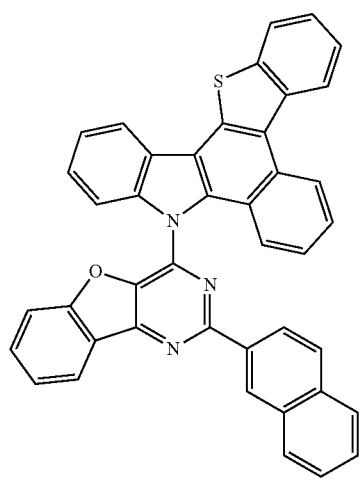
P 4-24
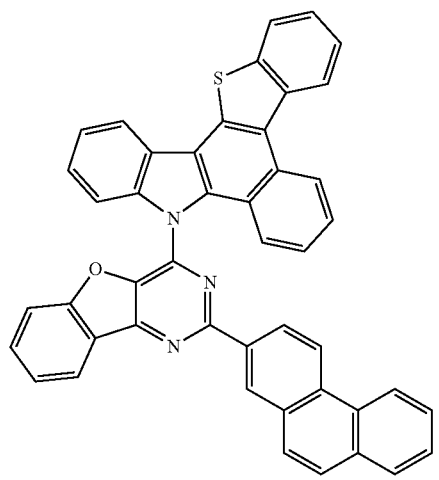
-continued
P 4-25
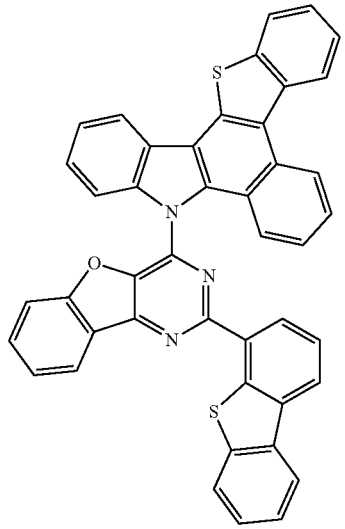
P 4-26
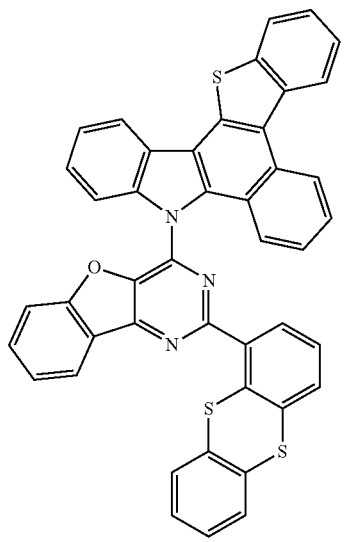
P 4-27
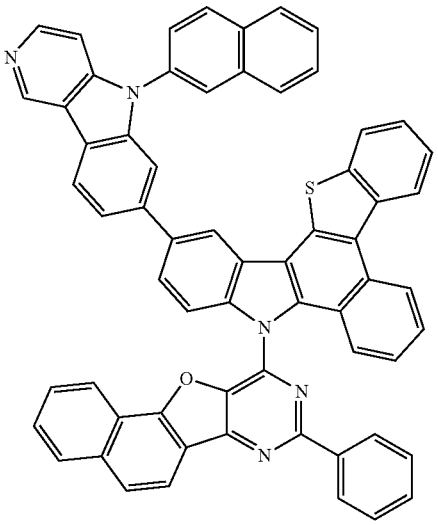

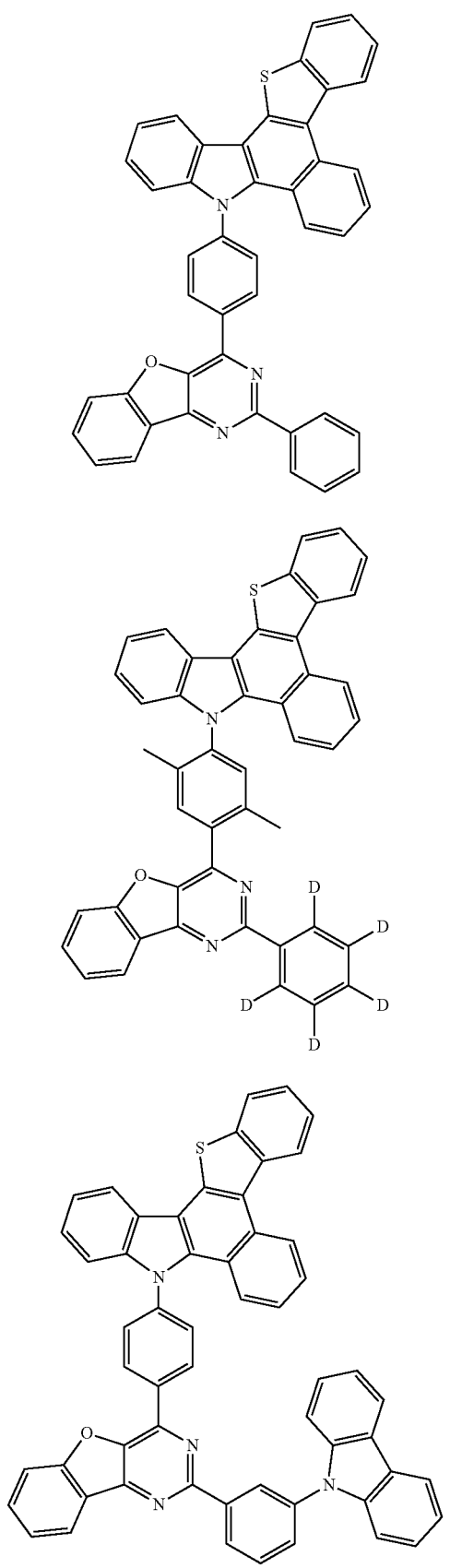
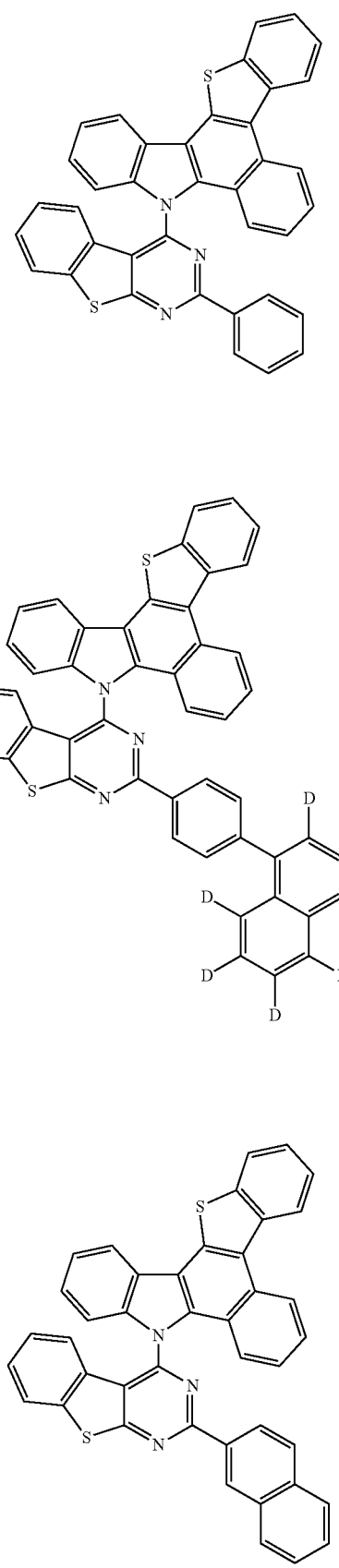

P 4-34
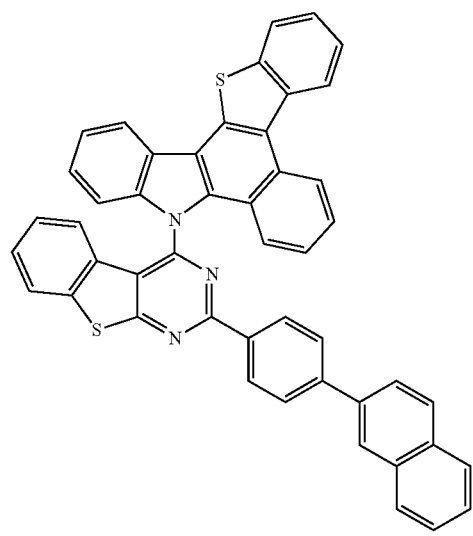
P 4-35
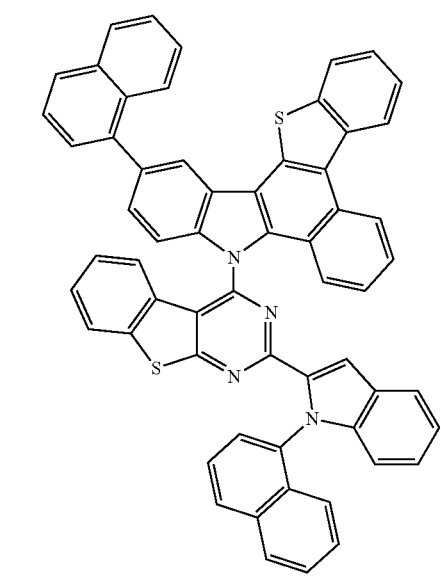
P 4-36
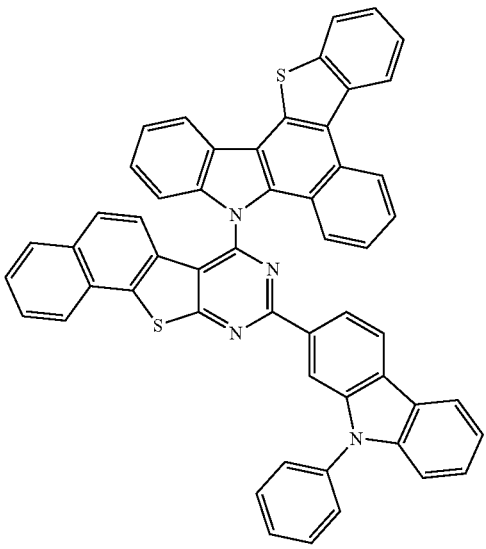
P 4-37
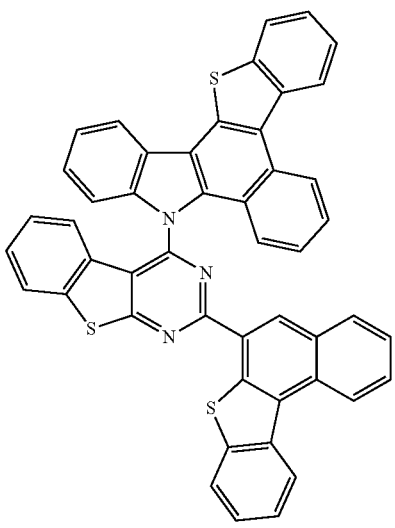
P 4-38
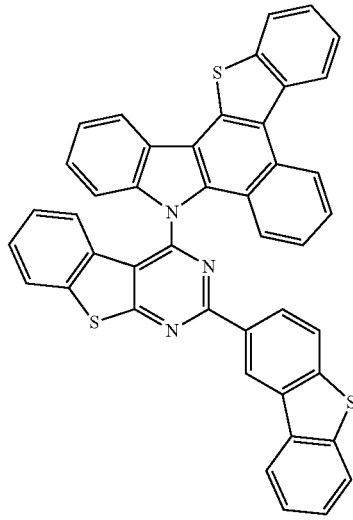
P 4-39
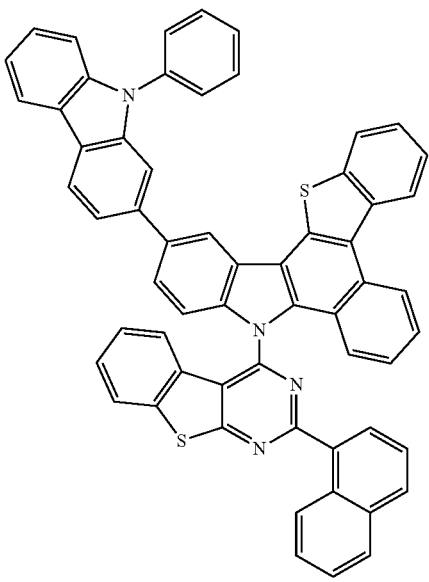

-continued
P 4-40
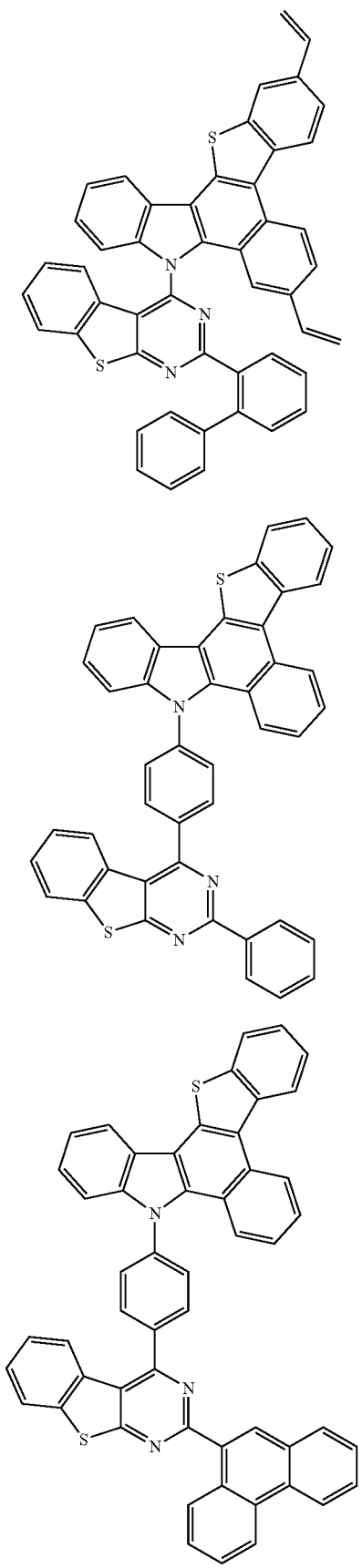
P 4-41
P 4-42
-continued
P 4-43
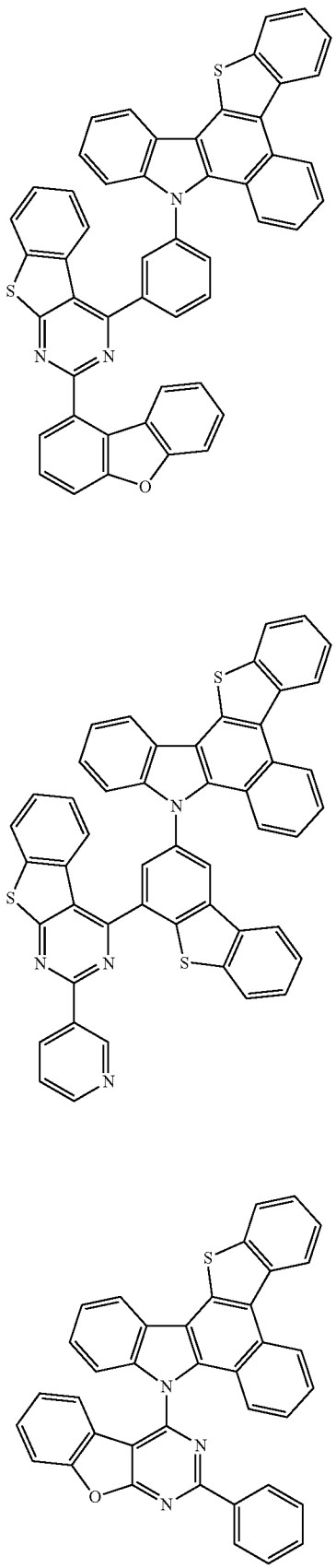
P 4-44
P 4-45

P 4-46

P 4-47

P 4-48

P 4-49

P 4-50

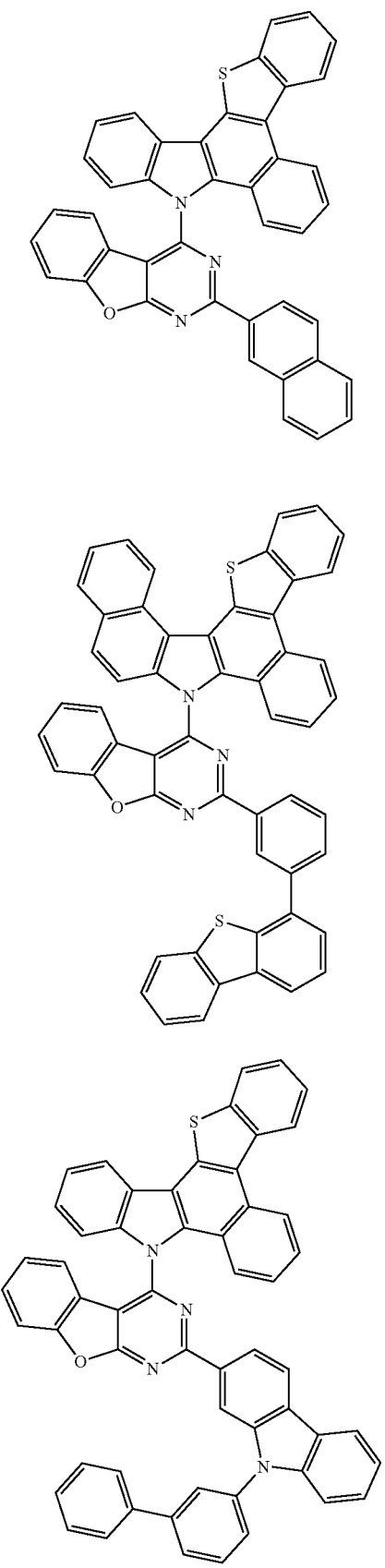

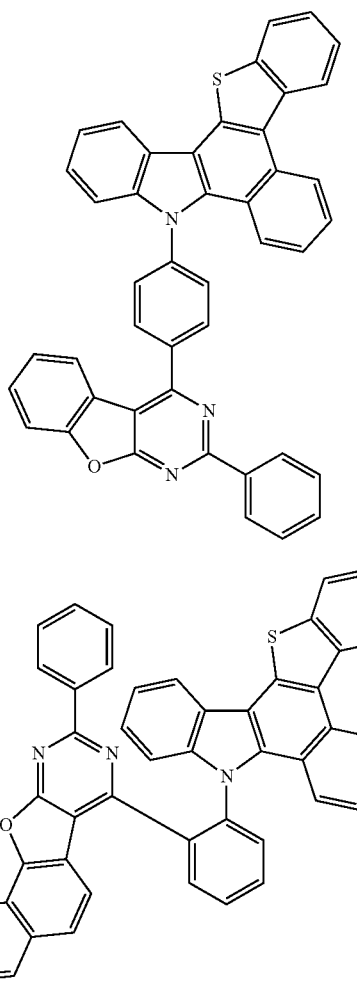

7. An organic electric element comprising a first electrode, a second electrode, and an organic material layer formed between the first electrode and the second electrode, wherein the organic material layer comprises the compound of claim 1.

8. The organic electric element of claim 7, wherein the compound is comprised as a single compound or a mixture of two or more different kinds in at least one layer of a hole injection layer, a hole transport layer, an emission-auxiliary layer and a light emitting layer of the organic material layer.

9. The organic electric element of claim 8, wherein the compound is used as phosphorescent host of the light emitting layer.

10. The organic electric element of claim 7, wherein the organic material layer is formed by any one of the processes of spin coating, nozzle printing, inkjet printing, slot coating, dip coating or roll-to-roll.

11. An electronic device comprising a display device and a control unit for driving the display device, wherein the display device comprises the organic electric element of claim 7.

12. The electronic device of claim 11, wherein the organic electric element is an organic light emitting diode, an organic solar cell, an organic photo conductor, an organic transistor, or an element for monochromatic or white illumination.

* * * * *